(12) United States Patent
Swager et al.

(10) Patent No.: US 12,274,993 B2
(45) Date of Patent: Apr. 15, 2025

(54) SYSTEMS AND METHODS FOR AFFECTING INTERACTIONS OF ELECTROMAGNETIC RADIATION WITH JANUS DROPLETS FOR SENSITIVE DETECTION OF SPECIES

(71) Applicant: Massachusetts Institute of Technology, Cambridge, MA (US)

(72) Inventors: Timothy Manning Swager, Newton, MA (US); Jie Li, Waltham, MA (US); Suchol Savagatrup, Cambridge, MA (US); Zachary P. Nelson, Cambridge, MA (US); Kosuke Yoshinaga, Cambridge, MA (US); Cassandra Zentner, Brighton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1130 days.

(21) Appl. No.: 16/932,392

(22) Filed: Jul. 17, 2020

(65) Prior Publication Data

US 2021/0080456 A1    Mar. 18, 2021

Related U.S. Application Data

(60) Provisional application No. 62/902,367, filed on Sep. 18, 2019.

(51) Int. Cl.
*B01L 1/00*     (2006.01)
*B01J 13/04*    (2006.01)
(Continued)

(52) U.S. Cl.
CPC ............. *B01J 13/14* (2013.01); *B01J 13/046* (2013.01); *C01B 33/145* (2013.01); *G01N 33/5432* (2013.01)

(58) Field of Classification Search
CPC ....... B01J 13/14; B01J 13/046; C01B 33/145; G01N 33/5432; G01N 33/56911; G01N 2333/32; G01N 33/54313
See application file for complete search history.

(56) References Cited

U.S. PATENT DOCUMENTS

| | | | |
|---|---|---|---|
| 3,826,613 A | 7/1974 | Parikh et al. |
| 4,663,277 A | 5/1987 | Wang |

(Continued)

FOREIGN PATENT DOCUMENTS

| | | | |
|---|---|---|---|
| EP | 135352 A | 3/1985 |
| EP | 161328 A | 11/1985 |

(Continued)

OTHER PUBLICATIONS

Sun, Xiao-Ting, Chun-Guang Yang, and Zhang-Run Xu. "Controlled production of size-tunable Janus droplets for submicron particle synthesis using an electrospray microfluidic chip." RSC advances 6.15 (2016): 12042-12047. (Year: 2016).*

(Continued)

*Primary Examiner* — Jyoti Nagpaul
(74) *Attorney, Agent, or Firm* — Wolf, Greenfield & Sacks, P.C.

(57) ABSTRACT

Embodiments described herein may be useful in the detection of analytes. The systems and methods may allow for a relatively simple and rapid way for detecting analytes such as chemical and/or biological analytes and may be useful in numerous applications including sensing, food manufacturing, medical diagnostics, performance materials, dynamic lenses, water monitoring, environmental monitoring, detection of proteins, detection of DNA, among other applications. For example, the systems and methods described herein may be used for determining the presence of a contaminant such as bacteria (e.g., detecting pathogenic bacteria in food and water samples which helps to prevent (Continued)

widespread infection, illness, and even death). Advantageously, the systems and methods described herein may not have the drawbacks in current detection technologies including, for example, relatively high costs, long enrichment steps and analysis times, and/or the need for extensive user training. Another advantageous feature provided by the systems and methods described herein includes fabrication in a relatively large scale. In some embodiments, the systems and methods may be used in conjunction with a detector including handheld detectors incorporated with, for example, smartphones (e.g., for the on-site detection of analytes such as pathogenic bacteria).

11 Claims, 85 Drawing Sheets

Specification includes a Sequence Listing.

(51) Int. Cl.
*B01J 13/14* (2006.01)
*C01B 33/145* (2006.01)
*G01N 33/543* (2006.01)

(56) References Cited

U.S. PATENT DOCUMENTS

| | | | |
|---|---|---|---|
| 4,870,026 A | 9/1989 | Wands et al. |
| 4,912,034 A | 3/1990 | Kalra et al. |
| 5,066,465 A | 11/1991 | Kano et al. |
| 5,217,648 A | 6/1993 | Beissinger et al. |
| 5,332,661 A | 7/1994 | Adamczyk et al. |
| 5,387,676 A | 2/1995 | Zavada et al. |
| 5,516,635 A | 5/1996 | Ekins et al. |
| 5,980,936 A | 11/1999 | Krafft et al. |
| 6,180,418 B1 | 1/2001 | Lee |
| 6,271,202 B1 | 8/2001 | Kudsk |
| 6,710,092 B2 | 3/2004 | Scher et al. |
| 7,067,590 B2 | 6/2006 | Sato et al. |
| 7,625,951 B2 | 12/2009 | Daunert et al. |
| 7,767,017 B2 | 8/2010 | Lahann et al. |
| 7,947,772 B2 | 5/2011 | Lahann et al. |
| 8,241,651 B2 | 8/2012 | Lahann |
| 9,415,392 B2 | 8/2016 | Ismagilov et al. |
| 10,005,058 B2 | 6/2018 | Swager et al. |
| 10,060,913 B2 | 8/2018 | Swager et al. |
| 10,252,231 B2 | 4/2019 | Swager et al. |
| 11,119,098 B2 | 9/2021 | Swager et al. |
| 11,229,892 B2 | 1/2022 | Swager et al. |
| 2002/0040065 A1 | 4/2002 | Scher et al. |
| 2002/0090608 A1 | 7/2002 | Palese et al. |
| 2004/0069857 A1 | 4/2004 | Leblans et al. |
| 2004/0176479 A1 | 9/2004 | Scher et al. |
| 2005/0145829 A1 | 7/2005 | Leyrer et al. |
| 2006/0154234 A1 | 7/2006 | Winther et al. |
| 2006/0201390 A1 | 9/2006 | Lahann et al. |
| 2007/0105972 A1 | 5/2007 | Doyle et al. |
| 2007/0237800 A1 | 10/2007 | Lahann et al. |
| 2008/0234394 A1 | 9/2008 | Hong et al. |
| 2008/0242774 A1 | 10/2008 | Lahann et al. |
| 2009/0232856 A1 | 9/2009 | Patel |
| 2009/0306311 A1 | 12/2009 | Reed |
| 2010/0062525 A1 | 3/2010 | Abbott et al. |
| 2010/0069726 A1 | 3/2010 | Levinson |
| 2010/0097687 A1 | 4/2010 | Lipovetskaya et al. |
| 2010/0099048 A1 | 4/2010 | Thomas et al. |
| 2011/0003401 A1 | 1/2011 | Oscarsson et al. |
| 2011/0104777 A1 | 5/2011 | Marquez et al. |
| 2011/0195394 A1 | 8/2011 | Selinfreund et al. |
| 2011/0195421 A1 | 8/2011 | Selinfreund et al. |
| 2011/0196085 A1 | 8/2011 | Selinfreund et al. |
| 2011/0223590 A1 | 9/2011 | Chiou et al. |
| 2012/0028342 A1 | 2/2012 | Ismagilov et al. |
| 2012/0045748 A1 | 2/2012 | Willson et al. |
| 2012/0248020 A1 | 10/2012 | Granick et al. |
| 2012/0288852 A1 | 11/2012 | Willson et al. |
| 2012/0319043 A1 | 12/2012 | Stepien et al. |
| 2012/0328654 A1 | 12/2012 | Huang et al. |
| 2014/0016177 A1 | 1/2014 | Aizenberg et al. |
| 2014/0227684 A1 | 8/2014 | Hindson et al. |
| 2014/0323330 A1 | 10/2014 | Bergo |
| 2014/0350168 A1 | 11/2014 | Bormashenko |
| 2015/0238636 A1 | 8/2015 | Homyk et al. |
| 2016/0114325 A1 | 4/2016 | Tang et al. |
| 2016/0151753 A1 | 6/2016 | Swager et al. |
| 2016/0151756 A1 | 6/2016 | Swager et al. |
| 2016/0193602 A1 | 7/2016 | Tsai et al. |
| 2016/0235670 A1 | 8/2016 | Mason et al. |
| 2017/0368865 A1 | 12/2017 | Macpherson et al. |
| 2017/0371151 A1 | 12/2017 | Brassard et al. |
| 2018/0080927 A1 | 3/2018 | Swager et al. |
| 2019/0170736 A1 | 6/2019 | Swager et al. |
| 2019/0170737 A1 | 6/2019 | Swager et al. |
| 2019/0184356 A1 | 6/2019 | Swager et al. |
| 2019/0212333 A1 | 7/2019 | Swager et al. |
| 2020/0166503 A1 | 5/2020 | Swager et al. |
| 2021/0041425 A1 | 2/2021 | Swager et al. |
| 2022/0205989 A1 | 6/2022 | Swager et al. |

FOREIGN PATENT DOCUMENTS

| | | |
|---|---|---|
| EP | 323909 A | 7/1989 |
| EP | 1365240 A2 | 11/2003 |
| JP | H05-99926 A | 4/1993 |
| JP | 2013-518167 A | 5/2013 |
| WO | WO 92/14154 A1 | 8/1992 |
| WO | WO 1992/17179 A1 | 10/1992 |
| WO | WO 1995/31500 A2 | 11/1995 |
| WO | WO 2004/063707 A2 | 7/2004 |
| WO | WO 2008/066463 A1 | 6/2008 |
| WO | WO 2009/061372 A1 | 5/2009 |
| WO | WO 2009/101113 A2 | 8/2009 |
| WO | WO 2010/092333 A1 | 8/2010 |
| WO | WO 2011/093733 A1 | 8/2011 |
| WO | WO 2013/059294 A1 | 4/2013 |
| WO | WO 2015/051179 A1 | 4/2015 |
| WO | WO 2016/103226 A2 | 6/2016 |

OTHER PUBLICATIONS

Ong et al., Dynamic self-correcting nucleophilic aromatic substitution. Nat Chem. Sep. 3, 2018;10:1023-30.
Claessens et al., Highly Efficient Synthesis of Chloro- and Phenoxy-Substituted Subphthalocyanines. Jun. 26, 2003;2003(14):2547-51.
Extended European Search Report mailed Jun. 11, 2018, for Application No. EP 15855674.6.
International Search Report and Written Opinion mailed Jan. 22, 2016, for Application No. PCT/US2015/058268.
International Preliminary Report on Patentability mailed May 11, 2017, for Application No. PCT/US2015/058268.
International Search Report and Written Opinion mailed Jan. 22, 2016, for Application No. PCT/US2015/058286.
International Preliminary Report on Patentability mailed May 11, 2017, for Application No. PCT/US2015/058286.
International Search Report and Written Opinion mailed Nov. 30, 2017, for Application No. PCT/US2017/052209.
International Preliminary Report on Patentability mailed Mar. 28, 2019, for Application No. PCT/US2017/052209.
International Search Report and Written Opinion mailed Dec. 3, 2020, for Application No. PCT/US2020/042599.
International Preliminary Report on Patentability mailed Mar. 31, 2022, for Application No. PCT/US2020/042599.
[No Author Listed], Definition of Associate. Retrieved from https://www.vocabulary.com/associate. Accessed on Apr. 22, 2020. 4 pages.
[No Author Listed], Definition of Fluidic. Retrieved from https://www.merriam-webster.com/dictionary/fluidic. Last accessed on Apr. 14, 2021. 10 pages.
Alino et al., Liquid crystal droplets as a hosting and sensing platform for developing immunoassays. Langmuir. Aug. 2011;27:11784-9.

(56) References Cited

OTHER PUBLICATIONS

Anker et al., Magnetically modulated optical nanoprobes. Appl Phys Lett. 2003. 82(7): 1102-4.
Aserin, Multiple Emulsions: Technology and Applications. John Wiley & Sons, Inc., 2008, 22 pages.
Augustin et al., Nano- and micro-structured assemblies for encapsulation of food ingredients. Chem Soc Rev. Apr. 2009;38(4):902-12. doi: 10.1039/b801739p. Epub Dec. 4, 2008.
Axenov et al., Thermotropic Ionic Liquid Crystals. Materials. 2011;4:206-59. Epub Jan. 14, 2011.
Bedford et al., Solubilities and Volume Changes Attending Mixing for the System: Perfluoro-n-hexane-n-Hexane. J. Am. Chem. Soc., 1958, 80(2): 282-285.
Belmonte et al., Patterned Full-Color Reflective Coatings Based on Photonic Cholesteric Liquid-Crystalline Particles. ACS Appl Mater Interfaces. Apr. 17, 2019;11(15):14376-14382. doi: 10.1021/acsami.9b02680. Epub Apr. 8, 2019.
Berger et al., Stimuli-responsive bicomponent polymer Janus particles by "grafting from"/"grafting to" approaches. Macromolecules. 2008;41:9669-76. Epub Nov. 21, 2008.
Besnard et al., Multiple emulsions controlled by stimuli-responsive polymers. Adv Mater. May 28, 2013;25(20):2844-8. doi: 10.1002/adma.201204496. Epub Mar. 11, 2013.
Bijlard et al., Functional Colloidal Stabilization. Advanced Materials Interfaces. Jan. 2019;4(1):1600443. Epub Nov. 8, 2016. 31 pages.
Brake et al., Biomolecular interactions at phospholipid-decorated surfaces of liquid crystals. Science. Dec. 19, 2003;302(5653):2094-7. doi: 10.1126/science. 1091749.
Braun et al., Functional liquid crystalline particles and beyond. Liquid Crystals. 2019;46(13-14):2023-41.
Broer et al., Functional organic materials based on polymerized liquid-crystal monomers: supramolecular hydrogen-bonded systems. Angew Chem Int Ed Engl. Jul. 16, 2012;51(29):7102-9. doi: 10.1002/anie.201200883. Epub May 15, 2012.
Brown et al., Stimuli-responsive surfactants. Soft Matter 2013; 9:2365-2374.
Brunsveld et al., Hierarchical Growth of Chiral Self-Assembled Structures in Protic Media. J. Am. Chem. Soc. 2000; 122(26):6175-82. Epub Jun. 17, 2000.
Chakravarti et al., Liquid membrane multiple emulsion process of chromium(VI) separation from waste waters. Colloid Surface A 1995; 103:59-71.
Chen et al., Janus particles templated from double emulsion droplets generated using microfluidics. Langmuir. 2009;25(8):4320-3. Epub Mar. 18, 2009.
Chen et al., Photoresponsive Monodisperse Cholesteric Liquid Crystalline Microshells for Tunable Omnidirectional Lasing Enabled by a Visible Light-Driven Chiral Molecular Switch. Adv Op Mat 2014; 2(9): 845-8.
Chevallier et al., Photofoams: remote control of foam destabilization by exposure to light using an azobenzene surfactant. Langmuir. Feb. 7, 2012;28(5):2308-12. doi: 10.1021/la204200z. Epub Jan. 27, 2012.
Choi et al., Microfluidic Design of Complex Emulsions. ChemPhysChem 2014; 15: 21-29.
Choi et al., One step formation of controllable complex emulsions: from functional particles to simultaneous encapsulation of hydrophilic and hydrophobic agents into desired position. Adv mater. 2013; 6 pages.
Choi et al., Patterned fluorescent particles as nanoprobes for the investigation of molecular interactions. Nano Letters. 2003;3(8):995-1000. Epub Jul. 11, 2003.
Cipparrone et al., Chiral self-assembled solid microspheres: a novel multifunctional microphotonic device. Adv Mater. Dec. 22, 2011;23(48):5773-8. doi: 10.1002/adma.201102828. Epub Nov. 15, 2011.
Concellón et al., Dynamic Complex Liquid Crystal Emulsions. J. Am. Chem. Soc. 2019;141(45):18246-55. Epub Nov. 1, 2019.

Craig et al., Effect of Spacer Length on the Thermal Properties of Side-Chain Liquid Crystal Polymethacrylates. 2. Synthesis and Characterization of the Poly[.omega.-(4'-cyanobiphenyl-4-yloxy)alkyl methacrylate]s. Macromolecules. 1995;28(10):3617-24. Epub May 1, 1995.
De La Fuente et al., Exploring the efficiency of gallic acid-based dendrimers and their block copolymers with PEG as gene carriers. Nanomed. 2012;7(11): 1667-81. Epub Jul. 20, 2012.
Dominguez et al., Modelling and understanding of the vapour-liquid and liquid-liquid interfacial properties for the binary mixture of n-heptane and perfluoro-n-hexane. J. Mol. Liq. 2013; 185:36-43.
Engel et al., Insulin: intestinal absorption as water-in-oil-in-water emulsions. Nature. Aug. 24, 1968;219(5156):856-7.
Erb et al., Towards holonomic control of Janus particles in optomagnetic traps. Adv Mater. Dec. 18, 2009;21(47):4825-9.
Eremin et al., Azodendrimers as a photoactive interface for liquid crystals. Liquid Crystals. 2018;45(13-15):2121-31. Epub Aug. 17, 2018.
Fleischmann et al., One-piece micropumps from liquid crystalline core-shell particles. Nat Commun. 2012;3:1178. doi: 10.1038/ncomms2193. Epub Nov. 6, 2012. 8 pages.
Forth et al., Building Reconfigurable Devices Using Complex Liquid-Fluid Interfaces. Advanced Materials. May 2019;31(18): 1806370. Epub Mar. 4, 2019. 39 pages.
Gao et al., Double Emulsion Templated Microcapsules with Single Hollow Cavities and Thickness-Controllable Shells. Langmuir, 2009, 25(6): 3832-3838.
Ge et al., Droplet topology control of Janus emulsion prepared in one-step high energy mixing. Soft Matter. 2014;10:4498-505. Epub Apr. 8, 2014.
Ge et al., Recent studies of Janus emulsions prepared by one-step vibrational mixing. Current Opinion in Colloid & Interface Science. Oct. 2016;25:58-66.
Gladysz et al., Structural, physical, and chemical properties of fluorous compounds. Top Curr Chem. 2012;308:1-23. doi: 10.1007/128_2011_282.
Gresham et al., Use of a sustained-release multiple emulsion to extend the period of radio protection conferred by cysteamine. Nature. Nov. 19, 1971;234(5325):149-50.
Guzowski et al., The structure and stability of multiple microdroplets. Soft Matter 2012; 8: 7269-7278.
Haase et al., Tailoring of high-order multiple emulsions by the liquid-liquid phase separation of ternary mixtures. Angew Chem Int Ed. 2014;53:1-6.
Han et al., Retroreflective Janus microparticle as a nonspectroscopic optical immunosensing probe. ACS Appl Mater & Interfaces. May 4, 2016;8(17):10767-74.
He et al., Interfacial Polymerization on Dynamic Complex Colloids: Creating Stabilized Janus Droplets. ACS Applied Materials & Interfaces. 2017;9(8):7804-11. Epub Feb. 15, 2017.
Heinze et al., Microfluidic immunosensor for rapid and sensitive detection of bovine viral diarrhea virus. Sensors and Actuators B. 2009;138:491-6.
Hessberger et al., Interfacial Self-Assembly of Amphiphilic Dual Temperature Responsive Actuating Janus Particles. Adv Funct Mater. 2018;28(21):1800629. 10 pages.
Jampani et al., Micrometer-Scale Porous Buckling Shell Actuators Based on Liquid Crystal Networks. Advanced Functional Materials. 2018;28(31):1801209. Epub Jun. 5, 2018. 9 pages.
Jeong et al., Liquid crystal Janus emulsion droplets: preparation, tumbling, and swimming. Soft Matter. Sep. 14, 2015;11(34):6747-54. doi: 10.1039/c5sm01053e. Epub Jul. 14, 2015.
Joyce, Fluidics—Basic Components and Applications. U.S. Army Electronics Research and Development Command. Harry Diamond Laboratories. Adelphi, MD. Aug. 1983. 24 pages.
Kang et al., Amplified Photon Upconversion by Photonic Shell of Cholesteric Liquid Crystals. J Am Chem Soc. Apr. 26, 2017;139(16):5708-5711. doi: 10.1021/jacs.7b01981. Epub Apr. 17, 2017.
Kato et al., Functional Liquid Crystals towards the Next Generation of Materials. Angew Chem Int Ed Engl. Apr. 9, 2018;57(16):4355-4371. doi: 10.1002/anie.201711163. Epub Mar. 13, 2018.

(56) References Cited

OTHER PUBLICATIONS

Kaufmann et al., "Sandwich" microcontact printing as a mild route towards monodisperse Janus particles with tailored bifunctionality. Adv Mater. 2011;23:79-83; Supporting Information pp. 1-8.

Kaufmann et al., Bifunctional Janus beads made by "sandwich" microcontact printing using click chemistry. J Mater Chem. 2012;22:6190-9. Epub Feb. 17, 2012. Electronic suppl info pp. 1-9.

Kim et al., Fabrication of monodisperse gel shells and functional microgels in microfluidic devices. Angew Chem Int Ed Engl. 2007;46(11):1819-22.

Kumar et al., Multiple emulsions: a review. Int J Rec Adv Pharm Rsch. Jan. 2012; 2(1):9-19.

Lemal, Perspective on fluorocarbon chemistry. J Org Chem. Jan. 9, 2004;69(1):1-11.

Li et al., Synthesis of biofunctional Janus particles. Macromol Rapid Comm. 2015;36:1200-4.

Lin et al., Endotoxin-Induced Structural Transformations in Liquid Crystalline Droplets. Science. Jun. 10, 2011; 332(6035): 1297-1300. Epub May 19, 2011. Author manuscript provided. 8 pages.

Lin et al., Morphology-Dependent Luminescence in Complex Liquid Colloids. J Am Chem Soc. Mar. 6, 2019;141(9):3802-3806. doi: 10.1021/jacs.8b13215. Epub Feb. 20, 2019. Author manuscript provided. 16 pages.

Lone et al., Fabrication of polymeric Janus particles by droplet microfluidics. RSC Adv. 2014 4: 13322-13333.

McClain et al., Interfacial roughness in a near-critical binary fluid mixture: X-ray reflectivity and near-specular diffuse scattering. Eur. Phys. J. B. 1999; 10: 45-52.

McClements et al., Factors that affect the rate of oil exchange between oil-in-water emulsion droplets stabilized by a nonionic surfactant: Droplet size, surfactant concentration, and ionic strength. J. Phys. Chem. Jun. 1993; 97(28): 7304-08. doi: 10.1021/j100130a030.

McClements et al., Structured emulsion-based delivery systems: controlling the digestion and release of lipophilic food components. Adv Colloid Interface Sci. Sep. 15, 2010;159(2):213-28. doi: 10.1016/j.cis.2010.06.010. Epub Jul. 3, 2010.

McNaughton et al., Compact sensor for measuring nonlinear rotational dynamics of driven magnetic microspheres with biomedical applications. J Magnet Magnet Materials. 2009; 321: 1648-52.

Miller et al., Design of Functional Materials based on Liquid Crystalline Droplets. Chem Mater. Jan. 14, 2014;26(1):496-506. doi: 10.1021/cm4025028. Author manuscript provided. 26 pages.

Miniewicz et al., Photochromic and nonlinear optical properties of azo-functionalized POSS nanoparticles dispersed in nematic liquid crystals. Journal of Materials C. 2014;2:432-40. Epub Oct. 30, 2013.

Mondiot et al., Liquid crystal-based emulsions for synthesis of spherical and non-spherical particles with chemical patches. J Am Chem Soc. Jul. 10, 2013;135(27):9972-5. doi: 10.1021/ja4022182. Epub Apr. 19, 2013. Author manuscript provided. 10 pages.

Mukerjee et al., Adsorption of fluorocarbon and hydrocarbon surfactants to air-water, hexane-water and perfluorohexane-water interfaces. Relative affinities and fluorocarbon-hydrocarbon nonideality effects. J. Phys. Chem., 1981, 85(15): 2298-2303.

Nagelberg et al., Reconfigurable and responsive droplet-based compound micro-lenses. Nat Commun. Mar. 7, 2017;8:14673. doi: 10.1038/ncomms14673. Epub Mar. 7, 2017. 9 pages.

Nie et al., Janus and ternary particles generated by microfluidic synthesis: design, synthesis, and self-assembly. J Am Chem Soc. Jul. 26, 2006;128(29):9408-12.

Nisisako et al., Synthesis of monodisperse bicolored Janus particles with electrical anisotropy using a microfluidic co-flow system. Adv Mater. 2006;18:1152-6.

Niu et al., Optical biosensor based on liquid crystal droplets for detection of cholic acid. Optics Commun. 2016;381:286-91.

Ohm et al., A continuous flow synthesis of micrometer-sized actuators from liquid crystalline elastomers. Adv Mater. Dec. 18, 2009;21(47):4859-62. doi: 10.1002/adma.200901522.

Patravale et al., Novel cosmetic delivery systems: an application update. Int J Cosmet Sci. Feb. 2008;30(1):19-33. doi: 10.1111/j.1468-2494.2008.00416.x.

Perro et al., Design and synthesis of Janus micro- and nanoparticles. J Mater Chem. 2005;15:3745-60. Epub Jul. 25, 2005.

Riess, Overview of progress in the fluorocarbon approach to in vivo oxygen delivery. Biomater Artif Cells Immobilization Biotechnol. 1992;20(2-4):183-202.

Roh et al., Biphasic Janus particles with nanoscale anisotropy. Nat Mater. Oct. 2005;4:759-63. Epub Sep. 25, 2005.

Schutt et al., Injectable microbubbles as contrast agents for diagnostic ultrasound imaging: the key role of perfluorochemicals. Angew Chem Int Ed Engl. Jul. 21, 2003;42(28):3218-35.

Schwartz et al., Cholesteric Liquid Crystal Shells as Enabling Material for Information-Rich Design and Architecture. Adv Mater. Jul. 2018;30(30):e1707382. doi: 10.1002/adma.201707382. Epub May 14, 2018. 19 pages.

Shah et al., Designer emulsions using microfluidics. Materials Today, 2011; 11: 18-27.

Shah et al., Janus Supraparticles by Induced Phase Separation of Nanoparticles in Droplets. Adv. Mater. 2009; 21: 1949-1953. doi: 10.1002/adma.200803115.

Shum et al., Droplet microfluidics for fabrication of non-spherical particles. Macromol Rapid Commun. Jan. 18, 2010;31(2):108-18. doi: 10.1002/marc.200900590. Epub Nov. 24, 2009.

Sivakumar et al., Liquid Crystal Emulsions as the Basis of Biological Sensors for the Optical Detection of Bacteria and Viruses. Advanced Functional Materials. 2009;19(14):2260-5. Epub Jul. 16, 2009.

Skarabot et al., Hierarchical self-assembly of nematic colloidal superstructures. Phys Rev E. Jun. 2008;77(6 Pt 1):061706. doi: 10.1103/PhysRevE.77.061706. Epub Jun. 12, 2008. 4 pages.

Song et al., Monodisperse w/w/w double emulsion induced by phase separation. Langmuir. 2012;28:12054-12059.

Tanaka et al., Dual stimuli-responsive "mushroom-like" Janus polymer particles as particulate surfactants. Langmuir. Jul. 20, 2010;26(14):11732-6. doi: 10.1021/la101237c.

Tschierske, Development of structural complexity by liquid-crystal self-assembly. Angew Chem Int Ed Engl. Aug. 19, 2013;52(34):8828-78. doi: 10.1002/anie.201300872. Epub Aug. 9, 2013.

Tu et al., One-step encapsulation and triggered release based on Janus particle-stabilized multiple emulsions. Chem Commun (Camb). Dec. 21, 2014;50(98):15549-52. doi: 10.1039/c4cc07854c. Epub Oct. 30, 2014.

Utada et al., Monodisperse double emulsions generated from a microcapillary device. Science. Apr. 22, 2005;308(5721):537-41.

Van Der Asdonk et al., Liquid crystal templating as an approach to spatially and temporally organise soft matter. Chem Soc Rev. Oct. 2, 2017;46(19):5935-5949. doi: 10.1039/c7cs00029d.

Walther et al., Janus particles. Soft Matter. 2008;4:663-8. Epub Feb. 26, 2008.

Wang et al., Janus magneto-electric nanosphere dimers exhibiting unidirectional visible light scattering and strong electromagnetic field enhancement. ACS Nano. Jan. 27, 2015;9(1):436-48. doi: 10.1021/nn505606x. Epub Jan. 6, 2015.

Wang et al., Liquid crystals: emerging materials for use in real-time detection applications. Journal of Materials Chemistry C. 2015;3:9038-47. Epub Aug. 4, 2015. Author manuscript provided. 23 pages.

Wang et al., Thermally reconfigurable Janus droplets with nematic liquid crystalline and isotropic perfluorocarbon oil compartments. Soft Matter. Mar. 20, 2019;15(12):2580-2590. doi: 10.1039/c8sm02600a. Author manuscript provided. 12 pages.

Wang et al., Topological defects in liquid crystals as templates for molecular self-assembly. Nat Mater. Jan. 2016;15(1):106-12. doi: 10.1038/nmat4421. Epub Sep. 21, 2015.

Wong et al., Bioinspired self-repairing slippery surfaces with pressure-stable omniphobicity. Nature. Sep. 21, 2011;477(7365):443-7. doi: 10.1038/nature10447.

Wu et al., Bioinspired nanocorals with decoupled cellular targeting and sensing functionality. Small. 2010;6(4):503-7.

(56) References Cited

OTHER PUBLICATIONS

Yang et al., Microfluidic synthesis of multifunctional Janus particles for biomedical applications. Lab Chip. Jun. 21, 2012;12(12):2097-102. doi: 10.1039/c2lc90046g. Epub May 14, 2012. Author manuscript provided. 14 pages.

Yi et al., Janus particles for biological imaging and sensing. Analyst. Jun. 21, 2016;141(12):3526-39. doi: 10.1039/c6an00325g. Epub Apr. 7, 2016. Author manuscript provided. 24 pages.

Yin et al., Versatile bifunctional magnetic-fluorescent responsive Janus supraballs towards the flexible bead display. Adv Mater. Jul. 12, 2011;23(26):2915-9. doi: 10.1002/adma.201100203. Epub Apr. 26, 2011.

Yoshida et al., Structurally Controlled Bio-hybrid Materials Based on Unidirectional Association of Anisotropic Microparticles with Human Endothelial Cells. Adv Mater. Dec. 2009;21:4920-5.

Yuet et al., Multifunctional Superparamagnetic Janus Particles. Langmuir. Mar. 16, 2010;26(6):4281-7. doi:10.1021/la903348s. Epub Oct. 20, 2009.

Yusa et al., Fluorescence Studies of pH-Responsive Unimolecular Micelles Formed from Amphiphilic Polysulfonates Possessing Long-Chain Alkyl Carboxyl Pendants. Macromolecules. 2002; 35(27): 10182-88. doi: 10.1021/ma0212947. Epub Nov. 27, 2002.

Zarzar et al., Dynamically reconfigurable complex emulsions via tunable interfacial tensions. Nature. Feb. 26, 2015;518(7540):520-4. doi: 10.1038/nature14168. Author manuscript provided. 20 pages.

Zeininger et al., Rapid Detection of *Salmonella enterica* via Directional Emission from Carbohydrate-Functionalized Dynamic Double Emulsions. ACS Cent Sci. May 22, 2019; 5(5): 789-795. Epub Apr. 23, 2019.

Zeininger et al., Waveguide-based chemo- and biosensors: complex emulsions for the detection of caffeine and proteins. Lab on a Chip. 2019;19:1327-31. Epub Mar. 21, 2019.

Zhang et al., Emulsion Agglutination Assay for the Detection of Protein-Protein Interactions: An Optical Sensor for Zika Virus. ACS Sens. Jan. 25, 2019;4(1):180-184. doi: 10.1021/acssensors.8b01202. Epub Jan. 9, 2019. Author manuscript provided. 12 pages.

Zhang et al., Fabrication of Janus droplets by evaporation driven liquid-liquid phase separation. Chemical Communications. 2016;52:5015-8. Epub Mar. 7, 2016.

Zhang et al., Interfacial bioconjugation on emulsion droplet for biosensors. Bioorg Med Chem. Oct. 15, 2018;26(19):5307-13. Author manuscript. 20 pages.

Zhang et al., Janus emulsions for the detection of bacteria. ACS Central Sci. Apr. 26, 2017;3(4):309-13.

Zhang et al., Janus Particle Synthesis, Assembly, and Application. Langmuir. 2017;33(28):6964-77. Epub Jul. 5, 2017.

Zhang et al., Toward Design Rules of Directional Janus Colloidal Assembly. Ann Rev Phys Chem. 2015;66:581-600. doi: 10.1146/annurev-physchem-040214-121241. Epub Feb. 4, 2015.

Zhang et al., Ultra-small droplet generation via volatile component evaporation. Lab Chip. Apr. 21, 2014;14(8):1395-400. doi: 10.1039/c3lc51183a.

Zhao et al., Microfluidic mass-transfer control for the simple formation of complex multiple emulsions. Angew Chem Int Ed. 2009;48:7208-11.

McNaughton et al., Single bacterial cell detection with nonlinear rotational frequency shifts of driven magnetic microspheres. Appl Phys Lett. 2007. 91: 224105.

Yu et al., Simultaneous detection of pathogenic bacteria using agglutination test based on colored silica nanoparticles. Curr Pharm Biotechnol. 2015; 16(8):716-23.

\* cited by examiner

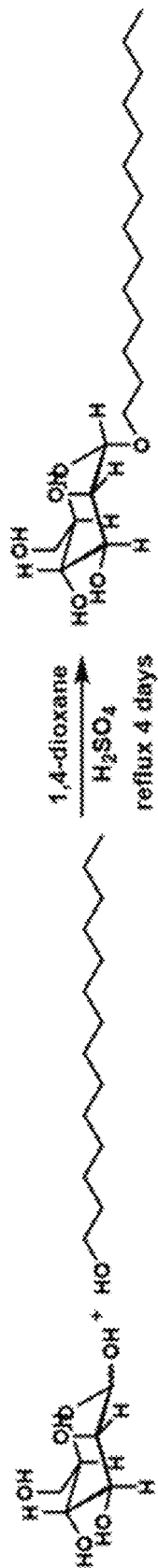
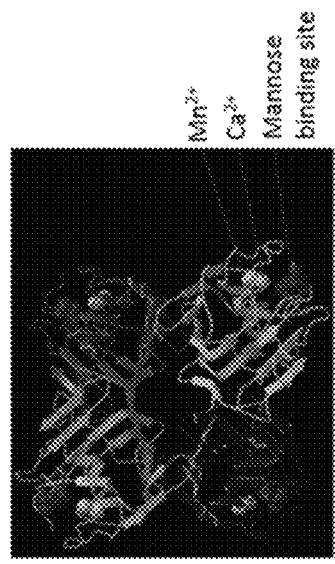
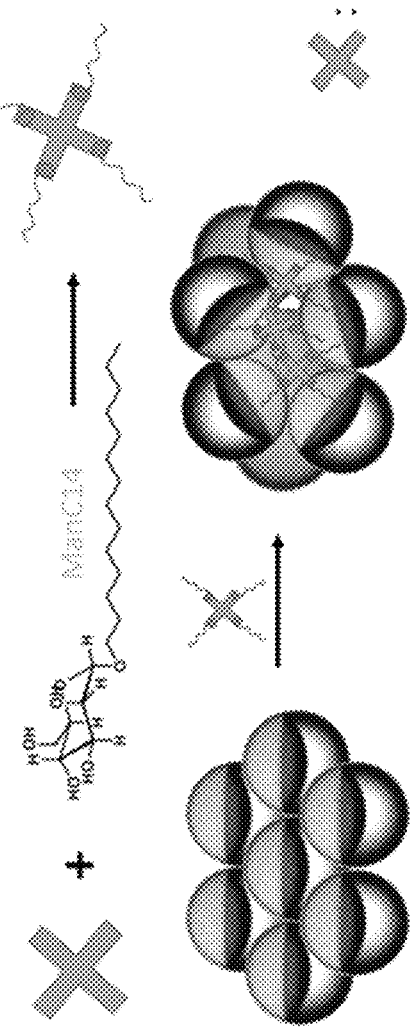
FIG. 4A
FIG. 4B

SEQUENCE LISTING

<160> NUMBER OF SEQ ID NOS: 2

<210> SEQ ID NO 1
<211> LENGTH: 19
<212> TYPE: DNA

-continued

```
<213> ORGANISM: Artificial Sequence
<220> FEATURE:
<223> OTHER INFORMATION: Synthetic polynucleotide

<400> SEQUENCE: 1 ttttttaga gttgagcat                                              19

<210> SEQ ID NO 2
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 2
tttttttatg ctcaactct                                             19
```

SYSTEMS AND METHODS FOR AFFECTING INTERACTIONS OF ELECTROMAGNETIC RADIATION WITH JANUS DROPLETS FOR SENSITIVE DETECTION OF SPECIES

RELATED APPLICATIONS

This application claims priority under 35 U.S.C. § 119(e) to U.S. Provisional Patent Application No. 62/902,367, filed Sep. 18, 2019, which is hereby incorporated by reference in its entirety.

STATEMENT OF GOVERNMENT SUPPORT

This invention was made with Government support under Grant No. CHE1740597 awarded by the National Science Foundation, under Grant No. FA9550-18-1-0341 awarded by the Air Force Office of Scientific Research, under Grant No. R01 GM095843 awarded by National Institutes of Health, and under Grant No. N00014-18-1-2878 awarded by the Office of Naval Research. The Government has certain rights in the invention.

INCORPORATION BY REFERENCE

The following patents and patent applications are incorporated herein by reference for all purposes:

U.S. Pat. No. 10,005,058, Issued Jun. 26, 2018, and entitled COMPOSITIONS AND METHODS FOR ARRANGING COLLOID PHASES.

U.S. patent application Ser. No. 16/284,722, filed Feb. 25, 2019, entitled COMPOSITIONS AND METHODS FOR FORMING EMULSIONS and published as US-2019-0184356-A1 on Jun. 20, 2019.

U.S. Pat. No. 10,252,231, Issued Apr. 9, 2019, and entitled COMPOSITIONS AND METHODS FOR FORMING EMULSIONS.

U.S. patent application Ser. No. 15/887,863, filed Feb. 2, 2018, and entitled TUNABLE MICROLENSES AND RELATED METHODS and published as US-2018-0246314-A1; on Aug. 30, 2018.

U.S. patent application Ser. No. 16/113,520, filed Aug. 27, 2018, and entitled SYSTEMS INCLUDING JANUS DROPLETS and published as US-2019-0212333-A1 on Jul. 11, 2019.

U.S. Pat. No. 10,060,913, Issued Aug. 28, 2018, and entitled SYSTEMS INCLUDING JANUS DROPLETS.

U.S. patent application Ser. No. 16/415,353 filed May 17, 2019, and entitled LIGHT EMITTING DROPLETS AND RELATED METHODS.

U.S. patent application Ser. No. 16/201,961, filed Nov. 27, 2018, and entitled SYSTEMS INCLUDING JANUS DROPLETS and published US-2019-0170736-A1 on Jun. 6, 2019.

U.S. patent application Ser. No. 16/202,007, filed Nov. 27, 2018, and entitled SYSTEMS INCLUDING JANUS DROPLETS and publication as US-2019-0170737-A1 on Jun. 6, 2019.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Sep. 29, 2020, is named M092570785US01-SEQ and is 1 kilobyte in size.

FIELD OF THE INVENTION

The present invention generally relates to systems and methods including Janus droplets.

BACKGROUND

Emulsification is a powerful age-old technique for mixing and dispersing immiscible components within a continuous liquid phase. Consequently, emulsions are central components of medicine, food, and performance materials. Complex emulsions, including multiple emulsions and Janus droplets, are of increasing importance in pharmaceuticals and medical diagnostics, in the fabrication of microdroplets and capsules for food, in chemical separations, for cosmetics, for dynamic optics, and chemical separations. However, quantitative detections of analytes with high sensitivity and selectivity using Janus droplets have yet to be realized. Accordingly, improved systems and methods are needed.

SUMMARY OF THE INVENTION

The present invention provides systems and methods including Janus droplets.

In one aspect, emulsions are provided. In some embodiments, the emulsion comprises an outer phase, a plurality of droplets dispersed within the outer phase, wherein the plurality of droplets comprise two or more components, wherein the two or more components are substantially miscible at a first temperature, and wherein the two or more components are substantially immiscible at a second temperature.

In another aspect, methods for forming an emulsion are provided. In some embodiments, the method comprises adjusting the temperature of a fluid to a first temperature, wherein the fluid comprises a first phase and a second phase substantially immiscible in the first phase, wherein the second phase comprises two or more components that are substantially miscible with each other, emulsifying the fluid, and adjusting the temperature of the fluid to a second temperature, such that the two or more components become substantially immiscible.

In another aspect, systems are provided. In some embodiments, the system comprises a plurality of Janus droplets associated with binding moieties to an analyte, the binding moiety and analyte selected such that when the analyte binds to the binding moiety at least a portion of the plurality of Janus droplets are changed in orientation sufficient to change electromagnetic radiation interacting with the plurality of Janus droplets in a detectable manner.

In some embodiments, the system comprises a plurality of Janus droplets associated with a plurality of binding moieties to an analyte and a detector positioned relative to the plurality of Janus droplets such that when sufficient numbers of the binding moieties bind to analyte at least a portion of the plurality of Janus droplets are changed in orientation sufficient to change electromagnetic radiation interacting with the Janus droplets in a manner determinable by the detector.

In certain embodiments, upon binding to the binding moieties, at least a portion of the plurality of Janus droplets agglutinate.

In certain embodiments, prior to binding to the binding moieties, the plurality of Janus droplets are oriented such that at least a portion of interfaces between a first phase and a second phase within each Janus droplet are aligned parallel with respect to one another.

In certain embodiments, prior to the analyte binding to the binding moieties, the plurality of Janus droplets are bound to a surface.

In certain embodiments, upon binding of the analyte to the binding moieties, at least a portion of the plurality of Janus droplets unbind from the surface.

In certain embodiments, the system comprises a source of external energy applicable to the composition to generate a determinable signal and a detector positioned to detect the signal.

In certain embodiments, the signal comprises electromagnetic radiation.

In certain embodiments, upon exposure of the article to a chemical or biological analyte, the system generates the determinable signal.

In another aspect, methods are provided. In some embodiments, the method comprises allowing an analyte to bind to binding moieties associated with a plurality of Janus droplets and determining a change in electromagnetic radiation interacting with the plurality of Janus droplets due at least in part to the binding of the analyte to the binding moieties.

In some embodiments, the method comprises exposing, to an article comprising an outer phase and a plurality of Janus droplets dispersed within the outer phase, a chemical or biological analyte, wherein the chemical or biological analyte, if present, interacts with at least a portion of the article such that at least a portion of the plurality of Janus droplets change orientation thereby producing a detectable change in an optical property of the article and determining the detectable change.

In some embodiments, the method comprises exposing, to an article comprising an outer phase and a plurality of Janus droplets dispersed within the outer phase, a chemical or biological analyte, wherein the chemical or biological analyte, if present, interacts with at least a portion of the article such that at least a portion of the plurality of Janus droplets change orientation thereby changing the optical transmission of the article.

In certain embodiments, the plurality of Janus droplets comprise one or more amphiphilic compounds including at least one binding moiety.

In certain embodiments, interacting with at least a portion of the article comprises binding of the chemical or biological analyte to the at least one binding moiety.

In certain embodiments, prior to exposing the article to a chemical or biological analyte, at least a portion of the plurality of Janus droplets are oriented such that at least a portion of interfaces between a first phase and a second phase within each Janus droplet are aligned parallel with respect to one another.

In certain embodiments, substantially all of the interfaces between a first phase and a second phase within each Janus droplet are aligned parallel with respect to one another.

In certain embodiments, upon exposing the article to a chemical or biological analyte, at least a portion of the plurality of Janus droplets agglutinate.

In certain embodiments, upon exposing the article to a chemical or biological analyte, at least a portion of the plurality of Janus droplets are oriented such that at least a portion of interfaces between a first phase and a second phase within each Janus droplet are not aligned parallel with respect to one another.

In certain embodiments, at least a portion of the plurality of Janus droplets are bound to a surface of the article via the binding moiety.

In certain embodiments, upon exposing the article to a chemical or biological analyte, at least a portion of the plurality of Janus droplets unbind from the surface.

In yet another aspect, articles are provided. In some embodiments, the article comprises an outer phase and a plurality of Janus droplets dispersed within the outer phase, wherein at least a portion of the plurality of Janus droplets comprise an amphiphilic compound including at least one binding moiety.

In certain embodiments, the plurality of Janus droplets is oriented such that at least a portion of interfaces between a first phase and a second phase within each Janus droplet are aligned parallel with respect to one another.

In certain embodiments, the at least one binding moiety is capable of binding with a chemical or biological analyte.

In certain embodiments, upon binding of the at least one binding moiety with a chemical or biological analyte, at least a portion of the plurality of Janus droplets change orientation.

In certain embodiments, the plurality of Janus droplets are substantively transmissive to electromagnetic radiation.

In certain embodiments, upon binding of the at least one binding moiety with a chemical or biological analyte, the plurality of Janus droplets decrease in optical transmission.

In some embodiments, the article comprises a surface, an outer phase deposited on at least a portion of the surface, and a plurality of Janus droplets dispersed within the outer phase, wherein at least a portion of the plurality of Janus droplets comprise an amphiphilic compound including at least one binding moiety, and wherein at least a portion of the plurality of Janus droplets are bound to the surface via the binding moiety.

In certain embodiments, at least a portion of the plurality of Janus droplets are oriented such that an interface between a first phase and a second phase within each Janus droplet are not aligned parallel to the surface.

In certain embodiments, upon exposure of the plurality of Janus droplets to a biological or chemical analyte, at least a portion of Janus droplets unbind from the surface.

In certain embodiments, upon exposure of the plurality of Janus droplets to a biological or chemical analyte, at least a portion of Janus droplets change orientation.

In certain embodiments, the article is substantively visible-light transmissive after exposure to the plurality of Janus droplets to the biological or chemical analyte.

In certain embodiments, upon exposure of the plurality of Janus droplets to a chemical or biological analyte, the plurality of Janus droplets increase in optical transmission.

In certain embodiments, each Janus droplet comprises a first phase and a second phase, immiscible with the first phase.

In certain embodiments, the outer phase is a hydrocarbon and/or aqueous phase.

In certain embodiments, the first phase comprises a hydrocarbon, a fluorocarbon, a silicone, a liquid crystal, an ionic liquid, a polymer, combinations thereof, or derivatives thereof.

In certain embodiments, the second phase comprises a hydrocarbon, a fluorocarbon, a silicone, a liquid crystal, an ionic liquid, a polymer, combinations thereof, or derivatives thereof, immiscible with the first phase.

In certain embodiments, the amphiphilic compound is selected from the group consisting of: ionic surfactants, non-ionic surfactants, zwitterionic surfactants, polymers, proteins, DNA, RNA, acids, carbohydrates, saccharides, enzymes, chromophores, lipids, graphene oxide, combinations thereof, and derivatives thereof.

In certain embodiments, an interface between the outer phase and the plurality of Janus droplets comprises the amphiphilic compound.

In certain embodiments, the Janus droplets comprise dyes, wherein a first dye partitions preferentially into a first phase and a second dye partitions into a second phase of the Janus droplets.

In certain embodiments, the first dye and the second dye have complementary absorption and emission properties, wherein the first dye is configured to substantially absorb a wavelength of light exciting the droplets and/or an emission from the second dye.

In certain embodiments, agglutination of the droplets results in increased light emission from a second dye as compared to droplets without agglutination.

In certain embodiments, the analyte comprises a biological compound, a drug, a macromolecule, a salt, an electrolyte, an enzyme, an acid, a nucleic acid, a carbohydrate, a peptide, a protein, a phosphate, a sulfonate, a virus, a pathogen, an oxidant, a reductant, a toxin, a chemical warfare agent, an explosive, carbon dioxide, or combinations thereof.

In certain embodiments, the analyte is a single analyte.

In some embodiments, the system comprises a plurality of Janus droplets comprising a first phase and a second phase and an amphiphilic compound associated with the first phase and capable of interacting with a biological analyte, wherein the amphiphilic compound does not associate with the second phase, and In certain embodiments, the amphiphilic compound comprises gallic acid or a derivative thereof.

In certain embodiments, wherein upon binding to the biological analyte, at least a portion of the plurality of Janus droplets agglutinate.

In certain embodiments, wherein, prior to binding to the biological analyte, the plurality of Janus droplets are oriented such that at least a portion of interfaces between a first phase and a second phase within each Janus droplet are aligned parallel with respect to one another.

In some embodiments, the system comprises an outer phase and a plurality of droplets dispersed within the outer phase, wherein at least a portion of the plurality of droplets comprise a first phase and a second phase, the first phase immiscible with the second phase and an amphiphilic compound associated with the first phase, the amphiphilic compound capable of binding with a biological analyte, wherein the plurality of droplets have a first configuration in which the amphiphilic compound is exposed to the outer phase, and wherein the plurality of droplets have a second configuration in which the amphiphilic compound is not exposed to the outer phase.

In some embodiments, the method comprises providing a colloid comprising an outer phase, a plurality of droplets dispersed within the outer phase, wherein at least a portion of the plurality of droplets comprise a first phase and a second phase, the first phase immiscible with the second phase, and an amphiphilic compound associated with the first phase, the amphiphilic compound capable of binding with a biological analyte, wherein the amphiphilic compound is not exposed to the outer phase, stimulating the colloid, such that the first phase and the second phase change arrangement and such that the amphiphilic compound is exposed to the outer phase and wherein the first phase and the second phase are immiscible with each other after changing arrangement.

In some embodiments, the method comprises allowing a biological analyte to bind to an amphiphilic compound associated with a plurality of Janus droplets and determining a change in electromagnetic radiation interacting with the plurality of Janus droplets due at least in part to the binding of the biological analyte to the amphiphilic compound.

In some embodiments, the method comprises exposing, to an article comprising an outer phase and a plurality of Janus droplets dispersed within the outer phase, a chemical or biological analyte, wherein the chemical or biological analyte, if present, interacts with an amphiphilic compound associated with a first phase of the Janus droplets such that at least a portion of the plurality of Janus droplets change orientation thereby producing a detectable change in an optical property of the article and determining the detectable change.

In certain embodiments, wherein interacting with at least a portion of the article comprises binding of the chemical or biological analyte to the amphiphilic compound.

In certain embodiments, wherein, prior to exposing the article to a chemical or biological analyte, at least a portion of the plurality of Janus droplets are oriented such that at least a portion of interfaces between a first phase and a second phase within each Janus droplet are aligned parallel with respect to one another.

In certain embodiments, wherein substantially all of the interfaces between a first phase and a second phase within each Janus droplet are aligned parallel with respect to one another.

In certain embodiments, wherein, upon exposing the article to a chemical or biological analyte, at least a portion of the plurality of Janus droplets agglutinate.

In certain embodiments, wherein, upon exposing the article to a chemical or biological analyte, at least a portion of the plurality of Janus droplets are oriented such that at least a portion of interfaces between a first phase and a second phase within each Janus droplet are not aligned parallel with respect to one another.

In certain embodiments, optical measurements can be performed continuously or at specific time intervals.

In certain embodiments, changes in optical signal from the droplets can indicate the presence and/or growth of live bacteria.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

FIG. 4A shows an exemplary surfactant for use in a system including Janus droplets, according to one set of embodiments.

FIG. 4B shows the agglutination of a plurality of Janus droplets in the presence of analyte, according to one set of embodiments.

FIGS. 7A-7F show image processing based of Janus droplets upon exposure to an analyte, according to one set of embodiments.

(FIG. 15A) In situ formation of GA12-NHS at droplet interface and subsequent amine conjugation. (FIG. 15B) Pre-synthesized GA12-NHS was dissolved in the droplet hydrocarbon phase and located at the hydrocarbon-water interface after trifluoethanol diffuses out to the continuous phase, followed by interfacial amine conjugation. (FIG. 15C) Pre-synthesized GA16-MA for interfacial thiol conjugation. FL in the schemes indicates generic fluorophores.

(FIG. 16A) Confocal z-stack images of emulsion droplets containing GA16-MA after covalent dye functionalization, 10× magnification. (FIG. 16B) Confocal cross-section of the droplet containing GA16-MA after covalent dye functionalization, 20× magnification.

(FIG. 20A) Microscope image of Protein A functionalized droplets in Janus morphology. (FIG. 20B) Microscope image of droplet in F/H/W after IgG bind to protein A. (FIG. 20C) Confocal cross section image of droplets with IgG at the hydrocarbon-water interface, in F/H/W morphology.

(FIG. 21A) Zonyl forced deformation of emulsion droplet on the side under microscope. (FIG. 21B) Confocal z-stack images of deformed droplets showing covalent bond formation at the droplet interface.

FIGS. 28A-28C show droplets after addition of $10^7$ CFU/mL of *Listeria* for 2 hours. FIG. 28D-28F shows addition of 100 CFU/mL of *Listeria* for 2 hours. Scale bar in 200 m (FIG. 28A, FIG. 28D). Scale bar in 50 m (FIG. 28B-28C, FIG. 28E-28F).

FIG. 34A shows fluorescence spectra (λex=350 nm) of droplet after addition of heat killed *listeria* at different concentrations.

FIG. 34B shows a correlation of concentration of heat killed *Listeria* and relative fluorescence intensity at 580 nm.

FIG. 35A shows non-agglutinated droplet (without addition of *listeria*). FIG. 35B shows agglutinated droplets (with the addition of *listeria*). Scale bar=50 μm.

FIG. 37B shows $^1$H NMR spectrum (400 MHz, Chloroform-d) and FIG. 37C shows $^{13}$C NMR spectrum (101 MHz, CDCl3).

FIG. 38B shows $^1$H NMR spectrum (600 MHz, Chloroform-d) and FIG. 38C shows $^{13}$C NMR spectrum (151 MHz, Chloroform-d).

FIG. 54A shows droplets in synthetic blood.

FIG. 54B shows droplets prepared in serum. Scale bar=50 μm.

FIG. 60A shows non-agglutinated droplet (without addition of *Listeria*). FIG. 60B shows agglutinated droplets (with $10^2$ CFU/mL of *Listeria*). FIG. 60C shows agglutinated droplets (with $10^7$ CFU/mL of *Listeria*). Scale bar=200 μm.

FIG. 61A shows non-agglutinated droplet (without addition of *Listeria*). FIG. 61B shows agglutinated droplets (with the addition of *Listeria* at 102 CFU/mL). FIG. 61C shows agglutinated droplets (with the addition of *Listeria* at 107 CFU/mL). Scale bar=200 μm.

FIG. 62A shows droplets without addition of *Listeria*. FIG. 62B shows droplets with addition of *Listeria*.

FIG. 64B shows the experiment set up under normal light. FIG. 64C shows the experimental set up under UV light.

Figure 1A:
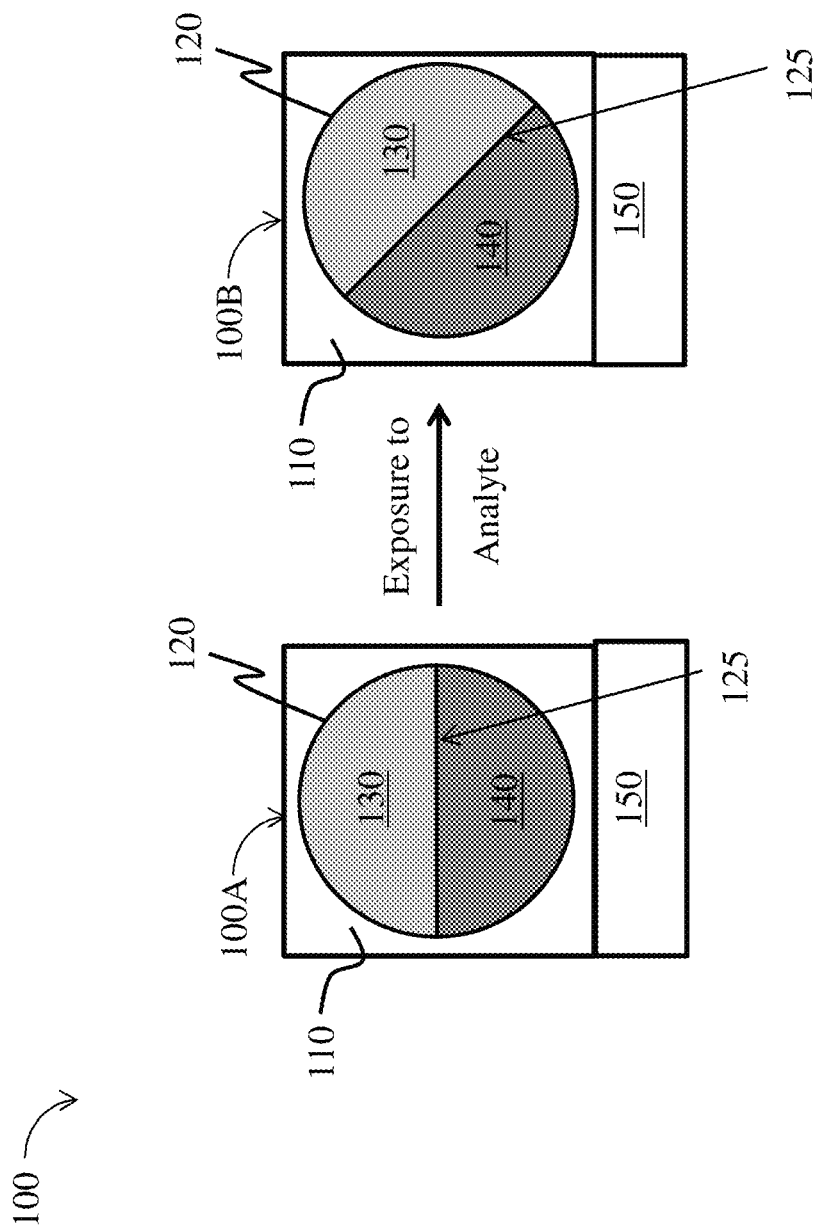
FIG. 1A illustrates a system including a Janus droplet, exposed to an analyte, according to one set of embodiments.

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

Embodiments described herein may be useful in the detection of analytes. The systems and methods may allow for a relatively simple and rapid way for detecting analytes such as chemical and/or biological analytes and may be useful in numerous applications including sensing, food manufacturing, medical diagnostics, performance materials, dynamic lenses, water monitoring, environmental monitoring, detection of proteins, detection of DNA, among other applications. For example, the systems and methods described herein may be used for determining the presence of a contaminant such as bacteria (e.g., detecting pathogenic bacteria in food and water samples which helps to prevent widespread infection, illness, and even death). Advantageously, the systems and methods described herein may not have the drawbacks in current detection technologies including, for example, relatively high costs, long enrichment steps and analysis times, and/or the need for extensive user training. Another advantageous feature provided by the systems and methods described herein includes fabrication in a relatively large scale. In some embodiments, the systems and methods may be used in conjunction with a detector including handheld detectors incorporated with, for example, smartphones (e.g., for the on-site detection of analytes such as pathogenic bacteria). For example, such systems could be used by the food industry to prevent extensive foodborne illnesses which may result in expensive medical treatment costs, lawsuits, government sanctions, product recalls, and/or tarnished long-term reputations. Articles comprising Janus droplets are also provided.

Advantageously, the systems and methods described herein may enable the functionalization to interact with a biological species (e.g., bioconjugation) on already formed droplets (e.g., having two or more internal phases) in an outer phase, without resulting in instability of the droplets. In some embodiments, the (bio)conjugation reaction may change the interfacial tension between two or more phases and, in some cases, may be used to change the configuration of a droplet as described herein. In some embodiments, an analyte such as a biological analyte binds to the conjugated droplet.

In some embodiments, the systems and methods comprise a plurality of Janus droplets. Janus droplets generally include two or more phases immiscible with one another and/or having distinct physical and/or chemical properties, within the droplet. In certain embodiments, when equal amounts of the two immiscible phases are present and the interfacial tensions are properly balanced, the Janus droplets will be spherical with each hemisphere of the sphere comprising one of the immiscible phases. The two immiscible phases need not be present in equal amounts, i.e., Janus droplets can be asymmetrical with one phase being present, e.g., in an amount 1.2, 1.4, 1.6, 1.8. 2, 3, 4, or more times the other phase, by volume.

The plurality of Janus droplets includes a first phase and a second phase immiscible with the first phase. In some embodiments, the plurality of Janus droplets may be dispersed within an outer phase (e.g., an hydrocarbon and/or aqueous phase). For example, in some embodiments, the system comprises an hydrocarbon and/or aqueous phase and a plurality of Janus droplets comprising a hydrocarbon and a fluorocarbon. In some cases, the plurality of Janus droplets may be associated a binding moiety (e.g., a binding moiety associated with the Janus droplets and/or a binding moiety present on a surfactant incorporated with the plurality of Janus droplets). In some embodiments, the binding moiety may bind with an analyte (e.g., a biological and/or chemical analyte) such that the orientation of at least a portion of the plurality of Janus droplets is changed. The change in orientation of a Janus droplet may result in a change in the interaction of electromagnetic radiation (e.g., visible light) with the Janus droplet in a detectable manner. In some embodiments, exposing a plurality of Janus droplets to an analyte causes a detectable change in an optical property of the Janus droplets, such that the analyte can be determined and/or quantified.

Embodiments described herein may be useful in the formation of emulsions (e.g., complex emulsions). The methods may allow for one-step fabrication of multi-phase (e.g., three-phase, four-phase) emulsions (e.g., complex emulsions), and may be useful in numerous applications including food manufacturing, drug delivery, medical diagnostics, performance materials, cosmetics, MRI and ultrasound contrast agents, artificial blood, among other applications. Furthermore, methods and emulsions described herein may allow for forming emulsions with controlled and reconfigurable morphologies. Another advantageous feature provided by emulsions and methods described herein is the ability to readily incorporate additional components (e.g., magnetic nanoparticles, biological materials, polymers, metals, etc.) into various applications. Emulsions (e.g., complex emulsions) are also provided.

Embodiments described herein may be useful for arranging phases (e.g., in response to a stimulus) and/or components within a colloid. Complex droplets of controllable compositions and dynamic reconfigurable morphologies provide a new active element for novel and existing applications of emulsions and may be useful in numerous applications including food manufacturing, drug delivery, medical diagnostics, performance materials, cosmetics, MRI and ultrasound contrast agents, artificial blood, among other applications. The dynamic rearrangement of droplet phases and/or components can be broadly applied using a wide variety of chemicals, materials, and surfactants, as described herein. Droplets triggered by stimuli could be used, for example, to target release of drugs at tumors, to induce changes in color or transparency (e.g., for applications including color changing mediums and camouflage), as vehicles for sequestration of pollutants, as tunable lenses, as controlled release droplets in response to an stimulus, or as sensors. Emulsions with the characteristic ability to selectively "present" and "hide" specific liquid interfaces and controllably alter droplet morphology and symmetry may be useful for numerous applications and devices. Another advantageous feature provided by emulsions and methods described herein is the ability to readily incorporate additional compounds (e.g., magnetic nanoparticles, biological materials, polymers, metals, etc.) into various applications.

In certain embodiments, upon exposure to an analyte, at least a portion of the plurality of Janus droplets may agglutinate. For example, in some cases, the analyte may facilitate the agglutination of at least a portion of the plurality of Janus droplets. The agglutination of some Janus droplets may result in a detectable change in the interaction of electromagnetic radiation (e.g., visible light) with the Janus droplets. In some cases, the agglutination of some Janus droplets may result in a change in orientation of each of the Janus droplets (e.g., relative to the orientation of the Janus droplets prior to exposure to the analyte). In other cases, the Janus droplets may be in an agglutinated state prior to exposure to an analyte and the exposure of the system to the analyte will disrupt agglutination and case a change in the orientation of the Janus droplet.

Advantageously, in some embodiments, the systems described herein may enable highly sensitive detection of analytes including, for example, detection of single analyte interaction events (e.g., binding events, chemical reactions, biological reactions). In an illustrative embodiment, a single analyte (e.g., one protein, one strand of DNA, one strand of RNA) may cause the agglutination of some Janus droplets and changing the orientation of each of the agglutinated Janus droplets, such that a single analyte (e.g., a single protein, a single strand of DNA, RNA etc.) is detected. In some such embodiments, the single analyte may bind to some Janus droplets such that the Janus droplets agglutinate. In another illustrative embodiment, a single analyte may cause the orientation of a single Janus droplet to change (e.g., via enzymatic degradation of a tether bound to the Janus droplet), such that a single analyte is detected. In some embodiments, a plurality of analytes and/or types of analytes may be detected (e.g., via the change in orientation of a plurality of Janus droplets and/or the agglutination of groups of Janus droplets). In certain embodiments, the concentration of an analyte exposed to the system may be determined by measuring the number of Janus droplets changing orientation upon exposure of the system to the analyte.

As illustrated in FIG. 1A, in some embodiments, system 100 comprises a plurality of Janus droplets such as Janus droplet 120. In certain embodiments, Janus droplet 120 comprises first phase 130 (e.g., comprising a hydrocarbon) and second phase 140 (e.g., comprising a fluorocarbon). As depicted illustratively in FIG. 1A, in some embodiments, first phase 130 and second phase 140 may have relatively the same volume in each Janus droplet. However, those skilled in the art would understand based upon the teaching of this specification that the volume of the first phase and the second phase may not be equal.

In some embodiments, as depicted in FIG. 1A, Janus droplet 120 has a particular orientation, such as orientation 100A. The orientation of a Janus droplet as described herein may be determined by measuring the angle of a planar surface defined by the interface (e.g., interface 125) between the first phase (e.g., first phase 130) and the second phase (e.g., second phase 140). In some embodiments, upon exposure of Janus droplet 120 to an analyte, the Janus droplet may change orientation (e.g., from orientation 100A to orientation 100B). In some such embodiments, the analyte may bind with a binding moiety present on the Janus droplet, resulting in the change in orientation of the Janus droplet. As illustrated in FIG. 1A, the orientation of interface 125 in orientation 100B is different than the orientation of interface 125 in orientation 100A. For example, in some embodiments, the Janus droplet may rotate upon exposure to the analyte (e.g., upon binding of the analyte with a binding moiety associated with the Janus droplet). In some embodiments, the change in orientation of the Janus droplet is determinable (e.g., measurable) such that it indicates the presence of an analyte.

The Janus droplets described herein may be useful in a number of applications. In an exemplary embodiment, the Janus droplets described herein may be used for sensing of an analyte. For example, in some such embodiments, the Janus droplets may change orientation upon exposure to an analyte such that the change in orientation can be detected (e.g., by a change in optical transmission, polarization, birefringence, etc. of the colloid). In another exemplary embodiment, the Janus droplets described herein may be used as tunable lenses. In certain embodiments, measurements of the optical properties (e.g., transmission, absorption, reflection, focal distance, and scattering) of the Janus droplets can be indicative of specific droplet orientations. For example, when a change in droplet orientation is correlated with an analyte of interest (i.e., enzyme, pollutant, virus, bacteria, DNA, RNA, etc.), then, the Janus droplets can be used as sensors in which an optical measurement serves as a readout mechanism of the presence of the analyte. In certain embodiments, for systems in which there is a change in an analyte of interest over time (e.g., progress of a chemical reaction, such as degradation of a chemical by an enzyme over time), tracking of the changes in optical properties of the Janus droplets over time can be used to, for example, analyze reaction rates or analyte concentrations. In some such embodiments, the orientation of the Janus droplets changes in the presence of an analyte such that the system obtains a transparent state over a particular range of time, or alternatively, obtains a relatively opaque state over a particular range of time. In some embodiments, a measurement of a property of the droplets may be made with the assistance of a microfluidic device. In some embodiments, the measurement is made using image analysis, and/or using fluorescence intensity. In some instances, the measurement may be a measurement of droplet agglutination.

Those skilled in the art would understand that changing a property of a Janus droplet refers to a property of the Janus droplet immediately before that differs in a substantially measurable way from the property of the Janus droplet at some relatively short time (e.g., seconds, minutes, hours) after exposure to the analyte. Those skilled in the art would also be capable of selecting methods for determining the change in the property of the Janus droplets (e.g., measuring the average birefringence, measuring the optical transmission at one or more wavelength, measuring the density, etc.) based upon the specification and examples below.

Figure 1B:
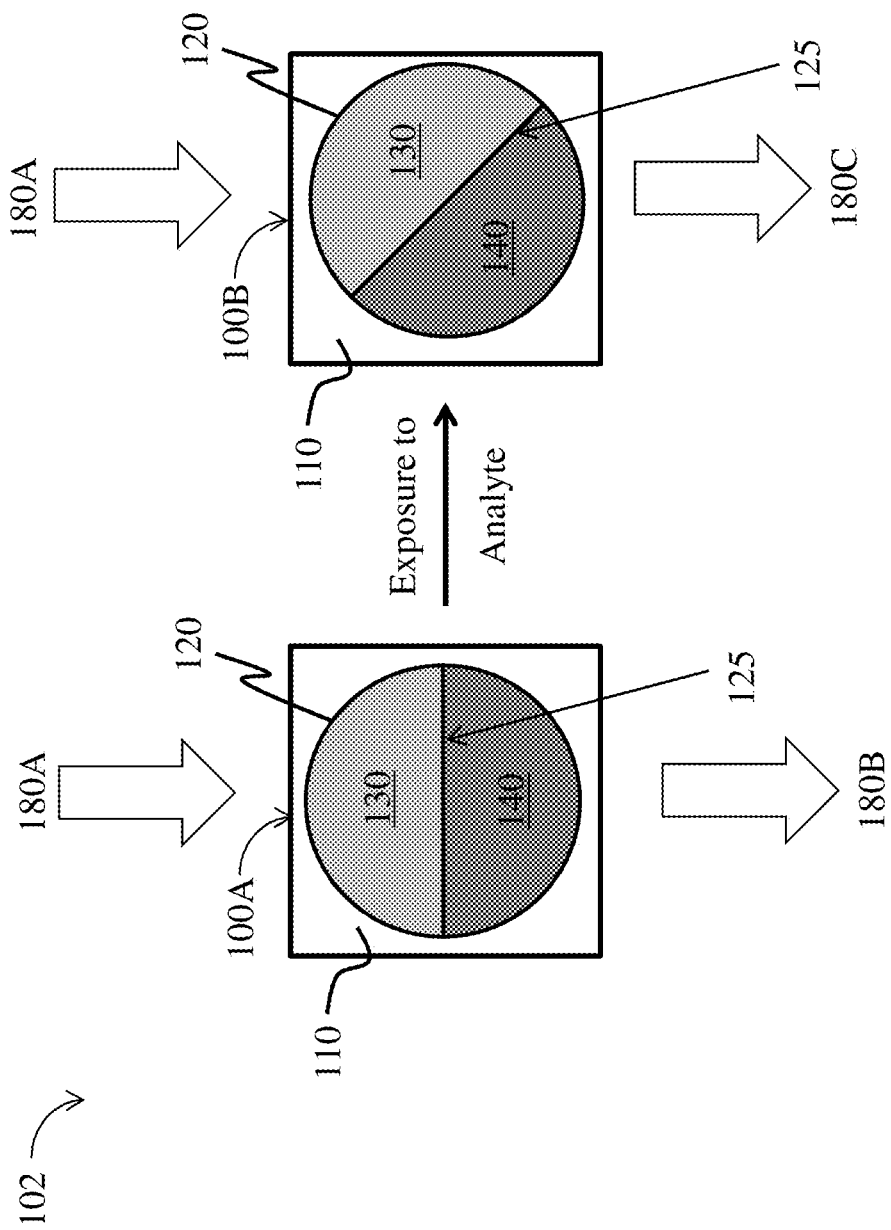
FIG. 1B illustrates a system including a Janus droplet, exposed to an analyte, according to one set of embodiments.

For example, as illustrated in FIG. 1B, system 102 comprises a plurality of Janus droplets such as exemplary Janus droplet 120. In some embodiments, electromagnetic radiation 180A interacts with Janus droplet 120. In certain embodiments, upon exposure of system 102 to an analyte (e.g., such that the analyte binds to a binding moiety associated with the Janus droplet), Janus droplet 120 changes orientation (e.g., from orientation 100A to 100B) sufficiently to change the interaction of electromagnetic radiation 180A with the Janus droplets as compared to the interaction of electromagnetic radiation 180A prior to exposure to the analyte. For example, prior to exposure to the analyte, Janus droplet 120 may interact with electromagnetic radiation 180A such that electromagnetic radiation 180B is produced. In some embodiments, electromagnetic radiation 180A and electromagnetic radiation 180B may be substantially the same. For example, Janus droplet 120 may have an orientation 100A such that electromagnetic radiation interacting with (e.g., transmitting perpendicular to interface 125 of Janus droplet 120) is not substantially changed in wavelength and/or amplitude.

For example, in some cases, the plurality of Janus droplets may be orientation such that the system is substantially optically transparent in a direction perpendicular to the surface of the interface between the first phase and the second phase (e.g., interface 125). In some cases, however, electromagnetic radiation 180B may be different than electromagnetic radiation 180A in wavelength and/or amplitude. In some embodiments, upon exposure of system 102 to an analyte, Janus droplet 120 changes orientation from orientation 100A to orientation 100B, such that electromagnetic radiation 180A interacts with Janus droplet 120 and produced electromagnetic radiation 180C, different than electromagnetic radiation 180B.

In some embodiments, the plurality of Janus droplets is changed in orientation (e.g., upon exposure to an analyte) sufficient to change electromagnetic radiation interacting with the plurality of Janus droplets in a detectable manner. In certain embodiments, at least a portion of the Janus droplets change orientation thereby changing the optical transmission of the article and/or thereby producing a detectable change in an optical property of the article. In some embodiments, the detectable change includes a change in color, average luminescence in one or more directions, and/or average optical transmission of the Janus droplet (or system comprising the plurality of Janus droplets).

In some embodiments the electromagnetic radiation (e.g., the electromagnetic radiation prior to interacting with the Janus droplet, the electromagnetic radiation after interacting with the Janus droplet) may comprise any suitable wavelength, including but not limited to infrared light (e.g., a wavelength between about 700 nm and about 1 cm), to visible light (e.g., a wavelength between about 400 nm and about 700 nm), and to ultraviolet (UV) light (e.g., a wavelength between about 10 nm and about 400 nm).

Figure 1C:
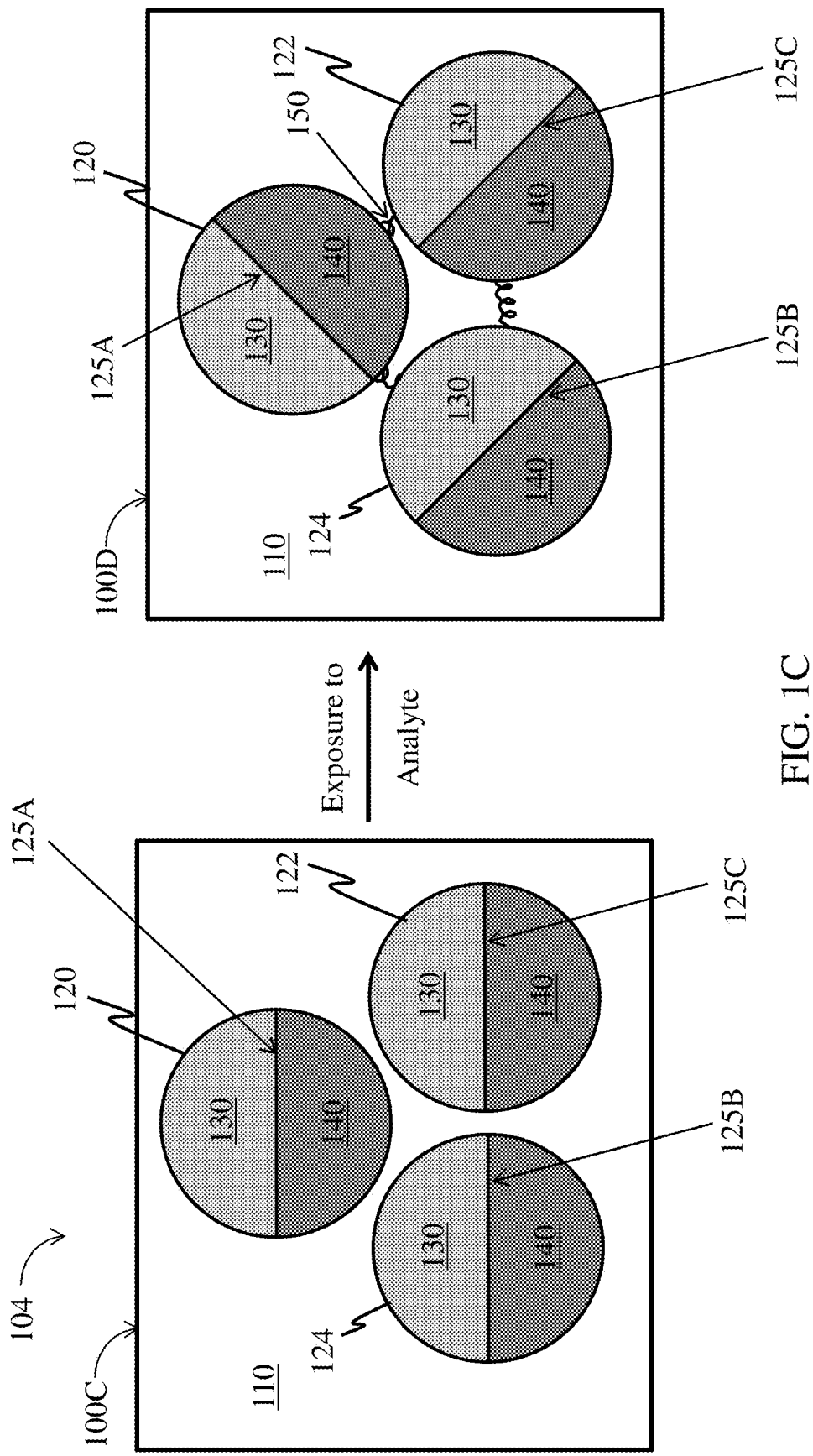
FIG. 1C illustrates a system including a plurality of Janus droplets, exposed to an analyte, according to one set of embodiments.

In certain embodiments, the plurality of Janus droplets (e.g., Janus droplets 120) is dispersed within an outer phase 110, as illustrated in FIGS. 1A-1C. In some embodiments, the outer phase is an hydrocarbon and/or aqueous phase (e.g., comprising water). The hydrocarbon and/or aqueous phase may also comprise, in some cases, solutes including organic molecules, proteins, ions, cells, DNA, RNA, cell lysates, or biological organisms. In some embodiments, exposing the system to the analyte comprises introducing the analyte into the outer phase. In certain embodiments, the analyte may be added to the outer phase such that the plurality of Janus droplets is exposed to the analyte.

In certain embodiments, the plurality of Janus droplets may be adjacent a surface 150, as illustrated in FIG. 1A. As used herein, when a component (e.g., a Janus droplet) is referred to as being "adjacent" another component (e.g., a surface), it can be directly adjacent to the component, or an intervening component (e.g., a fluid) also may be present. A component that is "directly adjacent" another component means that no intervening component is present (e.g., the component and another component are in contact with one another). Surface 150 may comprise a reflective surface such that exposing the system to an analyte causes a detectable change in an optical property of the Janus droplets such that the reflected electromagnetic radiation from surface 150 is also changed. In an exemplary embodiment, the plurality of Janus droplets is substantially transparent such that surface 150 is visible (e.g., when viewed perpendicular to surface 150) and, upon exposure to an analyte, the plurality of Janus droplets decrease in optical transmission such that at least a portion of surface 150 is obscured. Surface 150 may, in some cases, also be transparent such that light is transmitted through the surface and Janus droplets, such that exposure to an analyte will change the transmission of the light.

In some embodiments, at least a portion of the plurality of Janus droplets are orientated parallel (e.g., as measuring by the angle of a planar surface defined by the interface between the first phase and the second phase of the Janus droplet) to the surface. For example, referring again to FIG. 1A, in some embodiments, interface 125 of Janus droplet 120 (prior to exposure to an analyte) is orientated substantially parallel to surface 150 adjacent Janus droplet 120. In certain embodiments, the plurality of Janus droplets may be orientated substantially parallel to one another (e.g., substantially aligned). In some embodiments, prior to exposure to an analyte, the plurality of Janus droplets is aligned/oriented by the force of gravity (e.g., the first phase or the second phase having a greater density than the other phase) such that at least a portion of the plurality of Janus droplet are oriented substantially parallel with one another. In other embodiments, the forces that cause alignment of Janus droplets may include electrical or magnetic fields. For example, in certain embodiments, the plurality of Janus droplets may include a magnetic phase (e.g., including ferromagnetic particles)

In some embodiments, exposure to an analyte results in the agglutination of a plurality of Janus droplets. For example, as illustrated in FIG. 1C, system 104 comprises a plurality of Janus droplets (e.g., exemplary Janus droplets 120, 122, and 124). In certain embodiments, the plurality of Janus droplets may be orientated (relative to interfaces 125A, 125B, and 125C) substantially parallel to one another. In some embodiments, the interface between the first phase and the second phase of at least a portion the plurality of Janus droplet is aligned normal to the primary direction of the force of gravity such that the plurality of Janus droplets are oriented substantially parallel to one another. In some embodiments, upon exposure to an analyte, at least a portion of the Janus droplets agglutinate. In certain embodiments, agglutination of the Janus droplets results in a change of orientation of at least a portion of the Janus droplets (e.g., as measured by the change in angle of interfaces 125A, 125B, and 125C).

In certain embodiments, a binding moiety associated with the Janus droplet may bind with the analyte such that the Janus droplets agglutinate. For example, referring again to FIG. 1C, upon exposure to an analyte, the analyte may bind to a binding moiety on two or more Janus droplets (e.g., forming a bound complex 150 between two or more Janus droplets such as between Janus droplet 120 and Janus droplet 122). One of ordinary skill in the art would understand, based upon the teachings of this specification, that while bound complex 150 is illustrated as binding between first phase 130 and second phase 140, that formation of a bound complex between first phase 130 and first phase 130 of two droplets, is also possible. For example, as shown illustratively in FIG. 15, droplet 120 and droplet 122 are agglutinated via bound complex 152 between first phase 130 of droplet 120 and first phase 130 of droplet 122. Other configurations are also possible.

Figure 1D:
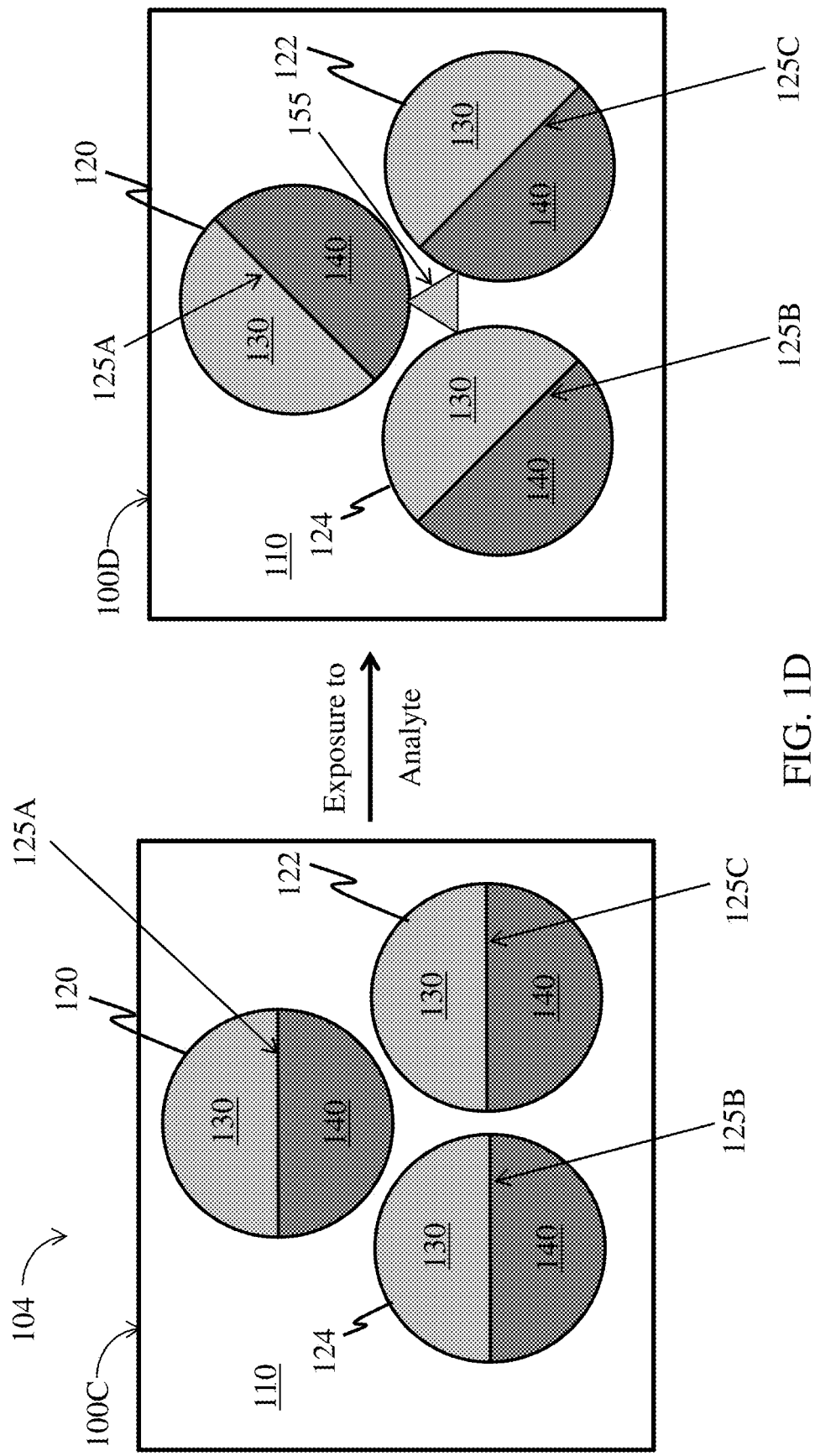
FIG. 1D illustrates a system including a plurality of Janus droplets, exposed to an analyte, according to one set of embodiments.

In some embodiments, a plurality of binding moieties (e.g., binding moieties associated with one or more Janus droplets) may bind with one or more analytes mutlivalently. For example, as illustrated in FIG. 1D, analyte 155 binds multivalently with Janus droplet 120, Janus droplet 122, and Janus droplet 124 such that the Janus droplets agglutinate. In some such embodiments, upon exposure and binding to the analyte, the Janus droplets change orientation sufficient to change electromagnetic radiation interacting with the plurality of Janus droplets in a detectable manner.

In some embodiments, upon agglutination of two or more Janus droplets, at least a portion of incident electromagnetic radiation may retroreflect amongst the droplets such that at least a portion of the electromagnetic radiation is reflected. For example, as shown illustratively in FIG. 15, system 106 comprises a plurality of Janus droplets (e.g., exemplary Janus droplets 120 and 122). In certain embodiments, the plurality of Janus droplets may be orientated (relative to interfaces 125A, and 125B) substantially parallel to one another (100C) and such that electromagnetic radiation 160 is transmitted through the interfaces. In some embodiments, upon exposure to an analyte, at least a portion of the Janus droplets agglutinate (100D). In certain embodiments, agglutination of the Janus droplets results in a change of orientation (100D) of at least a portion of the Janus droplets (e.g., as measured by the change in angle of interfaces 125A and 125B). In some embodiments, the Janus droplets change angle such that at least a portion of electromagnetic radiation 160 is reflected off of interfaces 125A and 125B. In some embodiments, at least a portion of electromagnetic radiation may still transmit through system 106. In some embodiments, the portion of electromagnetic radiation 160 that is reflected may be detected (e.g., by an optical detector, by a user) indicating the presence of the analyte (e.g., the analyte that results in agglutination of the Janus droplets) in the system.

Figure 2:
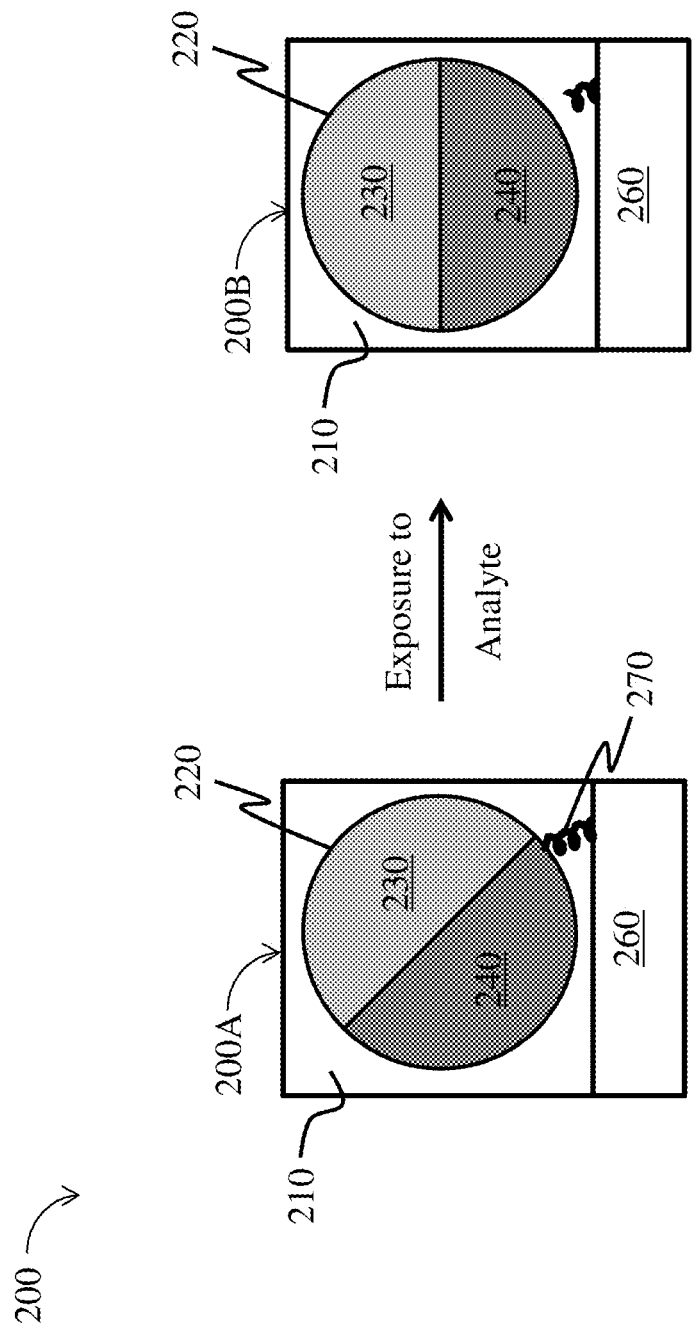
FIG. 2 illustrates a system including a Janus droplet, according to one set of embodiments.

In certain embodiments, the system may comprise a plurality of Janus droplets tethered (e.g., bound) to a surface. In some embodiments, exposure of the system to an analyte results in the breaking (e.g., cleavage) of the tether such that at least a portion of the Janus droplets change orientation (e.g., sufficient to change electromagnetic radiation interacting with the plurality of Janus droplets in a detectable manner). For example, as illustrated in FIG. 2, system 200 comprises Janus droplet 220 comprising first phase 230 and second phase 240, tethered to surface 260 adjacent Janus droplet 220 via tether 270. In some embodiments, exposure to an analyte results in the breaking of tether 270 such that Janus droplet 220 changes orientation (from orientation 200A prior to exposure to the analyte to orientation 200B upon exposure to the analyte). Those skilled in the art would understand based upon the teachings of this specification that surface 260 need not be planar and could be, for example, curved (e.g., the surface comprises a polymeric and/or inorganic particle). In some cases the surface may include an assembly of molecules such as proteins, DNA or RNA. In certain embodiments, the surface may comprise biological tissue (e.g., comprising skin (e.g., human skin), organ tissues, cells, or the like). In some cases, the surface may be a liquid immiscible with the outer phase and/or one or more phases present within the Janus droplets. In some embodiments, the surface comprises a polymeric material.

In some embodiments, the Janus droplet is tethered to the surface such that the interface between the first phase and the second phase is not parallel to the adjacent substrate and/or is not parallel with at least a portion of the plurality of Janus droplets. In some such embodiments, upon breaking of the tether by the analyte, at least a portion of the Janus droplets change orientation (e.g., such that at least a portion of the Janus droplets are parallel with one another and/or are parallel with an adjacent substrate). In some cases, breaking of the tether by the presence of an analyte resulting in an increase in the optical transmission of the system (e.g., such that a feature on the substrate is visible when viewed perpendicular to the surface). The tether may include, for example, one or more proteins, a polymer, one or more strands of DNA, one or more strands of RNA, or combinations thereof. Other tethers are also possible.

The analyte may break the tether in any suitable manner. For example, in some embodiments, the analyte may cleave the tether (e.g., via enzymatic degradation). In certain embodiments, the analyte may cleave the tether by changing the pH of the outer phase such that the tether breaks. In some embodiments, the analyte may cause the cleavage of the tether such that one or more binding moieties associated with (e.g., integrated within) the plurality of Janus droplets bind to the analyte. In some such embodiments, one or more binding moieties may be bound to the tether such that the Janus droplet is bound to the surface and, upon exposure to the analyte, the binding moiety unbinds from the tether and binds to the analyte.

In some cases, the binding moiety may comprise a biological or a chemical group capable of binding another biological or chemical molecule in a medium (e.g., hydrocarbon and/or aqueous phase). For example, the binding moiety may include a functional group, such as a thiol, aldehyde, ester, carboxylic acid, hydroxyl, and the like, wherein the functional group forms a bond with the analyte. In some cases, the binding moiety may be an electron-rich or electron-poor moiety wherein interaction between the analyte and the binding moiety comprises an electrostatic interaction. In some cases, the interaction between the analyte and the binding moiety includes binding to a metal or metal-containing moiety.

In some embodiment, the binding moiety and analyte interact via a binding event between pairs of biological molecules including proteins, nucleic acids, glycoproteins, carbohydrates, hormones, drugs, and the like. Specific examples include an antibody/peptide pair, an antibody/antigen pair, an antibody fragment/antigen pair, an antibody/antigen fragment pair, an antibody fragment/antigen fragment pair, an antibody/hapten pair, an enzyme/substrate pair, an enzyme/inhibitor pair, an enzyme/cofactor pair, a protein/substrate pair, a nucleic acid/nucleic acid pair, a protein/nucleic acid pair, a peptide/peptide pair, a protein/protein pair, a small molecule/protein pair, a glutathione/GST pair, an anti-GFP/GFP fusion protein pair, a Myc/Max pair, a maltose/maltose binding protein pair, a carbohydrate/protein pair, a carbohydrate derivative/protein pair, a metal binding tag/metal/chelate, a peptide tag/metal ion-metal chelate pair, a peptide/NTA pair, a lectin/carbohydrate pair, a receptor/hormone pair, a receptor/effector pair, a complementary nucleic acid/nucleic acid pair, a ligand/cell surface receptor pair, a virus/ligand pair, a Protein A/antibody pair, a Protein G/antibody pair, a Protein L/antibody pair, an Fc receptor/antibody pair, a biotin/avidin pair, a biotin/streptavidin pair, a drug/target pair, a zinc finger/nucleic acid pair, a small molecule/peptide pair, a small molecule/protein pair, a small molecule/target pair, a carbohydrate/protein pair such as maltose/MBP (maltose binding protein), a small molecule/target pair, or a metal ion/chelating agent pair. Specific non-limiting examples of binding moieties include peptides, proteins, DNA, RNA, PNA. Other binding moieties and binding pairs are also possible. Binding moieties can also be attached to polymers, organic nanoparticles, inorganic nanoparticles, or metal nanoparticles.

In some embodiments, the binding moiety and the tether interact via a binding event between pairs of biological molecules including proteins, nucleic acids, glycoproteins, carbohydrates, hormones, and the like. In other embodiments the binding moieties can be also bound to a nanoparticle.

In an exemplary embodiment, the binding moiety comprises a protein. In some embodiments, the protein is a hyperthermophilic protein.

The analyte may comprise any suitable material (e.g., a vapor analyte, a liquid analyte, a solid analyte) such that the incorporation of the analyte into the system causes at least a portion of the plurality of Janus droplets to change orientation (e.g., via breaking of a tether and/or agglutination of the Janus droplets). Those skilled in the art would be capable of selecting analytes and components suitable for Janus droplets based upon the teaching of the specification and the examples below. Non-limiting examples of analytes include a biological compound, a drug, a macromolecule, a salt, an electrolyte, an enzyme, a nucleic acid, a carbohydrate, a peptide, a protein, a lipid, a phosphate, a sulfonate, a virus, a pathogen (e.g., bacteria, virus), an oxidant, a reductant, a toxin, a chemical warfare agent, an explosive, carbon dioxide, a surfactant, or combinations thereof. In some embodiments, the tether is a biological compound, a drug, a macromolecule, a salt, an electrolyte, an enzyme, a nucleic acid, a carbohydrate, a peptide, a protein, a lipid, a phosphate, a sulfonate, a virus, a pathogen, an oxidant, a reductant, a toxin, a chemical warfare agent, an explosive, carbon dioxide, a surfactant, or combinations thereof. In an exemplary embodiment, the analyte is a bacterium.

In an exemplary embodiment, an enzyme may be added to the system comprising a plurality of Janus droplets such that the enzyme interacts with one or more of the components, binding moieties, tethers, and/or amphiphilic compounds present in the plurality of Janus droplets. In some such embodiments, the enzyme may interact with the component, binding moiety, tether, and/or amphiphilic compound (e.g., such as a surfactant which is cleaved in the presence of the enzyme) such that at least a portion of the plurality of Janus droplets change orientation as described herein. In certain embodiments, the Janus droplets change orientation at a particular critical concentration of the analyte.

In another exemplary embodiment, one or more Janus droplets may comprise an amphiphilic compound such as a surfactant that is capable of interacting with a biological analyte. In some such embodiments, the Janus droplet may change orientation in the presence of a biological analyte such that the change in orientation can be detected (e.g., by optical transmission).

In some embodiments, the interaction between a binding moiety and the analyte includes a chemical transformation between the binding moiety and the analyte and/or the binding moiety and a tether. Non-limiting examples of chemical transformations include enzymatic degradation, enzymatic synthesis, ionization, cleavage, coupling, hybridization, aggregation, hydrolysis, isomerization, reduction, oxidation, and host-guest interactions of one or more components (or component materials such as a surfactant). Other chemical transformations are also possible.

As described herein, in some embodiments, the methods and systems comprise an outer phase and a plurality of Janus droplets dispersed within the outer phase. In certain embodiments, the plurality of Janus droplets comprises two or more phases. The two or more phases (e.g., a first phase and a second phase) may be substantially miscible over a range of temperatures (e.g., below a critical temperature, above a critical temperature). The two or more phases may also be substantially immiscible over a different range of temperatures (e.g., above the critical temperature, below the critical temperature) than the range of temperatures over which they are miscible. The use of two or more phases with differing miscibility at different temperatures may allow for the one-step formation (e.g., bulk) of such Janus droplets, unconstrained by the limits of previous methods (e.g., low yield of microfluidic devices, multi-step processes, the need for solvent addition and/or extraction, etc.).

Janus droplets described herein may be formed using any suitable method. For example, in some embodiments, an outer phase material, a first phase, and a second phase are mixed and emulsified, forming an outer phase and a plurality of Janus droplets dispersed within the outer phase. Suitable methods for emulsifying the fluid are known in the art and may comprise sonication, high shear mixing, shaking, passing the fluid through a membrane, or injecting the two or more components into the outer phase through a small diameter channel.

Non-limiting examples of methods for forming Janus droplets are described in more detail in commonly-owned U.S. Patent Publication Number 2016/0151753, entitled "Compositions and Methods for Forming Emulsions", filed Oct. 30, 2015 and in U.S. Patent Publication Number 2016/0151756, entitled "Compositions and Methods for Arranging Colloid Phases", filed Oct. 30, 2016, each of which is incorporated herein by reference in its entirety.

In some embodiments, the methods and emulsions comprise an outer phase and a plurality of droplets dispersed within the outer phase. In certain embodiments, the plurality of droplets comprise two or more components. The two or more components may be substantially miscible over a range of temperatures (e.g., below a critical temperature, above a critical temperature). The two or more components may also be substantially immiscible over a different range of temperatures (e.g., above the critical temperature, below the critical temperature) than the range of temperatures over which they are miscible. The use of two or more components with differing miscibility at different temperatures may allow for the one-step formation (e.g., bulk) of emulsions (e.g., complex emulsions), unconstrained by the limits of previous methods (e.g., low yield of microfluidic devices, multi-step processes, the need for solvent addition and/or extraction, etc.)

In some embodiments, the plurality of droplets comprise two or more components, wherein the two or more components are immiscible below or above a critical temperature. In some embodiments, the critical temperature is an upper consolute temperature of the two or more components. That is to say, in some such embodiments, the two components are substantially miscible above the upper consolute temperature of the two or more components and substantially immiscible below the upper consolute temperature of the two or more components. In some embodiments, the critical temperature is a lower consolute temperature of the two or more components. That is to say, in some such embodiments, the two components are substantially miscible below the lower consolute temperature of the two or more components and substantially immiscible above the lower consolute temperature of the two or more components. In some embodiments, the miscibility of the two or more components is reversible. That is to say, the miscibility of the two or more components can be changed, in some embodiments, by increasing or decreasing the temperature to a temperature greater than, or less than, the critical temperature.

In some embodiments, two or more components may have an upper consolute temperature greater than or equal to about 0° C., greater than or equal to about 5° C., greater than or equal to about 8° C., greater than or equal to about 10° C., greater than or equal to about 15° C., greater than or equal to about 18° C., greater than or equal to about 20° C., greater than or equal to about 22° C., greater than or equal to about 25° C., greater than or equal to about 27° C., greater than or equal to about 30° C., greater than or equal to about 35° C., greater than or equal to about 40° C., greater than or equal to about 50° C., greater than or equal to about 55° C., or greater than or equal to about 60° C. In certain embodiments, the upper consolute temperature of the two or more components is less than about 70° C., less than about 60° C., less than about 55° C., less than about 50° C., less than about 40° C., less than about 35° C., less than about 30° C., less than about 27° C., less than about 25° C., less than about 22° C., less than about 20° C., less than about 18° C., less than about 15° C., less than about 10° C., less than about 8° C., or less than about 5° C. Combinations of the above-referenced ranges are also possible (e.g., a upper consolute temperature of greater than or equal to about 0° C. and less than about 70° C.). Other ranges are also possible. Those skilled in the art would be capable of selecting suitable methods for determining the upper consolute temperature of two or more components.

In some embodiments, two or more components may have a lower consolute temperature greater than or equal to about 0° C., greater than or equal to about 5° C., greater than or equal to about 8° C., greater than or equal to about 10° C., greater than or equal to about 15° C., greater than or equal to about 18° C., greater than or equal to about 20° C., greater than or equal to about 22° C., greater than or equal to about 25° C., greater than or equal to about 27° C., greater than or equal to about 30° C., greater than or equal to about 35° C., greater than or equal to about 40° C., greater than or equal to about 50° C., greater than or equal to about 55° C., or greater than or equal to about 60° C. In certain embodiments, the lower consolute temperature of two components is less than about 70° C., less than about 60° C., less than about 55° C., less than about 50° C., less than about 40° C., less than about 35° C., less than about 30° C., less than about 27° C., less than about 25° C., less than about 22° C., less than about 20° C., less than about 18° C., less than about 15° C., less than about 10° C., less than about 8° C., or less than about 5° C. Combinations of the above-referenced ranges are also possible (e.g., a lower consolute temperature of greater than or equal to about 0° C. and less than about 70° C.). Other ranges are also possible. Those skilled in the art would be capable of selecting suitable methods for determining the lower consolute temperature of two or more components.

In some embodiments, the two or more components have a greater miscibility at a first temperature as compared to a second temperature. That is to say, at the first temperature, the two or more components may be miscible to some extent, and miscible to some lesser extent (e.g., immiscible to some extent) at the second temperature. In some cases, the two or more components may be substantially miscible over a range of pressures (e.g., below a critical pressure, above a critical pressure). The two or more components may also be substantially immiscible over a different range of pressure (e.g., above the critical pressure, below the critical pressure) than the range of pressures over which they are miscible. The use of two or more components with differing miscibility at different pressures may allow for the one-step formation (e.g., bulk) of emulsions (e.g., complex emulsions), unconstrained by the limits of previous methods (e.g., low yield of microfluidic devices, multi-step processes, the need for solvent addition and/or extraction, etc.)

Those skilled in the art would be capable of selecting a suitable temperature and/or suitable pressure range for forming the emulsions described herein based upon the teachings of the specification and the examples below, and would generally understand these temperature ranges and/or pressure ranges to include ranges in which the two or more components remain substantially fluid (e.g., below the boiling point of the two or more components, above the freezing point of the two or more components.) In some embodiments, the two or more components are immiscible with the outer phase over the suitable temperature range and/or pressure range.

Immiscible, as used herein, refers to two components (or a phase and a component, or a first phase and a second phase) having an interfacial tension of greater than or equal to 0.01 mN/m as determined by an inverted pendant drop goniometer. Conversely, miscible, as used herein, refers to two components (or a phase and a component) having an interfacial tension of less than 0.01 mN/m as determined by an inverted pendant drop goniometer.

In some embodiments, at a temperature (and/or pressure) wherein the two or more components are immiscible, the two or more components comprise a first component and a second component at least partially encapsulated within the first component. In certain embodiments, at a temperature (and/or pressure) wherein the two or more components are immiscible, the two or more components do not encapsulate each other but interface with the outer phase (or an additional component at least partially encapsulating the two or more components) to form Janus droplets. Janus droplets are generally droplets where the droplet is divided into two or more distinct parts comprising two or more different components that do not encapsulate each other. For example, in some embodiments, the emulsion comprises an hydrocarbon and/or aqueous phase and a plurality of droplets comprising a hydrocarbon and a fluorocarbon, wherein the plurality of droplets are Janus droplets.

The term component, as used herein, generally refers to a portion of a droplet comprising a group of substantially similar molecules, a group of substantially similar compounds, and/or a phase (e.g., a non-hydrocarbon and/or aqueous phase, an hydrocarbon and/or aqueous phase). Those skilled in the art would understand that is not intended to refer to single molecules or atoms. In some embodiments, the component is a liquid phase (e.g., a gas phase, an hydrocarbon and/or aqueous phase, a non-hydrocarbon and/or aqueous phase) comprising a group of substantially similar compounds and/or molecules. For example, in some cases, each component may occupy at least about 1 vol %, at least about 2 vol %, at least about 5 vol %, at least about 10 vol %, at least about 20 vol %, at least about 50 vol %, at least about 70 vol %, at least about 90 vol %, at least about 95 vol %, or at least about 99 vol % of the total volume of the two or more components.

The term phase, as used herein, generally refers to a portion of a droplet or fluid comprising a group of substantially similar molecules, and/or a group of substantially similar compounds. Those skilled in the art would understand that is not intended to refer to single molecules or atoms. In some embodiments, the phase is a liquid phase (e.g., an hydrocarbon and/or aqueous phase, a non-hydrocarbon and/or aqueous phase) comprising a group of substantially similar compounds and/or molecules and/or polymers. For example, in some cases, each phase may occupy at least about 1 vol %, at least about 2 vol %, at least about 5 vol %, at least about 10 vol %, at least about 20 vol %, at least about 50 vol %, at least about 70 vol %, at least about 90 vol %, at least about 95 vol %, or at least about 99 vol % of the total volume of the two or more phases.

In some embodiments, at least one of the two or more phases (e.g., the first phase) comprises a hydrocarbon. Non-limiting examples of suitable hydrocarbons include alkanes (e.g., hexane, heptane, decane, dodecane, hexadecane), alkenes, alkynes, aromatics (e.g., benzene, toluene, xylene, benzyl benzoate, diethyl phalate), oils (e.g., natural oils and oil mixtures including vegetable oil, mineral oil, and olive oil), liquid monomers and/or polymers (e.g., hexanediol diacrylate, butanediol diacrylate, polyethylene glycols, trimethylolpropane ethoxylate triacrylate), alcohols (e.g., butanol, octanol, pentanol), ethers (e.g., diethyl ether, diethylene glycol, dimethyl ether), nitromethane, halogenated liquids (e.g., chloroform, dichlorobenzene, methylene chloride, carbon tetrachloride), brominated liquids, iodinated liquids, lactates (e.g., ethyl lactate), acids (e.g., citric acid, acetic acid), liquid crystals (4-cyano-4'-pentylbiphenyl), trimethylamine, liquid crystal hydrocarbons (e.g., 5-cyanobiphenyl), combinations thereof, and derivatives thereof, optionally substituted. In some embodiments, the hydrocarbon comprises a halogen group, sulfur, nitrogen, phosphorous, oxygen, or the like. Other hydrocarbons and solutes are also possible.

In some embodiments, at least one of the two or more phases (e.g., the second phase) comprises a fluorocarbon. Non-limiting examples of suitable fluorocarbons include fluorinated compounds such as perfluoroalkanes (e.g., perfluorohexanes, perfluorooctane, perfluorodecalin, perfluoromethylcyclohexane), perfluoroalkenes (e.g., perfluorobenzene), perfluoroalkynes, and branched fluorocarbons (e.g., perfluorotributylamine). Additional non-limiting examples of suitable fluorocarbons include partially fluorinated compounds such as methoxyperfluorobutane, ethyl nonafluorobutyl ether, 2H,3H-perfluoropentane, trifluorotoluene, perfluoroiodide, fluorinated or partially fluorinated oligomers, 2,2,3,3,4,4,5,5,6,6,7,7,8,8,9,9-hexadecafluorodecane-1,10-diyl bis(2-methylacrylate), perfluoroiodide, and 2-(trifluoromethyl)-3-ethoxydodecafluorohexane. Other fluorocarbons are also possible.

In some embodiments, at least one of the two or more components phases a silicone such as silicone oil. Non-limiting examples of suitable silicone oils include polydimethylsiloxane and cyclosiloxane fluids.

In some embodiments, at least one of the two or more phases comprises water.

In some embodiments, at least one of the two or more phases comprises an ionic liquid (e.g., an electrolyte, a liquid salt). In some embodiments, at least one of the two or more inner phases comprises an ionic liquid (e.g., an electrolyte, a liquid salt, 1-allyl-3-methylimidazolium bromide, 1-allyl-3-methylimidazolium chloride, 1-benzyl-3-methylimidazolium hexafluorophosphate, 1-butyl-1-methylpyrrolidinium hexafluorophosphate). In some embodiments, the outer phase comprises water. In certain embodiments, at least one of the two or more phases comprises a deuterated compound (e.g., a deuterated hydrocarbon).

In some embodiments, at least one of the two or more phases comprises a chlorinated solvent (e.g. chloroform, carbon tetrachloride).

In some embodiments, at least one of the two or more components comprises a polymer (e.g., polyethylene glycol). In certain embodiments, the polymer is a block copolymer. In certain embodiments, the polymer is a liquid crystal polymer (e.g., a thermotropic liquid crystal polymer). In certain embodiments, the polymer is a biopolymer (e.g. gelatin, alginate)

Non-limiting examples of combinations of components present in the emulsion described herein include hexane and perfluorohexane, carbon tetrachloride and perfluorohexane, chloroform and perfluorohexane, hexane and perfluorodecalin, hexane and perfluoromethylcyclohexane, hexane and perfluorotributylamine, isopropanol and hexadecane, ethyl lactate and heptane, acetic acid and decane, and triethylamine and water. Other combinations and materials are also possible.

In some embodiments, at least one of the two or more components comprises a gas (e.g., a perfluoropentane gas).

In some embodiments, at least one of the two or more phases comprises a combination of the materials described above (e.g., comprising a hydrocarbon, a fluorocarbon, a silicone, or combinations thereof). Non-limiting examples of combinations of phases present in the Janus droplets described herein include hexane and perfluorohexane, carbon tetrachloride and perfluorohexane, chloroform and perfluorohexane, hexane and perfluorodecalin, hexane and perfluoromethylcyclohexane, hexane and perfluorotributylamine, isopropanol and hexadecane, ethyl lactate and heptane, acetic acid and decane, and triethylamine and water. Other combinations and materials are also possible.

In some embodiments, at least one of the two or more components comprises a combination of the materials described above (e.g., comprising a hydrocarbon, a fluorocarbon, a silicone, or combinations thereof).

Those skilled in the art would be capable of selecting suitable phases based upon the teachings of the specification and the examples below such that the two or more phases are immiscible under a particular range of temperatures and/or conditions, as described above.

The outer phase may comprise any suitable material. Generally, the two or more phases comprising the plurality of Janus droplets may be substantially immiscible with the outer phase. In some embodiments, the outer phase is an hydrocarbon and/or aqueous phase (e.g., comprising water). The hydrocarbon and/or aqueous phase may, in some cases, have ions and/or be mixed with a biological fluid (e.g., sputum, blood, plasma, urine). In certain embodiments, the outer phase is a non-hydrocarbon and/or aqueous phase. In some embodiments, the non-hydrocarbon and/or aqueous phase comprises a hydrocarbon, a fluorocarbon, a silicone, or the like, as described above in the context of the two or more phases, substantially immiscible with the two or more phases. Those skilled in the art would be capable, based upon the teachings of the specification and the examples below, of selecting suitable materials for use as an outer phase based upon the miscibility of those materials (e.g., such that the two or more phases are substantially immiscible with the outer phase). The use of a non-hydrocarbon and/or aqueous outer phase may be advantageous in certain applications where the emulsion is used in low humidity environments. For example, a plurality of Janus droplets comprising fluorocarbon/hydrocarbon phases can be created in a liquid silicone matrix.

Those skilled in the art would be capable, based upon the teachings of the specification and the examples below, of selecting suitable materials for use as an outer phase based upon the miscibility of those materials (e.g., such that the two or more components are substantially immiscible with the outer phase). The use of an non-hydrocarbon and/or aqueous outer phase may be advantageous in certain applications where the emulsion is used in low humidity environments. For example, a plurality of droplets comprising fluorocarbon/hydrocarbon phases can be created in a liquid silicone matrix. The silicone can be crosslinked of polymerized to change its mechanical properties. In some embodiments, at least a portion of the droplets may be deformed and/or aligned by mechanically deforming (e.g., applying a mechanical force to) the outer phase.

In some embodiments, the Janus droplet comprises an amphiphilic compound. In certain embodiments, the binding moiety is associated with the amphiphilic compound. For example, the binding moiety may be bound to at least a portion of the amphiphilic compound.

In certain embodiments, the amphiphilic compound is miscible in the outer phase. In some embodiments, the amphiphilic compound is miscible in at least one of the two or more phases (e.g., the first phase, the second phase). In certain embodiments, the amphiphilic compound has a greater miscibility in at least one of the two or more phases than a miscibility in the outer phase. In other embodiments the amphiphilic compound is added to the Janus droplet though a dispersion, such as a hydrocarbon and/or aqueous micelle structure or dissolution method (e.g., comprising injecting a dispersion of the amphiphilic compound into the solution containing the Janus droplets). In some embodiments, the amphiphilic compound is disposed at the interface between the outer phase and the plurality of Janus droplets. Amphiphilic compounds may also be generated, in some embodiments, by reaction of a solute in one phase with solute in another phase. For example, without wishing to be bound by theory, a reactive group in an organic phase may, in some cases, react with a solute from a hydrocarbon and/or aqueous phase to create a amphiphilic molecule at the surface of a droplet. In certain embodiments, the amphiphilic compound is disposed at the interface between at least two of the two or more phases (e.g., the interface between the first phase and the second phase). The amphiphilic compound may preferentially interact with one or more phases or the outer phase. Those skilled in the art would be capable of selecting a suitable amphiphilic compound based upon the teachings of the specification and examples below.

In some embodiments, the amphiphilic compound is a surfactant. Non-limiting examples of suitable surfactants include ionic surfactants, non-ionic surfactants, and zwitterionic surfactants. In some embodiments, the surfactant is a fluorosurfactants (e.g., commercially available fluorosurfactants such as Zonyl® or Capstone®). In certain embodiments, the surfactant is anionic surfactants (e.g., sodium dodecyl sulfate (SDS)), cationic surfactants (e.g., alkyltrimethyl ammonium chloride, alkylmethyl ammonium bromide), non-ionic surfactants (e.g., alkyl poly(ethylene oxide)), zwitterionic surfactants (e.g., alkyl betain, C8-lecitin), polymeric surfactants, gemini surfactants, particulate surfactants (e.g., graphene oxide, silica particles, gold nanoparticles, polymer nanoparticles), and combinations thereof. Other surfactants are also possible. In some embodiments, the amphiphilic compound is a nucleic acid (e.g., DNA, RNA). In certain embodiments the amphiphilic compound comprises an amino acid (e.g., a peptide, a protein). In some embodiments, the amphiphilic compound comprises a biomaterial. Non-limiting examples of suitable biomaterials include carbohydrates or derivatives thereof, saccharides or derivatives thereof (e.g., sialic acid), lipids or derivatives thereof, enzymes, chromophores or the like. Those skilled in the art would be capable of selecting suitable biomaterials based upon the teachings of the specification and the examples below.

In some embodiments, the amphiphilic compound comprises a perfluorinated segment. In some embodiments, the amphiphilic compound comprises ethylene glycol.

In some embodiments, the amphiphilic compound is capable of forming metal complexes.

In some embodiments, the amphiphilic compound is gallic acid or derivatives thereof (e.g., tridodecyl gallic acid).

In some embodiments, the amphiphilic compound has a structure as in formula (I):

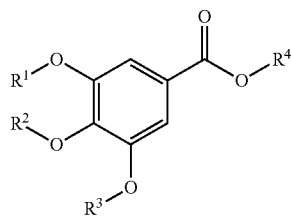

(I)

wherein each $R^1$-$R^3$ is the same or different and comprises hydrogen or alkyl, optionally substituted, and wherein $R^4$ is capable of binding to a biological analyte. In some embodiments, each of $R^1$-$R^3$ are the same or different and are $C_nH_{n+1}$, where n is an integer greater than or equal to 10 and less than or equal to 30 (e.g., 10, 11, 12, 13, 14, 15, 16, 17, 18, 19, 20, 21, 22, 23, 24, 25, 26, 27, 28, 29, 30). In some embodiments, $R^1$, $R^2$, and/or $R^3$ may be a saturated or unsaturated alkyl chain, optionally substituted. In some embodiments, $R^4$ comprises or is derived from methyl, carbonyl, carboxyl, N-hydroxysuccinimide, 1-ethyl-3-(3-dimethylaminopropyl)carbodiimide, and N-(2-aminoethyl) maleimide.

In some embodiments, the amphiphilic compound is capable of forming a bond with an analyte (e.g., a biological analyte). In some embodiments, $R^4$ is capable of forming the bond with the analyte. In some embodiments, $R^4$ is capable of interacting with the analyte via formation of a bond, such as an ionic bond, a covalent bond, a hydrogen bond, Van der Waals interactions, and the like. The covalent bond may be, for example, carbon-carbon, carbon-oxygen, oxygen-silicon, sulfur-sulfur, phosphorus, nitrogen, carbon-nitrogen, metal-oxygen, or other covalent bonds. The hydrogen bond may be, for example, between hydroxyl, amine, carboxyl, thiol, and/or similar functional groups.

In some embodiments, $R^4$ comprises one or more binding moieties as described herein.

In some embodiments, the amphiphilic compound may comprise a polymer (e.g., a block copolymer), as described herein. Non-limiting examples of suitable polymers for use as amphiphilic compounds include:

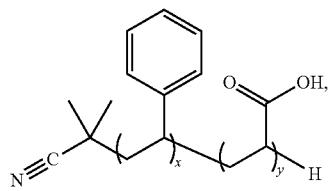

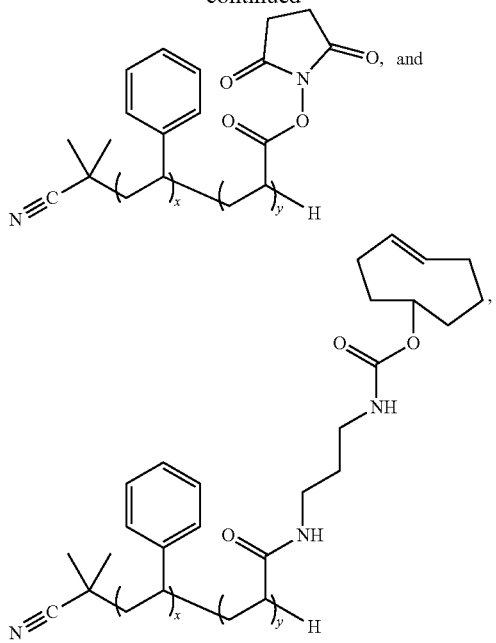

where x is 0-1, y is 0-1, and x+y=1. In some embodiments, a tetrazine click reaction may be used to form and/or react with the amphiphilic compound (e.g., the polymer).

In some embodiments, the one or more phases (e.g., the first phase, the second phase) and/or the outer phase comprises an additional compound dispersed in the one or more phases and/or the outer phase. In certain embodiments, the additional compound is miscible/dispersible in the first phase and immiscible/not dispersible in the second phases. In some cases, at least a portion of the additional compound is dispersible in the first phases and not dispersible in the second phases (e.g., a surfactant). In some embodiments, the additional compound may be dispersible or not dispersible in the outer phase. Non-limiting examples of suitable additional compounds include particles (e.g., magnetic particles/nanoparticles, silica particles), biological molecules (e.g., insulin), pharmaceutical compounds, polymers, surfactants, cells, bacteria, viruses, active pharmaceutical ingredients, and metals or metal particles. Other additional compounds are also possible and those skilled in the art would be capable of selecting such compounds based upon the teachings of this specification.

In some embodiments, the emulsion can be formed by adjusting the temperature of a fluid comprising the outer phase and the two or more immiscible components such that the two or more components become substantially miscible with each other, and emulsifying the fluid (e.g., thus forming the plurality of droplets). In certain embodiments, the method comprises adjusting the temperature of the fluid comprising the plurality of droplets such that the two or more components become substantially immiscible.

In some embodiments, the plurality of Janus droplets can be formed by adjusting the temperature of a fluid comprising the outer phase and the two or more immiscible phases such that the two or more phases become substantially miscible with each other, and emulsifying the fluid (e.g., thus forming the plurality of Janus droplets). In certain embodiments, the method comprises adjusting the temperature of the fluid comprising the two or more phases such that the two or more phases become substantially immiscible. In other embodiments, the method comprises the addition of a solvent that creates a stable uniform composition prior to emulsification, and the solvent is removed by evaporation or extraction to give phase separation and produce a Janus droplet.

Figure 3A:
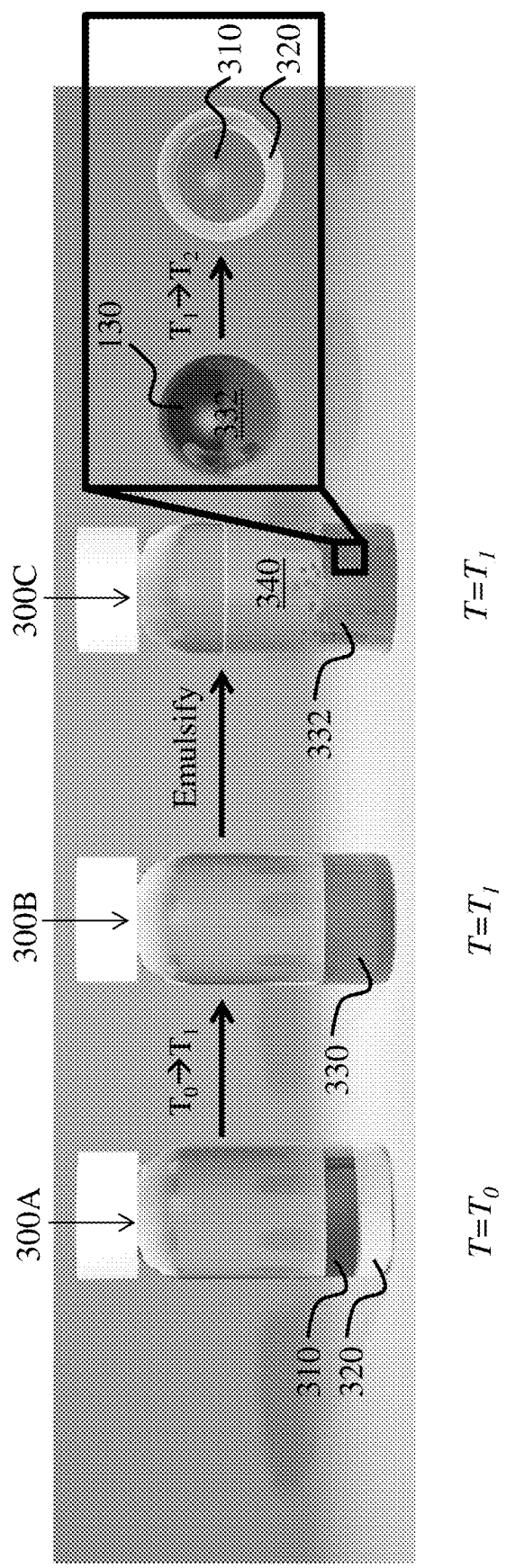
FIG. 3A illustrates the formation of complex emulsions, according to one set of embodiments.
Figure 3B:
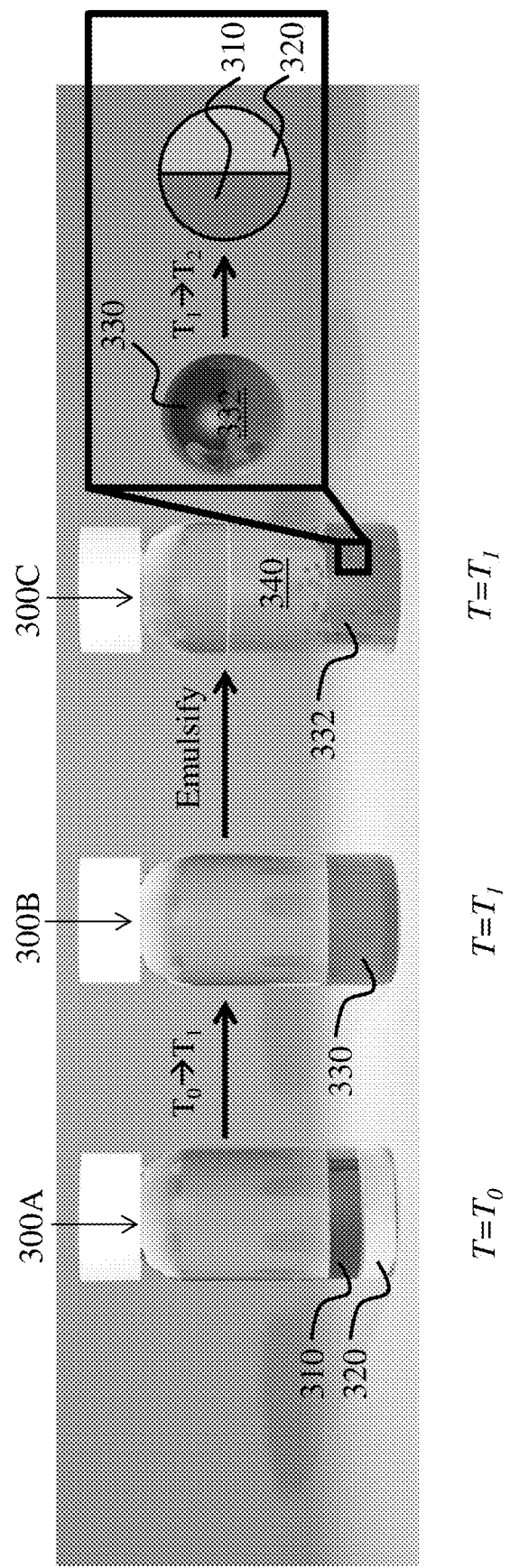
FIG. 3B illustrates the formation of complex emulsions, according to one set of embodiments.

For example, as illustrated in FIG. 3B, a fluid 300A comprises first phase 310 (e.g., a hydrocarbon) and second phase 320 (e.g., a fluorocarbon) which are immiscible at a first temperature $T_0$. In some embodiments, $T_0$ is adjusted to a second temperature $T_1$ (e.g., where $T_1$ is greater than $T_0$, or where $T_1$ is less than $T_0$) such that the first component and second component form a miscible mixture 330 in fluid 300B. For example, in some embodiments, the first phase and the second phase, which are initially substantially immiscible, may be heated such that they are miscible. In certain embodiments, the first phase and the second phase, which are initially substantially immiscible, may be cooled such that they are miscible. Miscible mixture 330 can, in certain embodiments, be emulsified to form emulsion 300C comprising plurality of droplets 332. Plurality of droplets 332 may comprise miscible mixture 330 and be present in an outer phase 340. In some cases, outer phase 340 may be added prior to changing the temperature from $T_0$ to $T_1$. In certain embodiments, outer phase 340 may be added after changing the temperature but prior to emulsification.

In some embodiments, T1 is adjusted to a temperature T2 (e.g., where T2 is greater than T1 or where T2 is less than T1) such that droplet 332 comprises first component 310, and second component 320 substantially immiscible with first component 310, contained within the droplet. In some such embodiments, first component 310 may be at least partially encapsulated by second component 320. In some embodiments, first component 310 and second component 320 are not encapsulated but form a Janus particle (FIG. 3B).

In some embodiments, $T_1$ is adjusted to a temperature $T_2$ (e.g., where $T_2$ is greater than $T_1$ or where $T_2$ is less than $T_1$) such that droplet 332 comprises first phase 310, and second phase 320 substantially immiscible with first component 310, forming a Janus droplet.

In some embodiments, $T_1$ is greater than a critical temperature of the two or more phases (e.g., an upper consolute temperature of the two or more phases). In certain embodiments, $T_1$ is less than a critical temperature of the two or more phases (e.g., a lower consolute temperature). Those skilled in the art will be capable of selecting suitable methods for determining the critical temperature (e.g., the upper consolute temperature, the lower consolute temperature) of two or more phases.

Suitable methods for emulsifying the fluid are known in the art and may comprise sonication, high shear mixing, shaking, passing the fluid through a membrane, or injecting the two or more components into the outer phase through a small diameter channel.

Colloids (e.g., droplets) described herein offer numerous advantages to colloids known in the art, including the ability to reversibly, dynamically, and/or controllably change the arrangement and/or configuration of the components within the colloid (e.g., in response to an external stimulus, a change in temperature, or an analyte). In some embodiments, the colloid comprises an outer phase and a plurality of droplets (or regions) comprising two or more components. For example, in certain embodiments, the colloid comprises an outer phase and a plurality of droplets comprising a first component and a second component. In some cases, the colloid comprises an outer phase, and a plurality of droplets (or regions) comprising a first component, a second component, and a third component. Additional components are also possible.

In certain embodiments, the colloid comprises an outer phase and a plurality of droplets where a first component encapsulates a second component. In some embodiments, the colloid may be stimulated (e.g., by a first stimulus such as a change in temperature or exposure to an analyte) such that the components change arrangement and the second component encapsulates the first component. Those skilled in the art would understand that changes in arrangement as described herein do not refer to the motion of immiscible phases in a colloid due to regular fluid motion driven by passive diffusion and/or Brownian motion, but instead refer to the controlled change in arrangement of phases as a result of the addition of a particular stimulus or condition not present prior to the rearrangement of phases (or removal of a particular stimulus or condition, present prior to the rearrangement of phases), and are described in more detail below. In certain cases, a change in temperature may increase the passive diffusion and/or Brownian motion of phases present in the colloid but does not result in rearrangement of phases as described herein (e.g., until the temperature reaches a critical temperature as described in more detail below).

Figure 3C:
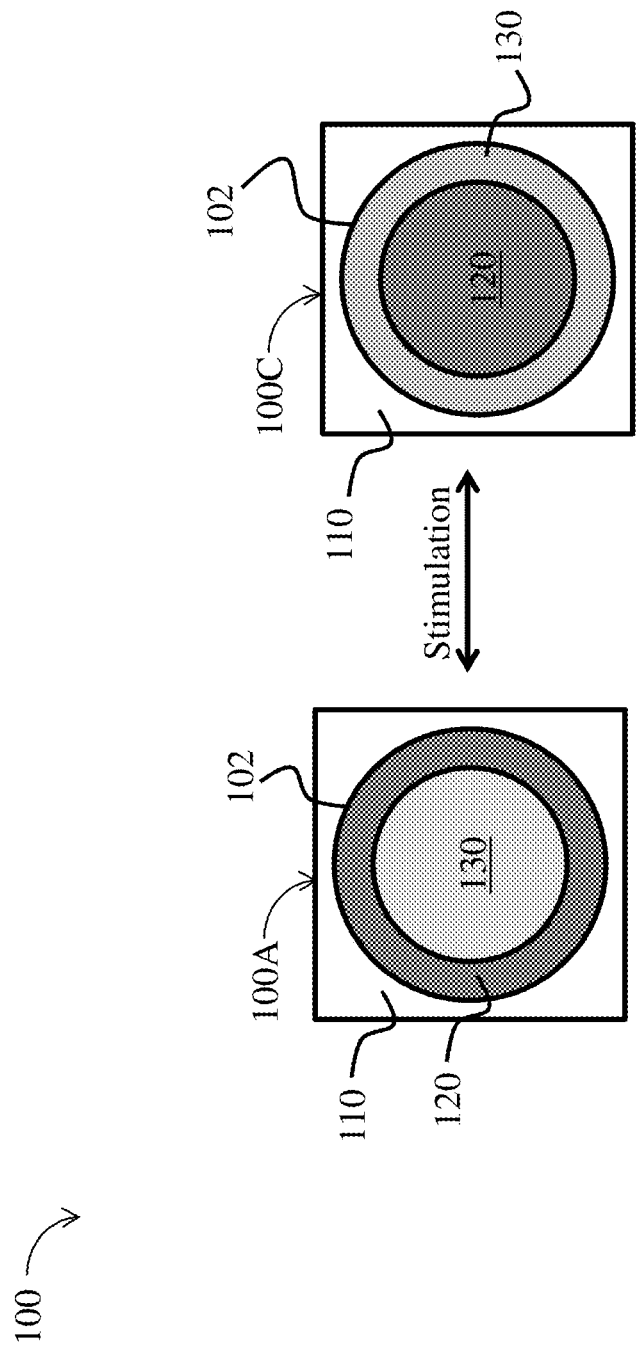
FIGS. 3C-3F are schematic drawings illustrating changing the arrangement of colloid droplet phases, according to one set of embodiments.

Referring to FIG. 3C, in some embodiments, colloid 100 comprises an outer phase 110, and a plurality of droplets (shown as exemplary droplet 102) comprising a first component 120 and a second component 130 at least partially encapsulated by the first component (configuration 100A). In certain embodiments, colloid 100 having configuration 100A may be stimulated (e.g., by a first stimulus) such that at least a portion of the plurality of droplets obtain a second configuration 100C, such that second component 130 at least partially encapsulates first component 120. That is to say, in certain embodiments, the first component and the second component may transpose. In some embodiments, the rearrangement between the first configuration and the second configuration may be reversible. For example, in some cases, colloid 100 comprising a plurality of droplets having second configuration 100C may be stimulated (e.g., by a second stimulus) such that at least a portion of the plurality of droplets return to first configuration 100A.

Figure 3D:
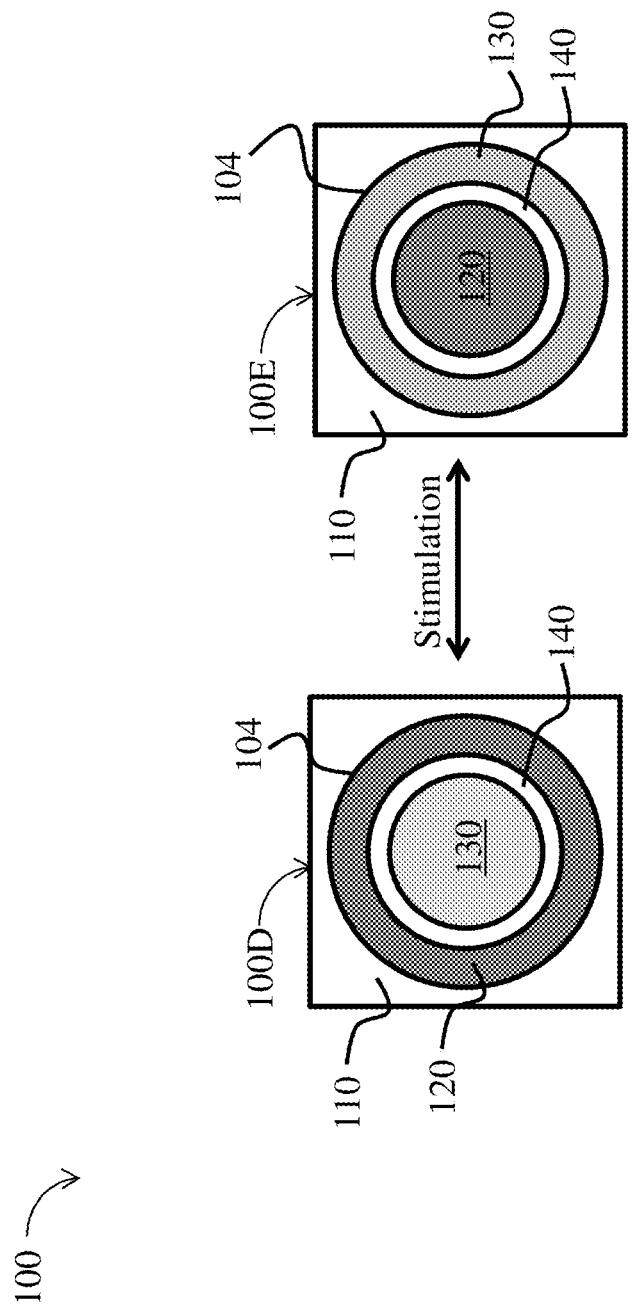

In some embodiments, the colloid comprises a plurality of droplets comprising three or more components. In some such embodiments, the colloid may be stimulated such that two or more of the three or more components change arrangement. In an exemplary embodiment, a colloid comprises a plurality of droplets comprising a first component at least partially encapsulating a second component, the second component at least partially encapsulating a third component, and upon stimulation, the first component changes arrangements with the second and/or third components. For example, as illustrated in FIG. 3D, colloid 100 may comprise outer phase 110 and a plurality of droplets (shown as exemplary droplet 104) comprising a first component 120, a second component 130, and a third component 140. In certain embodiments, the third component at least partially encapsulates the second component, and the first component at least partially encapsulates the second and third components. In certain embodiments, colloid 100 having configuration 100D may be stimulated (e.g., by a first stimulus) such that at least a portion of the plurality of droplets obtain a second configuration 100E, such that the second component at least partially encapsulates the first and third components. In some embodiments, the rearrangement between configuration 100D and 100E are reversible. For example, in some cases, colloid 100 comprising a plurality of droplets having configuration 100E may be stimulated (e.g., by a second stimulus) such that at least a portion of the plurality of droplets return to configuration 100D.

In certain embodiments, the colloid may be stimulated such that two or more components become miscible. Referring now to FIG. 3F, in some embodiments, the colloid comprises outer phase 110, and a plurality of droplets (shown as exemplary droplet 108) comprising a first component 120 and a second component 130 at least partially encapsulated by the first component (configuration 100A). In certain embodiments, colloid 100 having configuration 100A may be stimulated (e.g., by a first stimulus) such that at least a portion of the plurality of droplets obtain a second configuration 100F, such that the first component and the second component form a miscible mixture 125. Those skilled in the art would understand that droplets comprising two or more, three or more, or four or more components may, upon stimulation, have two or more, three or more, or four or more components form a miscible mixture.

In some cases, the colloid may comprises two or more miscible components that, upon stimulation, become immiscible. Referring again to FIG. 3F, in certain embodiments, the colloid having a plurality of droplets comprising mixture 125 such that (configuration 100F), upon stimulation, the mixture separates into first component 120 and second component 130, at least partially encapsulated by first component 120 (configuration 100A).

While exemplary configurations for a plurality of droplets having two or more components, are described above, those skilled in the art would understand based upon the teaching of this specification that additional reconfigurations and rearrangements are also possible (e.g., the third component encapsulating the first and second components, etc.). Those skilled in the art would also understand, based upon the teachings of this specification, that droplets comprising four or more, five or more, or six or more components are also possible and that such droplets may also be stimulated such that two or more of the components rearrange.

Those skilled in the art will understand that while much of the specification refers to a plurality of droplets, the colloid may comprises an outer phase and a plurality of regions comprising two or more components, such that the two or more components change configuration (e.g., after stimulation).

In some cases, the methods and colloids described herein may be useful for the formation of Janus droplets. For example, in certain embodiments, the first component and second component may change configuration upon stimulation such that neither component encapsulates the other component in the new configuration. In some such embodiments, the colloid may comprise a plurality of Janus droplets. In some such embodiments, the colloid is stimulated such that the plurality of droplets form Janus droplets.

Figure 3E:
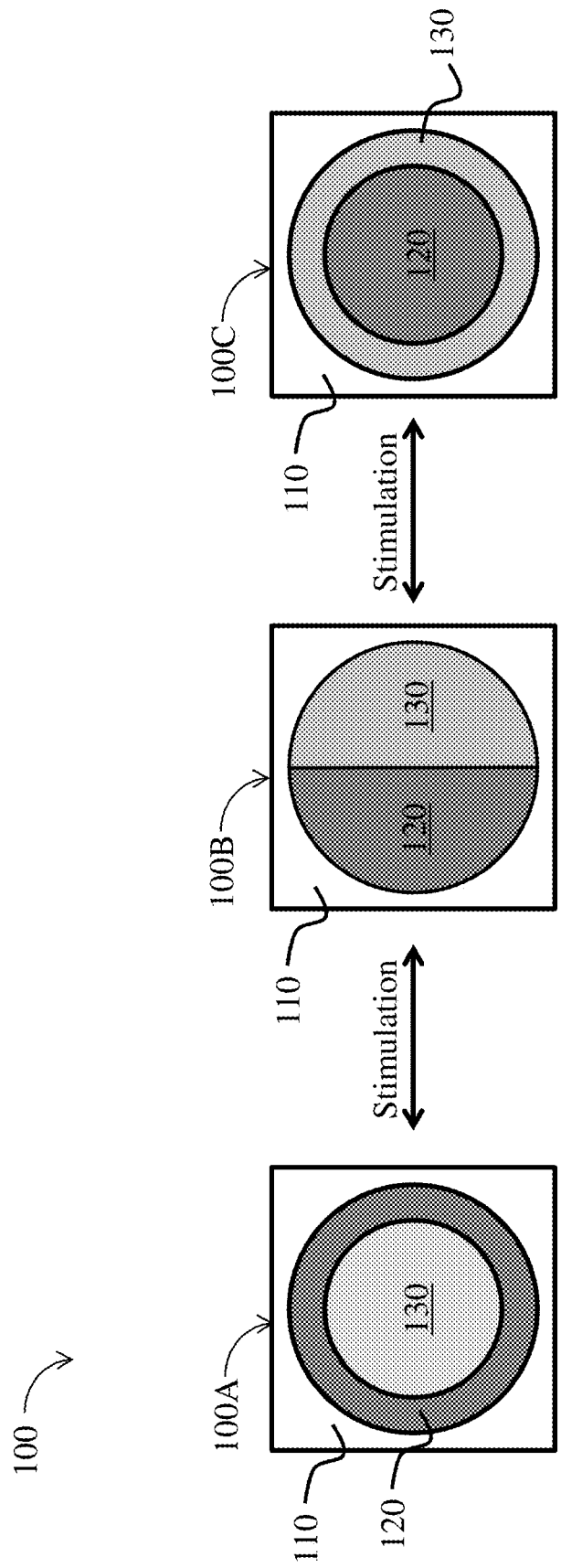
Figure 3F:
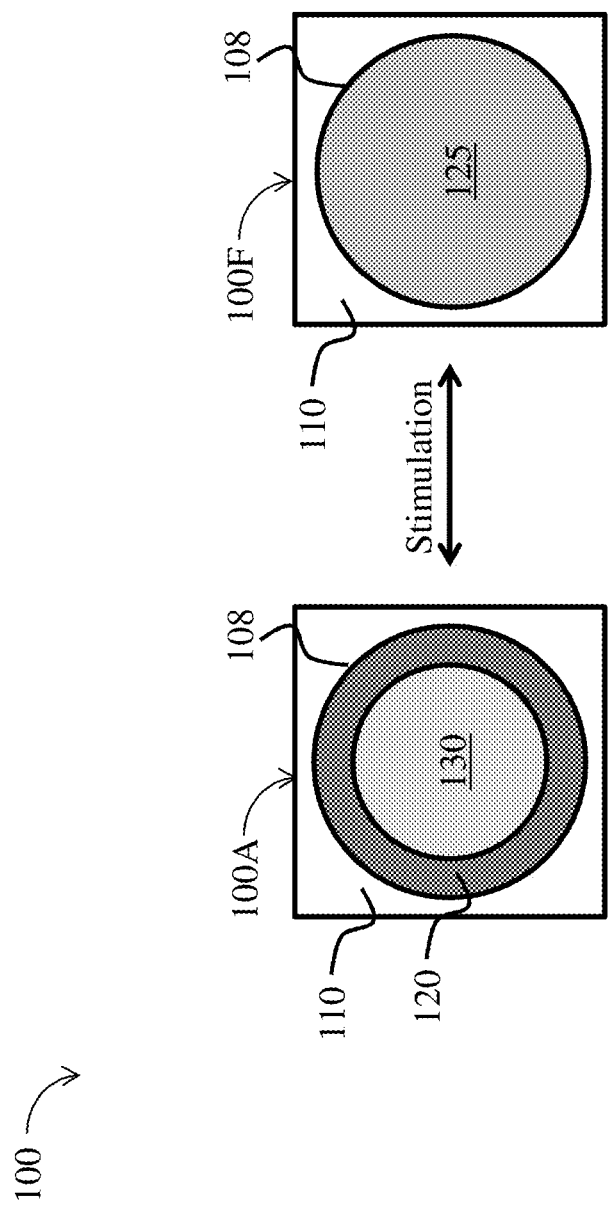

For example, as shown in FIG. 3E, second configuration 100B may comprise a Janus droplet. That is to say, in certain embodiments, the two or more components do not encapsulate each other but interface with the outer phase to form Janus droplets. Janus droplets are generally known in the art and comprise droplets wherein the droplet is divided into two distinct parts comprising two different components. For example, in some embodiments, the emulsion comprises an outer phase and a plurality of droplets comprising a first component and a second component, wherein the plurality of droplets are Janus droplets.

In some embodiments, colloid 100 may, upon stimulation, change configuration from first configuration 100A, to an intermediate configuration 100B. In some cases, colloid 100 may reversibly return (upon a second stimulation) to first configuration 100A, or obtain third configuration 100C. In certain embodiments, the change in configuration between configuration 100A and configuration 100B, or between configuration 100C and configuration 100B, is reversible. That is to say, in some embodiments, colloid 100 may change arrangement from the second configuration and/or the third configuration to the first configuration in the presence of a second stimulus, different than a first stimulus.

The first stimulus and the second stimulus may be the same type of stimulus (e.g., light, heat, force, an analyte, an acid) but differ in a property of the stimulus (e.g., different intensities of light, different magnitudes of temperature change, different magnitudes of force, different analytes, different analyte concentrations). In an exemplary embodiments, the first stimulus may be an analyte present at a first concentration, and the second stimulus comprises the analyte present in a second concentration, less than the first concentration (e.g., the degradation of an analyte below a particular concentration results stimulates the colloid).

In some cases, the first stimulus and the second stimulus may be different (e.g., a different type of stimulus, a different property of the stimulus).

An exemplary screening test for determining suitable stimuli includes preparing a colloid having a plurality of droplets comprising a first component and a second component at least partially encapsulated by the first component. The second component further comprises a dye (miscible in the outer phase but not present in the outer phase), dispersed within the second component, the dye being immiscible and not dispersed within the first component. Upon adding or exposing the colloid to the stimulus, as described herein, the first component and second component rearrange such that the second component at least partially encapsulates the first component and the dye is observed in the outer phase.

The colloid may be stimulated for any suitable amount of time. For example, in some cases, the stimulus is added to the colloid and not removed. In certain embodiments, the stimulus is applied for a specific amount of time. In some such embodiments, the stimulus may be applied for between about 1 second and about 10 seconds, between about 5 seconds and about 60 seconds, between about 30 seconds and about 2 minutes, between about 1 minute and about 5 minutes, between about 2 minutes and about 10 minutes, between about 5 minutes and about 15 minutes, between about 10 minutes and about 30 minutes, between about 15 minutes and about 60 minutes, between about 30 minutes and about 2 hours, between about 1 hour and about 6 hours, or between about 2 hours and about 24 hours. In some cases, the colloid may be stimulated for greater than 24 hours.

In certain embodiments, the second stimulus is the removal of the first stimulus. That is to say, in some embodiments, the two or more components in the plurality of droplets have a first configuration and change arrangement in the presence of a first stimulus to a second configuration. In some such embodiments, the two or more components may return to the first configuration upon removal of the first stimulus. Stimuli are described in more detail, below. The term component, as used herein, generally refers to a portion of a droplet comprising a group of substantially similar molecules, a group of substantially similar compounds, and/or a phase (e.g., a non-hydrocarbon and/or aqueous phase, a hydrocarbon and/or aqueous phase) comprising such molecules and/or compounds. Those skilled in the art would understand that the term component is not intended to refer to a single molecule or atom. In some embodiments, the component is a liquid phase (e.g., a gas phase, a hydrocarbon and/or aqueous phase, non-hydrocarbon and/or aqueous phase) comprising a group of substantially similar compounds and/or molecules. For example, in some cases, each component may occupy at least about 1 vol %, at least about 2 vol %, at least about 5 vol %, at least about 10 vol %, at least about 20 vol %, at least about 50 vol %, at least about 70 vol %, at least about 90 vol %, at least about 95 vol %, or at least about 99 vol % of the total volume of the two or more components present within each droplet.

In some embodiments, the plurality of droplets comprise two or more components (e.g., three or more components, four or more components, five or more components) such that at least two of the two or more components change configuration in the presence of a stimulus. In some cases, the two or more components may be substantially miscible over a range of temperatures (e.g., below a critical temperature of the two or more components, above a critical temperature of the two or more components). In some cases, the two or more components may also be substantially immiscible over a different range of temperatures (e.g., above the critical temperature of the two or more components, below the critical temperature of the two or more components) than the range of temperatures over which they are miscible.

In some embodiments, the two or more components may be selected such that the interfacial tension between the two or more components allows for slight changes in interfacial tension (e.g., in response to a stimulus that changes the conformation and/or a property of the one or more components) to change the configuration of the two or more components within at least a portion of the plurality of droplets. The morphology of the plurality of droplets is generally controlled by interfacial tension between two or more components within the droplets. For example, a complex emulsion of any immiscible liquids F and H (at a given volume ratio) in a third immiscible liquid W has interfacial tensions of the H-W interface, $\gamma_H$, the F-W interface, $\gamma_F$, and the F-H interface, $\gamma_{FH}$. In some cases, $\gamma_F$ and $\gamma_H$ may be greater than $\gamma_{FH}$ such that combinations of liquids H and F have low interfacial tension just below a critical temperature of the two liquids. Generally, such multi-phase droplets may have equilibrium spherical shapes and may exhibit, for example, thermodynamically-permissible internal configurations including (1) liquid H completely engulfs liquid F (FIG. 3G), (2) liquids H and F form a Janus droplet (FIG. 3I), and (3) liquid F completely engulfs liquid H (FIG. 3H). These droplet configurations may be characterized, in some cases, by two contact angles, $\theta_H$ between the H-W and F-H interfaces, and $\theta_F$ between the F-H and F-W interfaces. The three interfacial tensions acting along the interfaces must be in equilibrium for the droplet configuration to be stable as can be expressed by the following equations:

$$\cos\theta_H = \frac{\gamma_F^2 - \gamma_H^2 - \gamma_{FH}^2}{2\gamma_{FH}\gamma_H}$$

$$\cos\theta_F = \frac{\gamma_H^2 - \gamma_F^2 - \gamma_{FH}^2}{2\gamma_{FH}\gamma_F}$$

In some cases, $\theta_H$ approaches 0 and $\theta_F$ approaches 0, yielding the following two relationships:

$$\theta_H = 0 \Rightarrow \gamma_F = \gamma_H + \gamma_{FH}$$

$$\theta_F = 0 \Rightarrow \gamma_H = \gamma_F + \gamma_{FH}$$

These equations generally indicate that when $\gamma_F - \gamma_H \geq \gamma_{FH}$, the droplets can rearrange to configuration (1) in FIG. 2A.

Conversely, when $\gamma_H - \gamma_F \geq \gamma_{FH}$, the droplets can rearrange to configuration (3) in FIG. 2C. However, when the difference between $\gamma_H$ and $\gamma_F$ is on the order of $\gamma_{FH}$, the droplets can rearrange to a Janus droplet geometry associated with configuration (2) in FIG. 3H. As such, slight changes in the balance of TH and $\gamma_F$ may induce changes in the droplet's morphology. In some embodiments, the two or more components may be selected such that changes in the balance of $\gamma_H$ and $\gamma_F$ result in the reversible change of configuration of the two or more components within a portion of the plurality of droplets.

Those skilled in the art would be capable of selecting suitable components such that the components have a first configuration (i.e. arrangement) in the absence of a stimulus and a second configuration (i.e. arrangement) in the presence of the stimulus. In some embodiments, the components have a first configuration (i.e. arrangement) in the presence of a first stimulus and a second configuration (i.e. arrangement) in the presence of a second stimulus.

The term stimulating as used herein generally refers to the addition, removal, or change of a condition, a compound, or the environment (e.g., temperature, pressure, pH) such that the interfacial tension between two or more components is changed. Those skilled in the art will be capable of selecting suitable stimulus for use with the colloid described herein based upon the teachings of the specification and will understand stimulation does not comprise substantially removing a component and/or replacing the entirety of a component with a new component. However, in some embodiments, stimulating the colloid may result in a component, additional compound, and/or surfactant present in the colloid changing molecular conformation such that the component, additional compound, and/or amphiphilic compound is chemically distinguishable after stimulation (e.g., an acid cleavable component, additional compound, and/or amphiphilic compound that cleaves in the presence of an acid, a photosensitive component, additional compound, and/or amphiphilic compound that changes conformation or molecular structure after exposure to light) as compared to before stimulation. In certain embodiments, stimulating the colloid may result in a change in interfacial tension between two or more components such that the two or more component rearrange and/or mix.

In some embodiments, stimulating the colloid changes the arrangement of the colloid, as described herein. For example, in certain embodiments, stimulating the colloid changes the molecular conformation of at least one of the two or more components. In certain embodiments, stimulating the colloid releases at least one of the two or more components, additional compounds, and/or amphiphilic compounds, from a portion of the plurality of droplets. In some embodiments, stimulating the colloid changes an average birefringence of the colloid (e.g., increases the birefringence, decreases the birefringence). In certain embodiments, stimulating the colloid changes the color of the colloid and/or changes an average optical transmission of the colloid. In some cases, stimulating the colloid may change an average luminesce of the colloid. In certain embodiments, stimulating the colloid may change an average density of the colloid.

Those skilled in the art would understand that changing a property of a colloid refers to a property of the colloid immediately before that differs in a substantially measurable way from the property of the colloid at some relatively short time (e.g., seconds, minutes, hours) after stimulation. Those skilled in the art would also be capable of selecting methods for determining the change in the property of the colloid (e.g., measuring the average birefringence, measuring the optical transmission, measuring the density, etc.) based upon the specification and examples below.

In some embodiments, stimulating the colloid comprises exposing the colloid to an external stimulus (e.g., such that the configuration of two or more components is changed). In some such embodiments, the external stimulus comprises electromagnetic radiation, ionizing radiation, a magnetic field, an electric field, a mechanical force (e.g., pressure, direct contact), or combinations thereof. Those skilled in the art would be capable of selecting suitable components and methods of applying such external stimuli based upon the teachings of the specification and examples below. For example, in some such embodiments, at least one of the two or more components may comprise a magnetic particle such that, in the presence of a magnetic field, the at least one of the two or more components transposes or changes configuration with at least one additional component of the two or more components.

Figure 7B:
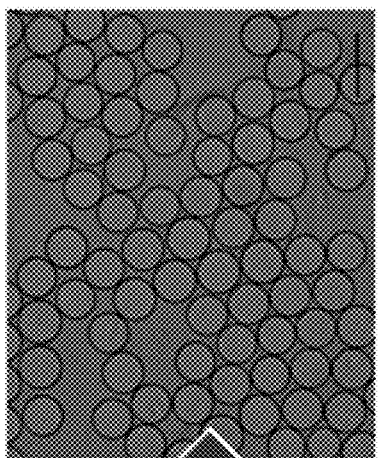
Figure 7B:
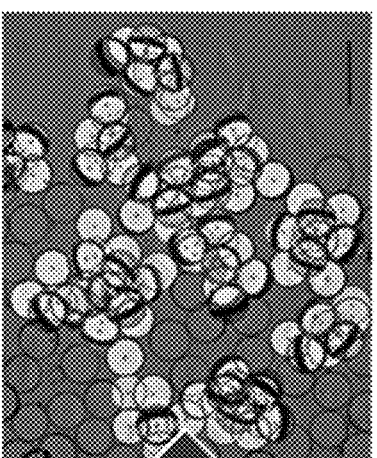
Figure 7B:
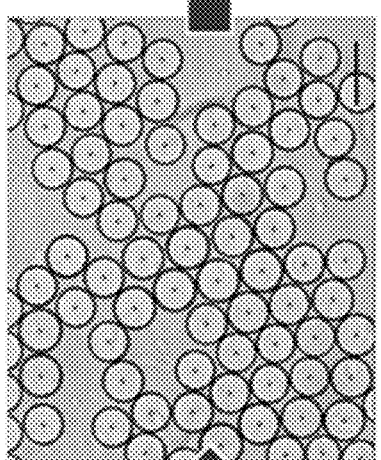

In certain embodiments, the external stimulus comprises photochemical stimulation (e.g., exposing the colloid to light). The light may comprise any suitable wavelength, including but not limited to radio waves (e.g., a wavelength between about 1 cm and about 100 m), infrared light (e.g., a wavelength between about 700 nm and about 1 cm), visible light (e.g., a wavelength between about 400 nm and about 700 nm), ultraviolet (UV) light (e.g., a wavelength between about 10 nm and about 400 nm), and x-rays (e.g., a wavelength between about 0.01 nm and about 10 nm). For example, in some embodiments, at least one of the two or more components comprises a light-sensitive surfactant (e.g., azobenzene) such that the light-sensitive surfactant reversibly changes molecular confirmation in the presence of UV light and/or visible blue light, causing the at least one component to transpose or change configuration with at least one additional component (FIG. 7B).

In some embodiments, stimulating the colloid comprises changing the temperature of the colloid (e.g., such that the configuration of two or more components is changed). In certain embodiments, changing the temperature of the colloid comprises heating the colloid. In some embodiments, changing the temperature of the colloid comprises cooling the colloid. In some embodiments, the colloid is at a first temperature, below a critical upper consolute temperature of two or more components, and the temperature is increased to a second temperature above the critical upper consolute temperature of the two or more components such that two or more of the two or more components change configuration. Those skilled in the art would be capable of selecting suitable methods of heating or cooling the colloid based upon the teaching of the specification and examples below.

In certain embodiments, stimulating the colloid comprises applying a force and/or pressure to the colloid such that the configuration of two or more components is changed.

In some embodiments, stimulating the colloid comprises adjusting the ionic strength and/or adjusting the pH of the colloid. For example, in some embodiments, adjusting the pH of the colloid comprises adding an acid (e.g., HCl) or a base (e.g., NaOH). For example, in some such embodiments, at least one of the two or more components comprises a pH-sensitive surfactant (e.g., N-dodecylpropane-1,3-diamine) and/or an acid-cleavable surfactant (e.g., sodium 2,2-bis(hexyloxy)propyl sulfate) such that the pH-sensitive surfactant and/or the acid-cleavable surfactant changes charge and/or cleaves in the presence of an acid or a base, causing the at least one component to transpose or change configuration with at least one additional component.

In certain embodiments, stimulating the colloid comprises adding an analyte to the colloid. The analyte may comprise any suitable material (e.g., a vapor analyte, a liquid analyte, a solid analyte) such that the incorporation of the analyte into a portion of the plurality of droplets or the outer phase causes the two or more components to change configuration. Those skilled in the art would be capable of selecting analytes and components suitable for colloid based upon the teaching of the specification and the examples below. Non-limiting examples of suitable analytes includes a biological compound, a drug, a macromolecule, a salt, an electrolyte, an enzyme, a nucleic acid, a carbohydrate, a peptide, a protein, a lipid, a phosphate, a sulfonate, a virus, a pathogen, an oxidant, a reductant, a toxin, a chemical warfare agent, an explosive, carbon dioxide, a surfactant, or combinations thereof. Components can be selected such that two or more components have a first interfacial tension in the absence of an analyte, and a second interfacial tension in the presence of the analyte such that the configuration of the two or more components is different in the presence of the analyte than in the absence of the analyte.

In an exemplary embodiment, an enzyme may be added to the colloid comprising a plurality of droplets such that the enzyme interacts with one or more of the components, additional compounds, and/or amphiphilic compounds present in the plurality of droplets. In some such embodiments, the enzyme may interact with the component, additional compound, and/or amphiphilic compound (e.g., such as a surfactant which cleaved in the presence of the enzyme) such that the two or more components change configuration, as described herein.

In another exemplary embodiment, one or more components may comprise an additional compound such as a surfactant that is capable of interacting with a biological analyte. Non-limiting examples of biological analytes include glucose, cholesterol, triglycerides, and bilirubin. In some such embodiments, the colloid may reversibly change arrangement of two or more components in the presence of a biological analyte such that the change in arrangement can be detected (e.g., by optical transmission). In certain embodiments, the colloid changes arrangement at a particular critical concentration of the biological analyte.

In some embodiments, stimulating the colloid causes a chemical transformation of one or more components present in the colloid such that two or more components change configuration. Non-limiting examples of chemical transformations which may result in two or more components changing configuration include enzymatic degradation, enzymatic synthesis, ionization, cleavage, coupling, hybridization, aggregation, hydrolysis, isomerization, reduction, oxidation, and host-guest interactions of one or more components (or component materials such as a surfactant). Other chemical transformations are also possible. In some embodiments, a portion of the plurality of droplets can be solidified (e.g., polymerized) such that a first configuration, a second configuration different than the first configuration, and/or a Janus droplet configuration solid droplets can be fabricated. Those skilled in the art will be capable of selecting appropriate materials for solidifying droplets and may include, in some embodiments, adding a crosslinker (e.g., a fluorinated acrylate) to the colloid such that the crosslinker crosslinks at least one of the two or more components, wherein the at least one of the two or more components comprises a crosslinkable polymer. In certain embodiments, solidifying droplets comprises adding a gelling agent (e.g., calcium-crosslinked alginate, gelatin, agar, or the like). In some embodiments, solidifying droplets comprises drying the droplets. In certain embodiments, solidifying droplets comprises changing the temperature such that one or more components solidify (e.g., a component comprising a liquid crystal or liquid crystal polymer that solidifies below the new temperature, a component comprising a liquid with a relatively high freezing point such that changing the temperature solidifies the liquid). Other methods of solidifying droplets are also possible and are known in the art.

Colloids described herein may be formed using any suitable method. For example, in some embodiments, an outer phase material, a first component, and a second component are mixed and emulsified, forming an outer phase and a plurality of droplets in the outer phase having a first component and a second component at least partially encapsulated by the first component. Suitable methods for emulsifying the fluid are known in the art and may comprise sonication, high shear mixing, shaking, passing the fluid through a membrane, or injecting the two or more components into the outer phase through a small diameter channel.

In certain embodiments, the outer phase material, the first component, and the second component may be mixed at a temperature at which the first component material and the second component material are miscible. In some such embodiments, the temperature of the mixture may be changed (e.g., increased, decreased) to a temperature such that the first component and the second component are immiscible and form a plurality of droplets in the outer phase having a first component and a second component at least partially encapsulated by the first component. While much of the description herein applies to two components, those skilled in the art would understand that such methods may be useful for the formation of colloids comprising a plurality of droplets having three or more, four or more, or five or more components.

The colloids described herein may be useful in a number of applications. In an exemplary embodiment, the colloids described herein may be used for sensing of an analyte. For example, in some such embodiments, two or more phases in the colloid may change arrangement in the presence of an analyte such that the change in arrangement can be detected (e.g., by a change in optical transmission, birefringence, etc. of the colloid). In another exemplary embodiment, the colloids described herein may be used as tunable lenses. In certain embodiments, measurements of the optical properties (e.g., transmission, absorption, reflection, focal distance, and scattering) of either individual droplets or of the bulk colloid can be indicative of specific droplet arrangements. For example, when a change in droplet arrangement is correlated with an analyte of interest (i.e., enzyme, pollutant, virus, etc.), then, the colloids can be used as sensors in which an optical measurement serves as a readout mechanism of the presence of the analyte. In certain embodiments, for systems in which there is a change in an analyte of interest over time (e.g., progress of a chemical reaction, such as degradation of a chemical by an enzyme over time), tracking of the changes in optical properties of the colloid over time can be used to, for example, analyze reaction rates or analyte concentrations. In some such embodiments, the arrangement of the components of the colloid changes in the presence of a stimulus such that the colloid obtains a transparent state over a particular range of time.

In yet another exemplary embodiment, the colloids described herein may be used for release of a macromolecule such as an active pharmaceutical ingredient or biomolecule (e.g., insulin). For example, in some such embodiments, the colloid comprising a plurality of droplets having two or more components may comprises an active pharmaceutical ingredient or biomolecule miscible and present within one of the components at least partially encapsulated by another component. In the presence of an analyte (e.g., glucose), two or more components may change arrangement such that the component containing the active pharmaceutical ingredient or biomolecule at least partially encapsulates the remaining components and the active pharmaceutical ingredient or biomolecule is released into the outer phase.

As used herein, the term "active pharmaceutical ingredient" (also referred to as a "drug") refers to an agent that is administered to a subject to treat a disease, disorder, or other clinically recognized condition, or for prophylactic purposes, and has a clinically significant effect on the body of the subject to treat and/or prevent the disease, disorder, or condition. Active pharmaceutical ingredients include, without limitation, agents listed in the United States Pharmacopeia (USP), Goodman and Gilman's The Pharmacological Basis of Therapeutics, 10th edition, McGraw Hill, 2001; Katzung, B. (editor), Basic and Clinical Pharmacology, McGraw-Hill/Appleton & Lange, 8th edition (Sep. 21, 2000); Physician's Desk Reference (Thomson Publishing); and/or The Merck Manual of Diagnosis and Therapy, 17th edition (1999), or the 18th edition (2006) following its publication, Mark H. Beers and Robert Berkow (editors), Merck Publishing Group, or, in the case of animals, The Merck Veterinary Manual, 9th edition, Kahn, C. A. (ed.), Merck Publishing Group, 2005. Preferably, though not necessarily, the active pharmaceutical ingredient is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention. In certain embodiments, the active pharmaceutical ingredient is a small molecule. Exemplary active pharmaceutical ingredients include, but are not limited to, anti-cancer agents, antibiotics, anti-viral agents, anesthetics, anti-coagulants, inhibitors of an enzyme, steroidal agents, steroidal or non-steroidal anti-inflammatory agents, antihistamine, immunosuppressant agents, antigens, vaccines, antibodies, decongestant, sedatives, opioids, pain-relieving agents, analgesics, anti-pyretics, hormones, prostaglandins, etc.

As used herein, a "fluid" is given its ordinary meaning, i.e., a liquid or a gas. A fluid cannot maintain a defined shape and will flow during an observable time frame to fill the container in which it is put. Thus, the fluid may have any suitable viscosity that permits flow. If two or more fluids are present, each fluid may be independently selected among essentially any fluids (liquids, gases, and the like) by those of ordinary skill in the art.

In some embodiments, a portion of the plurality of droplets can be solidified (e.g., polymerized) such that a first configuration, a second configuration different than the first configuration, and/or a Janus droplet configuration solid droplets can be fabricated. Those skilled in the art will be capable of selecting appropriate materials for solidifying droplets and may include, in some embodiments, adding a crosslinker (e.g., a fluorinated acrylate) to the colloid such that the crosslinker crosslinks at least one of the two or more component, wherein the at least one of the two or more component comprises a crosslinkable polymer. In some embodiments, the droplets can be gelled or solidified. In certain embodiments, solidifying droplets comprises adding a gelling agent (e.g., calcium-crosslinked alginate, gelatin, agar, or the like). In some embodiments, solidifying droplets comprises drying the droplets. In certain embodiments, solidifying droplets comprises changing the temperature such that one or more components solidify (e.g., a component comprising a liquid crystal or liquid crystal polymer that solidifies below the new temperature, a component comprising a liquid with a relatively high freezing point such that changing the temperature solidifies the liquid). Other methods of solidifying droplets are also possible and are known in the art.

The plurality of Janus particles may have any suitable average cross-sectional dimension. In some embodiments, the average cross-sectional dimension of the plurality of Janus particles is greater than or equal to 400 nanometers, greater than or equal to 500 nanometers, greater than or equal to 600 nanometers, greater than or equal to 800 nanometers, greater than or equal to 1 micron, greater than or equal to 2 microns, greater than or equal to 5 microns, greater than or equal to 10 microns, greater than or equal to 20 microns, greater than or equal to 30 microns, greater than or equal to 50 microns, greater than or equal to 60 microns, greater than or equal to 75 microns, greater than or equal to 100 microns, greater than or equal to 150 microns, greater than or equal to 200 microns, greater than or equal to 300 microns, or greater than or equal to 400 microns. In certain embodiments, the average cross-sectional dimension of the plurality of Janus particles may be less than or equal to 500 microns, less than or equal to 400 microns, less than or equal to 300 microns, less than or equal to 200 microns, less than or equal to 150 microns, less than or equal to 100 microns, less than or equal to 75 microns, less than or equal to 60 microns, less than or equal to 50 microns, less than or equal to 20 microns, less than or equal to 10 microns, less than or equal to 5 microns, less than or equal to 2 microns, less than or equal to 1 micron, less than or equal to 800 nanometers, less than or equal to 600 nanometers, or less than or equal to 500 nanometers. Combinations of the above-referenced ranges are possible (e.g., greater than or equal to 400 nanometers and less than or equal to 500 microns, greater than or equal to 400 nanometers and less than or equal to 100 microns, greater than or equal to 30 microns and less than or equal to 200 microns). Other ranges are also possible.

The present invention also provides, according to another aspect, the ability to select two species that can work together to enhance the ability of one or more Janus droplets (or Janus particles) to increase the effect of a change in an electromagnetic radiation (light) signal accompanying a change accompanying the droplet or droplets (e.g., binding of an analyte that can cause particle re-orientation and/or morphological (shape) change, or both, via agglutination or the like). One of the species can be selected to interact with electromagnetic radiation in a way that produces a detectable electromagnetic radiation signal (reflection of electromagnetic radiation, emission such as fluoroescense or phosphorescense, absorption of electromagnetic radiation, or the like), and a second species can be selected to attenuate, i.e., enhance or inhibit that signal. The different species can be positioned in different Janus droplets that interact with each other, or into different sections of the same Janus droplet.

For example, with reference to FIG. 1A, in one set of embodiments a first species is added to portion 130 of a Janus droplet and a second species can be added to portion 140. Upon exposure to an analyte, or other modification as described herein or as would be understood by those of ordinary skill in the art, the Janus droplet can change in orientation and/or morphology, resulting in a change in interaction with electromagnetic radiation. As described elsewhere herein, where the Janus droplet changes in orientation as illustrated in FIG. 1A, a change in emission of light can indicate a change in orientation, which can be caused by interaction of analyte with the Janus droplet. In this aspect of the invention, as noted, the two species, one introduced into section 130 and another into section 140, can be complementary in maximizing the distinction in electromagnetic radiation interaction. For example, one species can be a dye that emits light. Another species, introduced into another section of the particle, can be selected to absorb light thus blocking electromagnetic radiation emitted from the first dye, at least to some extent, and/or at least partially block incident light to which the dye is exposed, thus limiting its emission, or both.

With reference to FIG. 1A, if incident light or other electromagnetic radiation approaches the Janus droplet from above in the orientation of the figure, and section 130 of the Janus droplet includes a species that at least partially blocks (reflects, absorbs, etc.) that incident radiation, then an emissive dye in section 140 is inhibited or prevented from receiving that light, and emitting appreciably or at all. Where a dye in section 140 can receive incident radiation but a species in section 130 at least partially inhibits (blocks, absorbs, reflects, etc.) radiation emitted by the species in section 140, alone or in combination with the earlier-described species that inhibits passage of incident radiation, emission of radiation from the droplet is minimized and the droplet is in a stronger "off" position, at least with respect to a detector positioned above the droplet in the orientation of this Figure. Where exposure to an analyte causes re-orientation as shown in the right side of FIG. 1A, and emission from a species in section 140 can be detected (e.g., where a detector is positioned above the droplet in the orientation of the figure), then the blocking or reflective species in section 130 is bypassed and a signal can be observed.

The inhibiting species in section 130 can be, as mentioned, any species that inhibits incident electromagnetic radiation and/or emitted electromagnetic radiation. As described elsewhere herein, detection can take place from a detector (or a human eye) positioned to observe reflected, emitted, or transmitted electromagnetic radiation, or a combination. For example, in FIG. 1A, incident radiation can be applied from above, in the orientation of the figure, and a detector placed below, where absorption or reflection of incident electromagnetic radiation versus passage of that radiation is determined by the detector, and re-orientation of the droplet, as illustrated, changes a detected signal. In the original position (left side of FIG. 1A, there will be a low or zero signal. Upon re-orientation (right side of FIG. 1A), radiation will pass and a signal will be observed, or observed to increase in intensity, particle count, or a combination. In another arrangement the complementary nature of the two species positioned in sections 130 and 140 can include, for example, an emissive or reflective species in section 140 and a complementary reflective species in section 130 such that incident light from above is blocked from detection below when the droplet is oriented as in the left side of FIG. 1A but, when re-oriented as in the right side of FIG. 1A the species in section 140 becomes emissive and the species in section 130 reflects that emission to an enhance its detection from a detector below, or a detector in another orientation positioned to receive that reflected radiation (e.g., approximately the 7:30 clock position with respect to the particle of FIG. 1A.

As can be understood by those of ordinary skill in the art, a variety of combinations of complementary species or complementary dyes can be selected to inhibit or enhance signal production by Janus droplets based on re-orientation or change in morphology. Where a first species is used, and the detection of emission, absorption, reflection, or the like is desirably determined, a second species that is selected to block that electromagnetic radiation can be selected with a variety of blocking effectiveness levels. For example, an emissive species and blocking species can be selected where the peak wavelength of emission and the peak wavelength of blockage (reflection, absorption, or a combination) of the species, respectively, differs by no more than 10 nanometers, 20, 50, 100, or 200 nanometers in wavelength. In one set of embodiments, where an equal molar amount of an emissive species in section 140 and a blocking species in section 130 in the left side of FIG. 1A is selected, and incident electromagnetic radiation is applied from above, and a detector positioned below, at the most sensitive wavelength of detection (maximum wavelength of emission or other passage of radiation by the species in section 140), the ability of species 140 to emit or pass radiation is reduced by at least 10%, or in other embodiments 25%, 50%, 75%, 80%, or 90% relative to an essentially identical Janus droplet absent the blocking species in section 130.

In some embodiments, the plurality of Janus droplets may have a first orientation (and/or a first configuration) and, upon change in orientation and/or configuration, obtain a second orientation (and/or a second configuration) different than the first orientation (and/or first configuration) such that the change in orientation and/or configuration inhibits or enhances emission or transmission of electromagnetic radiation. In some embodiments, the electromagnetic radiation emitted or transmitted in the second orientation (and/or second configuration) is less than or equal to 99%, less than or equal to 95%, less than or equal to 90%, less than or equal to 80%, less than or equal to 75%, less than or equal to 70%, less than or equal to 60%, less than or equal to 50%, less than or equal to 40%, less than or equal to 30%, less than or equal to 25%, less than or equal to 20%, less than or equal to 10%, less than or equal to 5%, less than or equal to 2%, or less than or equal to 1% relative to the electromagnetic radiation emitted or transmitted in the first orientation (and/or first configuration). In some embodiments, the electromagnetic radiation emitted or transmitted in the second orientation (and/or second configuration) is greater than or equal to 0.5%, greater than or equal to 1%, greater than or equal to 2%, greater than or equal to 5%, greater than or equal to 10%, greater than or equal to 20%, greater than or equal to 25%, greater than or equal to 30%, greater than or equal to 40%, greater than or equal to 50%, greater than or equal to 60%, greater than or equal to 70%, greater than or equal to 75%, greater than or equal to 80%, greater than or equal to 90%, or greater than or equal to 95% relative to the electromagnetic radiation emitted or transmitted in the first orientation (and/or first configuration). Combinations of the above-referenced ranges are also possible (e.g., less than or equal to 99% and greater than or equal to 1%). Other ranges are also possible.

In another set of embodiments, the electromagnetic radiation emitted or transmitted in the first orientation (and/or first configuration) is less than or equal to 99%, less than or equal to 95%, less than or equal to 90%, less than or equal to 80%, less than or equal to 75%, less than or equal to 70%, less than or equal to 60%, less than or equal to 50%, less than or equal to 40%, less than or equal to 30%, less than or equal to 25%, less than or equal to 20%, less than or equal to 10%, less than or equal to 5%, less than or equal to 2%, or less than or equal to 1% relative to the electromagnetic radiation emitted or transmitted in the second orientation (and/or second configuration). In some embodiments, the electromagnetic radiation emitted or transmitted in the first orientation (and/or first configuration) is greater than or equal to 0.5%, greater than or equal to 1%, greater than or equal to 2%, greater than or equal to 5%, greater than or equal to 10%, greater than or equal to 20%, greater than or equal to 25%, greater than or equal to 30%, greater than or equal to 40%, greater than or equal to 50%, greater than or equal to 60%, greater than or equal to 70%, greater than or equal to 75%, greater than or equal to 80%, greater than or equal to 90%, or greater than or equal to 95% relative to the electromagnetic radiation emitted or transmitted in the second orientation (and/or second configuration). Combinations of the above-referenced ranges are also possible (e.g., less than or equal to 99% and greater than or equal to 1%). Other ranges are also possible.

In this manner, one can conduct a count of droplets affected by re-orientation or change in morphology, or measure total emitted or reflected or passed (unblocked) electromagnetic radiation, or a combination, as described herein and elsewhere in this specification, as a detection mechanism.

Referring again to FIG. 1A, and sections 130 and 140 of the exemplary Janus droplet, emissive and blocking species (for example, complementary dyes) can be selected to function in either phase, i.e., they can be tailored and controlled for ideal positioning and alignment. Where phases 130 and 140 are immiscible, for example, one being a primarily hydrocarbon phase and another a primarily fluorocarbon phase, either species can be selected to be primarily present in ether phase, selectively. In one set of embodiments, at least one of the species is more preferentially soluble in one phase versus the other, for example, being at least two times (2×), 4×, 8×, 10×, 20×, or 50× more soluble than in the other phase. In some embodiments, at least one of the species is more preferentially soluble in one phase versus the other, for example, less than or equal to 100 times (100×), 50×, 20×, 10×, 8×, or 4× more soluble than in the other phase. Combinations of the above-referenced ranges are also possible.

In another set of embodiments each species (emitter and blocker in that example) is preferentially soluble in one phase but not the other at any of the above preferential ratios.

As described elsewhere herein, Janus droplets can be initially oriented in a pre-reaction (pre-detection) orientation due to gravity, through inherent difference in density of phases and/or addition of particles adding mass and related density to one phase, a magnetic field (via magnetic particles added preferentially to one phase through control of solubility of magnetic particles in that phase, and corresponding orientation of a magnetic field relative to the particles), or the like. Upon exposure to an analyte, droplets can be re-oriented as illustrated for detection, from the initial orientation which can be controlled in manners described.

In another set of embodiments, which can be combined with embodiments described above or elsewhere herein, exposure of an analyte to Janus droplets does not necessarily cause re-orientation of the droplets (but can) but can cause a change in morphology (e.g., configuration, as described above and herein) in droplets that allows passage and/or emission of electromagnetic radiation from one phase of a droplet, potentially attenuated by another species in another phase of the droplet as described.

In some embodiments, the system further comprises polymers or particles configured to stabilize the plurality of Janus droplets and/or interfaces thereof. In one set of embodiments, a surfactant can be provided that stabilizes an interface between a first and second phase of Janus droplet and/or between the droplet and a continuous phase in which the droplet(s) is provided. The surfactant can respond to the presence of an analyte in a way that changes the structure of the droplet in a way that is detectable through interaction with electromagnetic radiation as described herein, on the basis of interaction of a species with electromagnetic radiation as attenuated (increase or inhibited) by a complementary species.

The invention provides as well a series of species that inhibit passage of electromagnetic radiation to attenuate signal, as described herein. At least one is provided that preferentially resides in a fluorocarbon phase of a Janus droplet and another that preferentially resides in an hydrocarbon phase, in preferential ratios described above.

Figure 13:
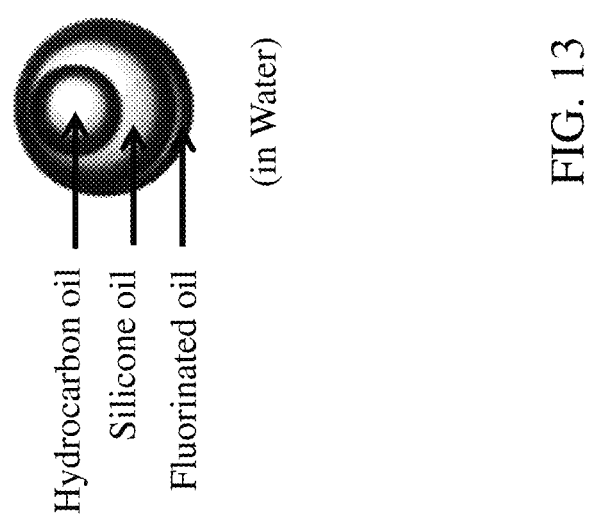
FIG. 13 shows a four-phase emulsion, formed according to one set of embodiments.

These and other embodiments of the invention allow significant sensitivity in measurement of analyte, by enhancing emission or passage of electromagnetic radiation in the absence of the attenuating species and/or blocking emission or blockage of electromagnetic radiation by the emissive species, thus increasing the distinction between an orientation and/or morphology of Janus droplets in the presence of analyte and/or in the absence of analyte.

EXAMPLES

The following examples illustrate embodiments of certain aspects of the invention. It should be understood that the methods and/or materials described herein may be modified and/or scaled, as known to those of ordinary skill in the art.

Example 1

The following example describes the general formation of an emulsion. For example, hydrocarbon and fluorocarbon liquids were heated until miscible and emulsified. The temperature required varied depending on the solutions. Solutions were emulsified either in bulk by shaking or by coaxial glass capillary microfluidics and cooled to induce phase separation. For hexane-perfluorohexane emulsions, the emulsions were chilled on ice prior to imaging and often imaged while immersed in a cool water bath to maintain a temperature below 20° C. For microfluidics, syringe pumps were used to inject the outer phase and inner phase using a glass capillary microfluidic device made from an outer square capillary and inner cylindrical capillary pulled to a 30 μm tip using a Micropipette Puller (Sutter Instrument Company). The microfluidic setup was heated above the Tc of the inner phase solution using a heat lamp. Emulsions were then cooled below Tc to induce phase separation. Emulsions were observed to be stable during the time periods used (e.g., on the order days).

Example 2

The following example describes the formation of an emulsion. According to the methods described in Example 1.

Fluorocarbons are generally lipophobic as well as hydrophobic and many fluorocarbon and hydrocarbon liquids are immiscible at room temperature but have a low upper consolute temperature ($T_c$) and mix with gentle heating. Hexane and perfluorohexane, for example, have a $T_c$ of 22.65° C. A 1:1 volume ratio of hexane and perfluorohexane was mixed and emulsified above $T_c$ in a hydrocarbon and/or aqueous solution of Zonyl FS-300 fluorosurfactant (FIG. 10, top left). Cooling below $T_c$ induced phase separation and yielded structured complex droplets (FIG. 2. Bottom right). Above $T_c$, hexane and perfluorohexane are miscible and emulsified in 0.1% Zonyl (FIG. 10, top left). Below $T_c$, hexane and perfluorohexane phase separate to create a hexane-in-perfluorohexane-in-water (H/F/W) double emulsion (FIG. 10, bottom right). This phase separation was reversible. These complex emulsions were readily produced in bulk by shaking warm hexane-perfluorohexane liquid in a surfactant solution (FIG. 11A). Although these droplets were polydisperse, the morphology and composition of the droplets was highly uniform. Chemical partitioning during phase separation gave directed compartmentalization of solutes (FIG. 11B), forming hexane/perfluorohexane/water double emulsion droplets in a microfluidic device. Therefore, temperature-induced phase separation of liquids provides a facile, scalable approach to fabrication of complex functional emulsions.

Example 3

The following example describes the formation of an emulsion comprising Janus droplets.

Liquid droplets and solid droplets with asymmetric properties were created by affecting different chemistries in the separate compartments of a fluorous-hydrocarbon Janus droplet. To create directionally-orientable and movable liquid Janus droplets, magnetic $Fe_3O_4$ nanoparticles stabilized with oleic acid were synthesized for preferential partitioning into the hydrocarbon phase. Magnetite nanoparticles were made as follows: 25 mL of concentrated NH3OH was added to an acidified solution of 1.6 g of $FeCl_3$ and 1 g of $FeCl_2 \cdot 4H_2O$ in 50 mL of water at 80° C. The magnetite nanoparticle precipitate was collected with a magnet, washed with water, and redispersed. 1 g of sodium oleate in 10 mL of water was added under stirring at room temperature. The oily black precipitate was extracted with hexanes. Solid was collected by evaporation of solvent and subsequently redispersed in dichlorobenzene. Janus droplets were obtained by heating the nanoparticle/dichlorobenzene solution and ethyl nonafluorobutyl ether above the Tc and shaking in 0.2% SDS and 0.2% Zonyl in a 2.5:1 ratio. The droplets were oriented using a neodymium magnet. Upon inclusion in a Janus emulsion of dichlorobenzene and ethyl nonafluorobutyl ether, the nanoparticle/dichlorobenzene hemispheres are rapidly oriented and move in the direction of a magnet (FIG. 12A).

To generate solid hemispherical droplets, an emulsion consisting of a liquid polymer precursor, 1,6-hexanediol diacrylate, as the hydrocarbon phase and methoxyperfluorobutane as the fluorous phase, was polymerized (FIG. 12B). 1-6,hexanediol diacrylate with 4% Darocur 1173 photoinitiator was heated with equal volume methoxyperfluorobutane above the Tc and emulsified. 1% SDS and 1% Zonyl in a 3:2 ratio yielded Janus droplets which were then polymerized under a UV lamp while kept cold on ice. By replacing methoxyperfluorobutane with a fluorinated acrylate oligomer and crosslinker, spherical solid Janus droplets with fluorinated and non-fluorinated sides were created (FIG. 12C).

Example 4

The same principles of droplet transformations observed in three-phase emulsions, and described in Example 1, were extended to a four-phase system thereby generating reconfigurable droplets of even higher order complexity. A system comprising of silicone oil (Si), hydrocarbon oil (H, mineral oil and octadecane), and fluorinated oil (F, ethyl nonafluorobutyl ether) was designed such that the liquids mixed with heating and separated into three phases at room temperature (FIG. 13). Light mineral oil with 20 wt % octadecane (used to reduce the Tc in a mixture with the other liquids), silicone oil, and ethyl nonafluorobutyl ether were used as the inner phases in a volume ratio of 6:7:13. The mineral oil and ethyl nonafluorobutyl ether both partitioned into the silicone oil such that upon phase separation, the silicone oil phase is enriched with some quantity of the two other phases. Hydrocarbon and/or aqueous mixtures of varying ratios of 1% Zonyl and 1% SDS were used as the outer phase, and emulsions were formed in the bulk by shaking.

Example 5

The following examples demonstrate the use of systems for the detection of analytes.

Surfactants specially designed with recognition elements to bind targeting analytes (species/molecules of interest) multivalently were synthesized. The binding interaction was able to transform a plurality of Janus droplets from an upright position to a horizontally tilted position against gravity. This transformation generated a distinct optical signal (scattering of a light beam) in the presence of analytes. The opposite response was also possible wherein a plurality of Janus droplets were pre-titled by binding to a surface or particle and is initially in a scattering position. In this case, the action of an analyte was to disrupt the linkage between the surface or particle and allow a relaxation to an upright position that allowed for reduced scattering. The optical signal could be recorded via a smartphone by for example using a QR code for binary on/off detection, using low magnification images that are processed computationally to quantify the amount of analytes in the emulsion mixture, and/or the monitoring the transmission of focused light beams through the samples. Such systems could be used in biosensor applications including hydrocarbon and/or aqueous liquid phase detection. The emulsions (comprising Janus droplets) with only low molecular weight surfactant molecules were relatively inexpensive to fabricate and stable over multiple weeks with no further precautions. In cases where greater emulsion stability may be required, polymeric surfactant molecules and structures could be employed. Additionally, the Janus droplets were highly selective and sensitive for detection of pathogens as, in some cases, small changes in the concentration and/or the identity of the surfactants lead to significant changes in the orientation of the Janus droplets. Janus droplets were fabricated using either bulk emulsification, which generated polydisperse droplets, or in a microfluidic device, which generated monodisperse droplets. For surfactants soluble in water, a solution containing the functionalized surfactants was used as the continuous phase. Hydrocarbon phase (such as hexane, ortho-dichlorobenzene, phthalate, etc.) and fluorocarbon phase (such as perfluorohexane, ethyl nonafluorobutyl ether, methoxy perfluorobutane) were mixed and heated over the upper critical temperature to generate the single droplet phase. When the droplet phase was dispersed into the continuous (outer) phase containing surfactants, single emulsions were generated; and upon cooling, the hydrocarbon and fluorocarbon phases separated to generate Janus droplets. The composition of each droplet was substantially similar because they were generated from the same single droplet phase. In addition, surfactants were able to be incorporated into the droplet phase. Surfactants that were not soluble in water were dissolved in the hydrocarbon phase or the fluorocarbon phase before mixing. The droplet phase containing surfactants could then be dispersed into the continuous water phase, which may contain additional surfactants and surfactant assemblies to generate the droplets. In both cases, Janus droplets were used as sensing particles with surfaces covered by with functionalized surfactants. The surfactants or surfactant assemblies could contain polymer surfactant/stabilizers or macromolecules of biological significance, including proteins, enzymes, nucleic acids, DNA, RNA.

Sensing of Pathogenic Bacteria

Our approach to detect pathogenic bacteria took advantage of the general affinity that different bacteria exhibit for specific patterns of carbohydrate. One of the targeting analytes, *Escherichia coli* (*E. coli*), is a bacterium that can be easily spread in contaminated food and water. While most strains of *E. coli* are harmless, certain strains that produce toxins could cause serious and fetal illness. To detect the *E. Coli* bacteria, surfactants were carefully designed that interact with the surfaces of the cell via the carbohydrate-lectin interaction. This weak interaction between lectin on the surfaces of *E. coli* and D-mannose typically creates a challenge to detect bacteria with high sensitivity when relying on a single interaction. Thus, a surfactant that functionalizes one phase of the Janus droplets to increase the concentration of the mannose moiety on the surface was designed. The increase in the concentration of the mannose moiety significantly enhanced binding affinity between the bacteria and the droplets, transforming a droplet into a selective sensing particle. The binding between Concanavalin A (ConA), a lectin known to bind D-mannose, was initially investigated using the Janus droplets as a model system. This technology could be relatively easily adapted for other analytes by, for example, changing the active surfactants. A novel surfactant bearing a D-mannose head group (ManC14) was synthesized (FIG. 4A). FIG. 4A shows the scheme for Mannose surfactant (ManC14) synthesis. FIG. 4B shows a schematic illustration of Janus droplets aligning with Concanavalin A (ConA). The denser perfluorohexane phase aligned at the bottom and the hexane on the top of the Janus droplets.

For this particular sensing platform, the Janus droplets were fabricated using the following method. The surfactants ManC14 and Zonyl® FS 300 (a commercially available fluorocarbon surfactant) were dissolved in a HEPES buffer solution (pH=7.5) as the continuous phase. A mixture of hexane and perfluorohexane (single droplet phase) was dispersed into the surfactant solution and cooled down to generate Janus droplets. The hexane phase on the Janus droplets was functionalized with mannose groups where the surfactant ManC14 aligned preferentially at the hexane/water interface. Without wishing to be bound by theory, due to gravity and the higher density of perfluorohexane in relative to that of hexane, Janus droplets aligned with perfluorohexane phase in the bottom (FIG. 4B). ConA was dissolved in HEPES buffer solution with final concentration of 0.5 mg mL$^{-1}$. An increasing amount of this solution (10 μL to 40 μL) was added to the Janus droplets; and after swirling the solution, the two-faced Janus droplets started aligning in a unique tilted configuration. The surfaces that were stabilized by ManC14 surfactant agglutinated together to form droplet complexes (FIG. 4B).

Without wishing to be bound by theory, the agglutination phenomenon occurred because ConA has four subunits, each with a binding site for mannose. This four-site binder acted similarly to an antibody that binds multiple particles and joins them together to make agglutinated droplet complexes.

When Janus droplets agglutinate, the solution changes from transparent to opaque. This large and easily observable change is particularly powerful because detection events will not generally require, for example, any external power input. The Janus droplet agglutination level could be characterized both qualitatively and quantitatively as described herein.

Tuning the Surface Chemistry

Surface recognition is a general phenomenon that can be applied to many different types of methods. The use of a ligand surfactant binding with a multivalent receptor, which can be a protein, cell, or pathogen, nanoparticle was described above. This scheme can be reversed where a receptor is immobilized at the surface of a droplet and then use a multivalent ligand scaffold (natural or synthetic) to bind the Janus droplets and hold them in a tilted (scattering) state relative to the aligned non-scattering state favored by gravity. The ligands can be designed to have a lower affinity than a target analyte and hence exposure to the analyte can result in a displacement that breaks the linkage (e.g., tether) between the polyvalent ligand and the droplet. Similarly, the tether between the droplet and the ligand can be cleaved. This could be affected by an enzyme that cleaves a peptide, such as an ester or a degraded RNA. It could also be affected by catalytic or heavy metal ions or select nucleophiles (sulfides). In some cases, the ligands could be bound to a surface. It is also possible that the ligands reside on another droplet.

Individual droplets that are tilted or alternatively not tilted (aligned by gravity) can be relatively easily quantified. This gives rise to the ability to, in some cases, detect single analytes. For example, it is possible that a single molecule of DNA can be detected if the droplet is anchored to a surface by a DNA duplex. Disruption of this duplex by a complementary target DNA analyte can be observed. One aligned droplet in a sea of other tilted droplets would be readily detected. This scheme has an advantage that, for example, there would be many potential binding sites for the DNA molecule and hence thus the target DNA would not be required to find a rare binding site. Similarly, a cluster of tilted droplets in a sea of aligned droplets can be detected and, in doing so, would be able to detect a single analyte.

Detection of Agglutinated Janus Droplets

Figure 5B:
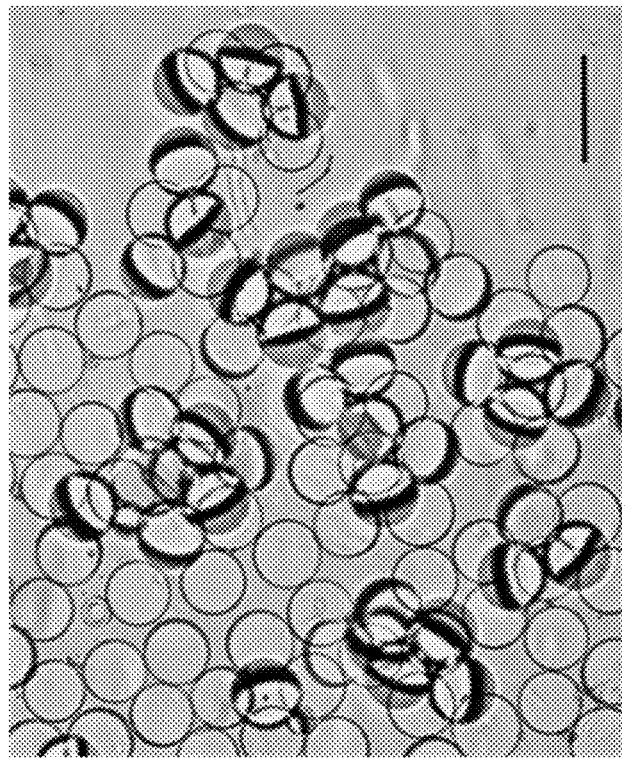
FIG. 5B shows a plurality of Janus droplets with altered orientation, according to one set of embodiments.
Figure 5A:
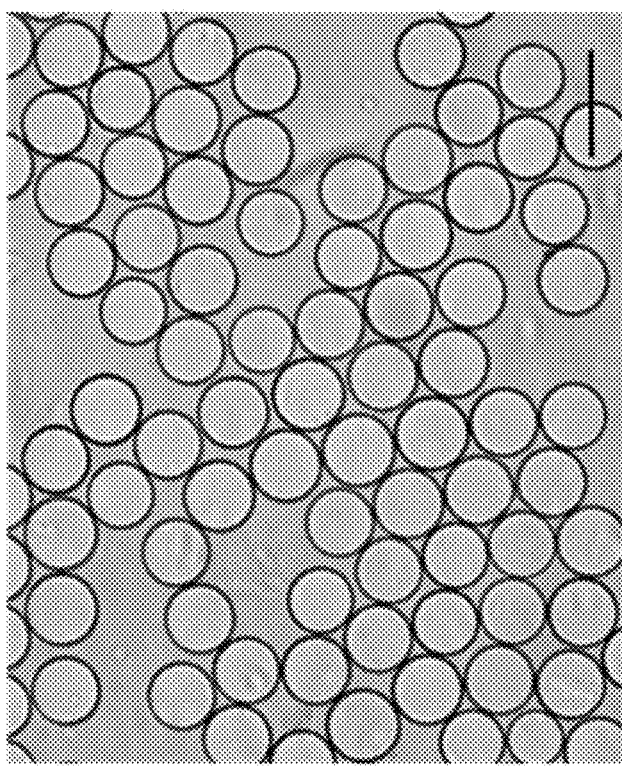
FIG. 5A shows a monodispersed plurality of Janus droplets, according to one set of embodiments.
Figure 6A:
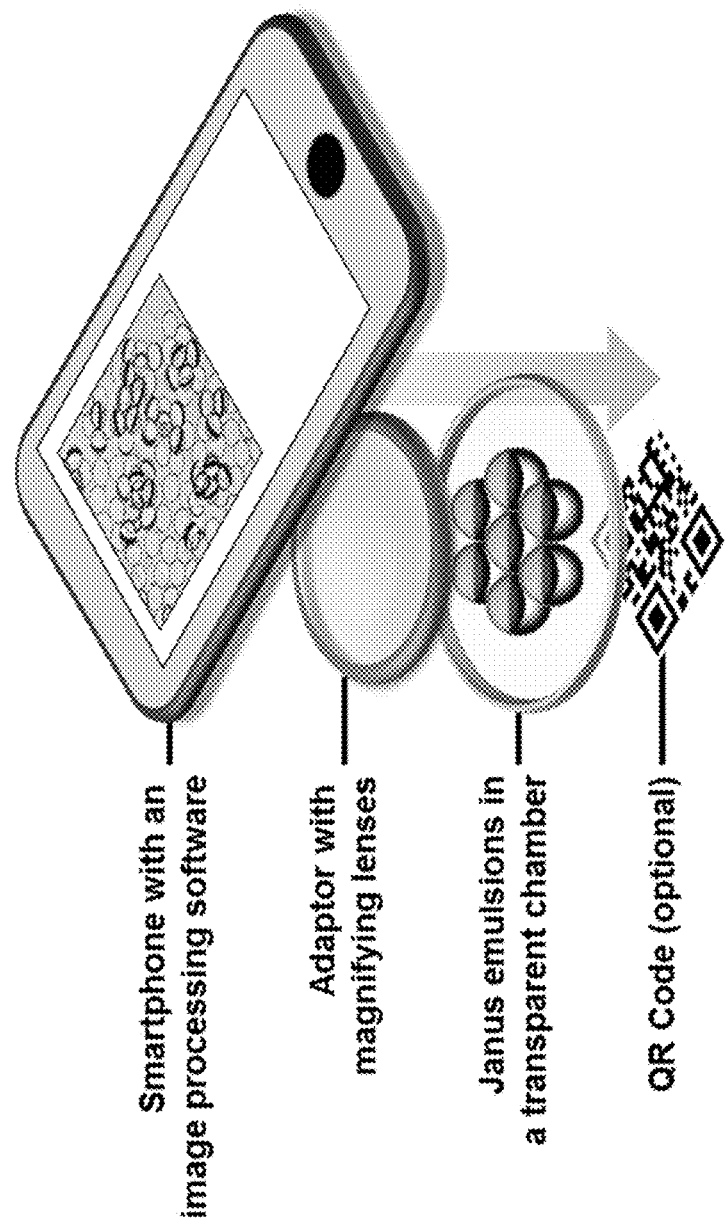
FIGS. 6A-6B show an exemplary system comprising a plurality of Janus droplets which, upon exposure to an analyte, changes an optical property of the system, according to one set of embodiments.

The solution of Janus droplets generally turns from transparent to opaque when the emulsions are agglutinated. FIG. 5A shows a solution of Janus droplets before exposure to an analyte. FIG. 5B shows a solution of Janus droplets after exposure to the analyte. Such large and easily observable differences may be incorporated into the use of image processing algorithms to analyze the optical micrographs. These optical micrographs are readily taken from, for example, any common smartphone equipped with magnifying lenses to enable low-magnification of 4× and 10× (FIG. 6A).

Figure 6B:
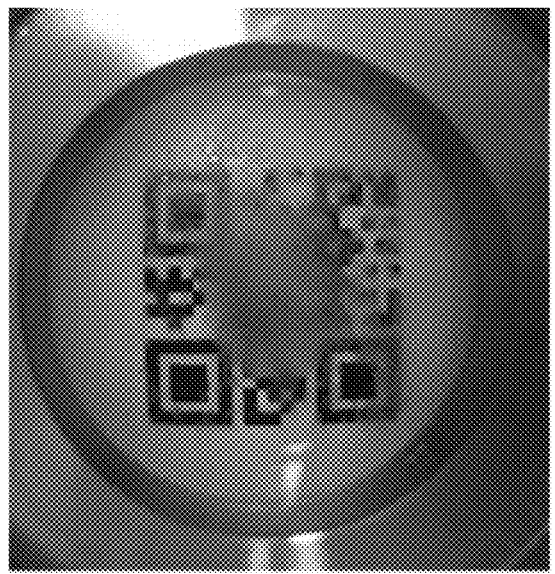
Figure 6B:

For qualitative purposes, the detection may use the significant changes in the optical transparency between pristine and agglutinated Janus droplets to generate a binary response. For example a transparent analysis chamber containing the Janus droplets was placed on top of a two-dimensional QR code, as shown in FIG. 6B. In the presence of ConA, the chamber became opaque and covered a portion of the QR code. This transformation inhibited a smartphone from reading the QR code.

Figure 7E:
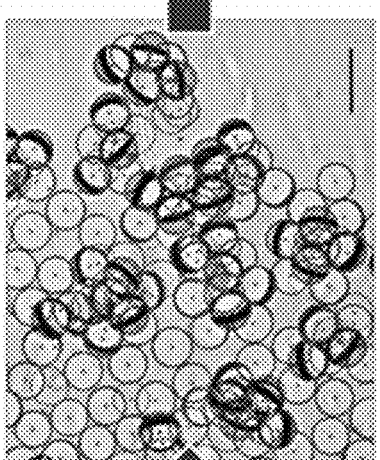
Figure 7A:
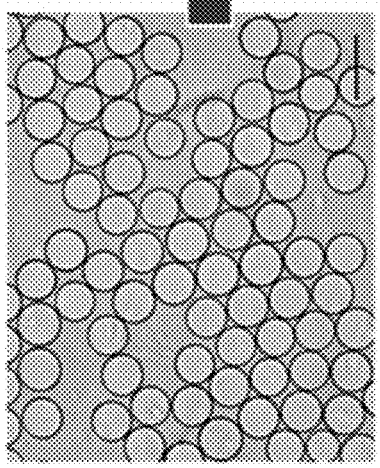
Figure 7D:
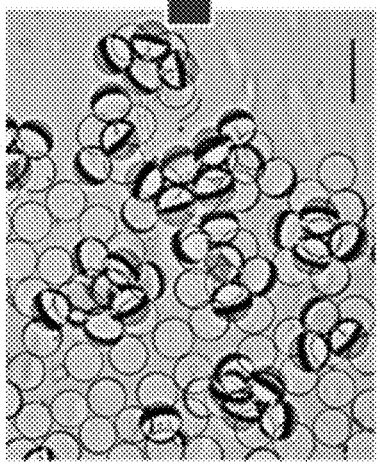
Figure 8A:
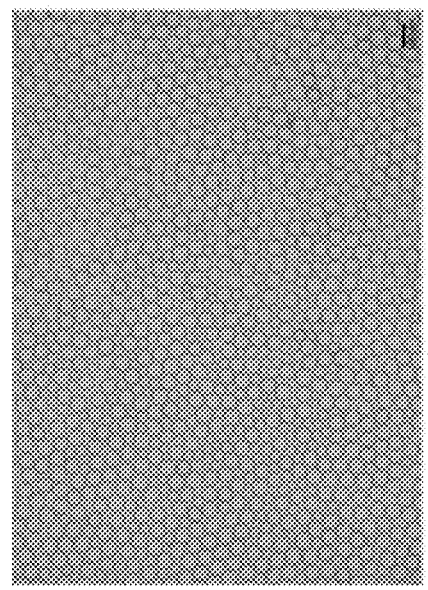
FIGS. 8A-8F show image processing based of Janus droplets upon exposure to an analyte, according to one set of embodiments.
Figure 8B:
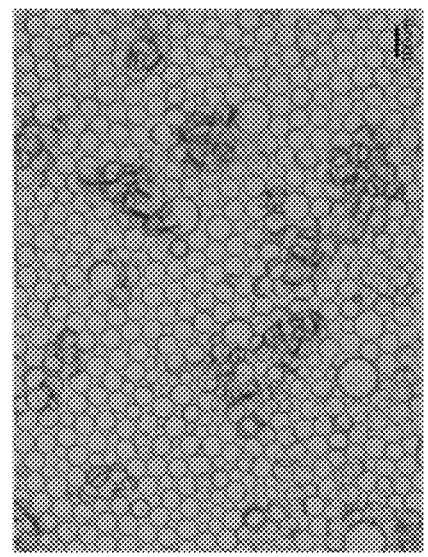
Figure 8C:
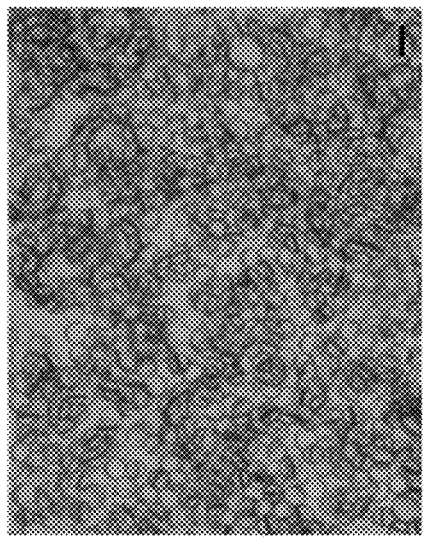
Figure 8D:
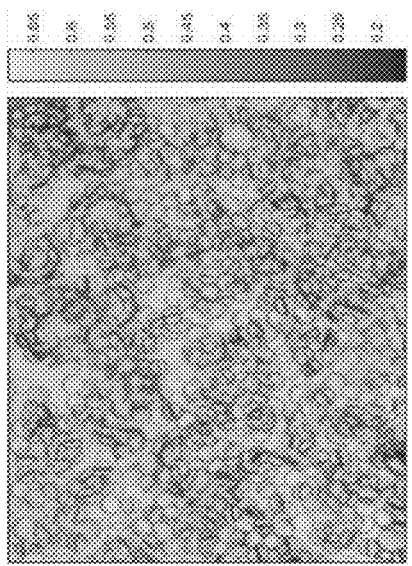
Figure 8E:
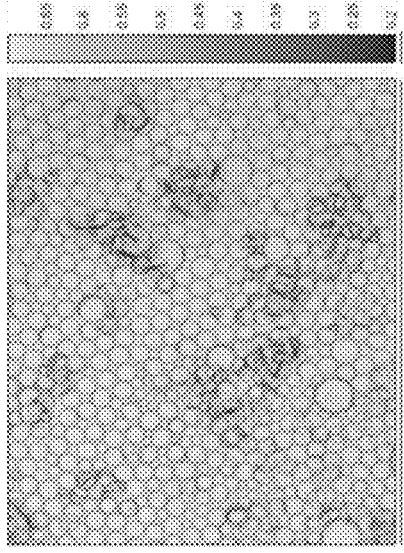
Figure 8F:
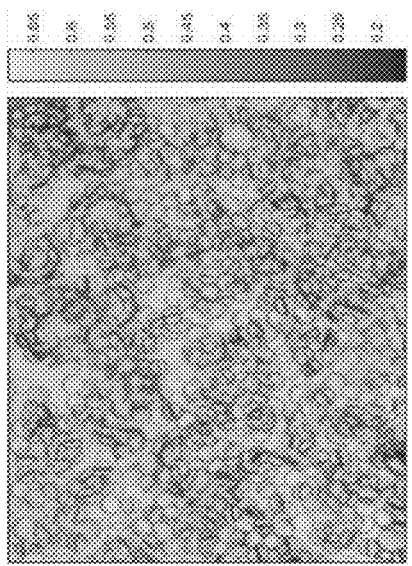

To quantify the degree of agglutination, an image processing program that calculates the percentage of area covered by agglutinated Janus droplets by two distinct logics was implemented: 1) the amount of overlapping droplets and 2) the difference in optical intensity of the images. FIGS. 7A-7C show the quantification of a plurality of Janus droplets in the absence of a targeted analyte. FIGS. 7D-7F show the quantification of a plurality of Janus droplets exposed to a targeted analyte.

Specifically, the image processing program analyzed the raw optical micrographs (FIG. 7A and FIG. 7D) by mapping out the locations of each Janus droplet and measuring their radii (FIG. 7B and FIG. 7E). Using this information, the program then sought overlapping emulsions. As described above, during agglutination the Janus droplets joined together to form droplet complexes of agglutinated Janus droplets. The program distinguished each droplet with more than two overlapping neighbors as a part of a droplet complex and rejected any droplet with zero, one, or two overlapping neighbors (FIG. 7C and FIG. 7F). The percentage of area covered by agglutinated Janus droplets were then calculated for both pristine sample (FIG. 7C) and agglutinated sample (FIG. 7F).

The area covered by these Janus droplet agglutinations were then further correlated with the analysis of optical intensity within the images. Similar to the qualitative detection, the image analysis can distinguish regions of agglutinated Janus droplets due to the lower optical transparency. The program used an adaptive thresholding algorithm to distinguish areas with higher transparency (pristine Janus droplets) from the opaque regions (agglutinated Janus droplets), FIGS. 8A-8F. The combination of the two distinct logics—identifying the overlapping Janus droplets and analyzing changes in optical intensity—can accurately detect the regions of agglutinated Janus droplets. Furthermore, the whole process can be completed within seconds from capturing the image to final calculation.

In some cases, the Janus droplets behave as individual lenses. Such droplets can be interrogated with a scanning light beam or a number of beams simultaneously. In this case (e.g., FIGS. 8A-8F), the light beams transmit through the sample and impinge on an array of light detectors. Signals can be deduced by changes in the intensity that represents the straight path of the light beam and the light that is refracted (e.g., deviating from a straight path). Without wishing to be bound my theory, lower intensity at the point of the straight path and higher intensity of light that is refracted from that path, indicate an increase in the tilt of one or more droplets. Similarly, higher intensity of light in the straight path and lower intensity that has been refracted may indicate a decrease in the tilt of the droplet. Such lensing permits detection of changes in a single droplet. For example, the ability to detect single events that can lead to the detection of single pathogens, cells, catalysts, or molecules.

Figure 9:
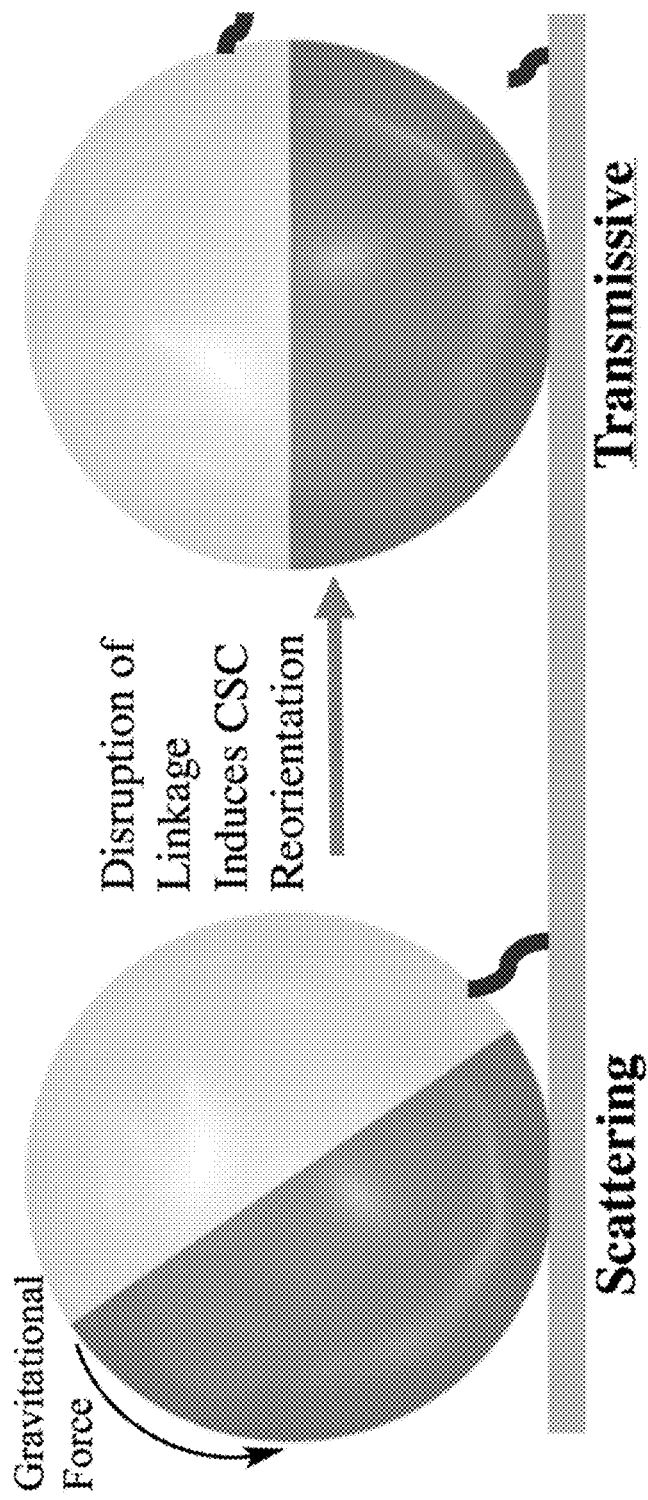
FIG. 9 shows an illustrative embodiment of interaction with an analyte resulting in the change of orientation of a Janus droplet, according to one set of embodiments.
Figure 10:
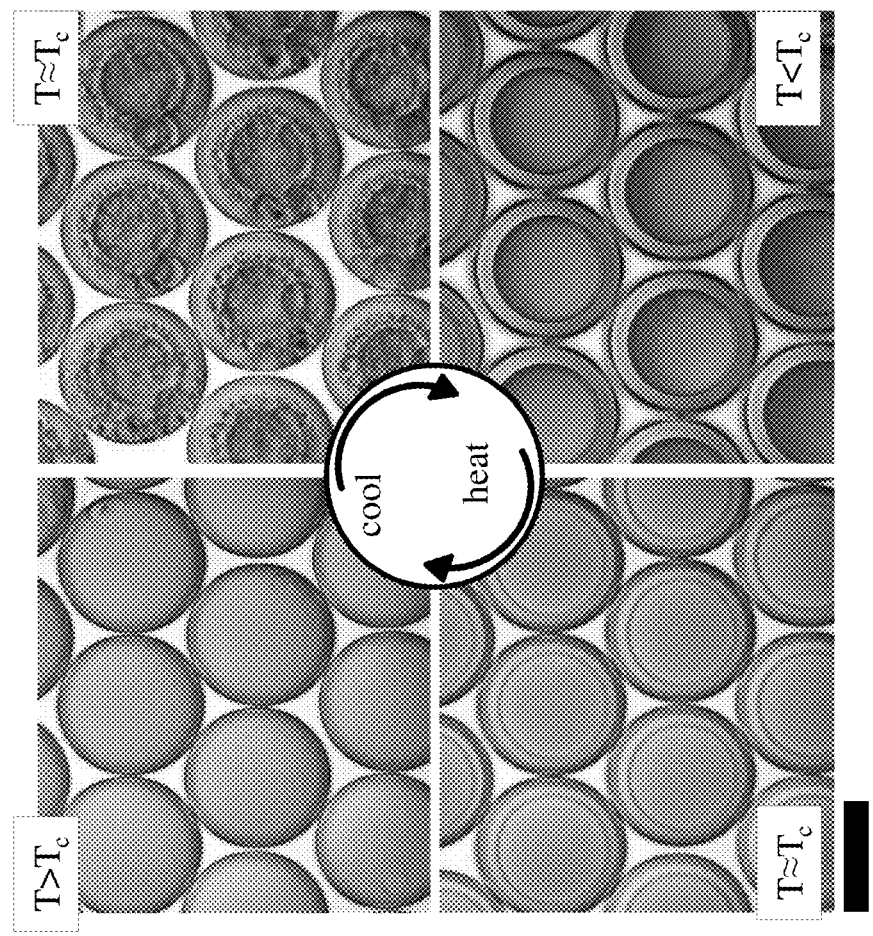
FIG. 10 shows photographs of the formation of complex emulsions comprising hexane and perfluorohexane, according to certain embodiments.
Figure 11A:
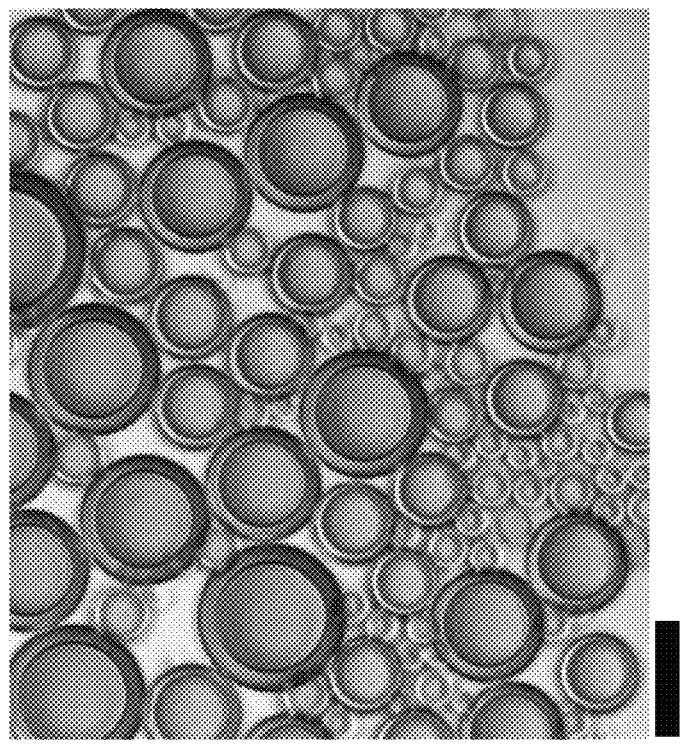
FIG. 11A shows photographs of a complex emulsion comprising hexane and perfluorohexane, formed according to one set of embodiments.
Figure 11B:
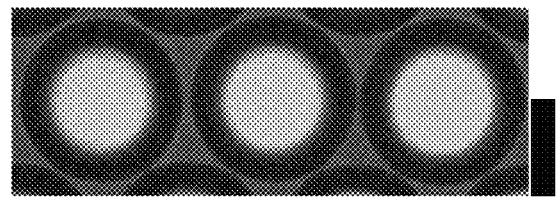
FIG. 11B shows a photograph of a complex emulsion comprising hexane and perfluorohexane, formed according to one set of embodiments.
Figure 12A:
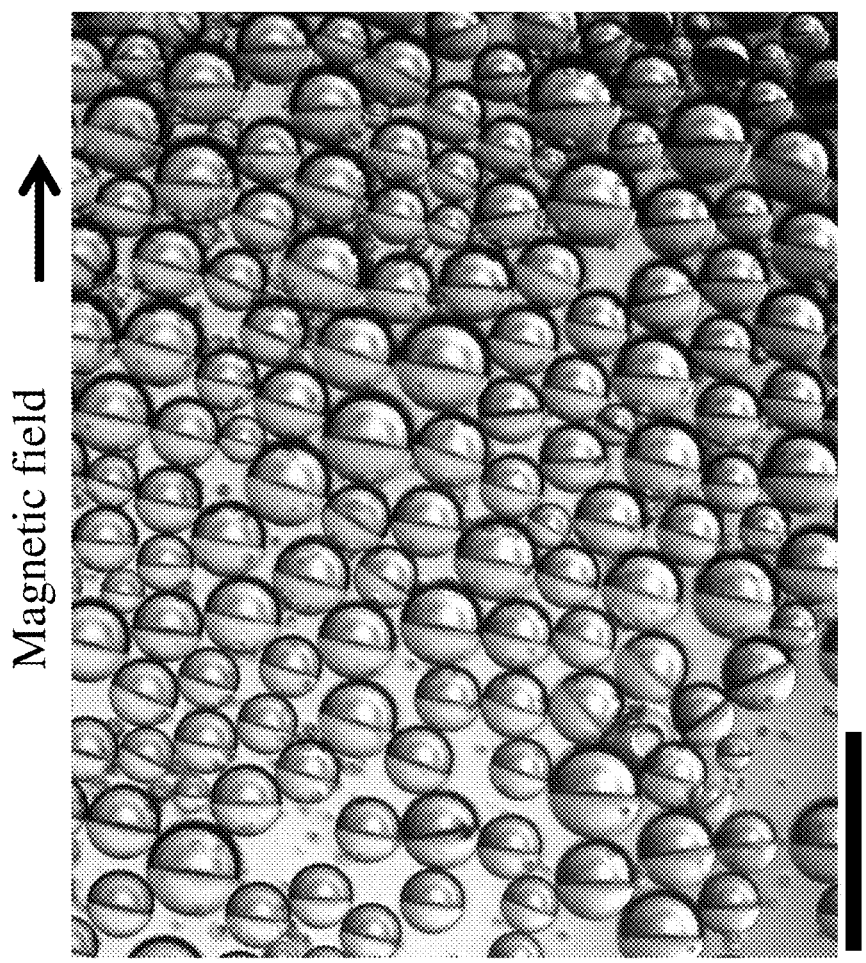
FIG. 12A shows a photograph of Janus droplets, formed according to one set of embodiments.
Figure 12B:
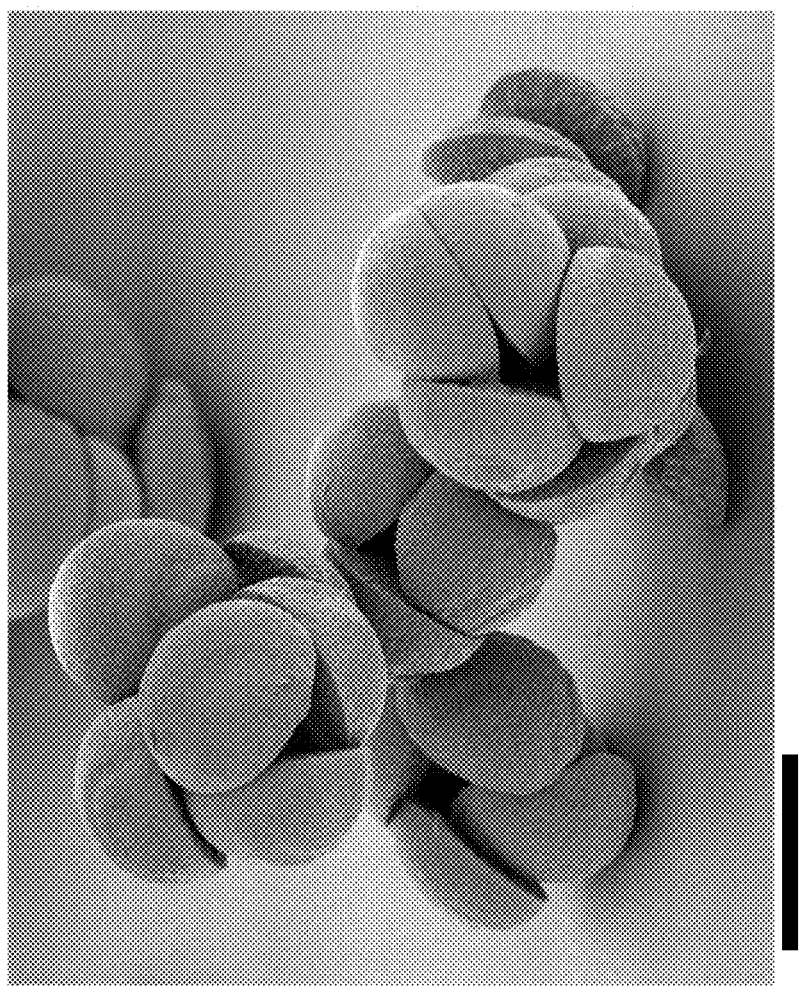
FIG. 12B shows a scanning electron micrograph of particles formed from polymerized Janus droplets, formed according to one set of embodiments.
Figure 12C:
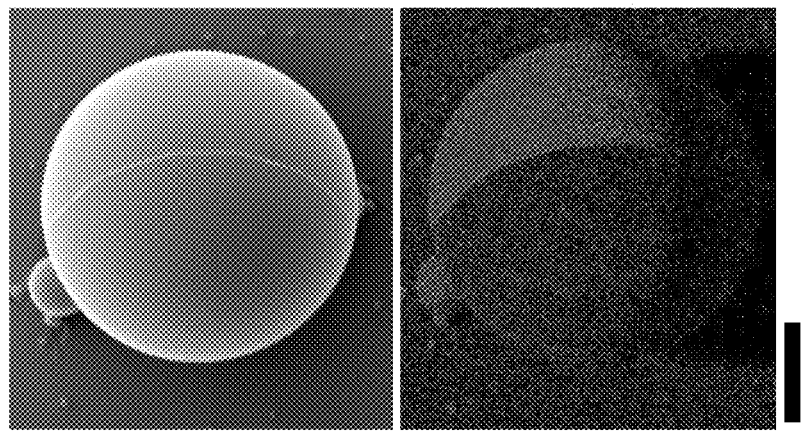
FIG. 12C shows a scanning electron micrograph (top) and an energy dispersive x-ray map highlighting fluorine (bottom) of a Janus particle, formed according to one set of embodiments.

FIG. 9 details a strategy wherein breaking a single linkage (tether) can potentially generate a sensor response that is visible to the naked eye. In this system, the red phase of the Janus droplet (CSC) had a higher density, and a gravitational force worked to orient the particles. Disrupting a chemical bond or complementary DNA interaction tether, which has pinned the Janus droplet in a tilted scattering configuration, produced a relaxation to the transmissive equilibrium orientation. An advantage of this method is, for example, that only one droplet in a multitude of droplets need be rotated to be detected. Additionally by tethering to patterned surfaces, arrays of sensors can be produced that can detect multiple types of analytes in a single device.

Formation of Droplets

Materials. For the detection of ConA, hexane and perfluorohexane were chosen as the hydrocarbon and fluorocarbon phases respectively. In other cases, different pairs of hydrocarbon (ortho-dichlorobenzene, phthalate, etc.) and fluorocarbon (ethyl nonafluorobutyl ether, methoxy perfluorobutane, etc.) phases can be substituted to tune the upper critical temperature ($T_c$) of the mixture and the differences in density for suitable applications. For the continuous water phase, surfactants ManC14 and Zonyl® FS 300 were chosen to stabilize and generate the Janus droplets. The two surfactants were dissolved in HEPES buffer solution (pH=7.5) separately with concentration of 0.0005% and 0.01% by weight, respectively. In both bulk emulsification and microfluidics method, the final volume ratio between ManC14 solution and Zonyl FS 300 solution was kept at 1.2:1 to generate two-hemisphere Janus droplets. For surfactants that are soluble in water (such as ManC14 and Zonyl® FS 300), a solution containing the functionalized surfactants was used as the continuous phase.

Bulk emulsification for polydispersed Janus droplets. To generate Janus droplets via bulk emulsions, we began by preparing an equal-mixture of hexane and perfluorohexane with a total volume of 1 mL in a 5 mL glass vial. The mixture initially formed an immiscible solution at room temperature. The vial containing the mixture was then heated to above the $T_c$ using a standard heat gun until the mixture was miscible; for hexane-perfluorohexane mixture, the $T_c$ is 20° C. For other combinations of hydrocarbon and fluorocarbon, the $T_c$ may vary depending on the two liquids. In another 5 mL glass vial, 1 mL of the continuous phase containing ManC14 and Zonyl FS 300 (concentrations of both reported in the previous section) was also heated to the same temperature as the vial containing hexane-perfluorohexane mixture. This precaution may mitigate the phase segregation of hexane and perfluorohexane upon addition before emulsification. 50 uL of heated and miscible hexane-perfluorohexane mixture was then injected into the heated continuous phase via a pipette. The Janus droplets were then generated by shaking the vial using a vortex mixer at 3000 RPM for 5 seconds. The solution of Janus droplets was then cooled down below Tc using an ice bath. This method of bulk emulsification generated polydispersed droplets with diameters ranging from 30 to 200 μm as observed by an optical microscope.

Generation of monodispersed Janus droplets via microfluidics. Both coaxial glass capillary microfluidics and commercial available microfluidic chips were used to generate emulsions. For coaxial glass capillary microfluidics, devices were made from an outer square capillary (OD=1.5 mm, ID=1.05 mm, AIT Glass) and inner cylindrical capillary (OD=1 mm, World Precision Instruments) pulled to a 30 μm tip using a P-1000 Micropipette Puller (Sutter Instrument Company). For commercial microfluidic device, Focused Flow Droplet Generator chip (channel width=100 μm, channel depth=20 μm, tip width=10 μm, glass) from Micronit was used. In both microfluidics system, Harvard Apparatus PHD Ultra syringe pumps were used to inject the outer phase (continuous phase) and inner phase (droplet phase). The flow rates were 50 μL min$^{-1}$ for the continuous phase and 30 μL min$^{-1}$ for the droplet phase. The solution of monodispersed droplets was first collected via 20 mL glass vial and later diluted with both ManC14 solution and Zonyl® solution to achieve a final droplet phase concentration of 6% by volume while maintaining the 1.2:1 volume ratio of the two surfactants. The microfluidic setup was heated above the Tc of the inner phase solution using a heat lamp. Janus droplets were then cooled below Tc to induce phase separation. For hexane-perfluorohexane emulsions, the emulsions were chilled on ice prior to imaging and often imaged while immersed in a cool water bath to maintain a temperature below 20° C. The average diameter of the monodispersed droplets generated from this setup were 60±10 μm. The composition of each droplet was nearly identical because each droplet was generated from the same single droplet phase.

Stability and sample storage. The Janus droplets generated from either method described above were observed to be stable on the order of weeks under room temperature. After emulsification, the Janus droplets were kept within the continuous phase at room temperature in a closed glass vial without mechanical perturbation. The diameter of the Janus droplets was not observed to change significantly after weeks of storage.

Sensing

Sample preparation for sensing of ConA. Monodispersed or polydispersed Janus droplets used for sensing experiments were fabricated using methods described above. Janus droplets were loaded into a stainless steel sample holder with a 1 cm deep well and a 1.5 cm diameter viewing window. 0.5 mL of mixed surfactant solution containing 30 μL of hexane-perfluorohexane droplet phase was loaded into sample holder to create a monolayer of Janus droplet that covered the whole viewing window. The sample holder and solution of the Janus droplets were kept below 20° C., the Tc of hexane-perfluorohexane mixture, during the sensing of ConA and image acquisition.

Model system: Sensing of ConA. ConA was dissolved in HEPES buffer solution with final concentration of 0.5 mg mL$^{-1}$ and used as the analyte. 10 μL of ConA solution was added using a micropipette to the sample holder containing Janus droplets. Solution was then swirled gently and agglutination of Janus droplets were observed within seconds. Image were recorded before and after adding ConA solution. An increasing volume (up to 40 μL) of ConA solution were added afterwards to get a correlation between agglutination level and analyte concentration. Agglutination level were analyzed both qualitatively and quantitatively as described below.

Surface Chemistry

Fabrication of DNA-functionalized surface. Glass substrates were cleaned by sonication in acetone and isopropyl alcohol for 5 min each to remove dust. After drying completely, the glass substrates were immersed in piranha solution ($H_2SO_4$: $H_2O_2$, 1:1, v/v) for 1 h, rinsed thoroughly with distilled water, and then dried under $N_2$. The glass substrates were then immersed and reacted with a toluene solution of trichlorosilane linker terminated with an N-hydroxysuccinimide (NHS) for 1 h to form NHS covalently functionalized glass substrates. Afterwards, a solution of 10 μM ssDNA dissolved in a sodium tetraborate buffer at pH 9 was reacted to form an amide bond, which attach the ssDNA onto surface of the glass slides. ssDNA was functionalized with alkyl chain to form a surfactant molecule. Janus droplets residing on the surface of ssDNA functionalized glass substrate were tilted against gravity. A solution of the complementary strand dissolved in 0.25 M NaCl solution was added to Janus droplets to hybridize the DNA strands. Janus droplets were released from the glass substrate to be aligned with gravity at areas where DNA strands were hybridized. X-ray photoelectron spectroscopy was used to analyze the elements on glass substrates to ensure successful functionalization of ssDNA.

Detection

Sample preparation for detection. For both qualitative and quantitative methods of detection, Janus droplets were imaged in a stainless steel sample holder. For qualitative detection, a two-dimensional QR code (1 cm×1 cm) was placed 1 cm below the viewing window of the analysis chamber. For quantitative detection, a white background was used instead of the QR code to provide contrast. The analysis chamber and the solution of the Janus droplets were kept in an ice bath, well below the Tc of the hexane-perfluorohexane mixture to maintain the morphology of the Janus droplets. Qualitative analysis using QR code. Qualitative analysis was performed using the QR code from unmagnified images taken from the smartphone. The distance from the phone to the analysis chamber containing the Janus droplets was approximately 10 cm. The exact distance was calibrated by the image processing software by using the known dimension of the QR code (1 cm×1 cm). The binary response measured was whether the QR code could be read via the software. If the QR code was readable, the Janus droplets were considered not agglutinated, and vice versa.

Image acquisition for quantitative analysis. To acquire the low-magnification images for quantitative analysis, an adaptor with magnifying lenses was adapted onto the smartphone. With this modification, optical micrographs with 4× and 1× magnification were obtained. The working distance from the smartphone to the analysis chamber was 1 cm. The working distance and the dimension of the images were calibrated by the calibrated marking underneath the analysis chamber with 10 µm tick marks. The image processing software then pre-processed the captured images by transforming them into greyscale images and adjusting the brightness and contrast to the reference image of blank analysis chamber. For each sample, 100 pictures were taken, forming a 10×10 array of images to span the majority of the area of the analysis chamber.

Identification of overlapping Janus droplets. From the pre-processed images with 1× magnification (greyscale images with adjusted brightness and contrast), the image processing program first estimated the range of diameters of the Janus droplets by using the calibrated marking underneath the analysis chamber. The program then sought out and mapped the centers and calculated the diameters of every Janus droplet. This process was done by a modified method based on the Circle Hough Transform. With the coordinates of the centers and the diameters of the Janus droplets, the program then evaluated overlapping droplets. Specifically, if the distance between two centers of two droplets was smaller than the sum of the two radii, the droplets were considered overlapping. Using this logic, the program could effectively map out the number of overlapping neighbors for every identified droplet.

Identification of droplet complexes. A Janus droplet was considered to be a part of a droplet complex if the number of its overlapping neighbor exceeded three. This threshold was set in some cases to prevent over-counting of the droplets at the edges of the droplet complexes and accidental overlapping of droplets. This measurement was further collaborated by the analysis based on the optical intensity. The area occupied by the agglutinated droplet complexes was then calculated.

Analysis of changes in optical intensity. Using the pre-processed images of 4× magnification (greyscale images with adjusted brightness and contrast), the program first applied the adaptive thresholding algorithm to distinguish the darker edges of the Janus droplets from the droplet complexes with tilted particles. More specifically, the program ignored the edges of the droplets that have inherent low-light intensity and only sought the area of droplet complexes. A threshold was set using areas with light intensity of less than 45% of the brightest regions to be considered part of the droplets complex. From this information, the area occupied by the droplet complexes was then calculated.

Example 6

The following example generally relates to bioconjugation of droplets, according to some embodiments.
Emulsion Assays and Surfactants Design
Dynamic Complex Emulsions Complex emulsions were fabricated at temperatures above the upper critical solution temperature of the internal phases to create materials with precisely determined compositions. Specifically, droplets containing equal volume of hydrocarbon (diethylbenzene) and fluorocarbon (HFE7500) liquid were emulsified around 40° C., which is above Tc (37° C.) in a hydrocarbon and/or aqueous continuous phase containing Zonyl FS-300 (hereafter 'Zonyl'), which is a nonionic fluorosurfactant. Surfactants generally lower the interfacial tension between two immiscible liquids and stabilize emulsion droplets. Droplets containing both hydrocarbon and fluorocarbon may switch morphologies between H/F/W (hydrocarbon-in-fluorocarbon-in-water), Janus, and F/H/W (fluorocarbon-in-hydrocarbon-in-water), with changes in the relative strength of the fluorocarbon and hydrocarbon surfactants.

Figure 14:
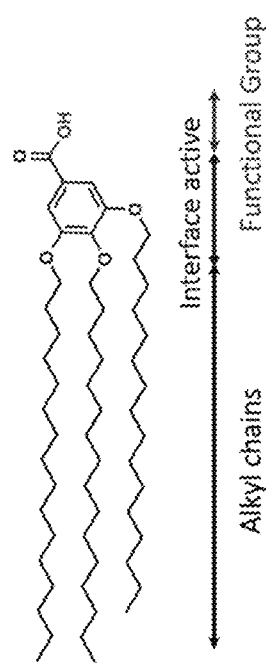
FIG. 14 shows the structure of exemplary tridodecyl gallic acid (GA120H) surfactant, according to one set of embodiments.

In some embodiments, the complex emulsion could be solidified or gelled by polymerization of the liquids within the droplet. In some such cases, the Janus structure could be preserved in the resultant solidified or gelled structure. Additionally, in certain instances, dyes could be selectively partitioned into separate phases of the droplets to place the dyes in the separate phases of the solidified or gelled structure. These solidified or gelled Janus structures could, in certain embodiments, function similarly to their liquid analogs and in some cases could provide enhanced stability.
Surfactant Design Creating surfactant molecules that interact with analytes is the helpful to create couplings to droplet morphology and orientation. The orientation in the absence of perturbation may be controlled by the density differences of the internal phases and gravity. The droplets are dynamic lenses and both morphology and orientation produce large optical signals. Optical transduction in these cases makes use of the light transparency because vertically aligned Janus droplets with internal phases having specific refractive indices. A transparency to highly scattering state may be triggered by small distortions in droplet morphology or agglutinated (tilting). To extend these methods, a generic surfactant platform was produced, shown in FIG. 14, for droplet bioconjugation with proteins, nucleic acids, and carbohydrates. The three alkyl chains in the tridodecyl gallic acid shown (GA12OH) provide for a robust hydrophobic anchor and the carbonyl based functional site provides for bioconjugation. The gallic structure was observed to be an intrinsic surfactant molecule that provides sufficient stability to prevent speciation of the generic reactive droplets. This design builds on the observation that aromatic rings with peripheral alkane chains organize at the oil-water interfaces to enhance the effectiveness at lowering interfacial tensions.

To validate the interfacial behavior of the gallic derived surfactant, emulsions with and without GA12OH in the hydrocarbon oil phase were produced in the same continuous phase (0.01 wt % Zonyl in PBS buffer). The pristine emulsion droplets without GA12OH, are in double emulsion morphology (FIG. 3E), namely hydrocarbon-in-fluorocarbon-in-water, whereas the emulsion droplets with 10 mg/mL GA12OH dissolved in the hydrocarbon phase appear in Janus configuration (FIG. 3E, 100B). These results confirm that GA12OH is a good surfactant that lowers the surface tension at the oil/water interface. Aside from helping with the control droplet formation, this feature indicates that the carboxylic acid groups are presented at the hydrocarbon and/or aqueous interface for chemical modification.

Emulsion Assays for Bioconjugation

Interfacial Functionalization on Emulsion Droplets

Figures 15A, 15B, 15C:
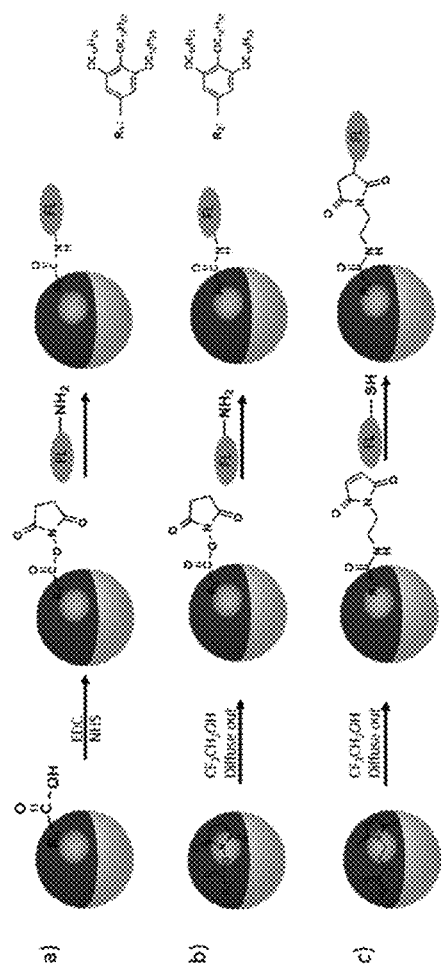
FIGS. 15A-15C show interfacial functionalization on a Janus droplet, according to one set of embodiments.

After confirming the surfactant behavior of GA12OH, the chemical reactivity at the droplet interface was studied using the EDC/NHS coupling reaction. As shown in FIG. 15A, GA12OH was loaded into the droplet phase and the droplets adopted a Janus morphology. EDC and NHS solutions were then added in the continuous phase. Fluoresceinamine was used as a model reactant for biomolecules bearing amine groups, and upon addition to the water phase reacts with the in situ generated NHS ester. The unreacted fluoresceinamine in the continuous water phase is removed by washing the droplets and a bright green fluorescence was observed at the hydrocarbon-water interface with confocal microscopy. The localized green fluorescence is attributed to the fluoresceinamine-NHS reaction to form a covalent amide bond at the droplet interface. Another dye, Sulfo-Cyanine 3 amine is separately functionalized to the droplet surface using the same method described above. When two batches of droplets functionalized with different dyes were combined together, no sign of mixing dyes was observed under microscopy even after extended period of time. This further confirmed the covalent bond formation at the hydrocarbon-water interface and that we can produce droplets that do not fuse or transfer functional groups between them. This latter feature is particularly useful for multiplexed detection schemes.

GA12-NHS Assay for Amine Conjugation

To investigate the scope of interfacial functionalization, surfactant GA12-NHS was pre-synthesized and dissolved in the droplet hydrocarbon phase (FIG. 15B). Trifluoroethanol was added the hydrocarbon and fluorocarbon droplet phase to lower the upper critical mixing temperature. After droplets are formed in the water phase, trifluoroethanol partitions into the continuous phase and internal phases then undergo phase separation to produce double emulsions. It was believed that the GA12-NHS has some portioning to hydrocarbon-water interface as a result of its surfactant behavior. The continuous phase was exchanged twice to remove the trifluoroethanol. This is facilitated because the droplets are denser than water and remain on the bottom of flask. The continuous phase solvent exchange does not affect the stability nor the morphology of the droplets. It was observed that fluoresceineamine functionalization with pre-synthesized GA12-NHS has a higher yield and resulted in 50% more intense fluorescence under confocal microscopy with relative to an internal dye reference (described later in this example). As a result, GA12-OH and in situ NHS formation is not quantitative.

GA16-MA Assay for Thiol Conjugation

Figures 16A, 16B:
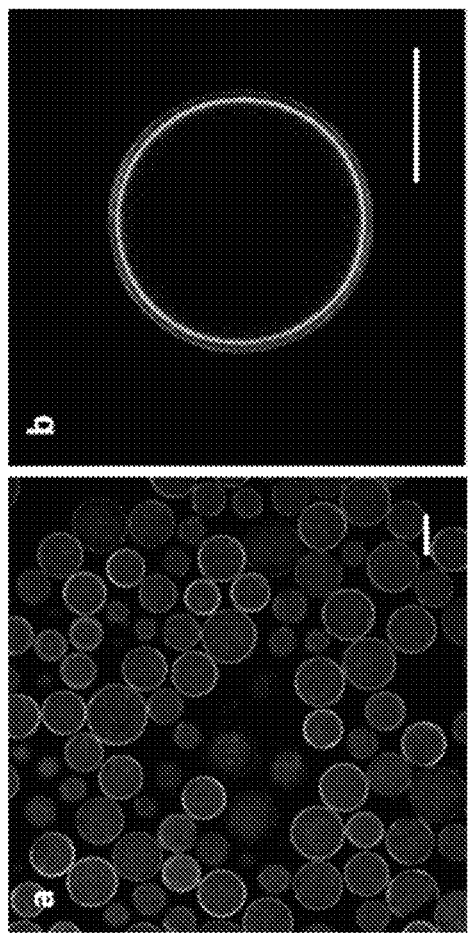
FIGS. 16A-16B show confocal microscopy images of cysteine-BODIPY functionalized droplets using interfacial maleimide-thiol chemistry. Scale bar in 50 µm.

To implement a maleimide-thiol bioconjugation scheme, GA16-MA (FIG. 15C) was pre-synthesized and loaded into the droplets. The longer hexadecyl chains increased the surfactant GA16-MA solubility in hydrocarbon phase. BODIPY-FL-Cysteine was used as the reactive model compound for biomolecules bearing thiol groups. Upon addition (FIG. 15C), this dye was covalently linked to the surface of the droplets and bright fluorescence from the BODIPY dye was observed at the hydrocarbon-water interface as shown in FIG. 16A-16B. In the control experiments under the same conditions without GA16-MA in the droplet phase, no fluorescent ring was observed by confocal microscopy.

Controlled Conjugation Reactivity of the Emulsion Assays

These complex emulsion assays generally use the interfacial functionalization and the recognition characteristics thereof. The droplet interface is dynamic and the morphology switches between H/F/W, Janus, and F/H/W with changes in the interfacial tensions between hydrocarbon-water interface and fluorocarbon-water interface. Another advantage of the emulsion droplets is that they can provide hydrolytic stability for the reactants that are localized in an internal phase that initially doesn't share an interface with water. With controlled activation the reactant can be used for functionalization later times.

Figure 17:
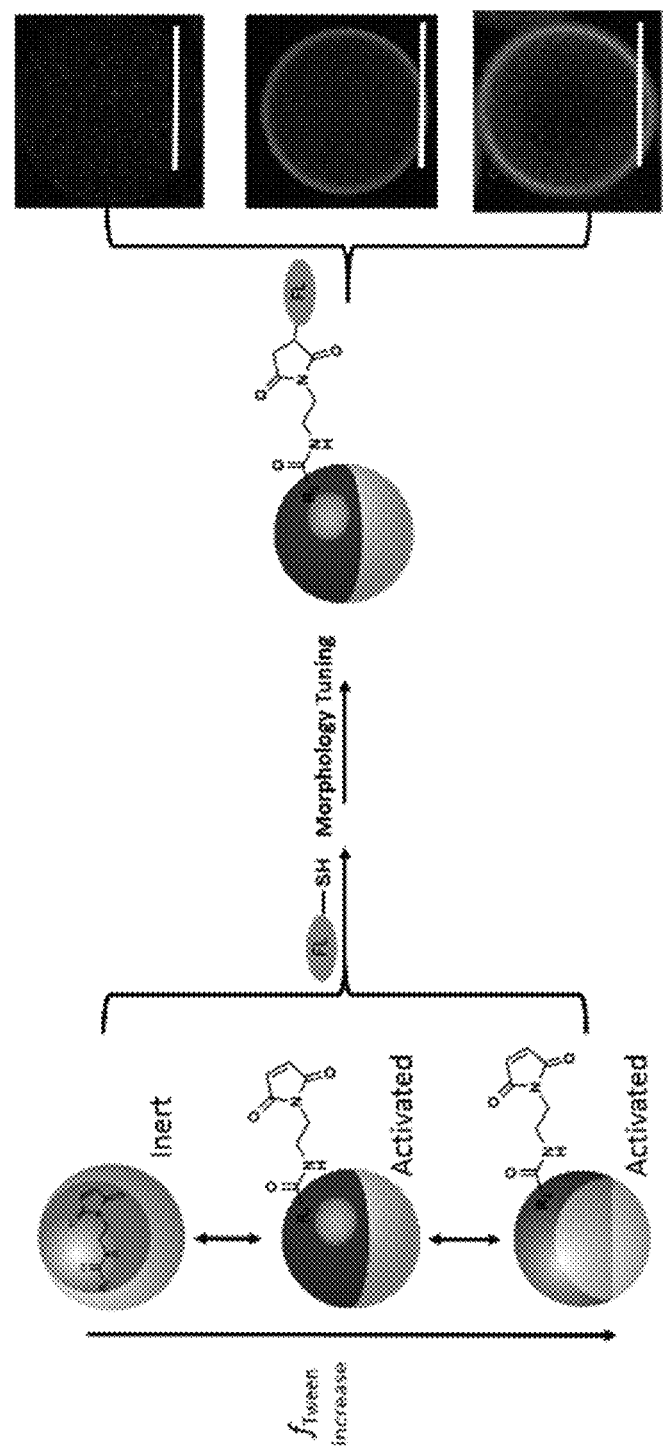
FIG. 17 shows dynamic emulsion droplets with controlled reactivity, according to one set of embodiments. Droplets start in different morphology and functionalized at the hydrocarbon-water interface. Droplets were then tuned to the Janus morphology for imaging. Higher intensity indicates higher level of functionalization at the interface.

As shown in FIG. 17, GA16-MA and BODIPY-FL-Cysteine was used to demonstrate the controlled interfacial conjugation. Tween 20 was chosen as the continuous phase "activating" hydrocarbon surfactant. Together with Zonyl as the continuous phase fluorocarbon surfactant, it is possible to tune the morphology of the droplets to facilitate maleimide-thiol conjugation. Tween 20 was chosen because of its mild surfactant behavior, which means it will not completely cover the hydrocarbon-water interface but is still able to change the morphology of the droplets. In the H/F/W morphology state, wherein the hydrocarbon oil was encapsulated inside the fluorocarbon phase, GA16-MA is rendered inert. When the droplet morphology was switched to Janus or F/H/W by the addition of Tween 20, the hydrocarbon phase now has a reactive interface with water and the interfaces are activated for functionalization reactions.

Quantification of the Interfacial Conjugation Reaction

Figure 18:
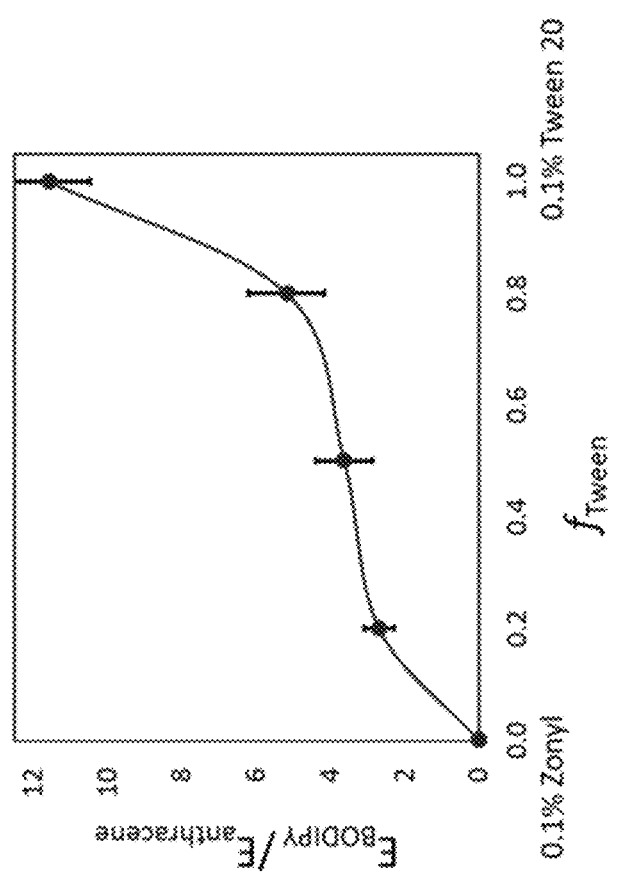
FIG. 18 shows the ratio of emission intensity at the interface ($E_{BODIPY}$) and inside ($E_{anthracene}$) relative to the continuous tween 20 surfactant concentration, according to one set of embodiments.

To further quantify the level of covalent functionalization at the interface, anthracene with different emission wavelength from BODIPY was used as an internal fluorescent reference to indicate the amount of fluorophore functionalized at the droplet interface. As shown in FIG. 17, the droplets with different starting morphology were functionalized with BODIPY using maleimide-thiol chemistry. After the reaction, the morphology of the droplets was tuned to the exact Janus state for confocal imaging by changing the continuous phase surfactant with either Zonyl or Tween 20. The fluorescent intensity of both fluorophores are analyzed through the open access software ImageJ (National Institute of Health, Bethesda, MD, USA; available for download at https://imagej.nih.gov/ij/) and the relative intensity ratio between $E_{anthracene}$ and $E_{BODIPY}$ was plotted against the initial droplet morphology, indicated by relative surfactant ratio $f_{Tween}$ (FIG. 18). The more surface area at the hydrocarbon-water interface during conjugation, the more thiol functionalization is to the droplets as indicated by the BODIPY fluorescent intensity.

Biomolecule Functionalized Emulsion Assays

Protein a Functionalized Assay for IgG Detection

Figure 19:
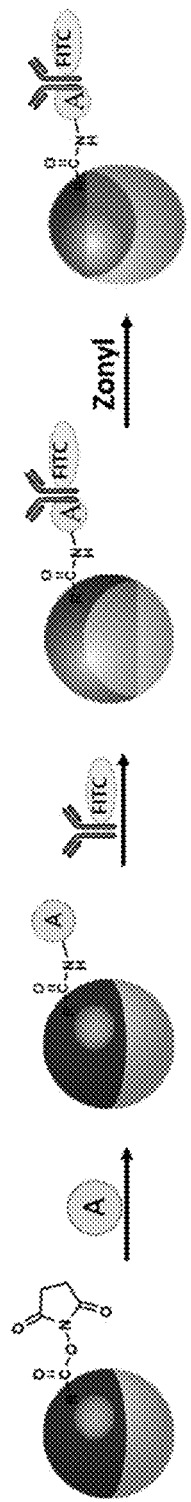
FIG. 19 shows exemplary droplet functionalization with protein A and detection scheme with immunoglobulin (IgG), according to one set of embodiments.
Figure 20A:
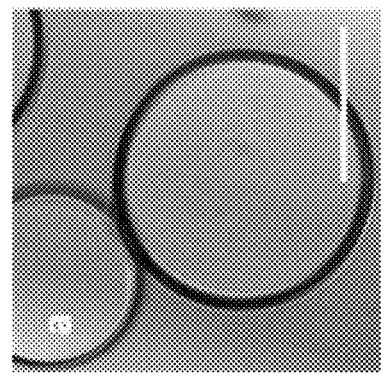
FIGS. 20A-20C show Protein A functionalized emulsion droplet for the detection of anti-mouse IgG, according to one set of embodiments. Scale bar in 50 µm.
Figure 20B:
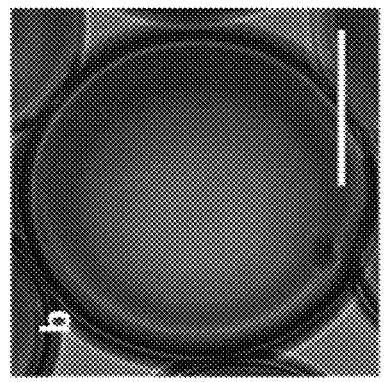
Figure 20C:
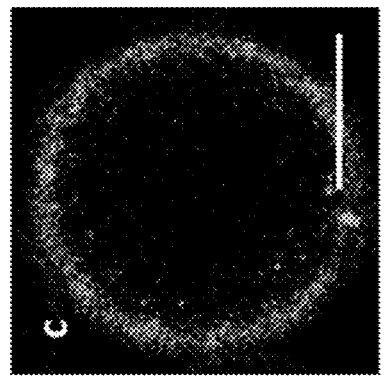

The examples above show that the emulsion droplets containing gallic acid (GA) based reactive surfactants can be functionalized with molecules bearing free amine or thiol group. Functionalization with biomolecules is useful to achieve broad utility in biosensing assays. As a prove-of-concept, a Protein A functionalized emulsion assay was targeted for the binding of anti-mouse IgG. As shown in FIG. 19, Protein A reacts through lysine amines with Janus emulsion droplets containing GA12-NHS. After functionalization, the emulsion droplets maintained a Janus morphology (FIG. 20A). Addition of FITC (fluorescein isothiocyanate) labelled anti-mouse IgG to the continuous phase results in binding to Protein A on the surface of droplets. This modification resulted in a change in droplet morphology from Janus to a F/H/W double emulsion (FIG. 20B). It was rationalized that the large IgG molecule provides additional hydrophilic character, which increases the surfactant strength at the hydrocarbon-water interface, thereby expanding the organic water interface. This morphology change from Janus (transparent) to F/H/W (opaque) is easily visualized with the transmission of natural light through thin gravity aligned layers of emulsion droplets. The binding of IgG to the droplet surface was further validated with confocal microscopy. The bright green fluorescence from the FITC labeled IgG was observed under confocal microscopy and was only located at the hydrocarbon-water interface (FIG. 20C). The GA12-NHS is therefore established as an active biomolecular reactive group for functionalization of the hydrocarbon-water interface.

Figure 21A:
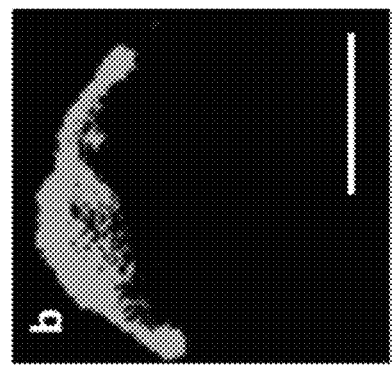
FIGS. 21A-21B show images of Zonyl forced droplets after IgG binding to protein A, according to one set of embodiments. Scale bar in 50 µm.
Figure 21B:
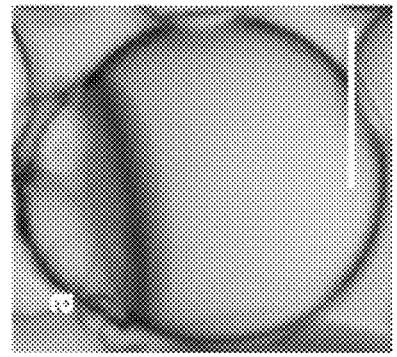

To demonstrate there is covalent bond between the droplet and Protein A/IgG complex, additional Zonyl surfactant was added in the continuous phase to force a morphology change from F/H/W to H/F/W. The Protein A/IgG complex is not dislodged from the hydrocarbon-water interface and the added Zonyl produces a deformation (FIG. 21) from a perfect sphere. If the droplet was not functionalized with proteins, the hydrocarbon phase would become an inner phase of a double emulsion, H/F/W. This experiment also shows that the interface was still dynamic after functionalization of either Protein A or IgG. Preserving a dynamic interface is central to sensing opportunities and producing changes in droplet morphology.

Nucleic Acid and Carbohydrate Functionalization

Figures 22A, 22B:
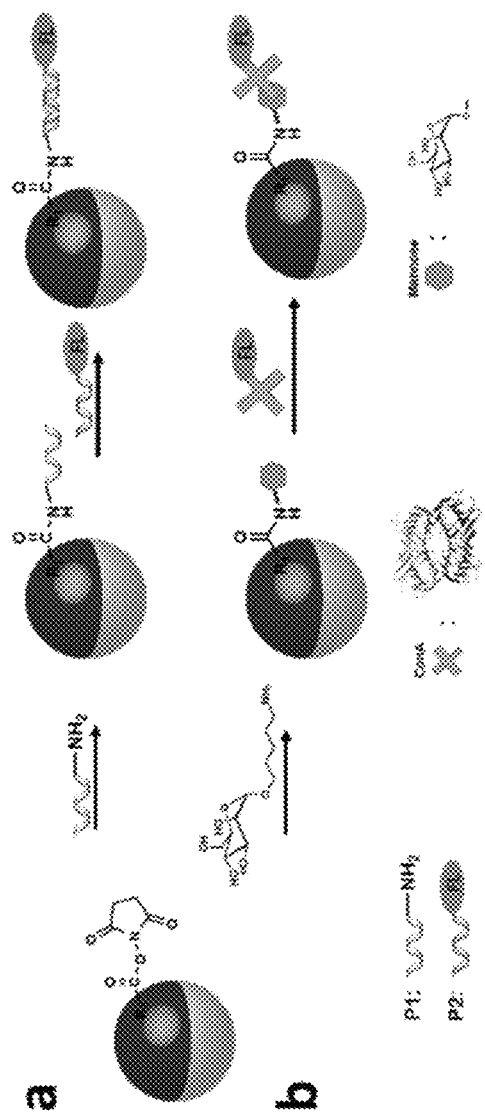
FIG. 22A shows bioconjugation with oligonucleotide followed by hybridization, according to one set of embodiments
FIG. 22B shows bioconjugation with mannose derivative for the binding of concanavalin A, according to one set of embodiments.

To demonstrate the generic bioconjugation capabilities of the emulsion assay, broader types of biomolecules were functionalized to the droplets (FIGS. 22A-22B). A strand of oligonucleotide 5'-amine C6 linker modified P1 was covalently functionalized to the droplet surface with GA12-NHS and amine reaction. A complementary strand P2 bearing a (6-carboxyfluorescein) 6-FAM tag at the 5' was added in the continuous phase. After removing unreacted oligonucleotide by washing, fluorescence from FAM was observed under confocal microscopy at the hydrocarbon-water interface, which indicates the oligonucleotide still maintains the reactivity. A mannose bearing amine was functionalized to the droplets using NHS-amine chemistry. Concanavalin A (ConA) labelled with FITC was added in the continuous phase. After washing the excess ConA from the mixture, fluorescence from FITC was observed under confocal microscopy, showing the carbohydrate-lectin binding interactions were preserved.

CONCLUSION

An emulsion assay capable of bioconjugation using NHS-amine or maleimide-thiol chemistry was designed. This assay has provided a generic platform for functionalization of biomolecules to the emulsion droplets as biosensors for the detection of antibodies, enzymes, nucleic acids and carbohydrates. The dynamic interface and droplet morphologies enable the controlled interfacial reactivity. The reactions modify the morphological changes that are easily detected with natural light transmission. Quantitative optical method and sensing of other targeted biomolecule will be demonstrated in follow-up studies.

Experimental Section
General Methods and Instrumentation

Diethylbenzene (DEB), 2-(trifluoromethyl)-3-ethoxydodecafluorohexane (HFE7500), hydroxylamine, trifluoroethanol, phosphate-buffered saline (PBS, pH=7.6) (1M), Tris buffer (pH=8.0), HEPES buffer (pH=7.6), Zonyl FS-300, fluoresceinamine, tris(2-carboxyethyl)phosphine hydrochloride (TCEP), N-(3-Dimethylaminopropyl)-N'-ethylcarbodiimide hydrochloride (EDC), N-hydroxysuccinimide (NHS), Concanavalin A-FITC, anti-mouse IgG-FITC and Protein A were purchased from Sigma-Aldrich. BODIPY FL L-Cystine was purchased from ThermoFisher. Sulfo-Cyanine3 amine was purchased from Lumiprobe. Solvents were purchased from Sigma-Aldrich and used as received. Oligonucleotides were purchased from Integrated DNA Technologies (IDT) and used without further purification.

EDC and NHS were dissolved in PBS at 1M and prepared fresh before each usage. Continuous phase surfactants were prepared as stock solution in PBS, including 0.1 wt % and 0.01 wt % Zonyl FS-300 as the fluorocarbon surfactant and 0.1 wt % Tween 20 as the hydrocarbon surfactant. Hydroxylamine was prepared as 1M solution in PBS to quench unreacted NHS groups at the droplet interface.

NMR spectra were recorded using a Bruker Avance 400 MHz NMR spectrometer and were referenced to the proton resonances resulting from incomplete deuteration of NMR solvent (1H). Confocal microscopy images were taken at room temperature with Nikon AIR Ultra-Fast Spectral Scanning Confocal Microscope.

Emulsion Assay Preparation
Bulk Emulsification for Polydispersed Complex Emulsion Droplets Complex emulsions, composed of equal volumes of diethylbenzene and HFE7500 in hydrocarbon and/or aqueous continuous phase were fabricated using bulk emulsification, which generates polydisperse droplets (20-100 m in diameter). In this process, the hydrocarbon phase (DEB) and fluorocarbon phase (HFE7500) were mixed and heated above the upper critical temperature (around 40° C.) to generate a single droplet phase. This single droplet phase was then dispersed into the hydrocarbon and/or aqueous phase containing the continuous phase surfactants to generate single phase emulsions and upon cooling to room temperature, the DEB and HFE7500 phases separated to generate complex emulsions. The composition of all droplets was identical because every droplet originated from the same single phase.[11]

A generic assay contains 0.5 mL of continuous phase and 20 µL droplet phase.

GA12OH Assay Preparation

To generate emulsion droplets containing GA12OH for interfacial functionalization, GA12OH was dissolved with gentle heat at 10 mg/mL in DEB. Polydispersed complex emulsion droplets were fabricated via bulk emulsification described above with 0.01 wt % Zonyl as the continuous phase surfactant. 25 µL of EDC solution was added to the emulsion and reacted for 15 min followed by addition of 25 µL of NHS solution. The reaction was set at room temperature for 1 h on a rocker (Rocker II from Boekel Scientific). The resulting assay is in equivalent to a GA12-NHS assay.

GA12-NHS Assay Preparation and Fluoresceinamine Functionalization

GA12-NHS was dissolved at 10 mg/mL in DEB. Trifluoroethanol was added at 10% in volume to the hydrocarbon and fluorocarbon mixture to decrease the mixing temperature. A mixture of 0.1 wt % Zonyl:0.1 wt % Tween 1:1 (v/v) was used as the continuous phase to increase the hydrocarbon-water surface area for bioconjugation. After emulsification, the continuous phase was exchanged twice with the same mixture of 0.1 wt % Zonyl:0.1 wt % Tween 1:1 (v/v) to remove the trifluoroethanol from the emulsion assay. Fluoresceinamine was prepared as 0.5 mg/mL solution in PBS.

25 µL of the fluoresceinamine solution was added to the GA12-NHS assay and reacted at room temperature overnight on a rocker. The continuous phase was washed 5 times after reaction to remove the excess amount of dye before imaging.

Sulfo-Cyanine 3 amine was prepared as 1 mg/mL 1 solution in PBS. 25 µL of the Sulfo-Cyanine 3 amine solution was added to the GA12-NHS assay. The reaction was carried out overnight at room temperature. Two vials containing different dye functionalized droplets were combined together. The mixture was settled for 48 h before imaging.

GA16-MA Assay Preparation and BODIPY-FL-Cysteine Functionalization

GA16-MA was dissolved at 10 mg/mL in DEB and the assay was prepared using the same method as described for the GA12-NHS assay.

BODIPY-FL-Cysteine was first dissolved in PBS at 1 mg/mL and activated with TCEP. The activated dye solution become bright green within 15 min and 25 µL of the activated dye solution was added to the GA16-MA assay. The continuous phase was washed 5 times after overnight reaction to remove excess amount of dye before imaging.

Protein A Functionalization and IgG Detection

Protein A was dissolved at 0.5 mg/mL in PBS buffer. 25 µL of the Protein A solution was added to a GA12-NHS assay and reacted overnight at room temperature on a rocker. The reaction was stopped with 25 µL of hydroxylamine solution to quench any unreacted NHS groups at the droplet surface. The continuous phase was washed with surfactant solution for three times. 25 µL anti-mouse IgG with FITC label from Sigma-Aldrich was added to the Protein A functionalized assay and reacted for 2 h. The continuous phase was then washed with surfactant solution for five times to remove unreacted IgG before imaging.

Oligonucleotide Functionalization

GA12-NHS assay was prepared as described in the previous section. 3 µL of oligonucleotide P1 with a sequence of 5'-NH$_2$—(CH$_2$)$_6$-TTT TTT T AGA GTT GAG CAT-3' (SEQ ID NO: 1) at 2 mM in PBS solution was added in the continuous phase. The conjugation reaction was carried out overnight at room temperature. The reaction was quenched with addition of 100 µL of 1M Tris buffer solution. 3 µL of complementary strand of oligonucleotide P2 with a sequence of FAM-5'-TTT TTT T ATG CTC AAC TCT-3' (SEQ ID NO: 2) at 1 mM in PBS solution was added. The solution was heated up to 50° C. and held for 15 min using a water bath. The emulsion assay was then allowed to cool down to room temperature and the continuous phase was washed 5 times to remove the unreacted oligonucleotide.

Carbohydrate Functionalization

GA12-NHS assay was prepared as described in the previous section. Man-C5-NH2 was dissolved in PBS at 1 mg/ml. 50 µL of Man-5-NH2 solution was added in the continuous phase and reacted overnight at room temperature. The reaction was quenched with 100 µL of 1M Tris buffer solution. 10 µL of 1 mg/mL FITC labelled Con A in HEPES buffer was added and reacted for 30 min. The solution was then washed 5 times to remove the excess lectin before imaging.

1. Synthetic Procedures 1.1. Synthesis of GA12OH

Figure 23A:
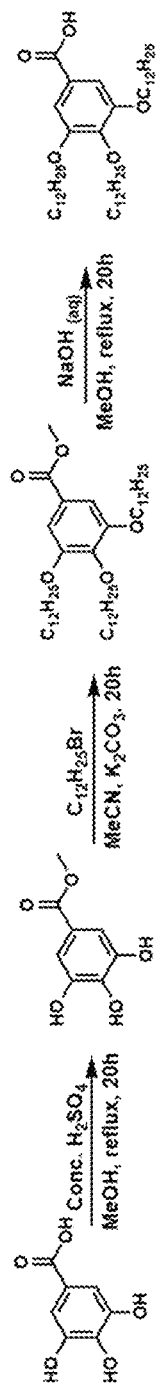
FIG. 23A shows a synthetic procedure for GA12OH, according to one set of embodiments.

GA12OH was synthesized as shown in FIG. 23A.

1.2. Synthesis of GA12-NHS

Figure 23B:
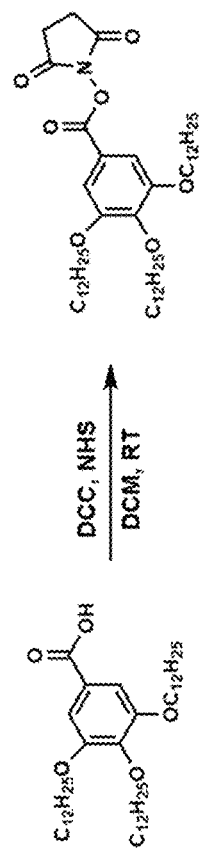
FIG. 23B shows a synthetic procedure for GA12-NHS, according to one set of embodiments.

GA12-NHS was synthesized as shown in FIG. 23B. GA12OH (1 g, 1.3 mmol), N,N'-dicyclohexylcarbodiimide (0.347 g, 1.7 mmol) and N-hydroxysuccinimide (0.194 g, 1.7 mmol) were dissolved in 50 mL dichloromethane followed by addition of catalytic amount of DMF. The solution was stirred at room temperature overnight. The crude material was purified by silica gel column chromatography using hexane and EtOAc (4/1).

$^1$H NMR (400 MHz, CDCl3): δ 7.32 (s, 2H), 4.07-3.99 (m, 6H), 2.92-2.89 (m, 4H), 1.85-1.78 (m, 4H), 1.75-1.70 (m, 2H), 1.50-1.43 (m, 6H), 1.36-1.26 (m, 48H), 0.89-0.86 (m, 9H)

1.3 Synthesis of GA16-MA

Figure 23C:
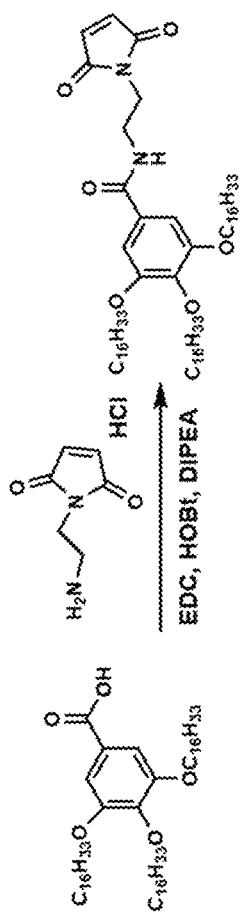
FIG. 23C shows a synthetic procedure for GA16-MA, according to one set of embodiments.

GA16OH was used for the synthesis of GA16-MA to increase the solubility in hydrocarbon (see FIG. 23C). To a solution of GA16OH (0.5 g, 0.60 mmol) in dichloromethane (10 mL) was added N,N-diisopropylethylamine (0.85 ml, 6 mmol). The mixture was treated with N-(3-dimethylaminopropyl)-N'-ethylcarbodiimide hydrochloride (0.19 g, 1 mmol), 1-hydroxybenzotriazole (0.13 g, 1 mmol) and N-(2-aminoethyl)maleimide hydrochloride (0.116 g, 0.66 mmol) and stirred at room temperature overnight. The reaction was quenched with droplet of HCl (1M) solution and washed with water for three times. The organic portion was dried over Na$_2$SO$_4$. The crude material was purified by silica gel column chromatography using hexane and EtOAc (4/1 to 3/1).

Example 7

The following example generally relates to detection of *Listeria* via agglutination of droplets, according to some embodiments.

1. Janus Emulsions for Biosensing of *Listeria*

This example describes the combination of in situ functionalization of Janus emulsions using reactive surfactant polymers to attach biorecognition groups including antibodies. The particles could readily agglutinate by interaction with target analytes and the agglutination events could be quantified using image analysis. The latter method could be used to make sensors using a magnifying lens and a smartphone camera. The image processing computational package could be performed on the smartphone or remotely by transmittal of the image. This method could allow for the detection of biological species with minimal hardware and has broad applicability in food and beverage production, as well as water quality monitoring, and health care.

Dynamic complex droplets could afford a novel and general platform for biosensing applications that may provide the suitable combination of speed, portability, and cost-effectiveness. As disclosed herein, it was demonstrated that complex droplets comprising equal volume of organic and fluorocarbon oils in Janus morphology could be used to detect biomolecules with minimal power consumptions. Specifically, upon exposure to the targeted analyte with multivalence interactions, the Janus droplets agglutinated to form clusters that inherently induced optical scattering. The degree of opacity could be measured both qualitatively and quantitatively, e.g., using image processing algorithm. This transduction mechanism could be further coupled with suitable recognition units (e.g., antibodies) to provide a generalizable sensor for the biomolecules of interest. An example of such a biomolecule is *Listeria*.

*Listeria* is a genus of gram-positive bacteria, which is responsible for listeriosis, a potentially lethal illness. As a foodborne bacterial illness, listeriosis could be serious problem for certain populations, e.g., pregnant women or people with impaired immune systems. Therefore, there was a need to develop an inexpensive, fast and sensitive biosensors for *listeria* detection.

A polymer surfactant was designed to be applied at the interface of continuous phase and hydrocarbon of droplets to allow for sensing of *Listeria* in hydrocarbon and/or aqueous solutions. *Listeria* antibodies was conjugated with the polymer surfactant on the droplets chemically such that the functionalized droplets could be used for detecting *Listeria*. When *Listeria* was present in the solution, the *Listeria* antibody on the droplets would bind to *Listeria*, which would lead to the formation of agglutinations of droplets since one *Listeria* could bind to multiple antibodies. By recording the morphology of droplets under microscope, the presence or absence of *Listeria* could be detected in the solution. Higher concentration of *Listeria* would result in a higher degree of agglutination of droplets. No agglutination would indicate that little to no *Listeria* existed in the solution.

2. Post Droplet Functionalization 2.1 Synthesis of Polymer Surfactant

Figure 24A:
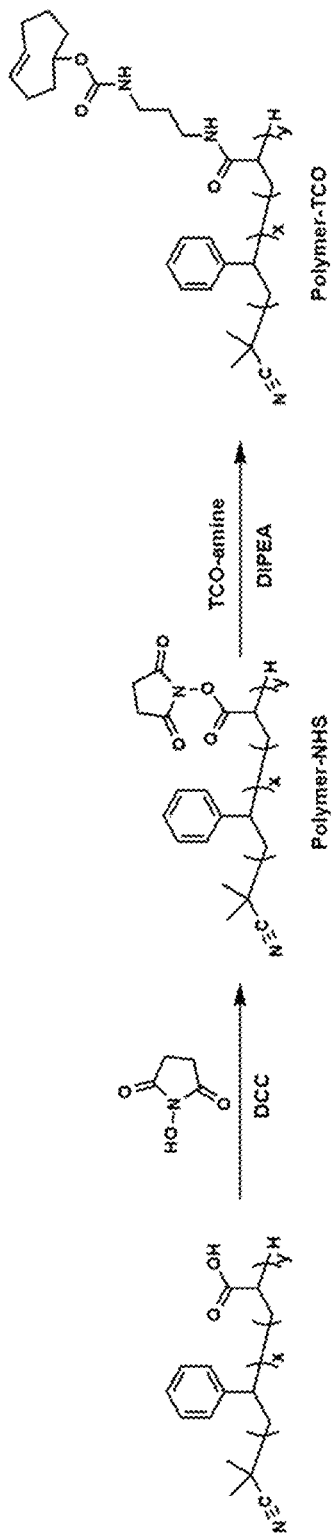
FIG. 24A shows a synthetic procedure for polymer-TCO, according to one set of embodiments.

All chemical reagents and solvents were purchased from Sigma-Aldrich, ThermoFisher or TCI without further purification. The synthesis scheme of polymer surfactant, i.e., polymer-TCO, is shown in FIG. 24A. To synthesize the polymer surfactant, 100 mg of polystyrene-block-poly (acrylic acid) was dissolved in 20 mL of DCM. 72 mg of N-hydroxysuccinimide (NHS) and 120 mg of N,N'-Dicyclohexylcarbodiimide (DCC) were added into the solution and stirred overnight at room temperature. The reaction mixture was then precipitated into 150 mL water. The product (Polymer-TCO) was washed with methanol, acetone and hexane after filtration.

2.2 Emulsion Assay Preparation

Figure 24B:
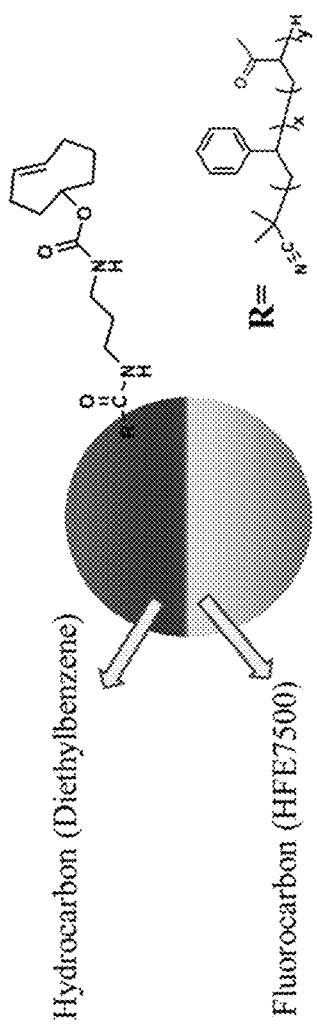
FIG. 24B shows an illustration of Janus droplet with polymer-TCO, according to one set of embodiments.

Bulk emulsification was used to fabricate complex emulsions that composed equal volumes of diethylbenzene and HFE7500 in hydrocarbon and/or aqueous continuous phase. The hydrocarbon phase (diethylbenzene, DEB) and fluorocarbon phase (HFE7500) were mixed and heated above a temperature of about 40° C. These polydispersed complex emulsions were readily produced in bulk by shaking warm DEB-HEF7500 liquid in a surfactant solution comprising a mixture of 0.1 wt % Zonyl:0.1 wt % Tween 20 1:1 (v/v). A generic assay contained 500 µL of continuous phase and 20 L of droplet phase. To generate emulsion droplets containing Polymer-TCO for interfacial functionalization, Polymer-TCO was dissolved at 1 mg/mL in the hydrocarbon phase DEB (FIG. 24B). Polydispersed complex emulsion droplets were fabricated by bulk emulsification as described previously.

Monodispersed droplets were fabricated by a microfluidic device at slightly above 40° C. Continuous phase (1.0 wt % tween 20) and the mixture of hydrocarbon phase (containing 1 mg/mL Polymer-TCO) and fluorocarbon phase were pumped into a chip with a diameter of 50 m to produce monodispersed droplets with a diameter of 50 µm. The monodispersed droplets were then washed with the mixture of 0.1 wt % Zonyl: 0.1 wt % Tween 20 1:1 (v/v) solution three times to produce Janus droplets.

2.3 Bioconjugation at the Interface of Droplets

Figure 24C:
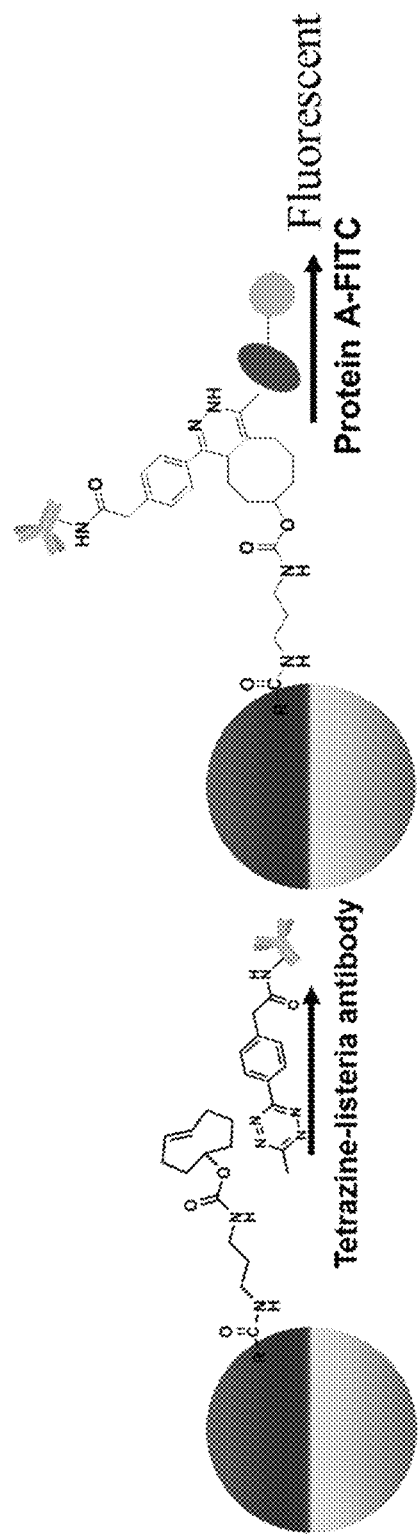
FIG. 24C shows a synthetic procedure for post droplet functionalization, according to one set of embodiments.

The post droplet functionalization with *Listeria* antibody is illustrated in FIG. 24C. As shown, 20 µL of droplet was transferred into a vial containing 0.5 mL of 0.1 wt % Zonyl:0.1 wt % Tween 20 1:1 (v/v) solution. 30 uL of tetrazine-*listeria* antibody (1 mg/mL) was added to the continuous phase and was stirred on a rocker overnight to allow the completion of trans-cyclooctene tetrazine bioconjugation. The unreacted tetrazine-*Listeria* antibody was removed by exchanging the continuous phase with 0.1 wt % Zonyl:0.1 wt % Tween 20 1:1 (v/v) solution for three times.

Figure 25:
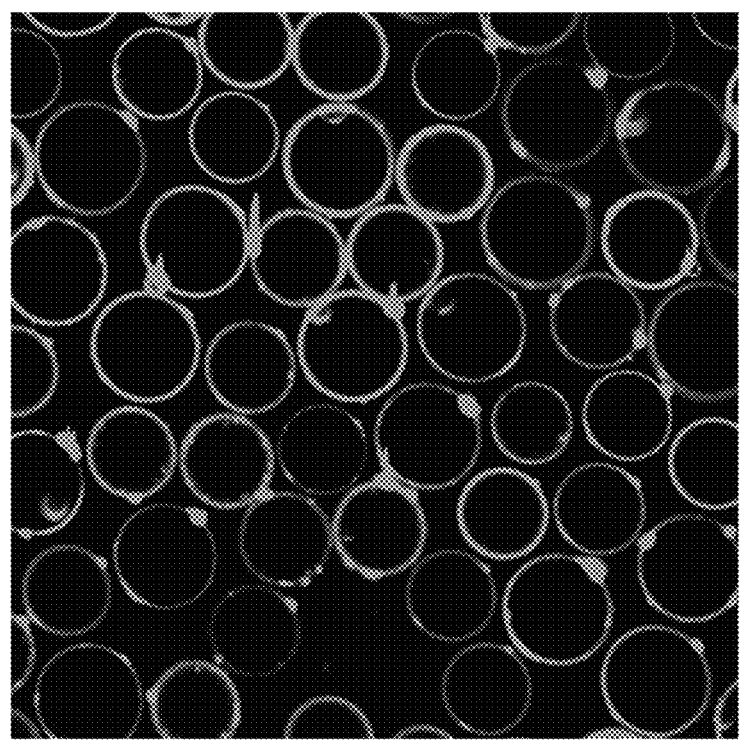
FIG. 25 shows confocal images of droplets showing successful bioconjugation of *Listeria* antibody at the interface of droplets, according to one set of embodiments.

To confirm the bioconjugation of *Listeria* antibody, after the bioconjugation step, 5 uL of protein A-FITC (1 mg/mL) was added to the continuous phase and stirred for 2 hours on a rocker. The un-binded protein A-FITC was removed by exchanging the continuous phase with 0.1 wt % Zonyl:0.1 wt % Tween 20 1:1 (v/v) solution three times. Fluorescent confocal images were taken with Zeiss 700 confocal Fluorescence Microscopy (FIG. 25). The fluorescence at the interface indicated successful bioconjugation of *Listeria* antibody.

3. Sensing of *Listeria* and Agglutination Protocols 3.1 Sensing of *Listeria*

Figure 26:
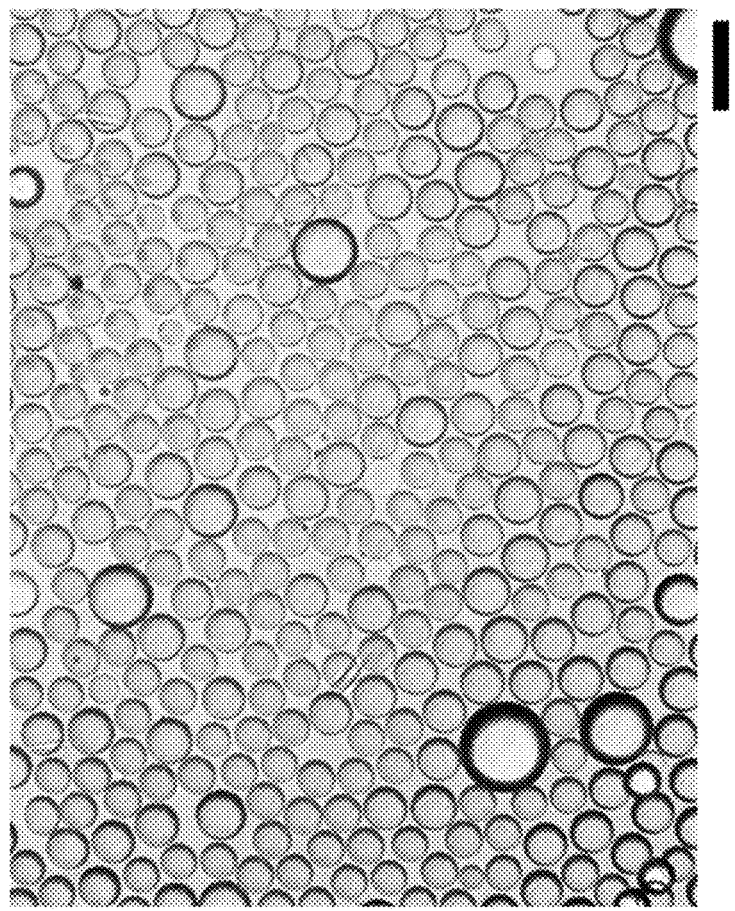
FIG. 26 shows optical images of droplets before the addition of *Listeria*, according to one set of embodiments.
Figure 27:
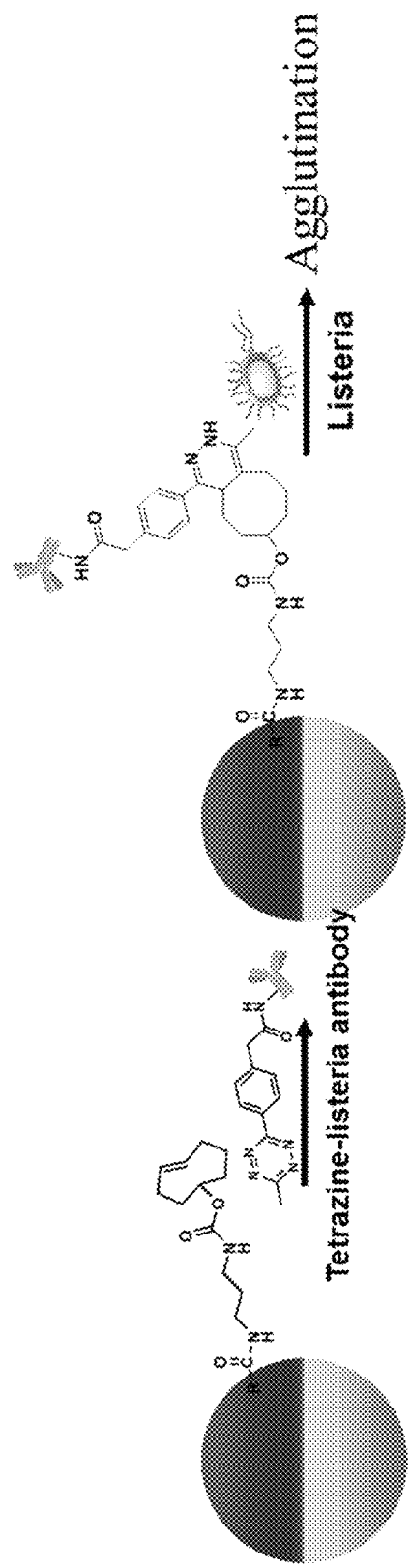
FIG. 27 shows a procedure for sensing *Listeria* using Janus droplets, according to one set of embodiments.

The conjugation of tetrazine *Listeria* antibody to Polymer-TCO via trans-cyclooctene tetrazine click chemistry had been experimentally validated. FIG. 26 shows an optical image of the droplets after bioconjugation with tetrazine *Listeria* antibody. To sense *Listeria*, heat killed *Listeria monocytogenes* (HKLM) were introduced into the continuous phase at different concentrations and the mixture was stirred on a rocker for 2 hours (FIG. 27). As shown in FIG. 27, the presence of *Listeria* would induce agglutination of the droplets.

Figures 28A, 28B, 28C, 28D, 28E, 28F:
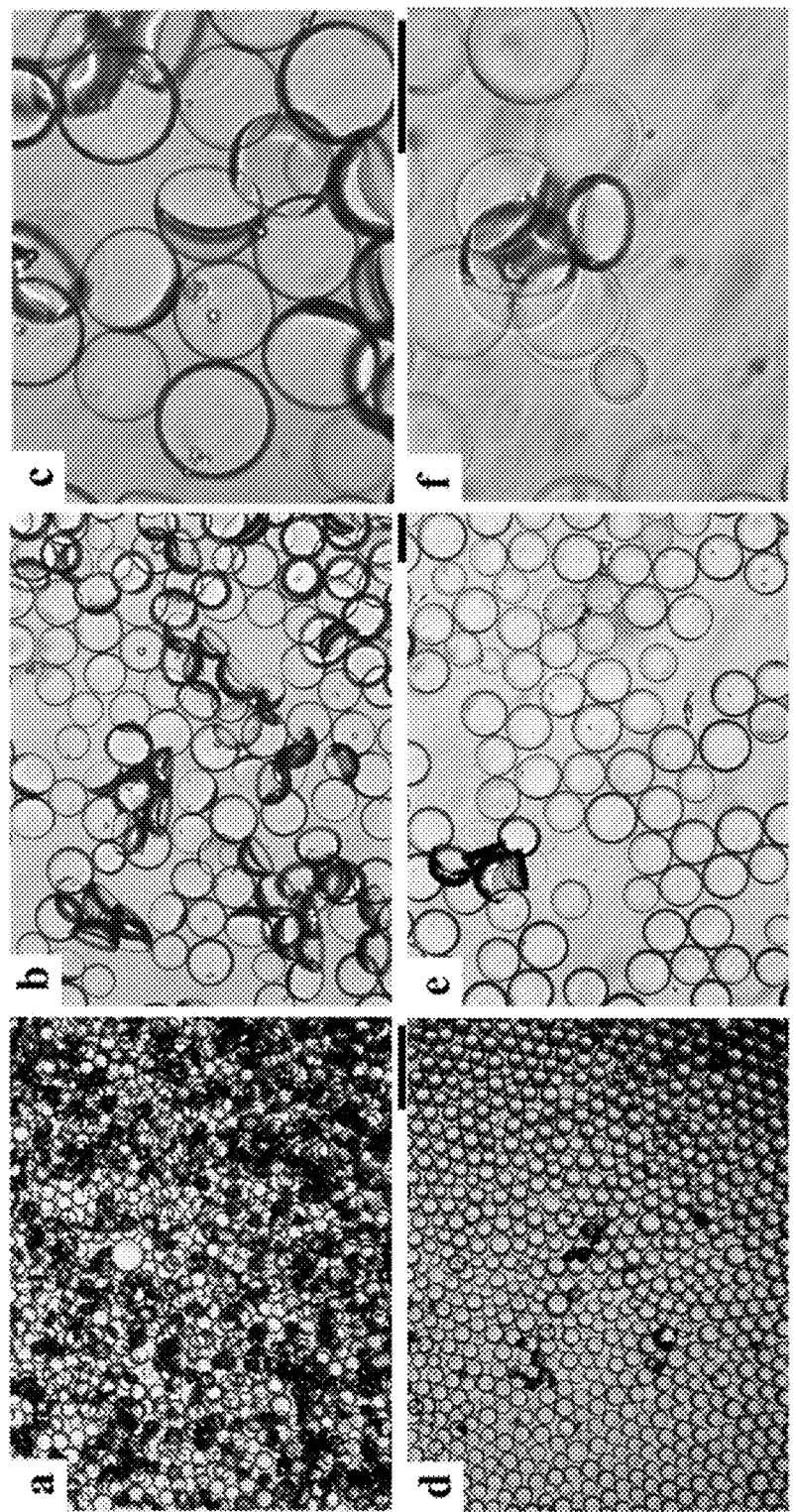
FIGS. 28A-28F show optical images of droplets after addition of *Listeria*, according to one set of embodiments.

10 µL of droplets was added to 1 mL of 0.1 wt % Zonyl:0.1 wt % Tween 20 1:1 (v/v) solution in a petri dish. An inverted microscope was used to record the agglutination of droplets after the addition of *Listeria*. Optical images of droplets after addition of *Listeria* at different concentrations were acquired after 2 hours. As shown, with the addition of *Listeria* at $10^7$ CFU/ml (FIGS. 28A-28C) or 100 CFU/mL (FIGS. 28D-28F), the formation of droplet agglutinations was observed at both concentrations. More agglutination was observed at $10^7$ CFU/mL of *Listeria* and less agglutination was observed at 100 CFU/mL.

3.2 Quantification of the Agglutinated Droplets

Figure 29:
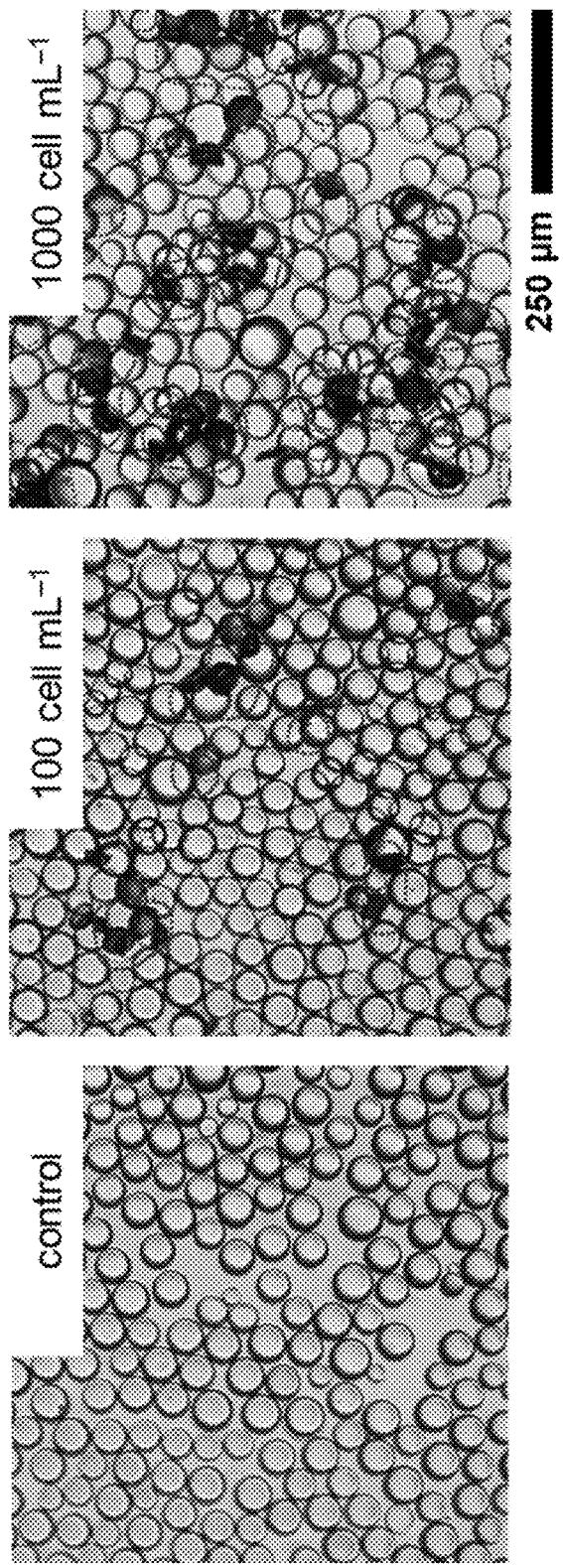
FIG. 29 shows optical images of droplets after addition of various concentrations of *Listeria* and the quantification of agglutination thereof, according to one set of embodiments. Scale bar in 250 μm.
Figure 30:
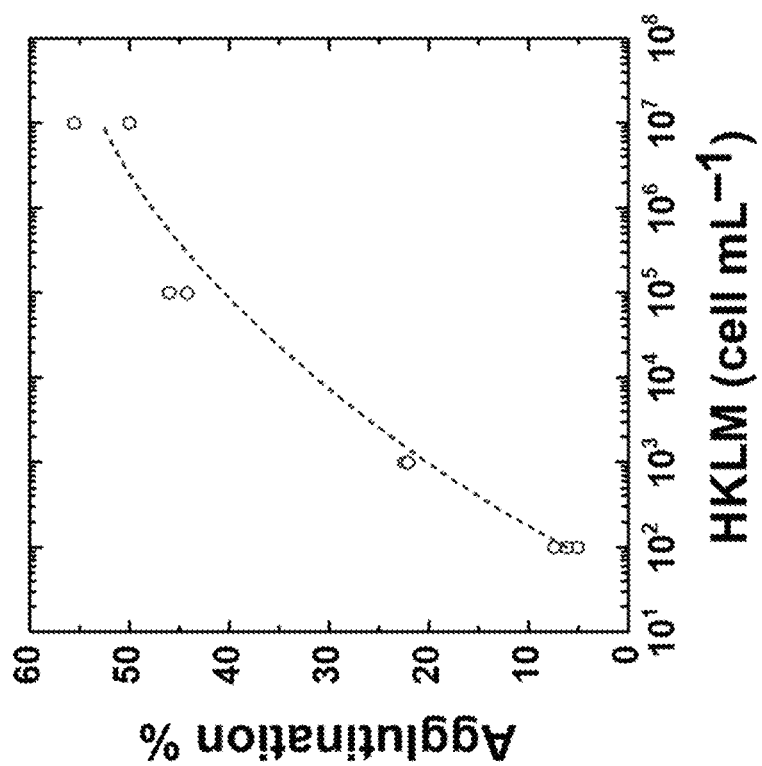
FIG. 30 shows a graph showing agglutination level of droplets as a function of heat killed *Listeria monocytogenes* (HKLM), according to one set of embodiments.
Figure 31:
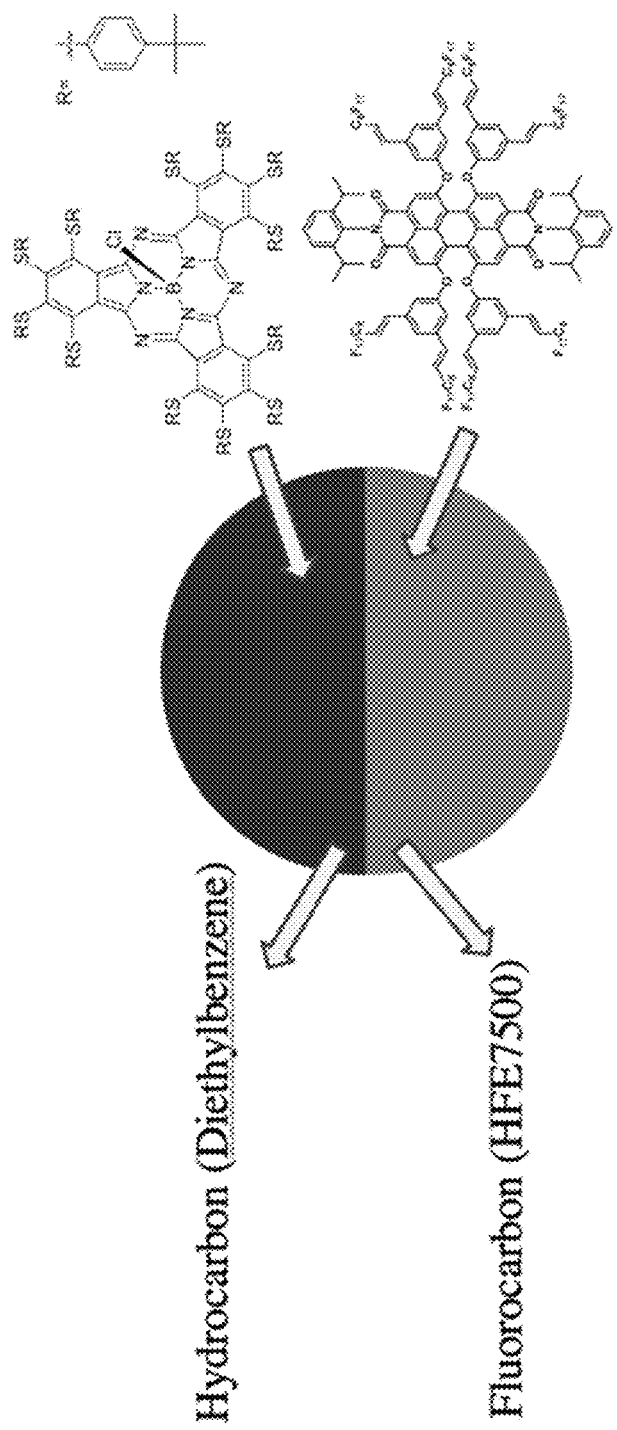
FIG. 31 shows a Janus droplet having a non-emissive sub-phthalocyanine dye in the organic phase and an emissive perylene dye in the fluorocarbon phase, according to one set of embodiments.

Quantification of the agglutinated droplets was performed using an in-house MATLAB code for image analysis. The image processing code first pre-processed the optical micrographs by transforming these micrographs into greyscale images, and then measured the average diameter of the droplets within the images. To locate the agglutinated areas, the program first used an adaptive thresholding algorithm, which optimized each set of images based on the original image contrast, and distinguished the darker regions where multiple droplets are tilted off their natural axes (as shown in FIG. 29). FIG. 29 shows optical images of droplets after addition of 0, 100 CFU/mL or 1000 CFU/mL of *Listeria* for 2 hours; these images were subsequently used in a processing algorithm for quantification of agglutination level. Using the average diameter and the area of the darker region, the percentage of the agglutinated area in each image was then calculated and plotted as a function of heat killed *Listeria monocytogenes* (HKLM) concentration (FIG. 30).

4. Emissive Methods for Enhanced Performance

The methods just discussed made use of light transmission through Janus droplets and the modulation thereof by agglutination. The use of emissive signals could be advantageous provided that the background could be made to be minimal, or ideally zero. A different method was demonstrated herein that made use of the placement of dyes into the different phases of a Janus droplet. Two different dyes having orthogonal solubilities were used. For example, while one of the dyes would be exclusively soluble in the organic phase, the other dye would be soluble in the fluorocarbon phase, as indicated in FIG. 3I.

Figure 3I:
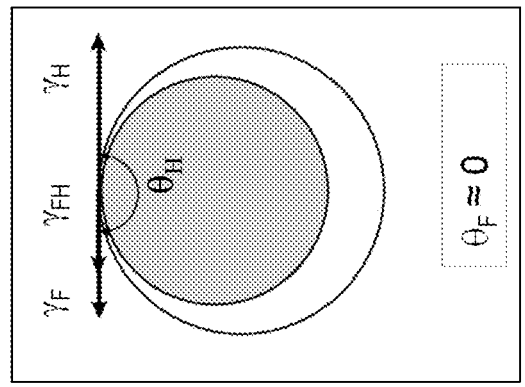
FIG. 3I is a schematic of the effect of interfacial tensions on the configuration of a complex droplet where encapsulation of a hydrocarbon (H) by a fluorocarbon (F) in water (W) is favored, according to one set of embodiments.
Figure 3H:
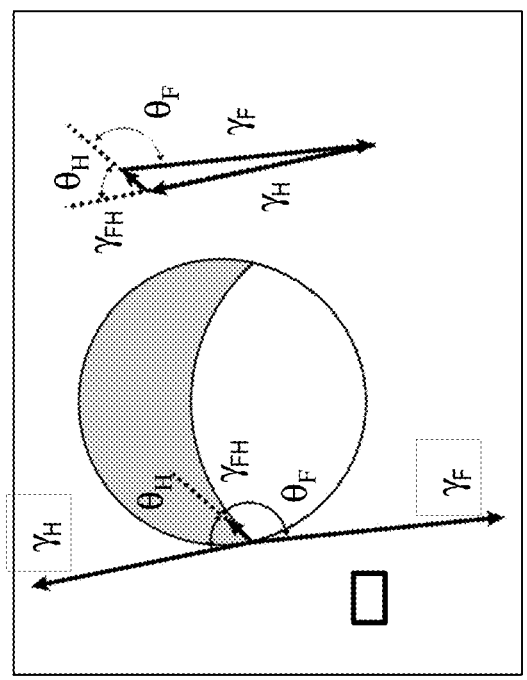
FIG. 3H is a schematic of the effect of interfacial tensions on the configuration of a complex droplet where the formation of a Janus droplet of a fluorocarbon (F) and a hydrocarbon (H) in water (W) is favored, according to one set of embodiments.
Figure 3G:
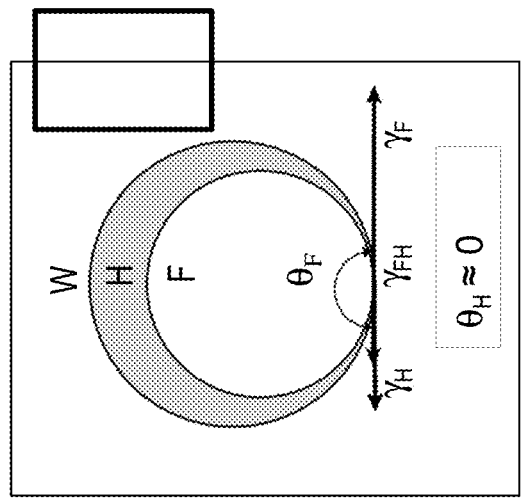
FIG. 3G is a schematic of the effect of interfacial tensions on the configuration of a complex droplet where encapsulation of a fluorocarbon (F) by a hydrocarbon (H) in water (W) is favored, according to one set of embodiments.

FIG. 3I shows a Janus droplet having a non-emissive sub-phthalocyanine dye in the organic phase and an emissive perylene dye in the fluorocarbon phase. The dyes were mostly insoluble in the phases that they were not shown in. For example, the sub-phthalocyanine was not soluble in water or the fluorocarbon phase and the emissive perylene dye was soluble in the fluorocarbon phase but not in the diethylbenzene or water phases.

Theoretically, for Janus droplets aligned normal to a surface by gravity, the application of a magnetic field, electrostatically, or by chemical potential optically excited, would have negligible emission in the direction normal to the surface. This state would be the state observed in the absence of an analyte. By matching the absorbance characteristics of the dye in the top phase of the Janus droplets, which in this case would be diethylbenzene (as shown in FIG. 3I), light could be prevented from transmitting through the droplet from the excitation source or from emitted light from the dye in the fluorocarbon phases of the Janus droplets. In this latter case, a precise matching of the absorbance of the non-emissive hydrocarbon dye and the emissive fluorocarbon dye was necessary. This was the case for the dyes shown in FIG. 3I. However, the dyes were not limited to these dyes only, other dyes could also be used.

Figure 32:
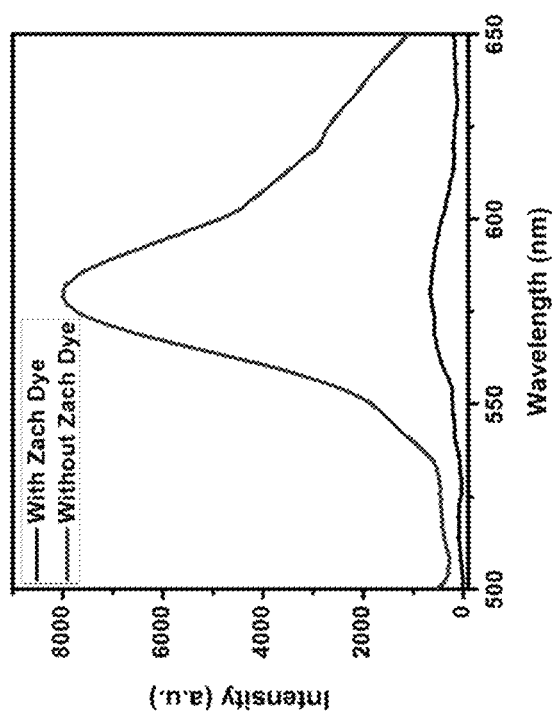
FIG. 32 shows a graph of an emission spectrum from Janus droplets aligned normal on a surface with or without the sub-phthalocyanine (Zach) dye in the organic phase, according to one set of embodiments.

When the aligned droplets possessed these characteristics described herein, minimal emission would be observed when monitoring the emissivity at about 580 nm and excitation at 350 nm. The sub-phthalocyanine dye would absorb at 350 nm and 580 nm, thereby absorbing the excitation light and any light emitted from the perylene dye in the fluorocarbon phase. The sub-phthalocyanine served as a filter that minimized emission from being generated or observed in the aligned Janus droplets. As shown later, this dye had large absorptions that allowed it to be a highly effective filter. The data showing the filtering effect of the sub-phthalocyanine dye (i.e., Zach dye) is illustrated in FIG. 32. FIG. 32 shows emission from Janus droplets aligned normal on a surface that either had the sub-phthalocyanine dye (i.e., Zach dye) or lack the sub-phthalocyanine (i.e., Zach dye) in the organic phase. Both droplets had the perylene dye as shown in FIG. 3I in the fluorocarbon phase.

Agglutination of droplets would result in a tilting of the droplets which would create a path for excitation light and emitted light, such that the light would not have to pass through the sub-phthalocyanine filter layer in the droplet. Hence, the action of tilting the dyes from their surface normal orientation as a result of agglutination would produce an emission signal normal to an array of droplets. This could be monitored by the use of a detector such as an image plate or a fiber optic. The excitation could be delivered from the top, such as shown in the fiber optic assembly in FIG. 33. Alternatively, the excitation could be accomplished at different angles or even by using the support upon which the droplets were aligned as a waveguide. In the latter case, the excitation could be accomplished by the use of ambient light. This latter feature could allow for a visual detection that would not require power. The fiber optic assembly in FIG. 33 would allow for excitation and monitoring of fluorescence coming from the dyed emulsions.

Figure 33:
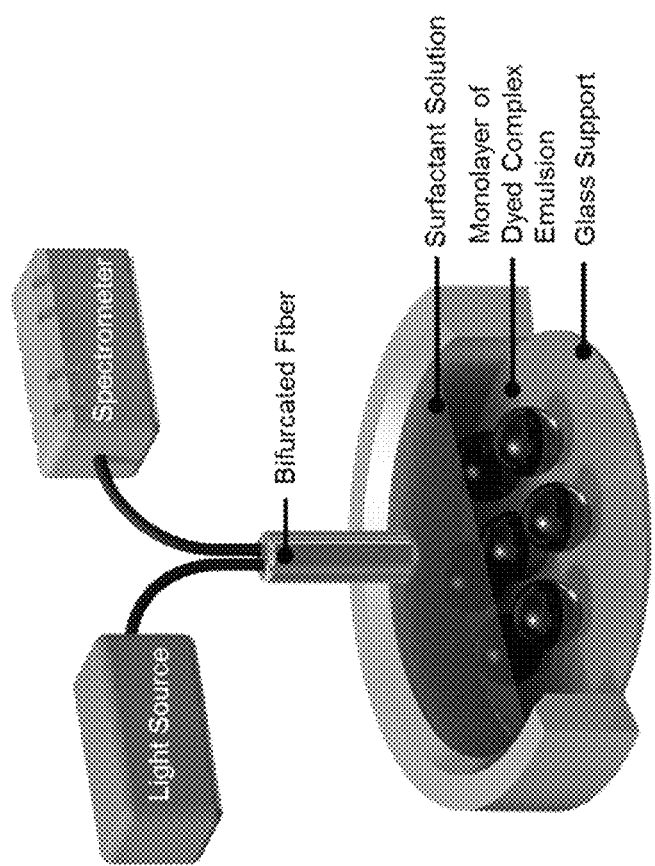
FIG. 33 shows a fiber optic assembly for excitation and monitoring fluorescence of dyed emulsion, according to one set of embodiments.
Figures 34A, 34B:
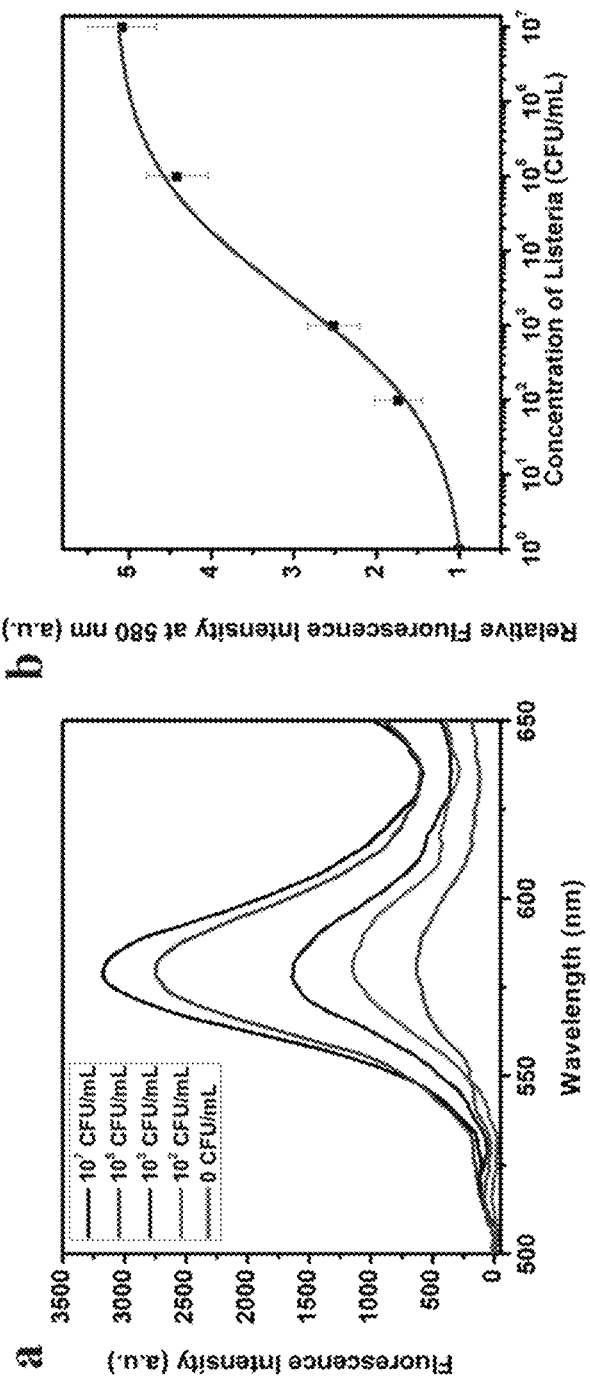
FIGS. 34A-34B show fluorescence spectra of droplets after addition of heat killed *Listeria*, according to one set of embodiments.

Droplets functionalized with the dyes shown in FIG. 3I and the antibodies shown in FIG. 27 were subjected to different concentrations of heat killed *Listeria*. Measurements were performed using the device in FIG. 33 and the fluorescence spectra were reported in FIG. 34A-34B. FIG. 34A shows the emission fluorescence spectra (λex=350 nm) of droplet after addition of heat killed *Listeria* at different concentrations using the measurement scheme shown in FIG. 33, and FIG. 34B shows a calibration curve for this measurement that depicted a correlation between concentration of heat killed *listeria* and relative fluorescence intensity at 580 nm. As shown in FIG. 34B, the limits of detection are less than 100 CFU/mL.

Figures 35A, 35B:
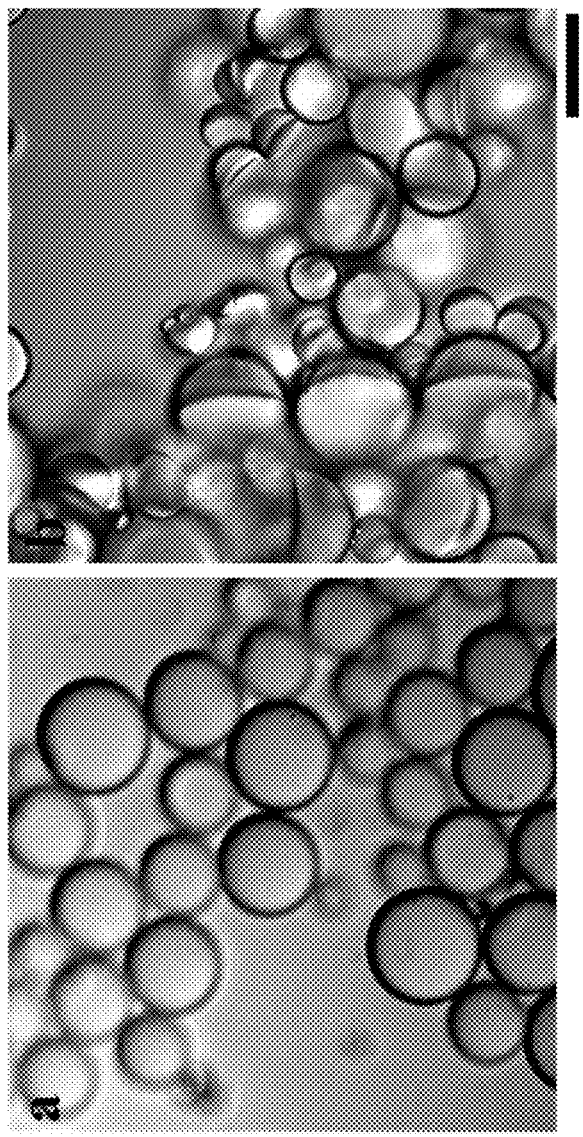
FIGS. 35A-35B show confocal microscope image of droplets containing dyes with and without agglutination, according to one set of embodiments.

The use of emissive dyes could also be used with image analysis and in this case could be used to create more robust methods. Specifically, the appearance of a new emission could be used to differentiate overlapping droplets or foreign objects that could otherwise be mistaken by image analysis as agglutination sites. This feature was illustrated by the images of droplets shown in FIGS. 35A-35B. As shown, FIG. 35 shows confocal microscope images (scale bar=50 m) of non-agglutinated droplets (without addition of *listeria*) (FIG. 35A), and agglutinated droplets (with the addition of *listeria* at $10^7$ CFU/mL) (FIG. 35B). The droplets comprised Zach dye (subphthalocyanine) in the hydrocarbon phase and perylene dye (F-PBI) in the fluorocarbon phase. As shown in FIG. 35B, the agglutinated droplets could readily be observed by the red perylene emission.

5. Two-Dye System with Opposite Phase Preference

Figure 36:
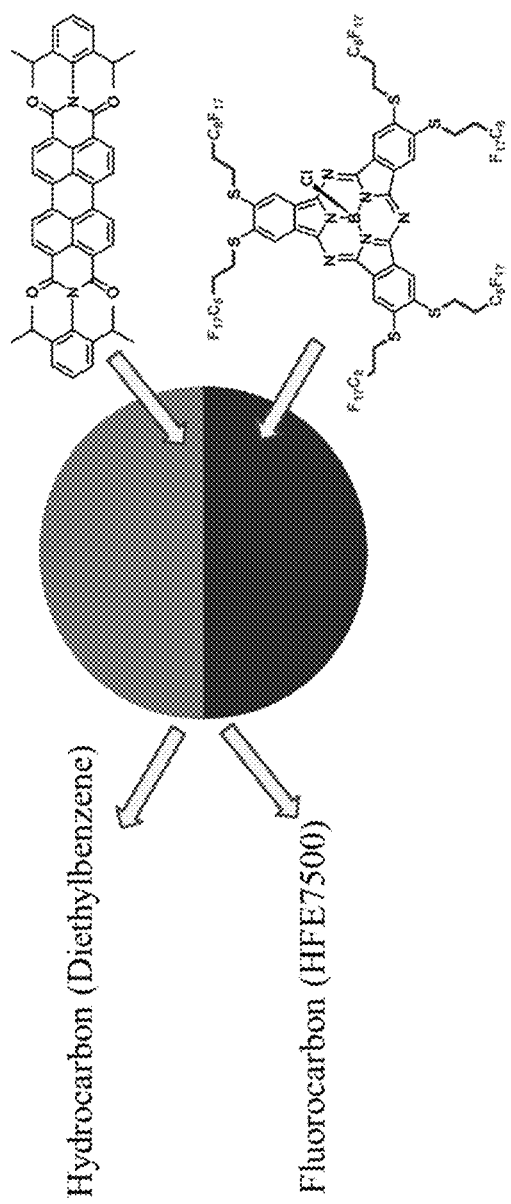
FIG. 36 shows a Janus droplet having a non-emissive F-SubPC dye in the fluorocarbon phase and an emissive Lumogen F Orange 240 dye in the hydrocarbon phase, according to one set of embodiments.

It should be noted that the arrangement of the dyes in the droplets needed not be in the form shown in FIG. 3I. For example, it could be possible to design dyes having the same spectral characteristics that have opposite phase preferences. For example, the sub-phthalocyanine could prefer the fluorocarbon phase and the perylene could favor the organic phase (as shown in FIG. 36). For instance, FIG. 36 shows a Janus droplet having a non-emissive F-SubPC dye in the fluorocarbon phase and an emissive Lumogen F Orange 240 dye in the hydrocarbon phase. The dyes were largely insoluble in the phases that they were not shown in. For example, the F-SubPC was not soluble in water or the hydrocarbon phase and the emissive Lumogen F Orange 240 dye was soluble in the hydrocarbon phase but not in the fluorocarbon phase or water phases.

This scheme could be useful in certain situations. For example, if the sample were excited from the bottom rather than from the top as shown in FIG. 33, then it would be desirable to have the filter dye (sub-phthalocyanine) in the fluorocarbon phase and the perylene in the organic phase. When the dyes became aligned, the sub-phthalocyanine dye would prevent light coming from the bottom to reach the perylene and a similar behavior to what was shown in FIGS. 34A-34B would be observed. An advantage of this method was that it could be performed in cases where the samples were turbid and optically absorbing, because the light path would be minimized through the solution as the droplets were organized at the surface.

6. Methods of Synthesis and Characterization

Unless stated otherwise all chemicals were of reagent grade and used as received. All air-sensitive and water-sensitive synthetic manipulations were performed in oven-dried glassware under an argon atmosphere using standard Schlenk techniques.

All the droplets were composed of diethylbenzene (hydrocarbon) and HFE7500 (fluorocarbon). Subphthalocyanine was dissolved in diethylbenzene at concentration of 1 mM and the perylene dye, F-PBI, was dissolved in HFE7500 at concentration of 0.1 mM. Poly-TCO was dissolved in diethylbenzene at concentration of 1 mg/mL. The continuous hydrocarbon and/or aqueous phase was a mixture of 0.1 wt % Zonyl:0.1 wt % Tween 20 1:1 (v/v)

NMR spectra were recorded with a Bruker Ascend-400 (400 MHz) or Ascend-600 (600 MHz) spectrometer. Chemical shifts δ were reported in ppm downfield from tetramethylsilane using the residual solvent signals (CDCl$_3$: $δ_H$ 7.26 ppm, $δ_C$ 77.16 ppm) as an internal reference. For $^1$H NMR, coupling constants J were given in Hz and the resonance multiplicity was described as s (singlet), d (doublet), t (triplet), p (quintet), and m (multiplet). Mass spectra were recorded with a Bruker Autoflex Speed Matrix-Assisted Laser Desorption/Ionization Time-of-Flight (MALDI-TOF) Mass Spectrometer in Reflectron Detection mode. Mass spectra were calibrated using poly(ethylene glycol) of the appropriate mass range as external standards. UV-Vis absorbance spectra were recorded on a Cary 4000 UV-Vis spectrophotometer using a quartz cuvette.

6.1 Experimental Procedure for Synthesis of Sub-Phthalocyanine

Figure 37A:
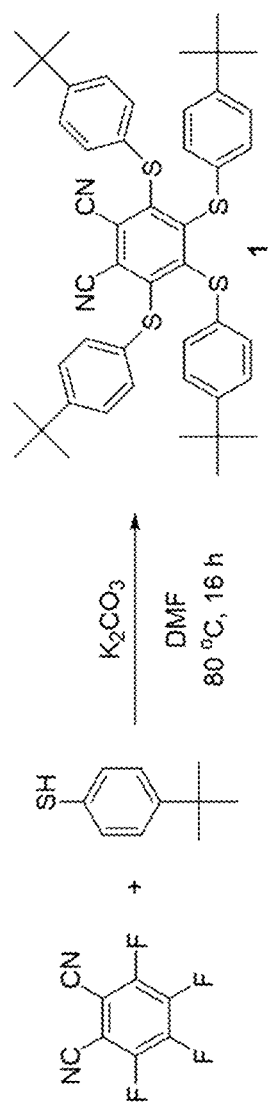
FIG. 37A shows synthetic procedure of 3,4,5,6-tetrakis ((4-(tert-butyl)phenyl)thio)phthalonitrile (1), according to one set of embodiments.
Figure 37B:
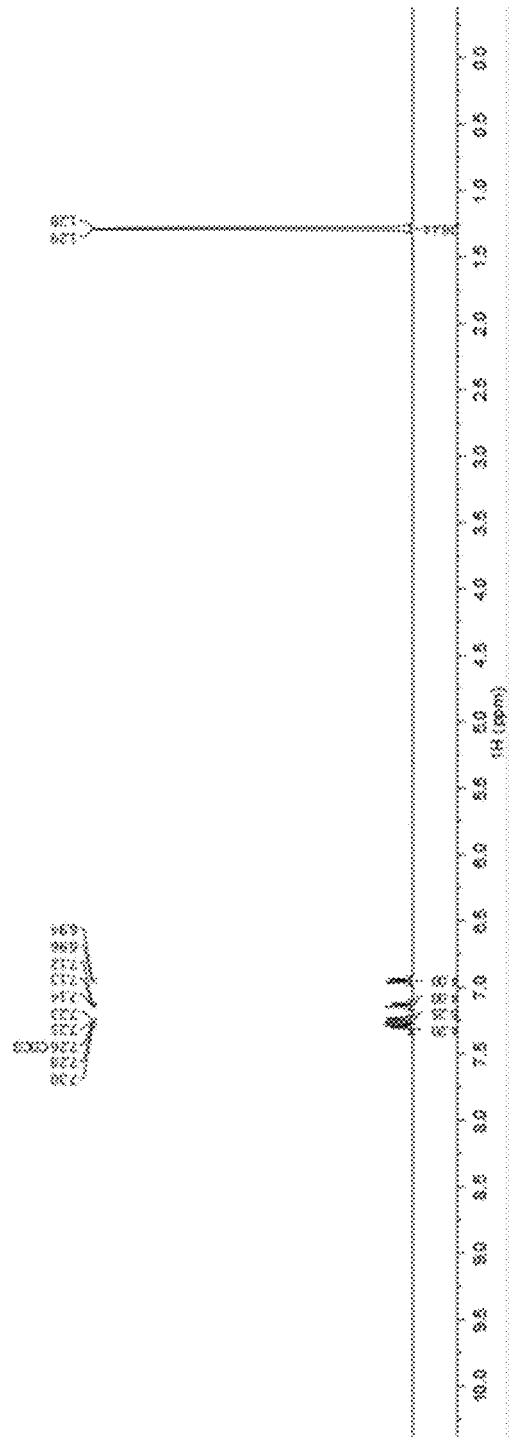
FIGS. 37B-37C show NMR spectra of 3,4,5,6-tetrakis((4-(tert-butyl)phenyl)thio)phthalonitrile (1), according to one set of embodiments.
Figure 37C:
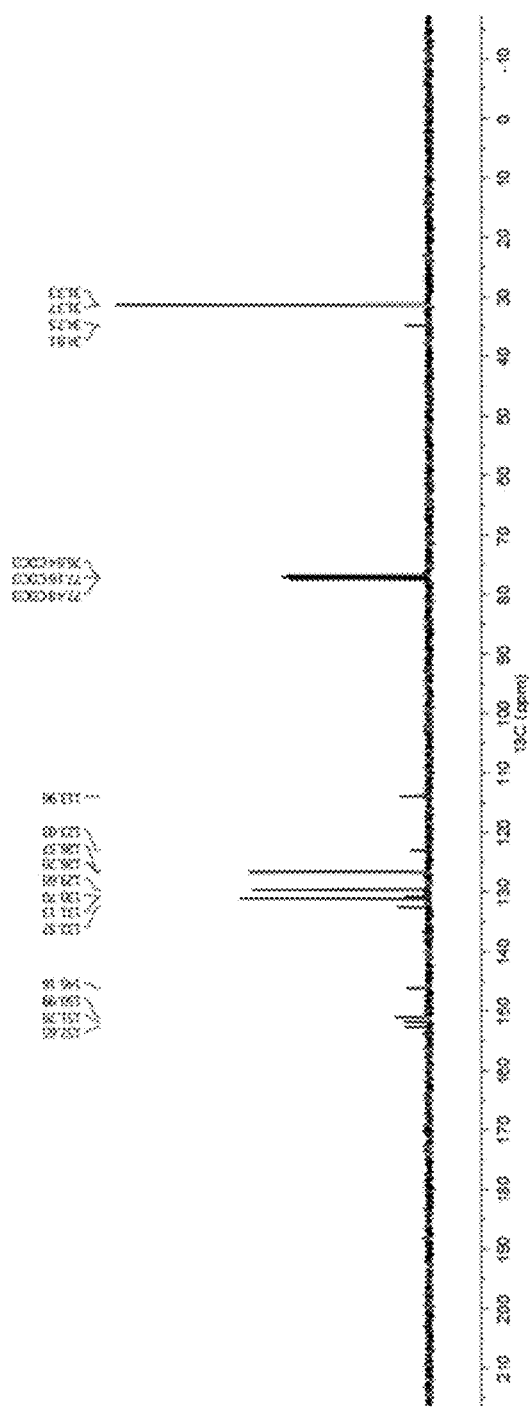

Synthesis of 3,4,5,6-tetrakis((4-(tert-butyl)phenyl)thio) phthalonitrile (1). Synthesis procedure was adapted from Ong, W. J.; Swager, T. M.; *Nature Chemistry* 2018, 10, 1023-1030, which is incorporated herein in its entirety for all purposes. FIG. 37A shows synthesis scheme of 3,4,5,6-tetrakis((4-(tert-butyl)phenyl)thio)phthalonitrile 1. To a 250 mL Schlenk flask with a stirrer containing 3,4,5-tetrafluorophthalonitrile (2.0 g, 10 mmol) under argon, dry DMF (100 mL) and 4-(tert-butyl)benzenethiol (7.1 mL, 41 mmol) were added. Then $K_2CO_3$ (8.3 g, 60 mmol) was added under a flow of argon. The reaction was stirred at 80° C. for 16 hours. The reaction mixture was cooled to room temperature and diluted with water and chloroform. The layers were separated, and the hydrocarbon and/or aqueous layer was extracted twice with chloroform. The combined organic layers were washed four times with water and once with brine, dried over $Mg_2SO_4$, and filtered. The filtrate was concentrated under reduced pressure and purified by recrystallization from hot acetonitrile to yield an orange powder (6.3 g, 81%). FIG. 37B shows $^1H$ NMR spectrum (400 MHz, Chloroform-d) of 3,4,5,6-tetrakis((4-(tert-butyl)phenyl)thio) phthalonitrile 1 with chemical shifts δ 7.29 (d, J=8.1 Hz, 4H), 7.25 (d, J=8.3f Hz, 4H), 7.13 (d, J=8.2 Hz, 4H), 6.95 (d, J=8.1 Hz, 4H), 1.29 (d, J=2.7 Hz, 36H). FIG. 37C shows $^{13}C$ NMR (101 MHz, Chloroform-d) of 3,4,5,6-tetrakis((4-(tert-butyl)phenyl)thio)phthalonitrile 1 with chemical shifts δ 152.65, 151.78, 150.99, 146.16, 132.57, 131.13, 130.70, 129.68, 126.70, 126.57, 123.03, 113.96, 34.81, 34.75, 31.37, 31.33.

Figure 38A:
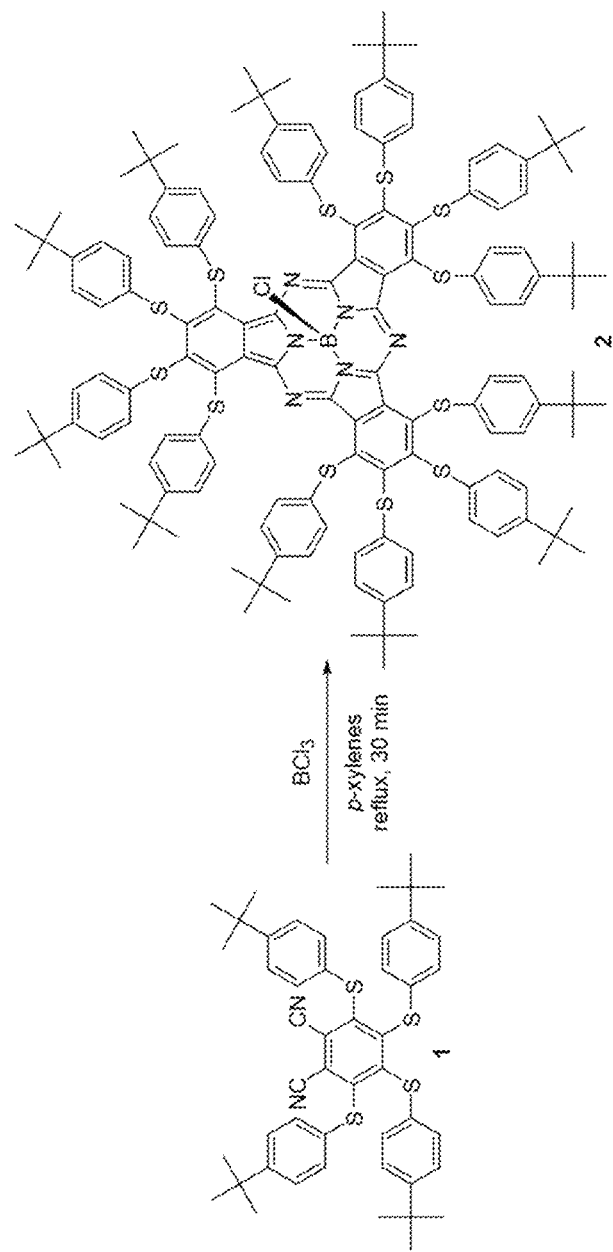
FIG. 38A shows synthetic procedure of subphthalocyanine (2), according to one set of embodiments.
Figure 38B:
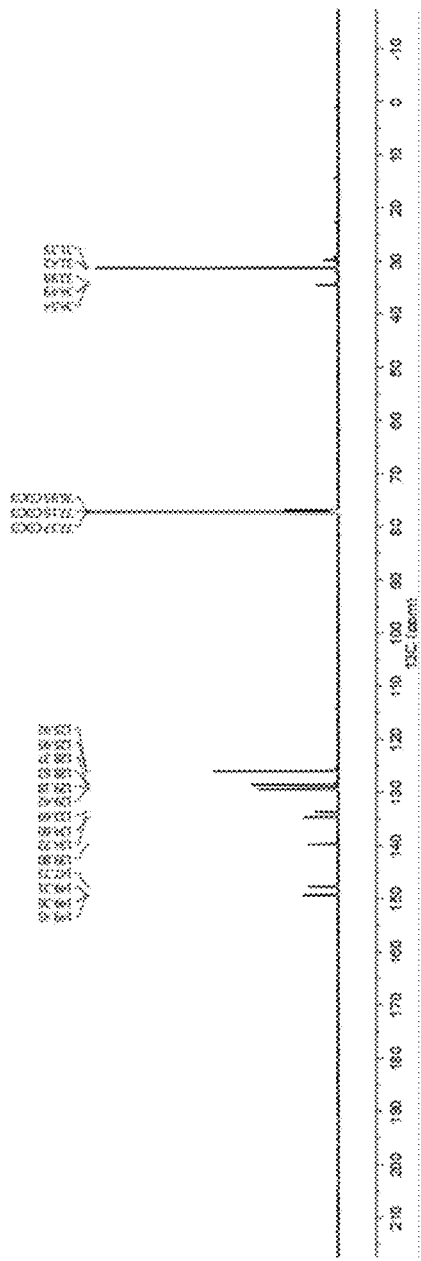
FIGS. 38B-38C show NMR spectra of subphthalocyanine (2), according to one set of embodiments.
Figure 38C:
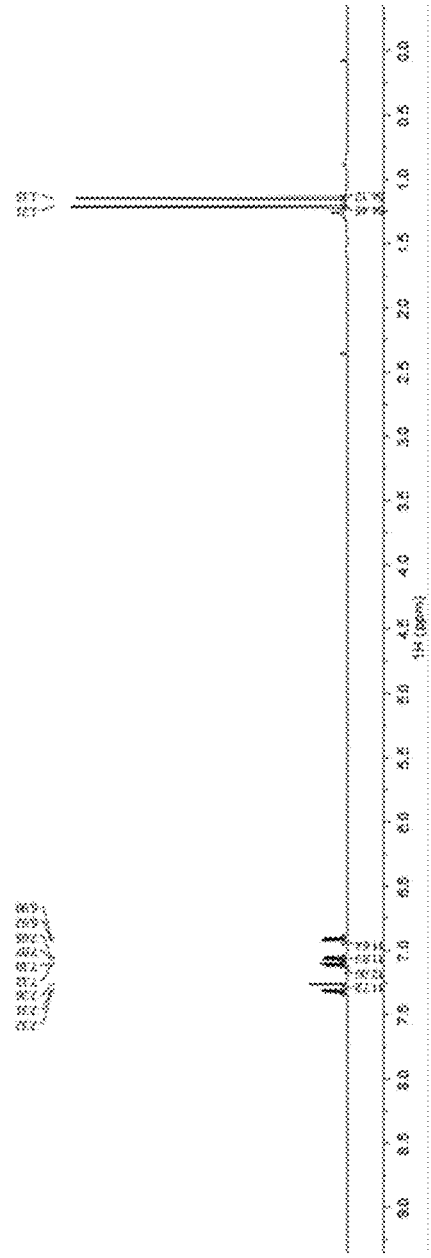
Figures 38D, 38E:
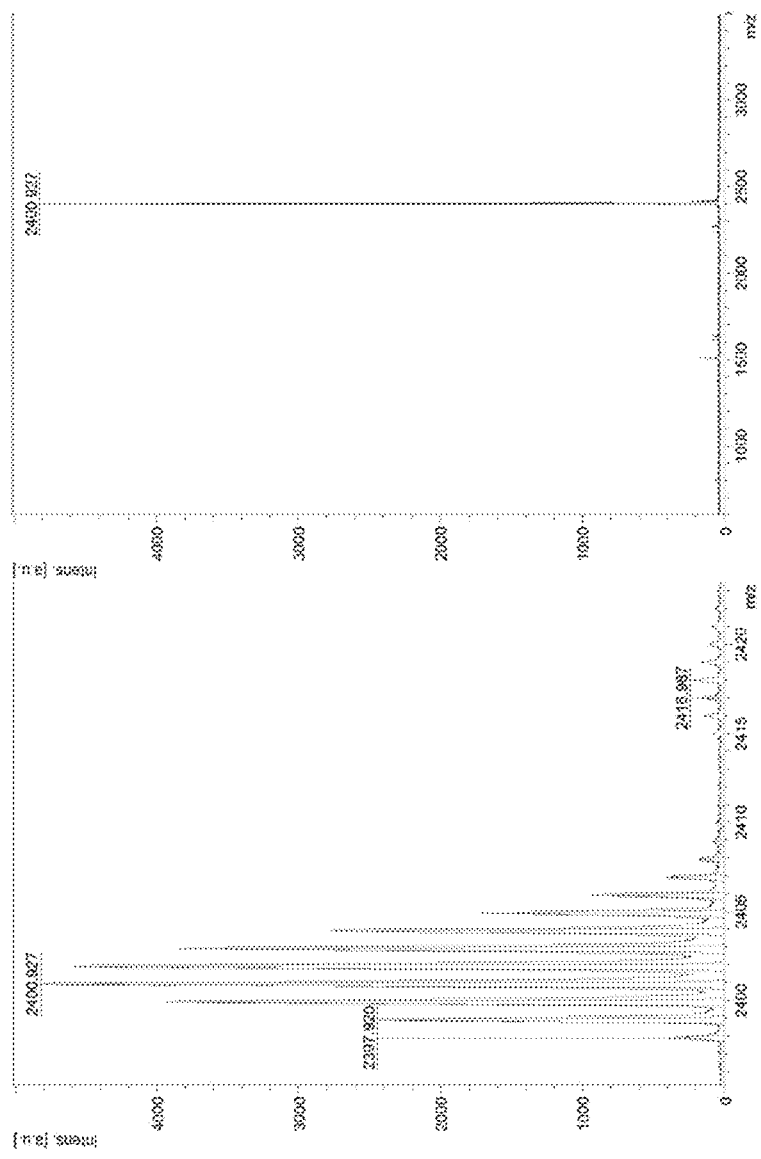
FIGS. 38D-38E show MALDI-TOF mass spectrometry spectrum of subphthalocyanine (2), according to one set of embodiments.
Figure 38F:
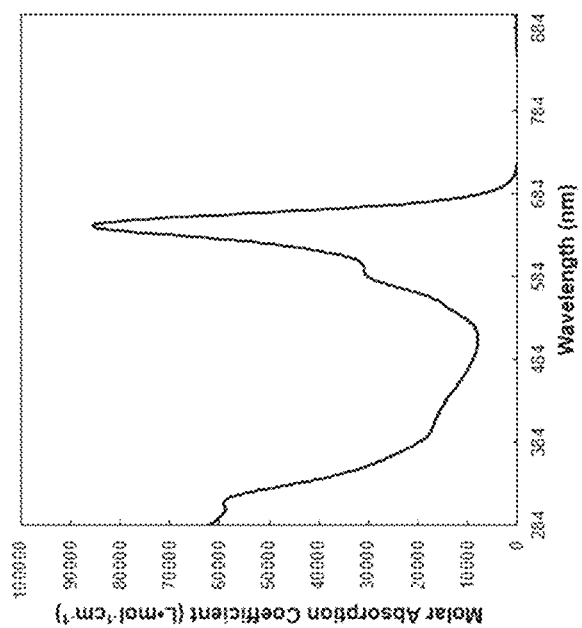
FIG. 38F shows UV/Vis spectrum of subphthalocyanine (2) in toluene, according to one set of embodiments.

Synthesis of Subphthalocyanine (2). Synthesis procedure was adapted from Claessens et al., *European J. Org. Chem.* 2003, 14, 2547, which is incorporated herein in its entirety for all purposes. FIG. 38A shows synthesis scheme of Subphthalocyanine 2 from phthalonitrile 1. As shown, $BCl_3$ (1.0 mL, 1 M solution in p-xylene) was added to phthalonitrile 1 (785 mg, 1 mmol), and stirrer under argon in a 25 mL two-necked round-bottomed flask fitted with a condenser and septum. The septum was replaced with a glass stopper, and the apparatus was placed in a pre-heated oil bath at 160° C. and stirred for 30 minutes. After cooling to room temperature, the solution was concentrated under reduced pressure. The resulting blue solid was subjected to silica gel column chromatography with toluene/hexanes (2:3, v:v) as eluent, yielding subphthalocyanine 2 as a dark blue solid (62 mg, 8%). The NMR spectra of subphthalocyanine 2 are shown in FIG. 38B-38C. Whereas FIG. 38B shows $^1H$ NMR (600 MHz, Chloroform-d) δ 7.32 (d, J=8.7 Hz, 12H), 7.11 (d, J=8.7 Hz, 12H), 7.06 (d, J=8.7 Hz, 12H), 6.92 (d, J=8.7 Hz, 12H), 1.21 (s, 54H), 1.15 (s, 54H), FIG. 38B shows $^{13}C$ NMR (151 MHz, Chloroform-d) δ 149.45, 149.36, 149.31, 147.73, 139.80, 134.72, 134.60, 133.69, 129.42, 128.63, 125.95, 125.92, 34.54, 34.49, 31.42, 31.35. MALDI-TOF mass spectrometry was performed for subphthalocyanine (2) as shown in FIG. 38D-38E. Both MALDI-TOF mass spectrometry spectrum of subphthalocyanine (2) and simulated isotopic distribution for $C_{144}H_{156}BClN_6S_{12}$ are shown in FIG. 38D-38E. MALDI-TOF m/z was calculated for $C_{144}H_{156}BClN_6S_{12}$ [M]$^+$, which was 2397.886, and compared to a measured value of 2397.920. UV/Vis spectrum of subphthalocyanine (2) in toluene was acquired. FIG. 38F shows UV/Vis (Toluene) at $\lambda_{max}$ (log ε)=310 (4.77), 645 (4.93).

6.2 Experimental Procedure for Synthesis of F-SubPC

Synthesis of Compound 1. Compound 1 was synthesized by slightly modifying the procedure, described above FIG. 39 shows the synthesis schematic of Compound 1. A mixture of 4,5-dichlorophthalonitrile (98.5 mg, 0.500 mmol), 1H,1H,2H,2H-perfluorodecanethiol (504 mg, 1.05 mmol), and anhydrous $K_2CO_3$ (400 mg, 2.89 mmol) in acetone (5 mL) was stirred at 60° C. for 48 h. Then, 1M HCl aq (10 mL) was added, and the precipitate was filtered and collected. The residue was recrystallized from chloroform to provide colorless crystals 1 (462 mg, 0.426 mmol, 85% yield). The specific details of $^1H$ and $^{19}F$ NMR were as follows: $^1H$ NMR (500 MHz, acetone-d6, 25° C.) with chemical shifts of δ (ppm) 8.06 (s, 2H), 3.59 (t, J=7.6 Hz, 4H), 2.68-2.84 (m, 4H); $^{19}F$ NMR (471 MHz, acetone-d6, 25° C.) with chemical shifts of δ (ppm) −81.56 (t, J=9.8 Hz, 6F), −114.23 (m, 4F), −122.14 (m, 4F), −122.37 (m, 8F), −123.19 (m, 4F), −123.67 (m, 4F), −126.66 (m, 4F).

Figure 39:
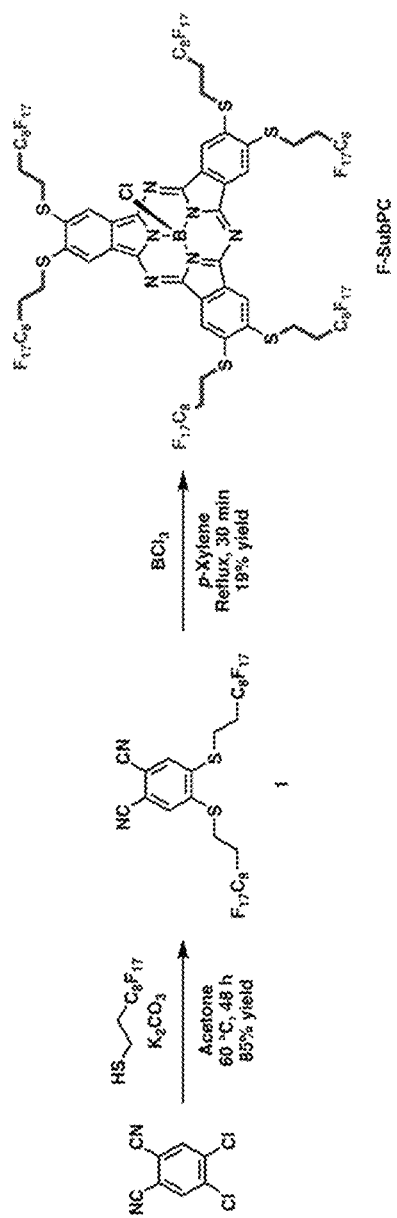
FIG. 39 shows synthetic procedure of F-SubPC, according to one set of embodiments.

Synthesis of F-SubPC. Compound 1 (462 mg, 0.426 mmol) was added to a dried flask, and $BCl_3$ (1.0 M in p-xylene, 0.450 mL) was added dropwise, as shown in FIG. 39. Then, the reaction mixture was stirred at 160° C. in a pre-heated oil bath for 30 min. Upon cooling the reaction mixture to room temperature, it was diluted with FC-770 (5 mL) and transferred to a separation funnel. The fluorous layer was washed with $CHCl_3$ (10 mL), acetone (10 mL), water, (10 mL), brine (10 mL), dried with $MgSO_4$, and evaporated to dryness under reduced pressure. Further purification was carried out by Soxhlet extraction with acetone for 72 h to obtain F-SubPC as a dark purple solid (63.2 mg, 0.0191 mmol, 13% yield). NMR spectra could not be obtained due to low solubility. MALDI-TOF MS was performed to confirm the presence of F-SubPC. The MALDI-TOF MS had a m/z calculated value for $C_{84}H_{30}BClF_{102}N_6S_6$ [M]$^+$ of 3297.9009, and a measured value of 3297.8978.

Example 8

The following example generally relates to detection and biosensing of *Salmonella Typhimurium* via agglutination of droplets (e.g., Janus emulsions), according to some embodiments.

1. General In Situ Emulsification Technique for Producing Janus Droplets

Amine-functionalized polymer was dissolved in water (0.1-1 mM). Aldehyde was dissolved in the oil phase (hydrocarbon (HC) or fluorocarbon (FC) phase, (50-200 mM). A 1:1 volume ratio of HC and FC were heated above their upper critical solution temperature ($T_c$) to form a homogeneous mixture. 25 μL of the heated HC/FC mixture was added to 500 μL of the continuous phase and vortexed for 5 s to emulsify. Upon cooling, double emulsions were generated.

2. In Situ Antibody Surfactant Fabrication Technique

Antibody (0.045 mg/mL) was dissolved in a hydrocarbon and/or aqueous buffer solution and reacted with an aldehyde (200 mM) in the HC/FC dispersed phase. By utilizing antibody and amine-polymer or co-surfactant in the buffer following the general procedure, double emulsions with precise compositions were generated. Examples of aldehydes could be 4-dodecoxybenzaldehyde, 1H,2H,2H-perfluoooctanal (and its hydrate). Examples of amines could be 2-(2-(2-methoxyethoxy)ethoxy)ethaneamine, peg-diamine. Examples of antibodies could be anti-b-actin, *listeria* antibody, *salmonella antibody, and avidin antibody.*

3. Heat Killed *Salmonella Typhimurium* (HKST) Sensing

Janus emulsions were prepared by following the general procedure outlined using 0.045 mg/mL *salmonella* antibody and 0.1 wt % Tween 20. Upon cooling, the Janus emulsions were exposed to $10^3$-$10^8$ HKST cells/mL (final concentration) and the chamber containing the emulsions was swirled to agitate the emulsions. Agglutination was observed directly after agitation.

Figure 40:
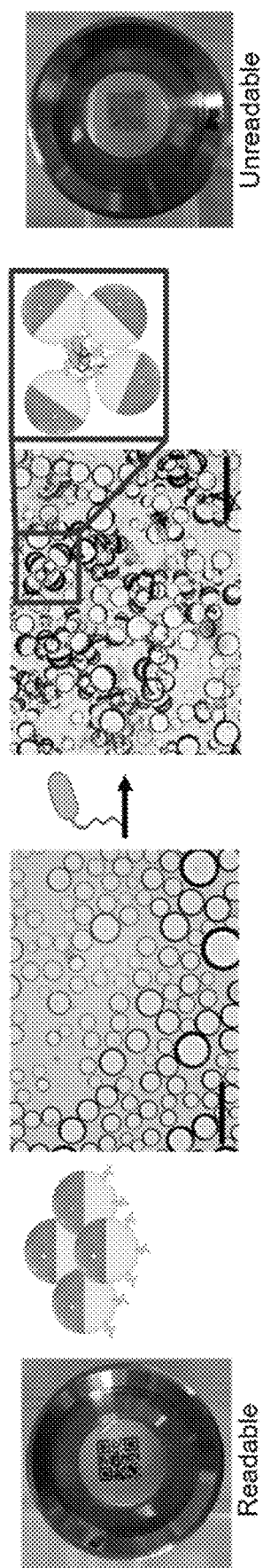
FIG. 40 shows procedure of an agglutination assay for heat killed *Salmonella Typhimurium* (HKST), according to one set of embodiments.
Figure 41:
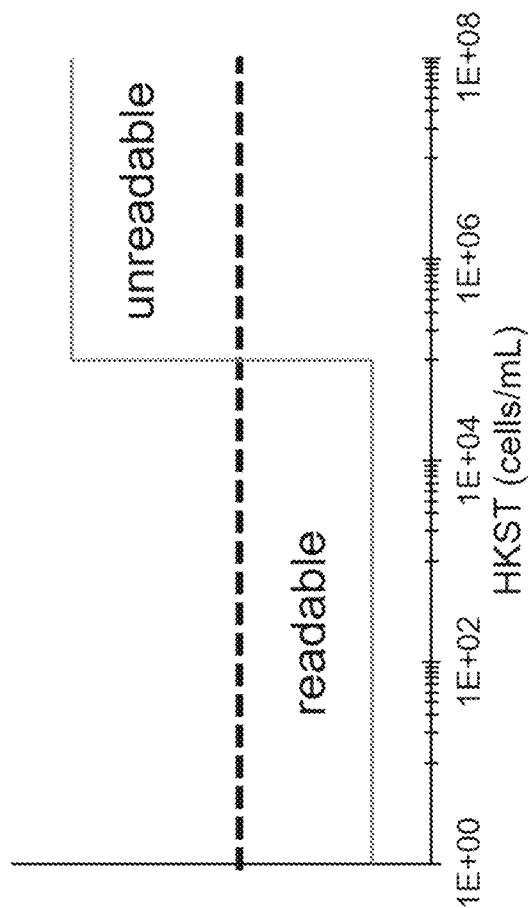
FIG. 41 shows a graph of QR code readability with different concentration of HKST, according to one set of embodiments.

The agglutinated emulsions were placed over a QR code to test readability of the QR code through the emulsions. A HKST agglutination assay was performed with $10^8$ HKST cells/mL, according to FIG. 40. For instance, as the emulsions agglutinated, the emulsions became opaque and obscured the QR code, thus rendering the QR code unreadable (as shown in FIG. 40). At a fixed distance from phone to QR code (10 cm) and fixed focal length (5 mm, distance from droplets to the QR code), an on/off reading was determined for the QR code in the presence of HKST. FIG. 41 shows QR code readability at different concentrations of HKST. For instance, at a concentration greater than or equal to $10^5$ HKST cells/mL, enough agglutination was present to render the QR code unreadable (as shown in FIG. 41).

Example 9

The following example generally relates to detection of live *Listeria Monocytogenes* via agglutination of droplets comprising a two-dye composition, according to some embodiments.

Detection of Live *Listeria Monocytogenes*.

Similar to the previous sensing scheme (e.g., Example 7), live *Listeria* ($10^7$ CFU/mL, $10^4$ CFU/mL, and 100 CFU/mL in FIGS. 42A-42C) was added to the continuous phase and mixed with the bacteria and Janus droplets on a rocker for 2 hours, after which images and fluorescence measurements were taken. Optical images of droplets containing 1 mg/mL of Poly-TCO in the hydrocarbon phase after adding $10^7$ CFU/mL, $10^4$ CFU/mL, and 100 CFU/mL of live *Listeria* for 2 hour were obtained and presented in FIGS. 42A-42C, respectively. As shown, a high degree of agglutination was observed after adding $10^7$ CFU/mL of *Listeria* and agglutination was still apparent after adding only 100 CFU/mL of live *Listeria*.

Figures 42A, 42B, 42C, 42D, 42E:
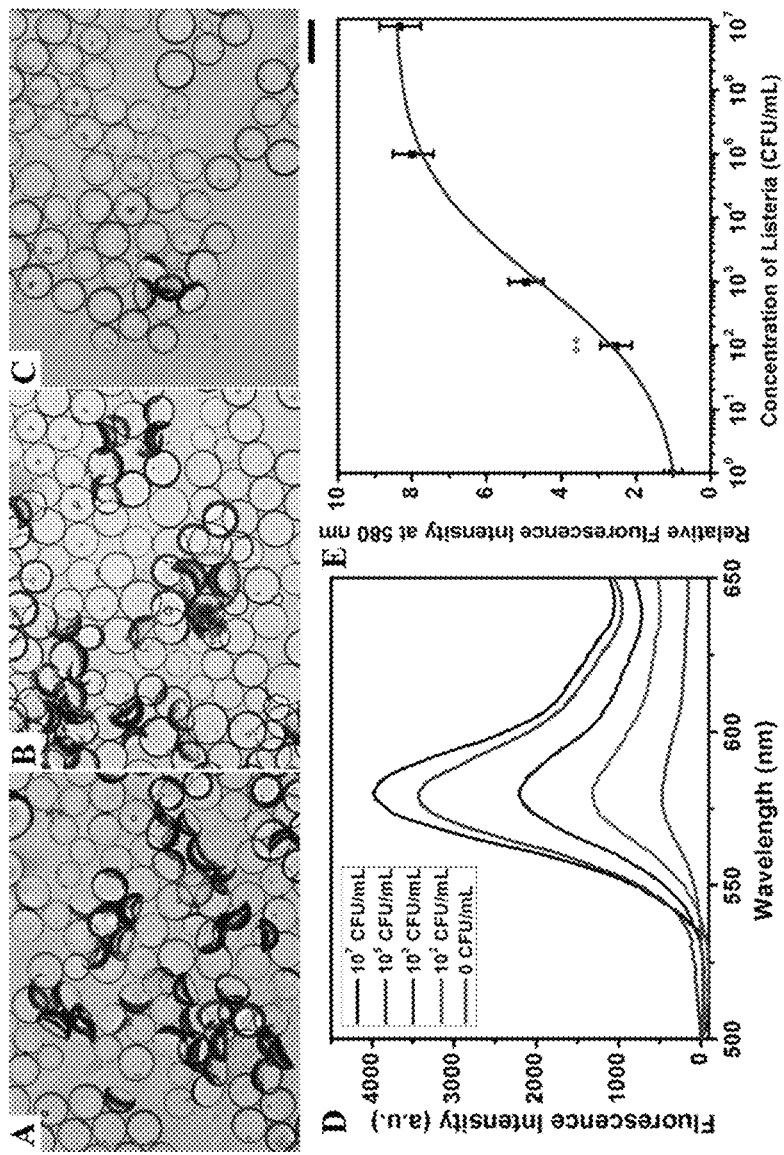
FIGS. 42A-42C show optical images of droplets containing 1 mg/mL of Poly-TCO in the hydrocarbon phase after adding *Listeria*, according to one set of embodiments. Optical images of droplets after adding of $10^7$ CFU/mL (FIG. 42A), $10^4$ CFU/mL (FIG. 42B), and 100 CFU/mL (FIG. 42C) of live *Listeria* for 2 hours. Scale bar=50 μm.
FIG. 42D shows a fluorescence spectrum (λex=361 nm) of droplets containing Poly-TCO and sub-PC dye in the hydrocarbon phase, and F-PBI dye in the fluorocarbon phase after addition of live *Listeria* at different concentrations, according to one set of embodiments.
FIG. 42E shows correlation of concentration of live *Listeria* and relative fluorescence intensity at 580 nm, according to one set of embodiments. Three replicate measurements were performed for the error bars, with p≤0.01.

Fluorescence spectra ($\lambda$ex=361 nm) of droplets containing Poly-TCO and sub-PC dye in the hydrocarbon phase, and F-PBI dye in the fluorocarbon phase after addition of live *Listeria* at different concentrations were obtained (FIG. 42D). As shown, the detected emission of F-PBI dye at 580 nm increased with an increase in the concentration of live *Listeria* (FIG. 42D) and a calibration curve in FIG. 42E was used to confirm the ability to detect live *Listeria* at 100 CFU/mL via fluorescence measurements.

Inverted Two-Dye System

Figure 43:
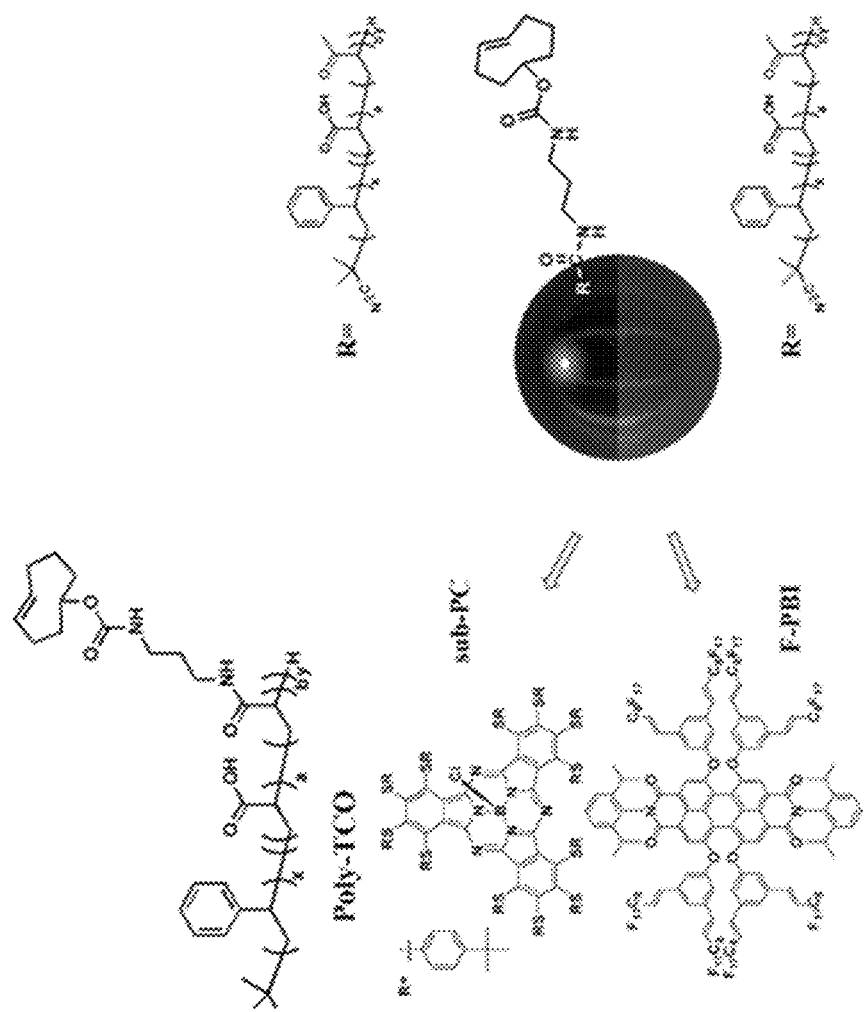
FIG. 43 shows a Janus droplet containing Poly-TCO and sub-PC dye in the hydrocarbon phase and the F-PBI dye in the fluorocarbon phase, according to one set of embodiments.

FIG. 43 shows a scheme of Janus droplet with Poly-TCO and sub-PC dye in the hydrocarbon phase and the F-PBI dye in the fluorocarbon phase. However, the arrangement of the dyes in the droplets needed not be in form given in FIG. 43. In some cases, an inverted arrangement of the blocking and signaling dyes could be advantageous. For example, in a highly scattering sample, the emission could alternatively be detected from the bottom directly through a glass support, thereby eliminating the pathlength through the solution. This situation was accomplished as shown in FIG. 44A, where the perylene dye Lumogen F Orange 240 was exclusively soluble in the hydrocarbon phase.

Figure 45:
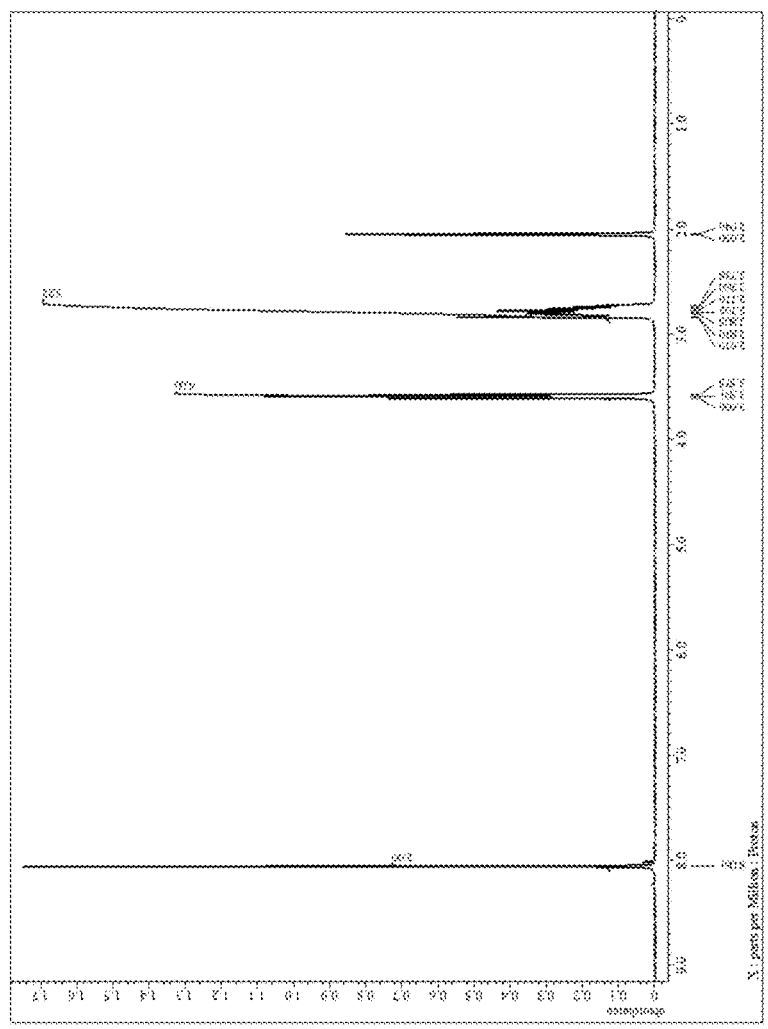
FIG. 45 shows $^1$H NMR (500 MHz, acetone-d6, 25° C.) spectrum of F-sub-PC, according to one set of embodiments.
Figure 46:
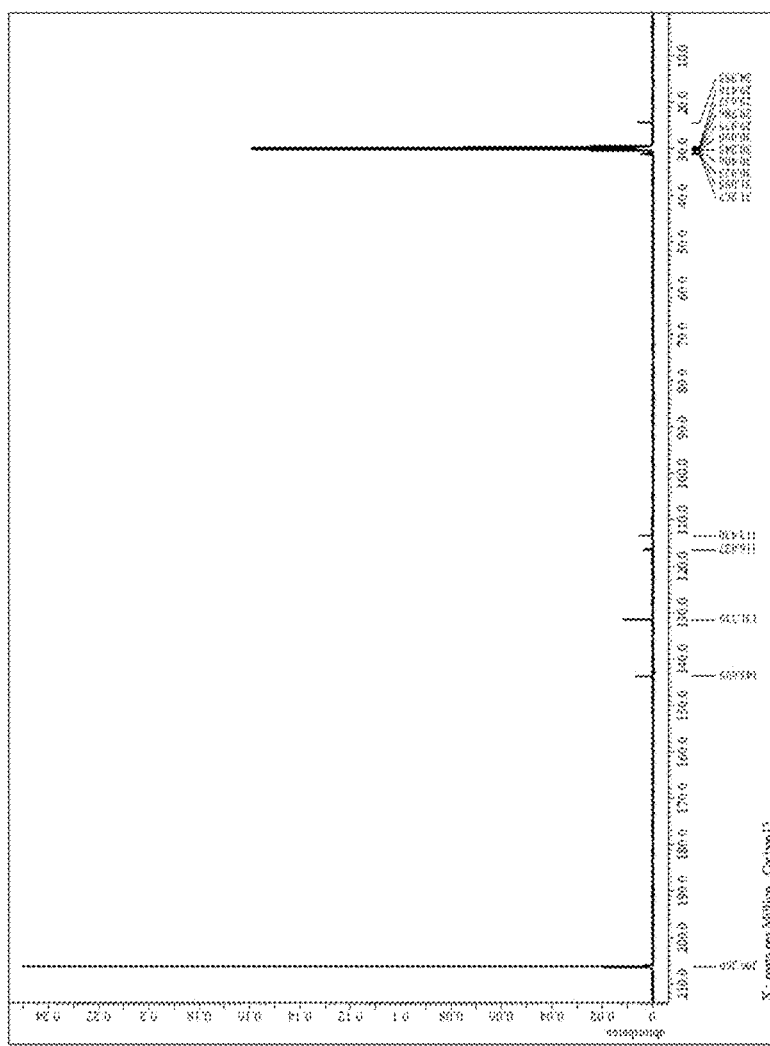
FIG. 46 shows $^{13}$C NMR (126 MHz, acetone-d6, 25° C.) spectrum of F-sub-PC, according to one set of embodiments.
Figure 47:
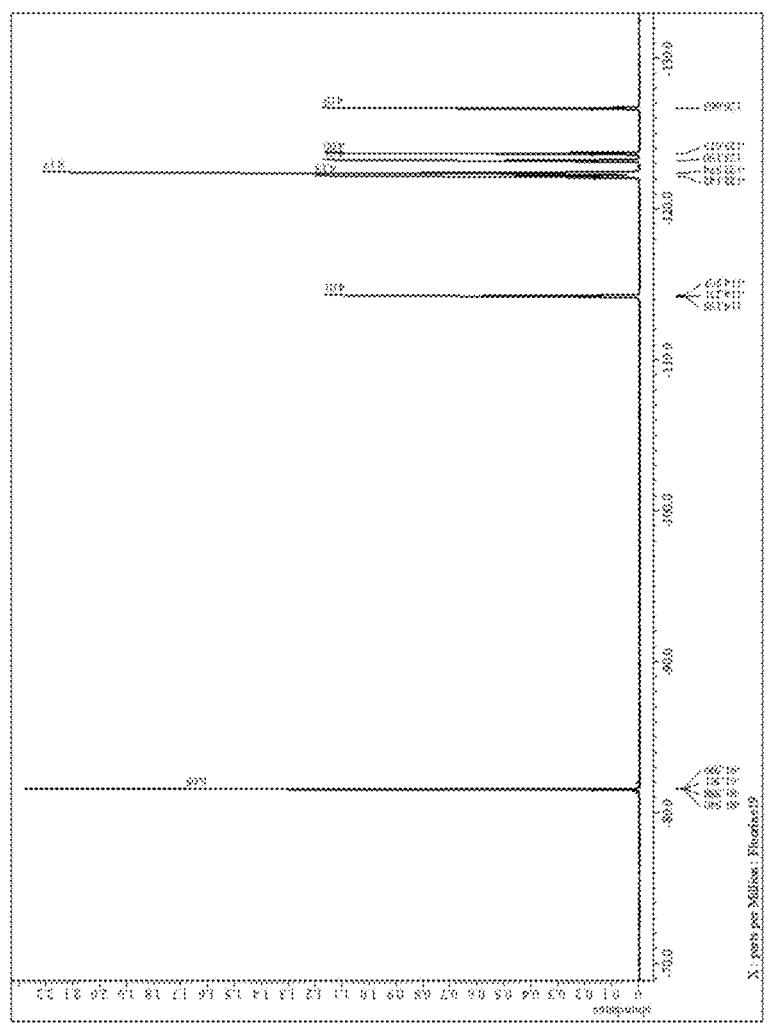
FIG. 47 shows $^{19}$F NMR (471 MHz, acetone-d6, 25° C.) spectrum of F-sub-PC, according to one set of embodiments.
Figure 48:
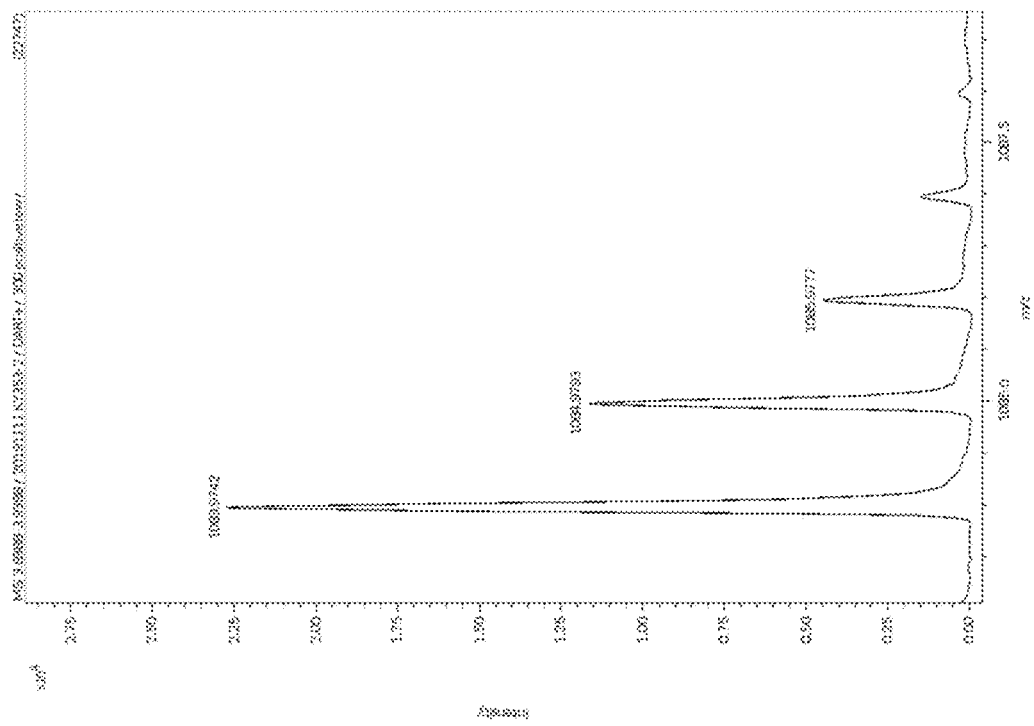
FIG. 48 shows DART MS spectrum of F-sub-PC, according to one set of embodiments.
Figure 49:
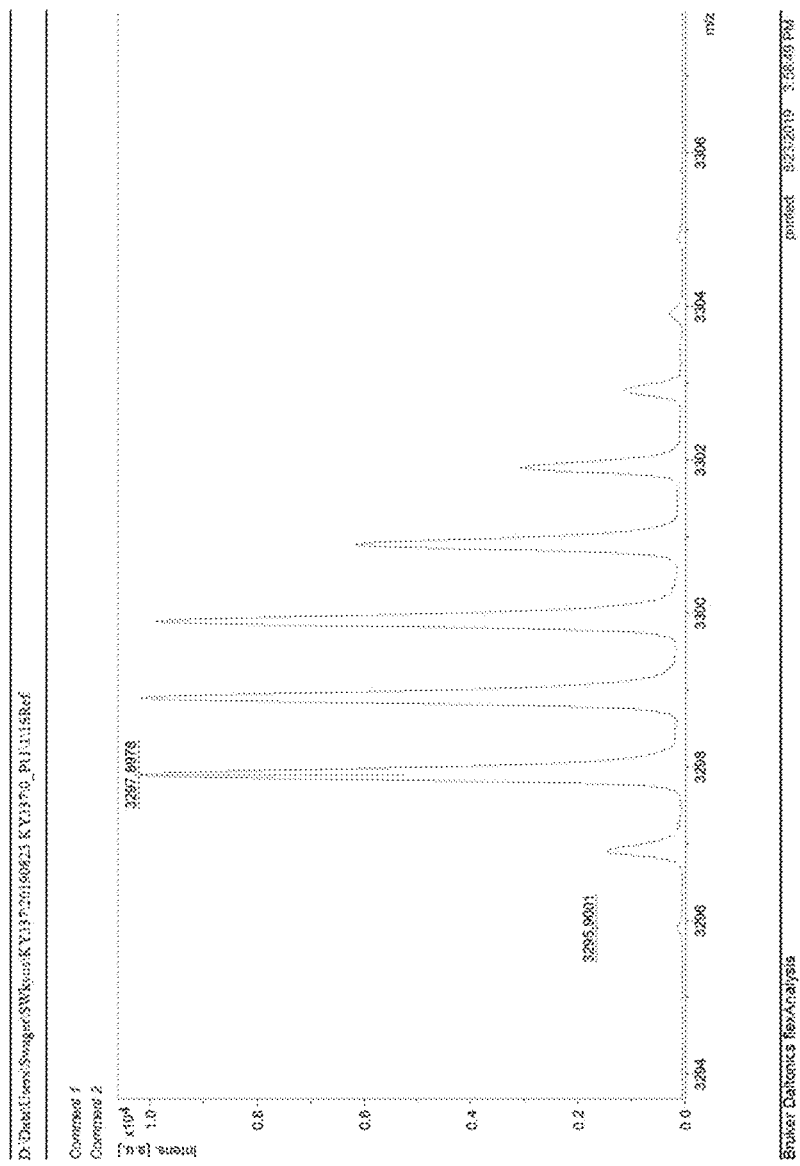
FIG. 49 shows MALDI TOF-MS spectrum of F-sub-PC, according to one set of embodiments.
Figure 50:
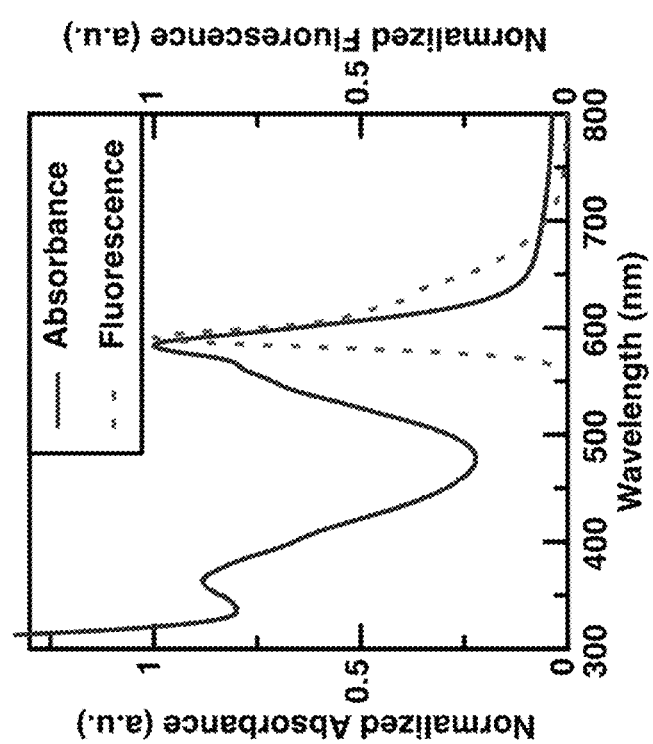
FIG. 50 shows UV/Vis absorbance and fluorescence of F-sub-PC, according to one set of embodiments.
Figure 51:
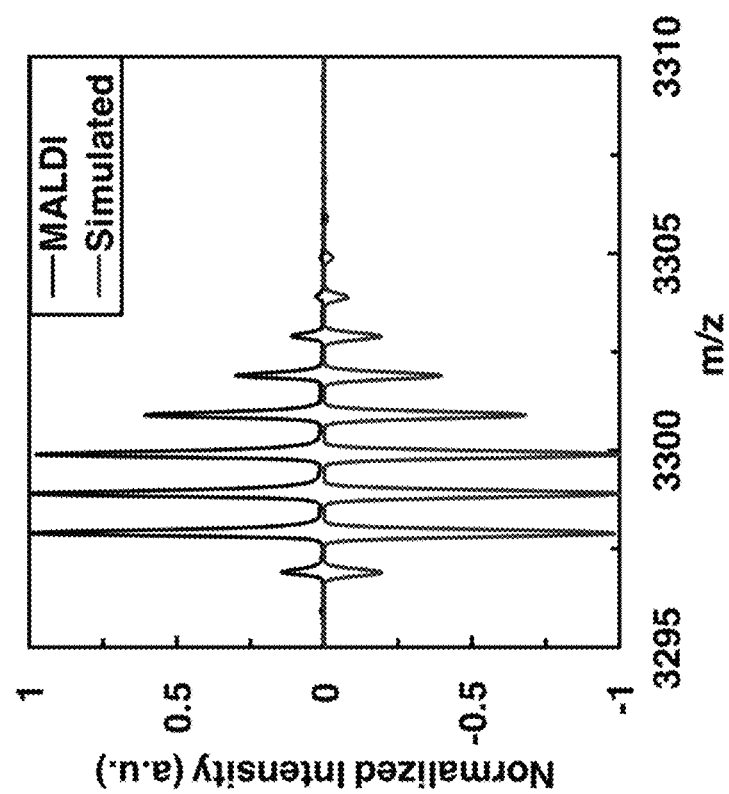
FIG. 51 shows MALDI TOF-MS Isotope Distribution Comparison of F-sub-PC, according to one set of embodiments.

A blocking sub-phthalocyanine dye (F-sub-PC) that was only soluble in the fluorocarbon phase was synthesized (FIGS. 45-51). As shown, the following analytical measurements were performed to confirm the successful synthesis of the dye: $^1$H NMR (500 MHz, acetone-d6, 25° C.) spectrum (FIG. 45); $^{13}$C NMR (126 MHz, acetone-d6, 25° C.) spectrum (FIG. 46); $^{19}$F NMR (471 MHz, acetone-d6, 25° C.) spectrum (FIG. 47); DART MS spectrum (FIG. 48); MALDI TOF-MS spectrum (FIG. 49); UV/Vis absorbance and fluorescence spectrum (FIG. 50); and MALDI TOF-MS Isotope Distribution Comparison (FIG. 51).

Figure 52:
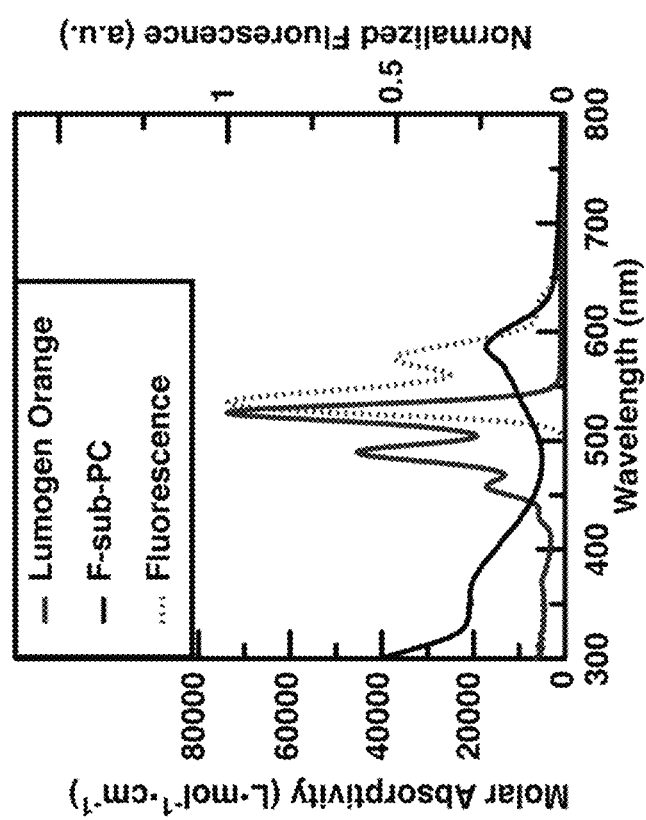
FIG. 52 shows UV/Vis spectra of F-sub-PC in HFE7500 and Lumogen F Orange 240 in diethylbenzene, overlayed with fluorescence spectrum of Lumogen F Orange 240 in diethylbenzene, according to one set of embodiments.
Figure 53:
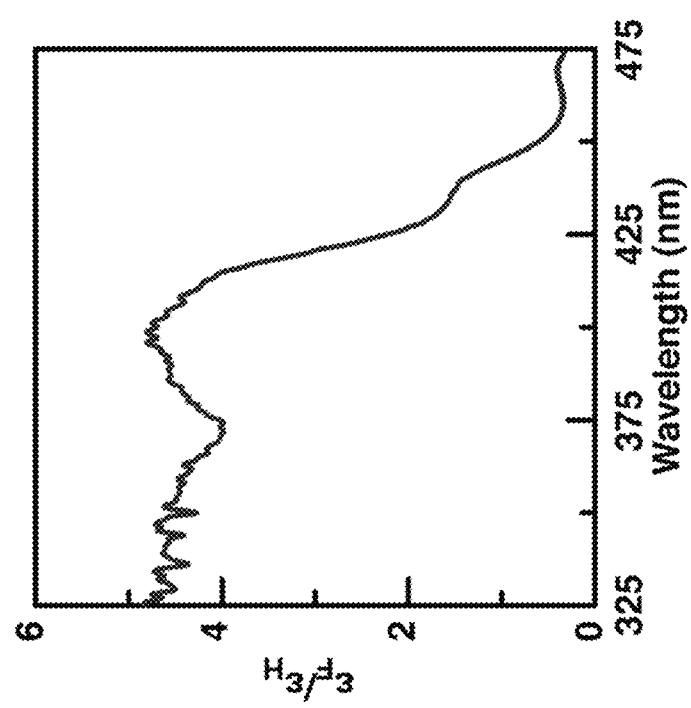
FIG. 53 shows a graph of ratio of molar absorptivity of F-sub-PC ($E_F$) and Lumogen F Orange 240 ($E_H$), according to one set of embodiments.
Figures 54A, 54B:
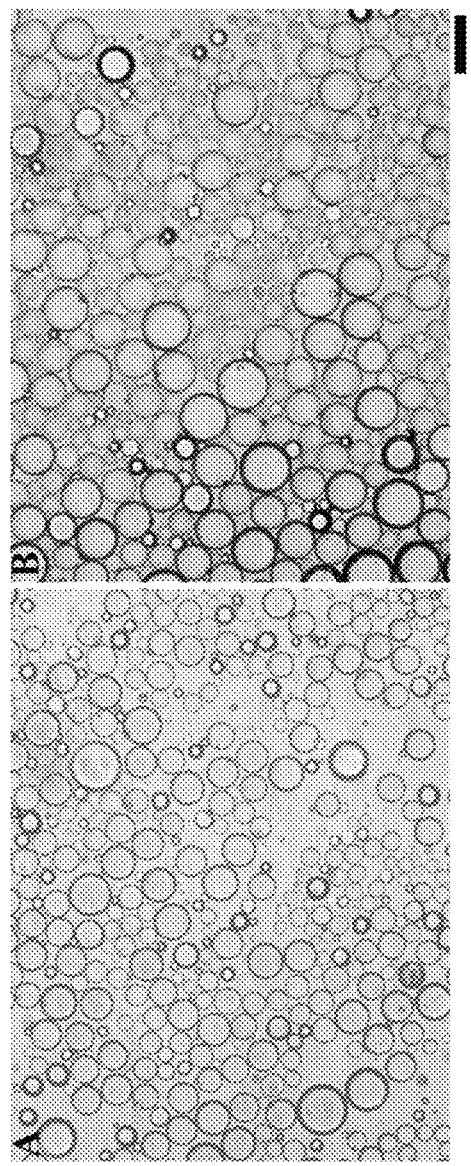
FIGS. 54A-54B show optical images of droplets prepared in different media, according to one set of embodiments.
Figures 55A, 55B:
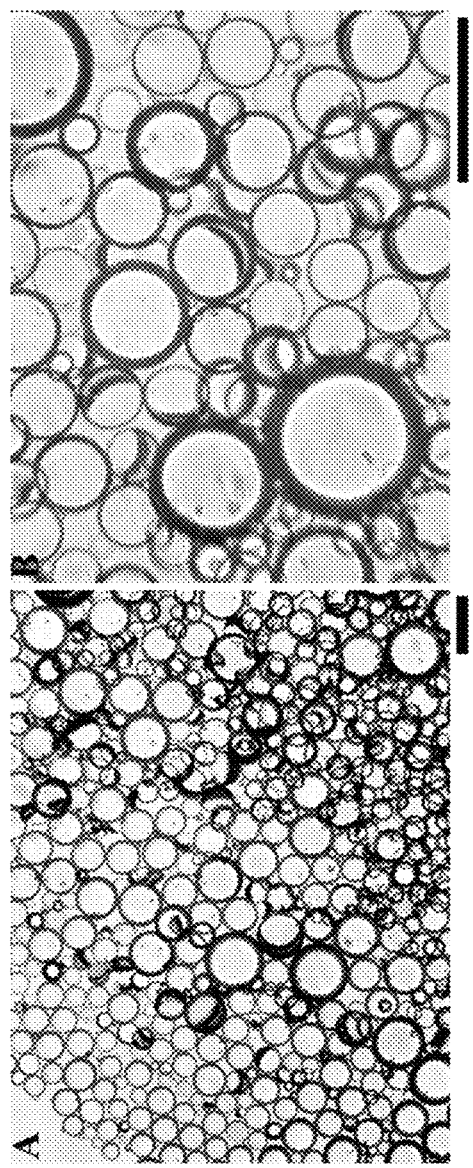
FIGS. 55A-55B show optical images of droplets bioconjugated with *Listeria* antibody and then incubated with $10^7$ CFU/mL of *Listeria* for 2 hour in serum, according to one set of embodiments. Scale bar=50 μm.
Figures 56A, 56B:
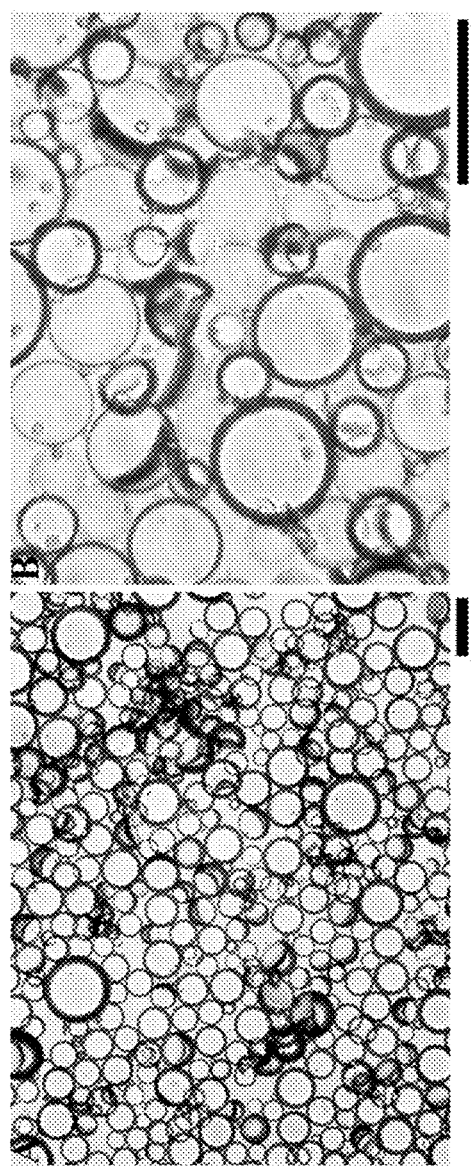
FIGS. 56A-56B show optical images of droplets bioconjugated with *Listeria* antibody and then incubated with $10^7$ CFU/mL of *Listeria* for 2 hours in synthetic blood, according to one set of embodiments. Scale bar=50 μm.

An UV/Vis spectra of F-sub-PC in HFE7500 and Lumogen F Orange 240 in diethylbenzene, overlayed with fluorescence spectrum of Lumogen F Orange 240 in diethylbenzene, was measured (FIG. 52). A plot of ratio of molar absorptivity of F-sub-PC ($\varepsilon$F) and Lumogen F Orange 240 ($\varepsilon$H) was generated (FIG. 53). As shown, the plot of ratio of the molar absorptivity of F-sub-PC and Lumogen F Orange 240 indicated that blocking of the excitation light was most efficient at 398 nm (FIGS. 52-53). Hence, the inverted two-dye system was excited at 398 nm. As shown, the F-sub-PC dye absorbed the 398 nm excitation and the Lumogen F Orange 240 emission was at 535 nm.

Figures 44A, 44B, 44C:
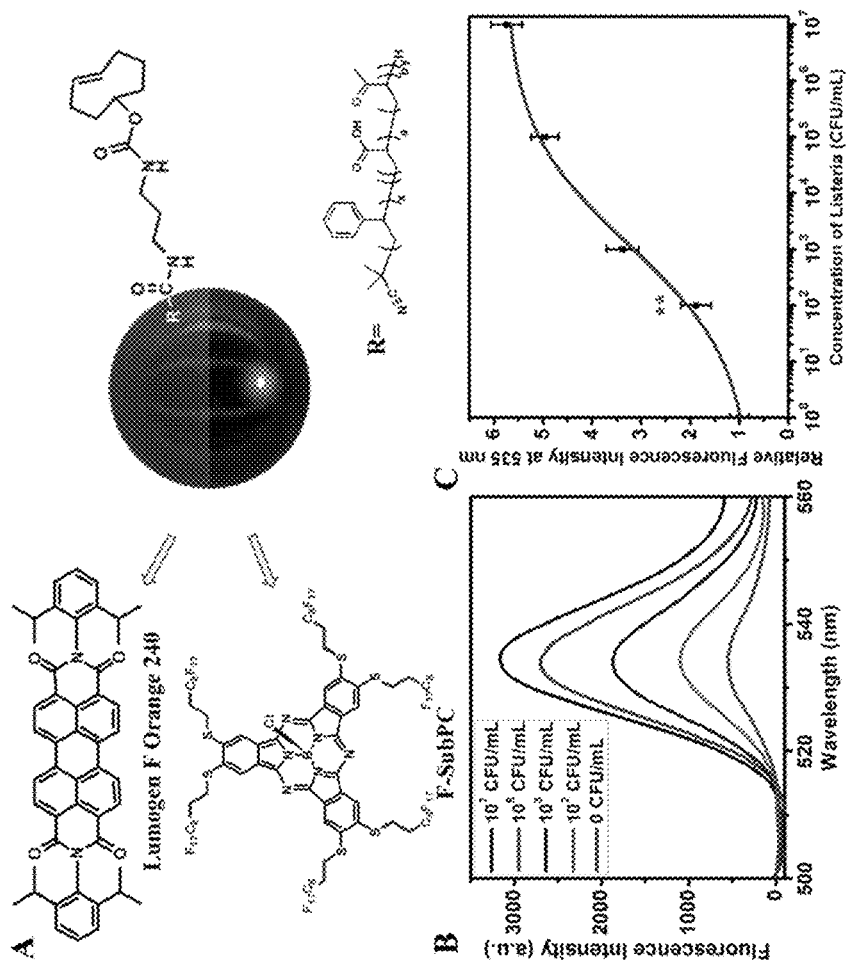
FIG. 44A shows a Janus droplet having a sub-phthalocyanine dye (F-Sub-PC) in the fluorocarbon phase and an emissive PBI dye (Lumogen F Orange 240) in the hydrocarbon phase, according to one set of embodiments.
FIG. 44B shows a fluorescence spectrum (λex=398 nm) of droplets containing Poly-TCO and Lumogen F Orange 240 in the hydrocarbon phase, F-sub-PC dye in the fluorocarbon phase after addition of *Listeria* at different concentrations, according to one set of embodiments.
FIG. 44C shows a correlation of concentration of *Listeria* and relative fluorescence intensity at 535 nm, according to one set of embodiments. Three replicate measurements were performed for the error bars, with p≤0.01, according to one set of embodiments.

Fluorescence spectra ($\lambda$ex=398 nm) of droplets containing Poly-TCO and Lumogen F Orange 240 in the hydrocarbon phase, F-sub-PC dye in the fluorocarbon phase after addition of *Listeria* at different concentrations were obtained and shown in FIG. 44B. Correlation of concentration of *Listeria* and relative fluorescence intensity at 535 nm was plotted in FIG. 44C. As shown, the antibody functionalized droplet agglutination assay was conducted with the fiber optic under the glass container and as shown in FIG. 44B, *Listeria* triggered an increased emission at 535 nm. The calibration curve suggests limits of detection of less than 100 CFU/mL, similar to the other methods (FIG. 44C).

Summary of Findings

In conclusion, a highly sensitive *Listeria* sensing method based on agglutination of Janus emulsion droplets with limits of detection less than 100 CFU/mL in 2 hours was reported in this example. Bioconjugation at the hydrocarbon phase-continuous phase interface of the droplets was accomplished by an efficient in situ click reaction between a tetrazine conjugated *Listeria* antibody and a trans-cyclooctene surfactant polymer. Exposure to *Listeria* induced agglutination and tilting of the droplets from their natural gravity induced alignment that could be quantified by image analysis. More robust agglutination assays were created using blocking and emissive dyes that were orthogonally partitioned between the hydrocarbon and fluorocarbon phases of the Janus droplet. These methods made use of an emission "turn on" triggered by agglutination which might be monitored from the top or the bottom with the proper selection of blocking and emissive dyes.

Figure 57:
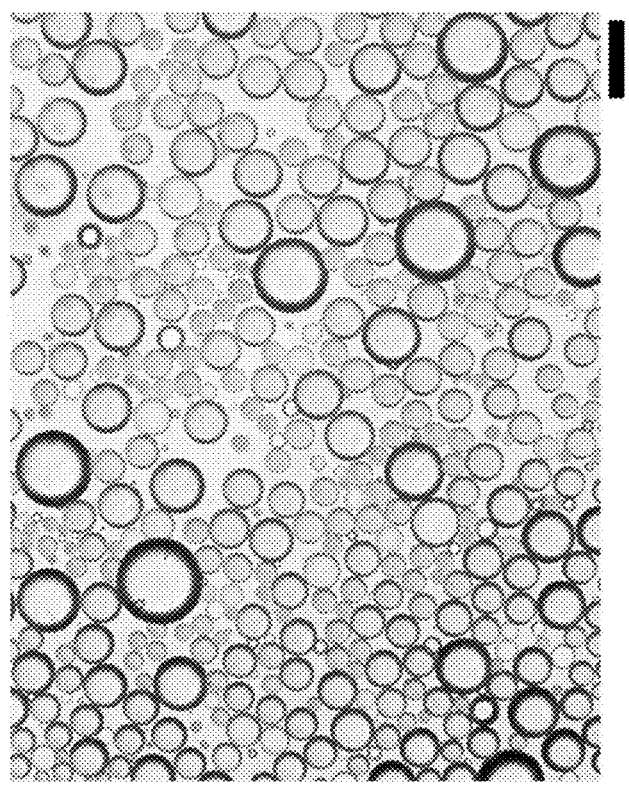
FIG. 57 shows optical image of droplets prepared in brain heart infusion broth, according to one set of embodiments. Scale bar=50 μm.

Assays monitoring from the bottom have the advantage that highly scattering solutions could be used because the emission signal did not need to travel through the solution. These droplet were robust and were stable in serum, synthetic blood, and brain heart infusion broth which guaranteed promising future applications in biomedical or biochemistry fields (FIGS. 54-57). Specifically, optical images of droplets prepared in different media were as follows: droplets in synthetic blood (FIG. 54A); droplets in serum (FIG. 54B); droplets bioconjugated with *Listeria* antibody and then incubated with $10^7$ CFU/mL of *Listeria* for 2 hours in serum (FIGS. 55A-55B); droplets bioconjugated with Listeria antibody and then incubated with $10^7$ CFU/mL of Listeria for 2 hours in synthetic blood (FIGS. 56A-56B); and droplets prepared in brain heart infusion broth (FIG. 57).

Figures 58A, 58B:
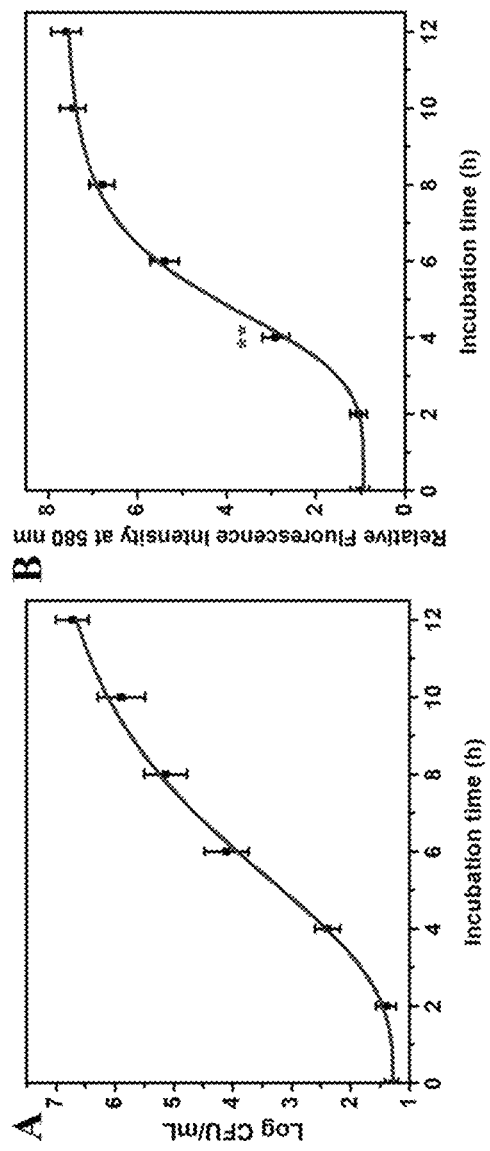
FIG. 58A shows graph of a growth curve for *Listeria monocytogenes* in brain heart infusion broth at 20 CFU/mL, according to one set of embodiments.
FIG. 58B shows graph of correlation of incubation time of *Listeria* (initial concentration at 20 CFU/mL) and relative fluorescence intensity, according to one set of embodiments. Three replicate measurements were performed for the error bars, with $p \leq 0.01$.

Through enrichment process, 20 CFU/mL of Listeria after incubating it at 37° C. for 4 hours could be easily determined (FIG. 58A-58B). Specifically, FIG. 58A shows growth curves for Listeria monocytogenes in brain heart infusion broth at 20 CFU/mL and the cultures were incubated at 37° C. in an incubator. FIG. 58B shows correlation of incubation time of Listeria (initial concentration at 20 CFU/mL) and relative fluorescence intensity (fluorescence spectra (λex=361 nm) of droplet containing Poly-TCO and sub-PC dye in the hydrocarbon phase, F-PBI dye in the fluorocarbon phase after addition of Listeria at different time points) at 580 nm.

Figures 59A, 59B:
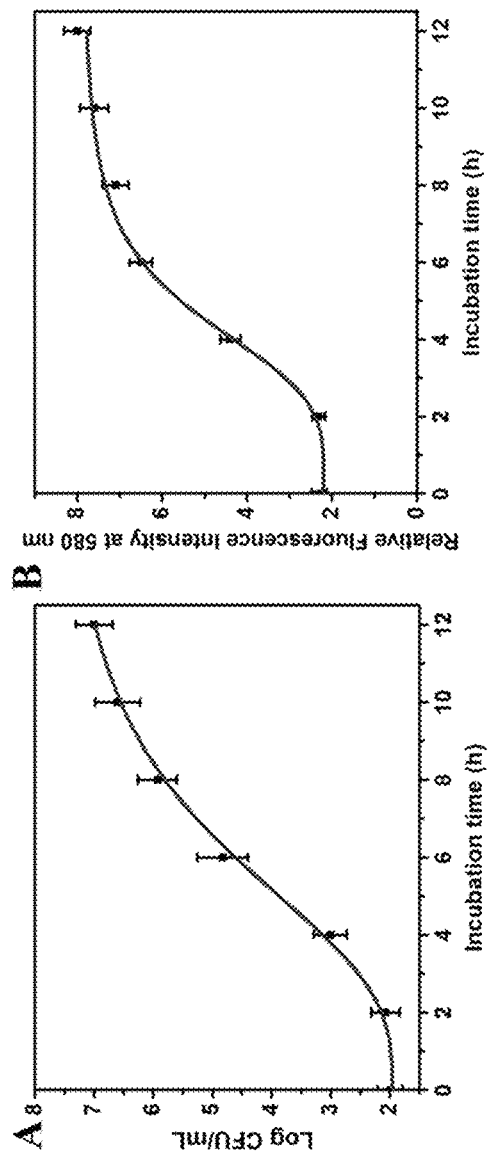
FIG. 59A shows graph of growth curve for *Listeria monocytogenes* in brain heart infusion broth at 100 CFU/mL, according to one set of embodiments.
FIG. 59B shows graph of correlation of incubation time of *Listeria* (initial concentration at 100 CFU/mL) and relative fluorescence intensity, according to one set of embodiments. Three replicate measurements were performed for the error bars, with $p \leq 0.01$.

Enhanced signal of 100 CFU/mL of Listeria could be acquired by incubating it at 37° C. for up to 12 hours and the relative intensity at 580 nm increased with an increase in incubation time (as shown in FIG. 59). Specifically, FIG. 59A shows growth curve for Listeria monocytogenes in brain heart infusion broth at 100 CFU/mL and the cultures were incubated at 37° C. in an incubator. FIG. 59B shows correlation of incubation time of Listeria (initial concentration at 100 CFU/mL) and relative fluorescence intensity (fluorescence spectra (λex=361 nm) of droplet containing Poly-TCO and sub-PC dye in the hydrocarbon phase, F-PBI dye in the fluorocarbon phase after addition of Listeria at different time points) at 580 nm.

Figures 60A, 60B, 60C:
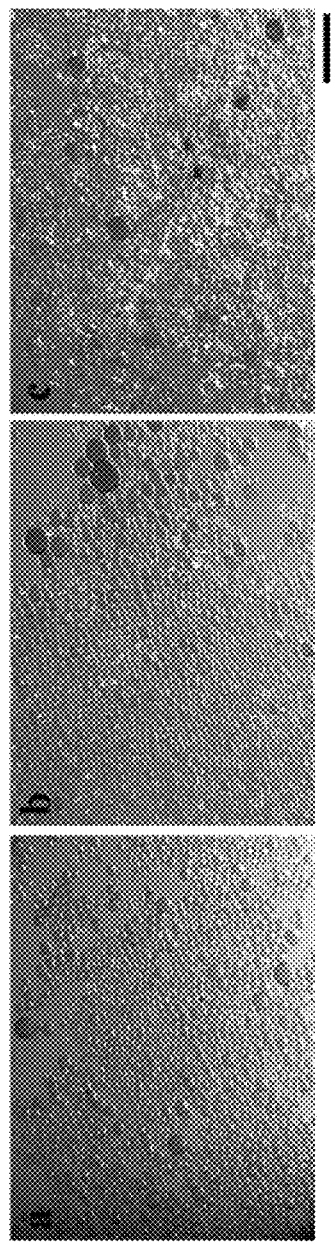
FIGS. 60A-60C show optical images taken by smartphone of droplets with sub-PC dye (subphthalocyanine) in the hydrocarbon phase and F-PBI dye in the fluorocarbon phase, according to one set of embodiments.
Figures 61A, 61B, 61C:
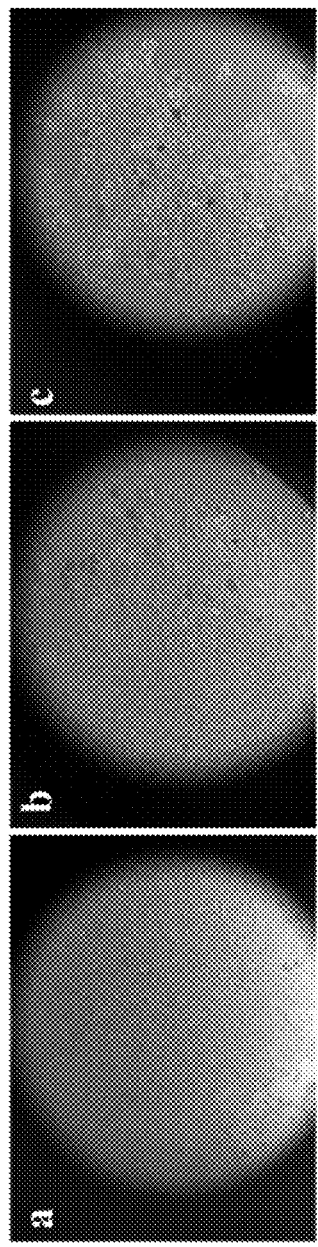
FIGS. 61A-61C show optical images taken by smartphone of droplets with sub-PC dye (subphthalocyanine) in the hydrocarbon phase and F-PBI dye in the fluorocarbon phase, according to one set of embodiments.

Overall, the method disclosed herein was simple and convenient, and agglutinations could even be detected by a smartphone camera with a magnifying lens (FIGS. 60-61). For instance, optical images were taken by smartphone of droplets comprising sub-PC dye (subphthalocyanine) in the hydrocarbon phase and F-PBI dye in the fluorocarbon phase. As shown, optical images were taken by smartphone of non-agglutinated droplet (without addition of Listeria) (FIG. 60A), and compared to agglutinated droplets (with the addition of Listeria at $10^2$ CFU/mL) and agglutinated droplets (with the addition of Listeria at $10^7$ CFU/mL) (FIGS. 60B and 60C, respectively).

Figures 62A, 62B:
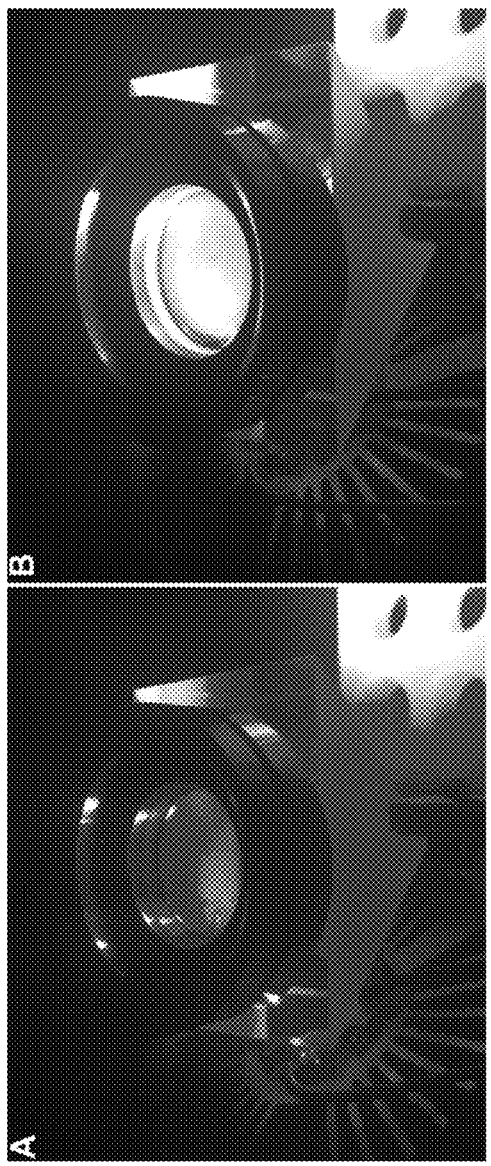
FIG. 62A-62B show images of Janus droplets on top of the waveguide device, according to one set of embodiments.

The effects reported could be detected in some cases by visual inspection. Specifically, agglutination could induce strong fluorescence in the sub-PC/F-PBI system when the excitation was performed under total internal reflection conditions using a glass prism at the glass interface (FIG. 62). For instance, FIG. 62 shows images of Janus droplets on top of the waveguide device taken without (FIG. 62A) and with (FIG. 62B) the addition of Listeria. The present assays readily achieve a detection limit of Listeria of 100 CFU/mL and can be extended to the detection of different analytes by the utilization of corresponding stable and selective antibodies.

Example 10

The following example generally relates to continuous visualization of complex droplets, e.g., using a microfluidic device, according to some embodiments.

Figures 63A, 63B, 63C:
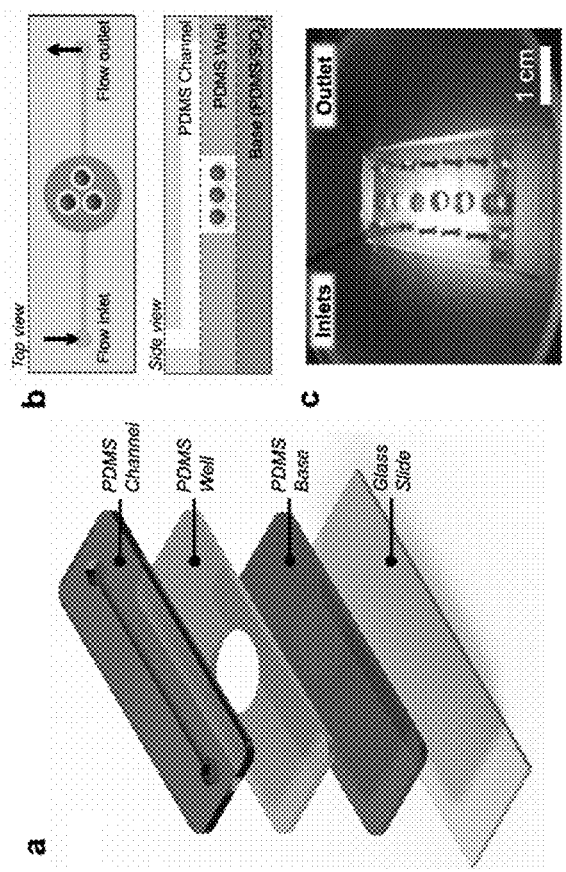
FIG. 63A shows a schematic diagram of the microfluidic device comprising three layers of polydimethylsiloxane (PDMS) and a glass slide, according to one set of embodiments.
FIG. 63B shows top and side views of the PDMS device with the complex droplets placed within the well, according to one set of embodiments.
FIG. 63C shows a photograph of the device in FIG. 63A comprising six separate wells and channels, according to one set of embodiments.

The reported method of measuring the degree of agglutination of complex droplets upon exposure to targeted analyte could be performed with continuous flow. To accomplish this, a microfluidic sampling device comprising a channel for fluid flow and a well for hosting the complex droplets was fabricated (FIG. 63). As shown, the microfluidic device comprised three layers of polydimethylsiloxane (PDMS) and a glass slide (FIG. 63A), where the layers were bonded using plasma treatment. FIG. 63B shows top and side views of the PDMS device with the complex droplets placed within the well. As shown in FIG. 63C, the device comprised six separate wells and channels, where the channel filled with blue liquid depicted one complete device.

This process could enable any mode of visualization of the complex droplets in addition to measuring the fluorescent emission upon agglutination, including optical microscopy and directional emission. The purpose of this method was to position a monolayer of complex droplets in the well and expose this layer to continuous flow of carrier liquid. An injection of a sample could then be introduced and measured in real time. This mode of operation could improve reproducibility by controlling the precise numbers of droplets in every experiment.

Figures 64A, 64B, 64C, 64D, 64E:
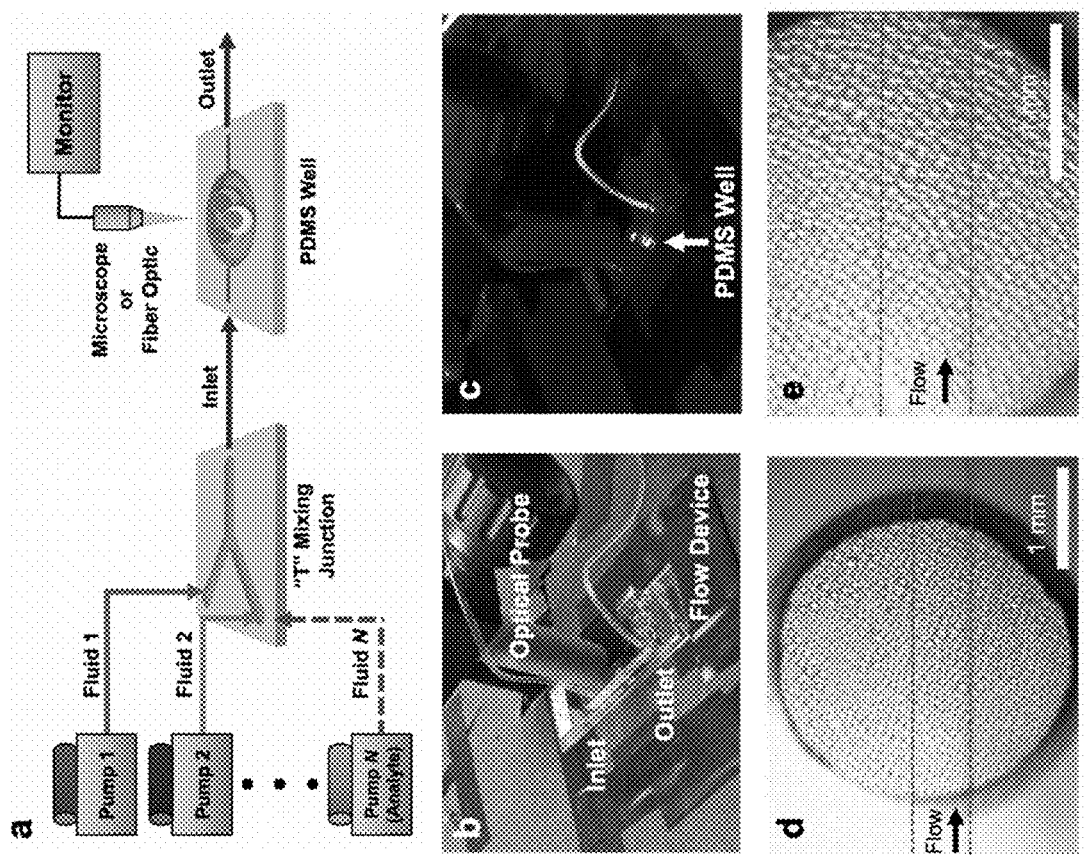
FIG. 64A shows a schematic of the device in operation, according to one set of embodiments.
FIGS. 64B-64C show photographs of the experimental set up of FIG. 64A, according to one set of embodiments.
FIGS. 64D-64E show optical micrographs of the complex droplets inside the PDMS well, according to certain embodiments.

The prototype of this device was made from polydimethylsiloxane (PDMS) and a glass slide using standard methods. Briefly, the channel features were created on silicon wafer with SU-8 photoresist using photolithographic technique. These features were then transferred to pre-crosslinked PDMS. After fully crosslinked, the PDMS layers (FIG. 63A) were bonded using plasma treatment to generate covalent bonds between PDMS layers and between PDMS and a glass slide. The inlet and outlet were then connected with PTFE tubes. FIG. 64A shows the schematic of the continuous operation of the microfluidic device. Upstream of the PDMS well containing the complex droplets, the carrier fluids and the analyte were introduced using syringe pumps or pressure pumps. A microscope or an optical fiber was placed on top of the droplet well to perform the measurement. These were first injected into the mixing junction before entering the PDMS well. FIGS. 64B and 64C show photographs of the experimental set-up where the optical probe was placed directly above the well containing complex droplets, under normal light (FIG. 64B) and UV light (FIG. 64C). FIGS. 64D and 64E show optical micrographs of a monolayer of complex droplets under continuous flow inside the PDMS well.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Any terms as used herein related to shape, orientation, alignment, and/or geometric relationship of or between, for example, one or more articles, structures, forces, fields, flows, directions/trajectories, and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter. Examples of such terms related to shape, orientation, and/or geometric relationship include, but are not limited to terms descriptive of: shape—such as, round, square, circular/circle, rectangular/rectangle, triangular/triangle, cylindrical/cylinder, elliptical/ellipse, (n)polygonal/(n)polygon, etc.; angular orientation—such as perpendicular, orthogonal, parallel, vertical, horizontal, collinear, etc.; contour and/or trajectory—such as, plane/planar, coplanar, hemispherical, semi-hemispherical, line/linear, hyperbolic, parabolic, flat, curved, straight, arcuate, sinusoidal, tangent/tangential, etc.; direction—such as, north, south, east, west, etc.; surface and/or bulk material properties and/or spatial/temporal resolution and/or distribution—such as, smooth, reflective, transparent, clear, opaque, rigid, impermeable, uniform(ly), inert, non-wettable, insoluble, steady, invariant, constant, homogeneous, etc.; as well as many others that would be apparent to those skilled in the relevant arts. As one example, a fabricated article that would described herein as being "square" would not require such article to have faces or sides that are perfectly planar or linear and that intersect at angles of exactly 90 degrees (indeed, such an article can only exist as a mathematical abstraction), but rather, the shape of such article should be interpreted as approximating a "square," as defined mathematically, to an extent typically achievable and achieved for the recited fabrication technique as would be understood by those skilled in the art or as specifically described. As another example, two or more fabricated articles that would described herein as being "aligned" would not require such articles to have faces or sides that are perfectly aligned (indeed, such an article can only exist as a mathematical abstraction), but rather, the arrangement of such articles should be interpreted as approximating "aligned," as defined mathematically, to an extent typically achievable and achieved for the recited fabrication technique as would be understood by those skilled in the art or as specifically described.

What is claimed is:

1. A system comprising:
a plurality of Janus droplets comprising an interface between a first phase and a second phase of the droplets, the second phase immiscible with the first phase; and
a binding moiety to a biological analyte associated with the plurality of Janus droplets,
wherein the first phase comprises an emissive species that interacts with electromagnetic radiation in a detectable manner,
wherein the second phase comprises a blocking species that at least partially absorbs and/or reflects electromagnetic radiation such that the blocking species at least partially blocks the passage of electromagnetic radiation that interacts with the first phase and/or at least partially blocks the passage of electromagnetic radiation emitted by the first phase,
wherein the plurality of Janus droplets have a first orientation in the absence of the biological analyte and a second orientation upon binding of the binding moiety to the biological analyte, such that the electromagnetic radiation emitted or transmitted in the second orientation is less than in the first orientation.

2. A system as in claim 1, wherein the plurality of Janus droplets is constructed and arranged to produce an electromagnetic radiation signal indicative of the presence and/or amount of the biological analyte exposed to the droplets.

3. A system as in claim 2, wherein the plurality of Janus droplets is constructed and arranged to change in orientation and/or morphology when exposed to the analyte in a manner that affects an electromagnetic radiation signal, determined by the detector.

4. A system as in claim 1, wherein the second phase contains an emissive species that emits light at a different wavelength than the emissive species in the first phase.

5. A system as in claim 1, further comprising at least one surfactant stabilizing the interface between the first and second phase and/or between the first phase and/or the second phase and a continuous phase in which the droplets are provided, wherein the at least one surfactant can respond to the presence of the analyte in a way that changes the structure of the droplet.

6. A system as in claim 5, wherein an analyte can cause a change in emission detectable with respect to alignment of the droplet and changes in the detected emission indicate the presence of an analyte.

7. A system as in claim 5, comprising at least one magnetic material associated with at least one droplet, optionally added to the droplet.

8. A system as in claim 5, comprising an emissive species comprising a sub-phthalocyanine dye, a perylene dye, or a phthalocyanine dye.

9. A system as in claim 5, wherein, upon exposure of the system to a chemical or biological analyte, the system generates the determinable signal.

10. A system as in claim 5, comprising a first emissive species associated with the first phase and a second emissive species associated with the second phase.

11. A system as in claim 1, wherein a peak wavelength of emission of the emissive species and a peak wavelength of blockage of the blocking species differ by no more than 200 nanometers in wavelength.

* * * * *

UNITED STATES PATENT AND TRADEMARK OFFICE
CERTIFICATE OF CORRECTION

| | | |
|---|---|---|
| PATENT NO. | : 12,274,993 B2 | Page 1 of 1 |
| APPLICATION NO. | : 16/932392 | |
| DATED | : April 15, 2025 | |
| INVENTOR(S) | : Timothy Manning Swager et al. | |

It is certified that error appears in the above-identified patent and that said Letters Patent is hereby corrected as shown below:

In the Specification

Column 1, Lines 8-11, STATEMENT OF GOVERNMENT SUPPORT section should read:
This invention was made with government support under FA9550-18-1-0341 awarded by the Air Force Office of Scientific Research, N00014-18-1-2878 awarded by the Office of Naval Research, GM095843 awarded by the National Institutes of Health, and CHE1740597 awarded by the National Science Foundation. The government has certain rights in the invention.

Signed and Sealed this
Twenty-seventh Day of May, 2025

Coke Morgan Stewart
*Acting Director of the United States Patent and Trademark Office*